(12) United States Patent
Sahin et al.

(10) Patent No.: US 8,399,210 B2
(45) Date of Patent: Mar. 19, 2013

(54) AUTOANTIGENES FOR IMPROVED DIAGNOSIS, PROGNOSIS AND TREATMENT OF INFLAMMATORY NEUROLOGICAL DISEASES

(75) Inventors: Ugur Sahin, Mainz (DE); Özlem Türeci, Mainz (DE); Alexander Zaigler, Hainburg (DE)

(73) Assignees: Ganymed Pharmaceuticals AG, Mainz (DE); Johannes Gutenberg-Universitat, Mainz (DE)

( * ) Notice: Subject to any disclaimer, the term of this patent is extended or adjusted under 35 U.S.C. 154(b) by 130 days.

(21) Appl. No.: 12/420,627

(22) Filed: Apr. 8, 2009

(65) Prior Publication Data

US 2009/0252714 A1    Oct. 8, 2009

Related U.S. Application Data

(63) Continuation of application No. PCT/EP2007/008776, filed on Oct. 9, 2007.

(30) Foreign Application Priority Data

Oct. 11, 2006  (DE) .......................... 10 2006 048 201

(51) Int. Cl.
*G01N 33/53* (2006.01)
*G01N 33/537* (2006.01)
*G01N 33/567* (2006.01)

(52) U.S. Cl. ........ 435/7.92; 435/7.1; 435/7.21; 435/7.8; 435/7.9; 436/501; 436/503

(58) Field of Classification Search .................. None
See application file for complete search history.

(56) References Cited

U.S. PATENT DOCUMENTS 7,807,777 B2 * 10/2010 Suzuki et al. ................. 530/300
2005/0142616 A1   6/2005 Hanson et al.

FOREIGN PATENT DOCUMENTS

| WO | WO 02/22819 | 3/2002 |
|---|---|---|
| WO | WO 03/042701 | 5/2003 |
| WO | WO 2006/032126 | 3/2006 |

OTHER PUBLICATIONS

O' Dwyer et al., "Pituitary autoantibodies in lymphocytic hypophysitis target both gamma- and alpha-enolase: A link with pregnancy?" Archives of Physiology and Biochemistry, vol. 110, No. 1-2, Apr. 2002. XP009099986.
International Preliminary Report on Patentability for International Patent Application Serial No. PCT/EP2007/008776, mailed May 14, 2009.
Maruyama et al., "Autoimmune mechanisms in molecular pathology of glaucomatous optic neuropathy." Nippon Ganka Gakkai Zasshi; April 105(4):205-12 (2001).
Lisiany et al., "Humoral link of autoimmune reactions to neuron-specific enolase in post-radiation encephalopathy patients." Ukr Biokhim Zh; Nov.-Dec. 70(6):76-82 (1998).
Patricia Krause "SeroGRID: an improved method for the rapid selection of antigens with disease related immunogenicity", Journal of Immunological Methods 283 (2003) 261-267.

* cited by examiner

*Primary Examiner* — Olga N Chernyshev
(74) *Attorney, Agent, or Firm* — McAndrews, Held & Malloy Ltd.

(57) ABSTRACT

According to the invention, autoantibodies, the appearance of which is characteristic of neurological autoimmune diseases, especially multiple sclerosis, are detected and the respective autoantigens identified. It can further be shown that many of these autoantigens are expressed specifically in the brain. The identification of the autoantigens and autoantibodies is useful for diagnosis and treatment. A brain-specific expression of the autoantigens further emphasizes an important role of the antigens and antibodies in the origin and development of neurological autoimmune diseases.

9 Claims, 10 Drawing Sheets

Fig. 3

| class | number | gene |
|---|---|---|
| brain specific antigens | 8 | ARPP-19, NAP1L3, CLSTN1, CMTM2, CPE, LITAF, ENO2, TUBG1 |
| other autoantigens | 4 | SDCCAG8, HSP90B1, SAT, EXOSC5 |
| unknown antigens | 10 | chromosome 20 sequence; CEP63; LOC115648; chromosome 18 sequence; chromosome 14 sequence 1; chromosome 14 sequence 2; IQWD1; c6ORF199; chromosome 22 sequence; LOC400843 |
| other cellular antigens | 17 | IRF2BP2, SREBF1, XPO4, ZFP64, FNPB1, CCL4, COPA, GHITM, NGLY1, KTN1, SFRS11, NME1-NME2, RPS15, APC2, GLS2, TECAL8, PPIF |
| mitochondrial antigens | 5 | ND4; ATP5H; COX1; COX2; COX3 |
| summary | 44 autoantigens | |

AUTOANTIGENES FOR IMPROVED DIAGNOSIS, PROGNOSIS AND TREATMENT OF INFLAMMATORY NEUROLOGICAL DISEASES

RELATED APPLICATIONS

This application is a Continuation Application of International Application Number PCT/EP2007/008776, filed Oct. 9, 2007, and claiming priority benefit of German Patent Application Number 10 2008 048 201.8, filed on Oct. 11, 2006, the contents of which are incorporated herein by reference in their entireties.

FEDERALLY SPONSORED RESEARCH OR DEVELOPMENT

[Not Applicable]

BACKGROUND OF THE INVENTION

A maximally comprehensive analysis of the autoimmune response of the immune system is necessary for developing efficient serodiagnostic agents and therapeutic agents for neurological autoimmune diseases. The serodiagnosis of autoimmune diseases is based on detection of autoantibodies which circulate in the blood and are specifically directed against immunogenic constituents (antigens) of autologous proteins. These antigens are also the sites of action of preventive and therapeutic strategies for autoimmune diseases. Knowledge of these antigens therefore permits the development of methods for the specific diagnosis and therapy of inflammatory neurological diseases.

Inflammatory neurological diseases, and especially multiple sclerosis (MS), are widespread diseases. According to statements by the WHO, multiple sclerosis is the commonest neurological disease in young adults around the world, with a prevalence of about 1:800 in Europe and North America. The chronic inflammatory disease of the nervous system, which appears for the first time in patients between 15 and 40 years of age, leads to a demyelinization of dendrites of the central nervous system (CNS). This results in a progressive paralysis of the muscles, losses of sensitivity and psychological disorders. Both the clinical course and the pathology of the cerebral disease are extremely heterogeneous (Lucchinetti et al., 2000 Ann Neurol 47, 707), The disease has either a chronic progressive or episodic course. General neurological symptoms appear initially and can be differentiated only with difficulty from other neurological diseases.

The etiology of the neurological autoimmune diseases and especially of MS has not been completely elucidated as yet, despite intensive research. An important role is ascribed to genetic and immunological and viral/bacterial factors (Kalman et al., 1999, Biomed Pharmac 53, 358; Lucchinetti et al., 2001, Curr Opin Neurol 14, 259; Kurtzke, 2001, J Clin Epidemiol 54, 1). A crucial role is, however, played by autoimmune processes, and various hypotheses concerning the immune dysregulation have been suggested. Thus, for example, the loss of regulatory mechanisms of autoreactive T cells has been described. The pathogenesis of MS lesions (Lucchinetti et al., 2000, Ann Neurol 47, 707) additionally supports the importance of autoimmune processes in the course of the disease. The reasons for the autoimmunity might be for example the similarity of viral antigens to encephalitogenic antigens ("Molecular mimicry") or traumatic tissue death (Levin et al., 2002, Nat Med 8, 509; Ludewig et al., 2004, J Exp Med 200, 837) as underlying mechanism. The significance of the immune dysregulation in inflammatory neurological diseases is additionally supported by numerous experiments in model organisms in which an "experimental autoimmune encephalitis" (EAE) can be induced by autoimmunological processes ('t Hart et al., 2003, Curr Opin Neurol 18, 375).

The diagnosis of neurological autoimmune diseases and of MS in particular is currently a great problem. The first symptoms such as, for example, vision or coordination impairments and signs of paralysis and deafness apply to numerous neurological diseases, and differential diagnosis from autoimmune diseases is scarcely possible (Schmitt, 2003, Biomed Pharmacother 57, 261). A reliable diagnosis of MS is ultimately obtained only by combination with other criteria such as, for example, the number of inflammatory brain lesions which are obtained with the aid of MRI spectroscopy (magnetic resonance imaging), or analysis of oligoclonal IgG bands in the CSF. A rapid and reliable diagnosis using serum or urine is not at present possible, although various markers have been analyzed for their diagnostic power (Berger et al., 2003, New Engl J Med 349, 139; Chamczuk et al., 2002, J Imm Methods 262, 21; Vojdani et al., 2003, J Int Med 254, 383) and immunological tests in the form of ELISA and RIA are commercially available (e.g. from Diagnostics Systems Laboratory, Dakocytomation). There is as yet furthermore no laboratory diagnostic method which characterizes the course of MS in relation to imminent pathological episodes, and characterizes the course of pathological episodes and determines whether the disease is about to take a more active or aggressive course in patients (e.g. episodic course of the disease to chronic progressive). Ultimately, there is no diagnostic method which gives prognostic indications of possible MS and/or a diagnostic method which characterizes the course of treatment of MS.

A disease-specific treatment of MS has not been established to date. The treatment of MS is currently predominantly symptomatic using antiinflammatory medicaments. Steroids and various interferons are employed in particular (Jacobs et al., 2003, J Exp Med 343, 598; EP1289541). In principle, these medicaments reduce the inflammatory immune response through toxic effects on lymphocytes, but do not prevent the further episodic or chronic progressive course of the disease. Other substances currently being tested are statins (US2002159974) and glatiramer acetate, which is said to inhibit T-cell proliferation by competition (Duda et al., 1999, J Clin Invest 105, 987; EP1487783; WO2004078145). In addition, some antigen-specific approaches are currently being analyzed. Attempts to treat MS by T-cell vaccinations are still in the early stages (WO9115225). Therapeutic approaches with various monoclonal antibodies directed against the antigens $\alpha_4$-integrin (Bielekova et al. 2000, Nat Med 6, 1145), CD40 (patent publication: WO03045978) and CD52 (patent publication: EP1455826) are moreover in different clinical phases. It has moreover been possible to test successfully an antigen-specific tolerance therapy in EAE models (Robinson et al., 2003, Nat Biotechn 21, 1033).

It has not been possible to utilize the information obtained to date in order to provide maximally sensitive and specific test methods enabling reliable and generally accepted diagnostic methods using serum for neurological autoimmune diseases, especially multiple sclerosis. Nor has it been possible on the basis of the antigens known to date to establish either an effective preventive or a therapeutic vaccination, although a wide variety of methods have been published, and some substances are still being tested.

There is thus a need for an effective diagnosis, prognosis and therapy of neurological autoimmune diseases, and especially multiple sclerosis.

It was the object of the present invention to provide target structures for a diagnosis, prognosis and therapy of neurological autoimmune diseases such as multiple sclerosis. It was the particular object of the present invention to identify molecular markers which enable differential diagnosis between neurological autoimmune diseases such as multiple sclerosis and other neurological diseases.

This object is achieved according to the invention by the subject matter of the claims.

BRIEF SUMMARY OF THE INVENTION

According to the invention, autoantibodies whose occurrence is characteristic of neurological autoimmune diseases, especially multiple sclerosis, are detected and the respective autoantigens are identified. It has further been possible to show according to the invention that some of these autoantigens are specifically expressed in the brain. Identification of the autoantigens and autoantibodies is of diagnostic and therapeutic use, with brain-specific expression of the autoantigens further underlining an important role of the antigens and antibodies in the development and course of neurological autoimmune diseases.

Accordingly, the invention relates to methods which enable assessment and/or prognosis of a neurological autoimmune disease. The methods of the invention preferably make it possible to state whether a neurological autoimmune disease has been contracted or will be contracted. The methods of the invention preferably allow a distinction to be made between a neurological disease which is not an autoimmune disease, and a neurological autoimmune disease, especially between a neurological disease which is not multiple sclerosis, and multiple sclerosis. The methods of the invention may also give information about the success of a treatment of a neurological autoimmune disease. In this embodiment, success of a treatment of a neurological autoimmune disease is preferably indicated by a decrease in one or more of the auto-antibodies or T lymphocytes described herein. The methods of the invention also make it possible to monitor the course of the disease, and if the disease deteriorates, as indicated for example by an increase in one or more of the autoantibodies or T lymphocytes described herein, the planning of a more aggressive therapy such as a treatment by immunosuppression is made possible.

In one aspect, the invention relates to a method for the diagnosis, prognosis and/or monitoring, i.e. determination of the regression, progression and/or course, of a neurological autoimmune disease in a patient, comprising the detection and/or determination of the amount of an antibody which is specific for a protein or peptide which is encoded by a nucleic acid which is selected from the group consisting of:

(a) a nucleic acid which comprises a nucleic acid sequence which is selected from the group consisting of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, a part and a derivative thereof, (b) a nucleic acid which hybridizes under stringent conditions with the nucleic acid of (a), (c) a nucleic acid which is degenerate in relation to the nucleic acid of (a) or (b), and (d) a nucleic acid which is complementary to the nucleic acid of (a), (b) or (c), or is specific for a part or a derivative of the protein or peptide, in a biological sample isolated from a patient. The protein or peptide for which the antibody is specific preferably comprises a sequence which is selected from the group consisting of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, a part and derivative thereof.

In one embodiment of the invention, the method of the invention further comprises the detection and/or determination of the amount of the antibody in a biological sample isolated from a patient without the autoimmune disease and/or without a risk of the autoimmune disease.

Presence of the antibody and/or an amount of the antibody which is increased by comparison with a patient without the autoimmune disease and/or without a risk of the autoimmune disease in the biological sample indicates preferentially the presence of the autoimmune disease or a risk of the development of the autoimmune disease.

In a preferred embodiment, the detection and/or determination of the amount of the antibody takes place with an immunoassay. The detection and/or determination of the amount of the antibody preferably comprises (i) contacting the biological sample with an agent which specifically binds to the antibody, and (ii) detecting the formation of a complex between the agent and the antibody. The agent which specifically binds to the antibody is preferably immobilized on a support material and/or is preferably a protein or peptide or derivative thereof which specifically binds to the antibody. In a preferred embodiment, the protein or peptide which specifically binds to the antibody comprises a sequence which is encoded by a nucleic acid which is selected from the group consisting of: (a) a nucleic acid which comprises a nucleic acid sequence selected from the group consisting of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 89, 71, 73, 75, 77, 79, 81, 83, 85, 87, a part and a derivative thereof, (b) a nucleic acid which hybridizes under stringent conditions with the nucleic acid of (a), (c) a nucleic acid which is degenerate in relation to the nucleic acid of (a) or (b), and (d) a nucleic acid which is complementary to the nucleic acid of (a), (b) or (c). The protein or peptide which specifically binds to the antibody preferably comprises a sequence which is selected from the group consisting of SEQ ID NO: 2, 4, 6, 8, 10, 12, 14, 18, 18, 20, 22, 24, 26, 28, 30, 32, 34, 36, 38, 40, 42, 44, 46, 48, 50, 52, 54, 56, 58, 60, 62, 84, 68, 68, 70, 72, 74, 78, 78, 80, 82, 84, 88, 88, and a part thereof. A derivative of the protein or peptide is accordingly preferably derived from such a protein or peptide.

In a further aspect, the invention relates to a method for the diagnosis, prognosis and/or monitoring of a neurological autoimmune disease in a patient, comprising the detection and/or determination of the amount of a T lymphocyte which is specific for a protein or peptide which is encoded by a nucleic acid which is selected from the group consisting of: (a) a nucleic acid which comprises a nucleic acid sequence which is selected from the group consisting of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, a part and a derivative thereof, (b) a nucleic acid which hybridizes under stringent conditions with the nucleic acid of (a), (c) a nucleic acid which is degenerate in relation to the nucleic acid of (a) or (b), and (d) a nucleic acid which is complementary to the nucleic acid of (a), (b) or (c), or is specific for a part or a derivative of the protein or peptide, in a biological sample isolated from a patient. The protein or peptide for which the T lymphocyte is specific preferably comprises a sequence selected from the group consisting of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, a part and derivative thereof.

In one embodiment of the invention, the method of the invention further comprises the detection and/or determination of the amount of the T lymphocyte in a biological sample isolated from a patient without the autoimmune disease and/or without a risk of the autoimmune disease.

Presence of the T lymphocyte and/or an amount of the T lymphocyte which is increased by comparison with a patient without the autoimmune disease and/or without a risk of the autoimmune disease in the biological sample indicates preferentially the presence of the autoimmune disease or a risk of the development of the autoimmune disease.

In a preferred embodiment, the detection and/or determination of the amount of the T lymphocyte takes place with a lymphocyte proliferation test. The detection and/or determination of the amount of the T lymphocyte preferably comprises (i) contacting the biological sample with an agent which specifically binds to the T lymphocyte, and (ii) detecting the formation of a complex between the agent and the T lymphocyte. The agent which specifically binds to the T lymphocyte is preferably immobilized on a support material. In one embodiment, the agent which specifically binds to the T lymphocyte is a protein or peptide or a derivative thereof which specifically binds to the T lymphocyte. In a further embodiment, the agent which specifically binds to the T lymphocyte is a complex which comprises an MHC molecule or a part thereof and a protein or peptide or derivative thereof and which specifically binds to the T lymphocyte. In one embodiment, the complex is presented by a cell such as an antigen-presenting cell.

The protein or peptide which specifically binds to the T lymphocyte, or which is comprised in the complex which specifically binds to the T lymphocyte, preferably comprises a sequence which is encoded by a nucleic acid which is selected from the group consisting of: (a) a nucleic acid which comprises a nucleic acid sequence selected from the group consisting of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 81, 83, 65, 87, 69, 71, 73, 75, 77, 79, 81, 83, 85, 87, a part and a derivative thereof, (b) a nucleic acid which hybridizes under stringent conditions with the nucleic acid of (a), (c) a nucleic acid which is degenerate in relation to the nucleic acid of (a) or (b), and (d) a nucleic acid which is complementary to the nucleic acid of (a), (b) or (c). The protein or peptide which specifically binds to the T lymphocyte, or which is comprised in the complex which specifically binds to the T lymphocyte, preferably comprises a sequence selected from the group consisting of SEQ ID NO: 2, 4, 8, 8, 10, 12, 14, 18, 18, 20, 22, 24, 28, 28, 30, 32, 34, 36, 38, 40, 42, 44, 48, 48, 50, 52, 54, 56, 58, 60, 82, 64, 68, 88, 70, 72, 74, 78, 78, 80, 82, 84, 86, 88, and a part thereof. A derivative of the protein or peptide is accordingly preferably derived from such a protein or peptide.

In one embodiment, the methods of the invention for monitoring a neurological autoimmune disease comprise a determination of the regression, the course or the onset of the disease in a sample from the patient. In particular embodiments, the methods of the invention for monitoring a neurological autoimmune disease serve to monitor a successful therapy of the neurological autoimmune disease, in which case a decrease in the level of antibodies and/or T lymphocytes which are detected and/or determined according to the invention indicates a successful therapy.

In particular embodiments, the methods of the invention for the diagnosis, prognosis and/or monitoring of a neurological autoimmune disease comprise a detection or determination of the amount in a first sample at a first time and in a further sample at a second time and comparison of the two samples.

A biological sample comprises according to the invention preferably body fluid and/or body tissue, where the body fluid is preferably selected from serum, plasma, urine and cerebrospinal fluid.

The neurological autoimmune disease is preferably according to the invention multiple sclerosis.

In a particularly preferred embodiment, the invention in the foregoing aspects relates to a method for the diagnosis of a neurological autoimmune disease, especially multiple sclerosis.

In particular embodiments of the methods of the invention for the diagnosis, prognosis and/or monitoring of a neurological autoimmune disease, the patent is suffering from a neurological disease, in particular from a neurological autoimmune disease, and displays in particular symptoms of such a disease, is suspected of suffering from a neurological disease, in particular from a neurological autoimmune disease, or of developing such a disease, or exhibits a risk of a neurological disease, in particular a neurological autoimmune disease.

In a preferred embodiment, the biological sample isolated from a patient is compared with a comparable normal biological sample such as a sample from a healthy individual.

The agent used for a detection or determination of the amount of antibodies or T lymphocytes, in particular the protein, peptide or derivative thereof, or the agent which binds to a complex formed between an antibody or T lymphocyte and an agent binding thereto, in particular an anti-immunoglobulin antibody or an antibody directed against T lymphocytes, are preferably detectably labeled. In particular embodiments, the detectable marker is a radioactive marker, fluorescent marker or enzyme marker.

In particular embodiments, the methods of the invention comprise a detection of a plurality of the autoantibodies and/or T lymphocytes described herein.

In a further aspect, the invention relates to a kit which comprises one or more agents which make it possible to detect and/or determine the amount of the antibodies or T lymphocytes described herein in a biological sample isolated from a patient. Such agents are described herein and known to the person skilled in the art.

The invention in this aspect relates in particular to a kit for the diagnosis, prognosis and/or monitoring of a neurological autoimmune disease in a patient, comprising a protein or peptide which comprises a sequence selected from the group consisting of SEQ ID NO: 2, 4, 8, 8, 10, 12, 14, 18, 18, 20, 22, 24, 26, 28, 30, 32, 34, 36, 38, 40, 42, 44, 48, 48, 50, 52, 54, 56, 58, 60, 82, 64, 68, 88, 70, 72, 74, 78, 78, 80, 82, 84, 86, 88, and a part thereof or a derivative of the protein or peptide. The protein or peptide or the derivative thereof is preferably immobilized on a support.

The kit of the invention preferably further comprises instructions for use of the kit in a method for the diagnosis, prognosis and/or monitoring of a neurological autoimmune disease in a patient, where the method is preferably a method of the invention.

In one embodiment, the kit further comprises a reagent for detecting a binding of an antibody to the protein or peptide contained therein, or the derivative thereof, where the reagent preferably comprises a detectably labeled binding partner for the antibody. The binding partner for the antibody is preferably an anti-immunoglobulin antibody, in particular an anti-human immunoglobulin antibody coupled to a detectable marker such as an enzyme. The kit of the invention may further also comprise an enzyme substrate, and positive controls and negative controls.

In a further aspect, the invention relates to a pharmaceutical composition comprising one or more components which are selected from the group consisting of (i) a protein or peptide which comprises a sequence which is selected from the group consisting of SEQ ID NO: 2, 4, 8, 8, 10, 12, 14, 18, 18, 20, 22, 24, 26, 28, 30, 32, 34, 36, 38, 40, 42, 44, 46, 48, 50, 52, 54, 58, 58, 80, 62, 64, 86, 68, 70, 72, 74, 76, 78, 80, 82, 84, 86, 88, and a part thereof or a derivative of the protein or peptide, (ii) a nucleic acid which expresses the protein or peptide or the derivative thereof in (i), and (iii) a host cell which comprises the nucleic acid in (ii). The nucleic acid may be present in an expression vector. The host cell will preferably express the peptide or protein or derivative thereof.

A host cell present in the pharmaceutical composition of the invention may secrete the protein or peptide or derivative thereof, express it on the surface or may additionally express an MHC molecule which binds to the protein or peptide or derivative thereof or to a processed form thereof. In one embodiment, the host cell expresses the MHC molecule endogenously. In a further embodiment, the host cell expresses the MHC molecule and/or the protein or peptide or derivative thereof recombinantly. The host cell is preferably non-proliferative. In a preferred embodiment, the host cell is an antigen-presenting cell.

A pharmaceutical composition of the invention may comprise a pharmaceutically acceptable carrier and/or an adjuvant, and is preferably suitable for the treatment of a neurological autoimmune disease, especially for the treatment of multiple sclerosis.

The invention further relates to a method for the treatment of a neurological autoimmune disease, especially multiple sclerosis, comprising the administration of a pharmaceutical composition of the invention.

BRIEF DESCRIPTION OF SEVERAL VIEWS OF THE DRAWINGS

FIG. 3. Classification of the antigens identified according to the invention.

Figure 1:
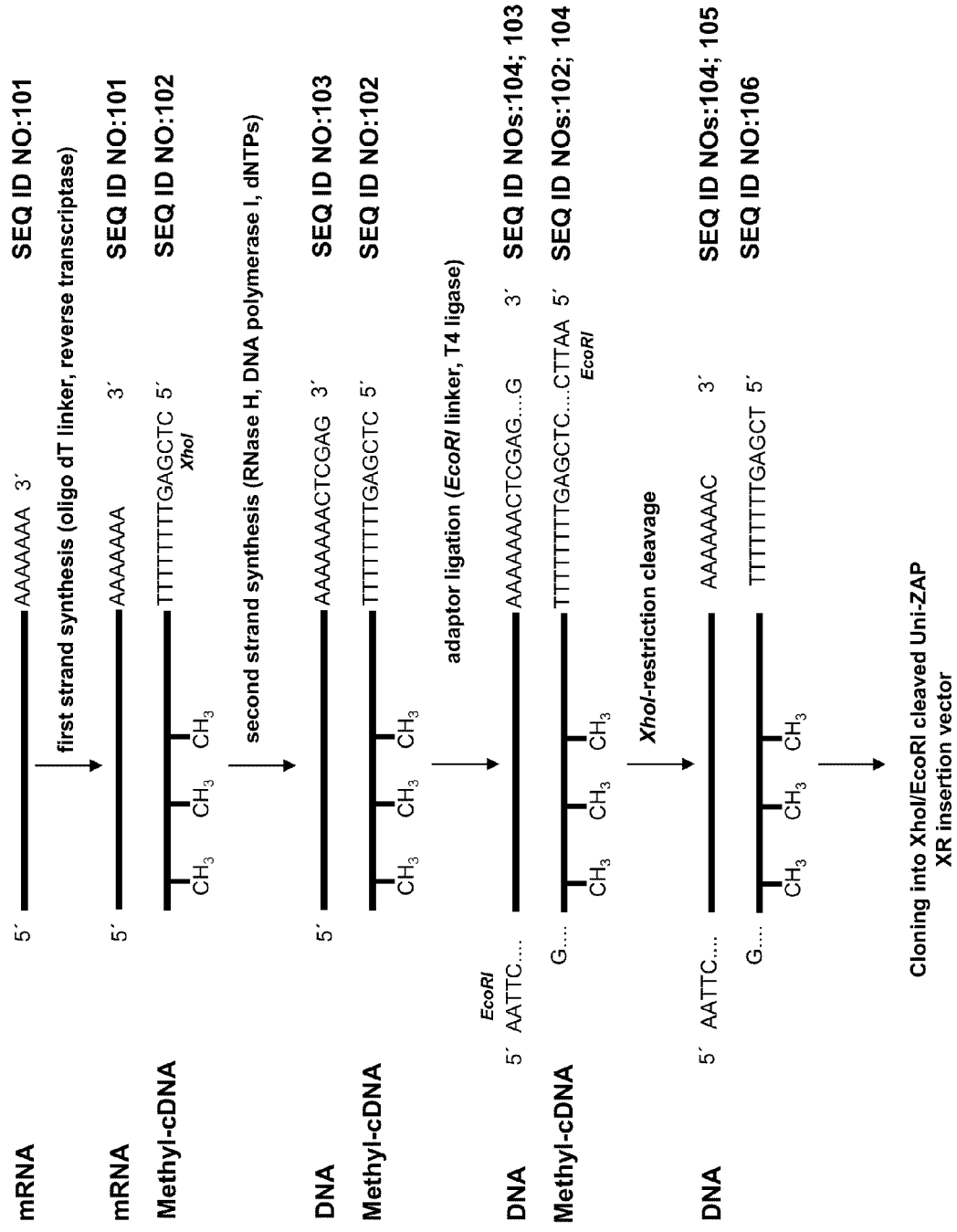
FIG. 1. Diagrammatic representation of the strategy for producing a brain-specific cDNA expression library.

B: Summary of the signal intensities of all the antigens depicted in FIG. 10 A after incubation with sera from MS patients compared with healthy control sera.

DETAILED DESCRIPTION OF THE INVENTION

The term "autoantigen" relates according to the invention to a substance which generates an immune response such as the production of antibodies in the creature from which it is derived. In particular, the term "autoantigen" relates according to the invention to a protein or peptide which is encoded by a nucleic acid which is selected from the group consisting of:

(a) a nucleic acid which comprises a nucleic acid sequence selected from the group consisting of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 83, 65, 67, 89, 71, 73, 75, 77, 79, 81, 83, 85, 87, a part and a derivative thereof, (b) a nucleic acid which hybridizes under stringent conditions with the nucleic acid of (a), (c) a nucleic acid which is degenerate in relation to the nucleic acid of (a) or (b), and (d) a nucleic acid which is complementary to the nucleic acid of (a), (b) or (c), or a part or a derivative of the protein or peptide. The term "autoantigen" refers according to the invention in particular to a protein or peptide which comprises a sequence which is selected from the group consisting of SEQ ID NO: 2, 4, 8, 8, 10, 12, 14, 18, 18, 20, 22, 24, 26, 28, 30, 32, 34, 38, 38, 40, 42, 44, 48, 48, 50, 52, 54, 58, 58, 80, 82, 84, 86, 88, 70, 72, 74, 76, 78, 80, 82, 84, 88, 88, a part and derivative thereof.

The term "autoantibody" relates according to the invention to antibodies which are directed against an autoantigen. Autoantibodies recognize an endogenous antigen and occur inter alia in association with autoimmune diseases. In particular, the term "autoantibody" relates according to the invention to an antibody which is directed against an autoantigen described above and in particular specifically binds thereto.

The term "detection and/or determination of the amount" in relation to a substance relates according to the invention to the determination of the occurrence or absence and/or the absolute and/or relative amount of the substance. The term also includes situations in which no substance is detected, either because it is not present, or its amount is below the limit of detection of the detection system.

It is generally possible according to the invention to employ all methods suitable for a detection and analysis of antibodies or T lymphocytes for a detection and/or determination of the amount thereof. Possibilities for carrying out a detection and/or determination of the amount of antibodies and T lymphocytes in the methods of the invention are known to the person skilled in the art.

It is possible in particular to use according to the invention any direct or indirect method for detecting antibodies.

In the direct methods, the binding of the antibodies to be detected to the antigen is determined via a change in the chemical or physical properties, so that subsequent detection steps with labeled binding partners are unnecessary.

It is preferred according to the invention for antibodies to be detected in an immunoassay, preferably in a solid-phase immunoassay, with direct or indirect coupling of a binding partner.

The detection can particularly preferably take place in an ELISA, an RIA or a fluorescence immunoassay. The procedure for these detection methods is known to the person skilled in the art.

It is possible to use as solid phase for example any support able to bind to antigen or antibody. Such supports include materials such as glass, polystyrene, polypropylene, polyethylene, dextran, nylon, natural or modified celluloses, polyacrylamides, agaroses and magnetite. The support may have any possible structural configuration as long as the molecule bound thereto, such as antigen or antibody, is able to bind to its binding partner. Suitable configurations include a spherical configuration, a cylindrical configuration such as the inside of a test vessel, or a flat configuration such as test strips etc.

In an ELISA for example antigen is bound directly or indirectly to a support substance such as polystyrene. Incubation with the antibodies to be detected is followed by detection of antigen-bound antibodies directly or indirectly by means of enzyme-coupled substances. These substances may be antibodies, fragments of antibodies or high-affinity ligands. Examples of suitable enzymes are peroxidase, alkaline phosphatase, β-galactosidase, urease or glucose oxidase. It is possible by adding a chromogenic substrate for the bound enzymes, and thus for example the bound antibodies, to be quantified.

In a radioimmunoassay, the antigen is bound directly or indirectly to a support substance such as polystyrene. Incubation with the antibodies to be detected is followed by detection of antigen-bound antibodies by means of substances having a radioactive label such as $^{125}$I. These substances may be antibodies, fragments of antibodies or high-affinity ligands. The bound radioactivity can be quantified by means of a suitable measuring instrument.

By the same principle, in a fluorescence immunoassay the antigen-bound antibodies are detected by means of substances which have a fluorescent label such as fluorescein isothiocyanate (FITC). These substances may be antibodies, fragments of antibodies or high-affinity ligands. The bound amount of fluorescent dye is then quantified by means of a suitable measuring instrument.

It is also possible according to the invention to detect antibodies in an agglutination test or gel diffusion test. These detection methods are also known to the person skilled in the art.

In the gel diffusion test, the antigen solutions or antibody solutions are preferably put into neighboring, adjacent wells of agar or agarose plates. If the substances diffuse out of their wells, concentration gradients form, starting from the wells. If the overlapping antigen and antibody concentrations in the gel are within certain proportions, and the antibody solution contains antibodies against the antigen, visible precipitates are formed in the gel.

In the agglutination test, antigen-carrying particles such as particles of latex or polystyrene are crosslinked by antibodies. The aggregates formed can be detected for example by turbodimetry.

A detection or determination of the amount of a T lymphocyte can take place according to the invention with a cell which presents a complex, for which the T lymphocyte is specific, between a protein, peptide or derivative thereof and an MHC molecule, where the cell is preferably an antigen-presenting cell. Detection or determination of the amount of a T lymphocyte takes place where appropriate through detection of its proliferation, cytokine production and/or cytotoxic activity which is induced by the specific stimulation with the complex between the protein, peptide or derivatives thereof and an MHC molecule. A detection or determination of the amount of a T lymphocyte can moreover take place through a recombinant MHC molecule or a complex of two or more MHC molecules which are loaded with one or more proteins, peptides, or derivatives thereof.

In one embodiment, the cell expresses the MHC molecule endogenously. In a further embodiment, the cell expresses the MHC molecule and/or the protein or peptide or derivative thereof recombinantly. The host cell is preferably non-proliferative. In a preferred embodiment, the host cell is an antigen-presenting cell.

A binding agent such as antibody is specific for its target, such as an antigen, if it binds thereto. The term "binding" relates according to the invention preferably to a specific binding. "Specific binding" means that a binding to a target such as an epitope for which a binding agent such as an antibody is specific is stronger by comparison with the binding to another target. A "stronger binding" can be characterized for example by a lower dissociation constant.

It is possible according to the invention to use a "reference" such as a reference sample or a reference organism in order to correlate or compare the results obtained in the methods of the invention. A reference organism is typically a healthy organism, especially an organism which is not suffering from a neurological autoimmune disease, especially from multiple sclerosis.

A "reference value" can be determined on the basis of a reference empirically by measuring a sufficient number of references.

A nucleic acid is according to the invention preferably deoxyribonucleic acid (DNA) or ribonucleic acid (RNA). Nucleic acids include according to the invention genomic DNA, cDNA, mRNA, recombinantly prepared and chemically synthesized molecules. A nucleic acid may according to the invention be in the form of a single-stranded or double-stranded and linear or covalently circularly closed molecule.

The nucleic acids described according to the invention are preferably isolated. The term "isolated nucleic acid" means according to the invention that the nucleic acid (i) has been amplified in vitro, for example by polymerase chain reaction (PCR), (ii) has been produced recombinantly by cloning, (iii) has been purified, for example by cleavage and fractionation by gel electrophoresis, or (iv) has been synthesized, for example by chemical synthesis. An isolated nucleic acid is a nucleic acid which is available for manipulation by recombinant DNA techniques.

A degenerate nucleic acid is according to the invention a nucleic acid which differs from a reference nucleic acid in terms of the codon sequence on the basis of the degeneracy of the genetic code.

The term "nucleic acid" also includes according to the invention derivatives of nucleic acids. By "derivative" of a nucleic acid is meant according to the invention that single or multiple, preferably at least 2, at least 4, at least 6 and preferably up to 3, up to 4, up to 5, up to 6, up to 10, up to 15 or up to 20, substitutions, deletions and/or additions of nucleotides are present in the nucleic acid.

The term "derivative" of a nucleic acid further includes also a chemical derivatization of a nucleic acid on a nucleotide base, on the sugar or on the phosphate and nucleic acids which contain non-naturally occurring nucleotides and nucleotide analogs.

The degree of identity between a nucleic acid and a nucleic acid which is a derivative of the first nucleic acid, which hybridizes with the first nucleic acid and/or which is degenerate in relation to the first nucleic acid is preferably according to the invention at least 70%, in particular at least 75%, at least 80%, at least 85%, at least 90%, at least 95%, at least 98%, at least 97%, at least 98%, and preferably at least 99%. The degree of identity is preferably indicated for a region of at least about 30, at least about 50, at least about 70, at least about 90, at least about 100, at least about 150, at least about 200, at least about 300, at least about 400, at least about 500, at least about 1000, or at least about 2000 consecutive nucleotides. In preferred embodiments, the degree of identity is indicated for the complete length of the reference nucleic acid like the nucleic acid sequences indicated in the sequence listing.

A nucleic acid is "complementary" to another nucleic acid if the two sequences are able to hybridize together and enter into a stable duplex, the hybridization preferably taking place under conditions which permit a specific hybridization between polynucleotides (stringent conditions). Stringent conditions are described for example in Molecular Cloning: A Laboratory Manual, J. Sambrook et al., editors, $2^{nd}$ edition, Cold Spring Harbor Laboratory Press, Cold Spring Harbor, N.Y., 1989 or Current Protocols in Molecular Biology, F. M. Ausubel et al., editors, John Wiley & Sons, Inc., New York, and relate for example to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After the hybridization, the membrane to which the DNA has been transferred is washed for example in 2×SSC at room temperature and then in 0.1-0.5×SSC/0.1×SDS at temperatures up to 68° C.

Percent complementarity indicates the percentage of consecutive nucleotides in a nucleic acid which are able to form hydrogen bonds (e.g. by Watson-Crick base pairing) with a second nucleic acid. Complementary nucleic acids preferably exhibit according to the invention at least 40%, in particular at least 50%, at least 80%, at least 70%, at least 80%, at least 90% and preferably at least 95%, at least 98% or at least 99% complementary nucleotides. Complementary nucleic acids are preferably completely complementary, meaning that all consecutive nucleotides can enter into hydrogen bonds with the same number of consecutive nucleotides in a second nucleic acid.

"Sequence similarity" indicates the percentage of amino acids which either are identical or represent conservative amino acid substitutions. "Sequence identity" between two polypeptides or nucleic acids indicates the percentage of amino acids or nucleotides which are identical between the sequences.

The term "% identity" is intended to refer to a percentage of nucleotides which are identical between two sequences to be compared with an optimal alignment, this percentage being purely statistical, it being possible for the differences between the two sequences to be distributed at random and over the complete sequence length, and it being possible for the sequence to be compared to include additions or deletions by comparison with the reference sequence in order to achieve an optimal alignment between two sequences. Sequence comparisons between two sequences are generally carried out by comparing the sequences after an optimal alignment in relation to a segment or "comparison window" in order to identify local regions of sequence agreement. The optimal alignment for a comparison can be carried out manually or with the aid of the local homology algorithm of Smith and Waterman, 1981, Ads App. Math. 2, 482, with the aid of the local homology algorithm of Neddleman and Wunsch, 1970, J. Mol. Biol. 48, 443, and with the aid of the similarity search algorithm of Pearson and Lipman, 1988, Proc. Natl. Acad. Sci. USA 85, 2444, or with the aid of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percent identity is obtained by determining the number of identical positions in which the sequences to be compared agree, dividing this number by the compared positions and multiplying this result by 100.

It is for example possible to use the program BLAST "BLAST 2 sequences" which is obtainable from the website http://www.ncbi.nlm.nih.gov/blast/bl2seq/wblast2.cgi.

Derivatives of a particular nucleic acid relate in particular to variants of the nucleic acid, especially splice variants, isoforms and species homologs of the nucleic acid, especially those which are expressed naturally.

Nucleic acids can be analyzed in relation to variants such as splice variants according to the invention in a manner known per se. Techniques for analyzing splice variants include reverse transcription polymerase chain reaction (RT-PCR), Northern blotting and in situ hybridization.

A technique called "RNAse protection" can also be used in order to identify alternatively spliced mRNAs. RNAse protection includes transcription of a gene sequence into synthetic RNA, which is hybridized onto RNA derived for example from other cells. The hybridized RNA is then incubated with enzymes which recognize RNA:RNA hybrid mismatches. Fragments which are smaller than expected indicate the presence of alternatively spliced mRNAs. The putative alternatively spliced mRNAs can be cloned and sequenced in a manner known per se.

RT-PCR can also be used in order to identify alternatively spliced mRNAs. In RT-PCR, mRNA is converted into cDNA by the enzyme reverse transcriptase in a manner known per se. The complete coding sequence of the cDNA is then amplified by means of PCR using a forward primer which is located in the 3'-nontranslated region, and a reverse primer which is located in the 5'-nontranslated region. The amplification products can be analyzed for alternative splice forms for example by comparing the size of the amplified products with the size of the expected product from normally spliced mRNA for example by means of agarose gel electrophoresis. Any changes in the size of the amplification products may indicate alternative splicing.

mRNA derived from mutated genes can also be easily identified with the aid of the techniques described above for identifying alternative splice forms. Thus, for example, allelic forms of genes, and the mRNA produced thereby, which are considered according to the invention to be "mutants", can be identified.

Nucleic acids may according to the invention be present alone or in combination with other nucleic acids, which may be homologous or heterologous. In particular embodiments, a nucleic acid is present according to the invention functionally connected to expression control sequences which may be homologous or heterologous in relation to the nucleic acid, where the term "homologous" here indicates that a nucleic acid is also naturally functionally connected to the expression control sequence, and the term "heterologous" indicates that a nucleic acid is not naturally functionally connected to the expression control sequence.

A nucleic acid, preferably a transcribable nucleic acid, and especially one which codes for a peptide or protein, and an expression control sequence are "functionally" connected together if they are covalently linked together in such a way that transcription or expression of the nucleic acid is under the control or under the influence of the expression control sequence. If the nucleic acid is to be translated into a functional peptide or protein, when an expression control sequence is functionally connected to the coding sequence an induction of the expression control sequence leads to a transcription of the coding sequence without there being a shift in the reading frame in the coding sequence or an inability of the coding sequence to be translated into the desired peptide or protein.

The term "expression control sequence" includes according to the invention promoters, ribosome binding sequences, enhancers and other control elements which control the transcription of a gene or the translation of mRNA. In particular embodiments of the invention, the expression control sequences are regulatable. The exact structure of expression control sequences may vary depending on species or depending on cell type, but generally includes 5'-nontranscribed and 5'- and 3'-nontranslated sequences which are involved in the initiation of transcription or translation, such as TATA box, capping sequence, CAAT sequence and the like. 5'-Nontranscribed expression control sequences include in particular a promoter region which includes a promoter sequence for transcriptional control of the functionally connected nucleic acid. Expression control sequences may also include enhancer sequences or activator sequences located upstream.

The term "promoter" or "promoter region" relates to a nucleic acid sequence which is located upstream (5') of the sequence to be expressed and controls the expression of the sequence by providing a recognition and binding site for RNA polymerase. The promoter region may include further recognition or binding sites for further factors involved in regulating the transcription of a gene. A promoter can control the transcription of a prokaryotic or eukaryotic gene. A promoter may be "inducible" and initiate transcription in response to an inducer, or it may be "constitutive" if the transcription is not controlled by an inducer. An inducible promoter is not expressed or is expressed to only a very small extent if an inducer is absent. In the presence of the inducer, the gene is "switched on" or the transcription level is raised. This is ordinarily mediated by binding of a specific transcription factor.

Promoters preferred according to the invention are for example promoters for SP6, T3 or T7 polymerase, human U6 RNA promoter and CMV promoter.

The term "expression" is used according to the invention in its most general meaning and includes the production of RNA or of RNA and protein/peptide. It also includes partial expression of nucleic acids. The expression may furthermore take place transiently or stably.

It is further possible for a nucleic acid which codes for a protein or peptide to be present according to the invention in conjunction with another nucleic acid which codes for a peptide sequence which controls secretion of the protein or peptide encoded by the nucleic acid from a host cell. It is also possible for a nucleic acid to be present according to the invention in conjunction with another nucleic acid which codes for a peptide sequence which brings about anchoring of the encoded protein or peptide on the cell membrane of a host cell or its compartmentalization in particular organelles of this cell. Conjunction with a nucleic acid which represents a reporter gene or any type of "tag" is equally possible.

In a preferred embodiment, a nucleic acid is present according to the invention in a vector, where appropriate with a promoter which controls the expression of the nucleic acid. The term "vector" is used in this connection in its most general meaning and includes all intermediate vehicles for a nucleic acid which make it possible for example for the nucleic acid to be introduced into prokaryotic and/or into eukaryotic cells and, where appropriate, be integrated into a genome. Such vectors are preferably replicated and/or expressed in the cell. Vectors include plasmids, phagemids, bacteriophages or viral genomes. The term "plasmid" as used herein relates generally to a construct of extrachromosomal genetic material, usually a circular DNA duplex, which can replicate independently of chromosomal DNA.

The term "host cell" relates according to the invention to any cell which can be transformed or transfected with an exogenous nucleic acid, preferably DNA or RNA. The term "host cell" includes according to the invention prokaryotic (e.g. E. coli) or eukaryotic cells (e.g. mammalian cells, especially human cells, yeast cells and insect cells). Mammalian cells such as human cells, mouse cells, hamster cells, pig cells, goat cells and primate cells are particularly preferred. The cells can be derived from a large number of tissue types and include primary cells and cell lines. Specific examples include keratinocytes, peripheral blood leukocytes, bone marrow stem cells and embryonic stem cells. In further embodiments, the host cell is an antigen-presenting cell, where the term "antigen-presenting cell" includes according to the invention dendritic cells, monocytes and macrophages. A nucleic acid may be present in the host cell in a single or in a plurality of copies and is expressed in one embodiment in the host cell.

In the cases of the invention in which an MHC molecule presents a protein or peptide, it is possible for an expression vector also to include a nucleic acid sequence which codes for the MHC molecule. The nucleic acid sequence which codes for the MHC molecule may be present on the same expression vector as the nucleic acid which codes for the protein or peptide, or the two nucleic acids may be present on different expression vectors. In the latter case, the two expression vectors may be cotransfected into a cell. If a host cell expresses neither the protein or peptide nor the MHC molecule, the two nucleic acids coding therefor may be transfected either on the same expression vector or on different expression vectors into the cell. If the cell already expresses the MHC molecule, it is possible for only the nucleic acid sequence which codes for the protein or peptide to be transfected into the cell.

The term "peptide" relates according to the invention to substances which include at least 2, at least 3, at least 4, at least 8, at least 8, at least 10, at least 13, at least 16, at least 20 and preferably up to 8, 10, 20, 30, 50, or 100 consecutive amino acids which are connected together by peptide linkages. The term "protein" relates to large peptides, preferably peptides having more than 100 amino acids, but the terms "peptide" and "protein" are generally used exchangeably herein. The term "protein or peptide" is also intended to include, unless indicated otherwise, derivatives thereof.

The proteins and peptides described according to the invention are preferably isolated. The terms "isolated protein" or "isolated peptide" mean that the protein or peptide is separated from its natural environment. An isolated protein or peptide may be in an essentially purified state. The term "essentially purified" means that the protein or peptide is essentially free of other substances with which it is present in nature or in vivo.

Proteins and peptides are used according to the invention for example for preparing antibodies and can be employed in immunological or diagnostic assays or as therapeutic agents. Proteins and peptides described according to the invention can be isolated from biological samples such as tissue or cell homogenates and can also be expressed recombinantly in a large number of prokaryotic or eukaryotic expression systems. It is further possible according to the invention for proteins and peptides to be synthesized on solid or liquid phase in a manner known per se.

The proteins, peptides or derivatives thereof described herein can be used in their free or bound form for the diagnosis or treatment of patients with a neurological autoimmune disease, where the proteins, peptides or derivatives thereof have the ability in particular to bind, neutralize and/or selectively remove autoantibodies.

"Derivatives" of a protein or peptide or of an amino acid sequence in the context of this invention include amino acid insertion variants, amino acid deletion variants and/or amino acid substitution variants.

Amino acid insertion variants include amino- and/or carboxy-terminal fusions, and insertions of individual or a plurality of amino acids in a particular amino acid sequence. In amino acid sequence variants with an insertion, one or more amino acid residues are introduced into a predetermined position in an amino acid sequence, although random insertion with suitable screening of the resulting product is also possible.

Amino acid deletion variants are characterized by the removal of one or more amino acids from the sequence.

Amino acid substitution variants are distinguished by at least one residue in the sequence being removed and another residue being inserted in its place. The modifications are preferably located at positions in the amino acid sequence which are not conserved between homologous proteins or peptides, and/or amino acids are replaced by others having similar properties, such as hydrophobicity, hydrophilicity, electronegativity, volume of the side chain and the like (conservative substitution). Conservative substitutions relate for example to the exchange of one amino acid by another amino acid mentioned below in the same group as the substituted amino acid:

1. mall aliphatic, nonpolar or slightly polar residues: Ala, Ser, Thr (Pro, Gly)
2. egatively charged residues and their amides: Asn, Asp, Glu, Gln
3. ositively charged residues: His, Arg, Lys
4. arge aliphatic, nonpolar residues: Met, Leu, Ile, Val (Cys)
5. arge aromatic residues: Phe, Tyr, Trp.

Three residues are placed in parentheses because of their particular role for protein architecture. Gly is the only residue without a side chain and thus confers flexibility on the chain. Pro has an unusual geometry which greatly restricts the chain. Cys can form a disulfide bridge.

The degree of similarity, preferably identity, between one amino acid sequence and an amino acid sequence which is a derivative of the former amino acid sequence is preferably at least 70%, in particular at least 75%, at least 80%, at least 85%, at least 90%, at least 95%, at least 98%, at least 97%, at least 98%, and preferably at least 99%. The degree of identity is preferably indicated for a range of at least about 10, at least about 30, at least about 50, at least about 70, at least about 90, at least about 100, at least about 150, at least about 200, at least about 300, at least about 400, or at least about 500 consecutive amino acids. In preferred embodiments, the degree of identity is indicated for the complete length of the reference amino acid sequence like the amino acid sequences indicated in the sequence listing.

The amino acid variants described above can easily be prepared with the aid of known peptide synthesis techniques such as, for example, by "solid-phase synthesis" (Merrifield, 1964) and similar methods or by recombinant DNA manipulation. The manipulation of DNA sequences for preparing proteins and peptides with substitutions, insertions or deletions is described in detail for example in Sambrook et al. (1989).

"Derivatives" of proteins or peptides include according to the invention also single or multiple substitutions, deletions and/or additions of any molecules associated with the protein or peptide, such as carbohydrates, lipids and/or proteins or peptides. The term "derivative" also extends further to all functional chemical equivalents of the proteins and peptides and substances which comprise not only amino acid constituents but also non-amino acid constituents such as sugars and phosphate structures and also include substances which comprise linkages such as ester linkages, thioether linkages and disulfide linkages. A derivative of a protein or peptide preferably has a better stability, preferably a longer in vivo half-life, than the protein or peptide from which it is derived.

Derivatives of a particular protein or peptide also relate to post-translationally modified variants, isoforms and species homologs of the protein or peptide, especially those which are expressed naturally.

A part, i.e. fragment, or derivative of a protein or peptide preferably displays according to the invention a functional property of the protein or peptide from which it is derived. Such functional properties include for example immunoreactivity, especially the interaction with antibodies or the interaction with other peptides or proteins. An important property is the ability to enter into a complex with MHC molecules and where appropriate to generate or prevent an immune response for example by stimulating or inhibiting cytotoxic or helper T cells. A part of a protein or peptide preferably includes a sequence of at least 6, at least 8, at least 1, at least 1, at least 1, at least 2, at least 30 and preferably up to , up to 1, up to 1, up to 1, up to 2, up to 30 or up to 50 consecutive amino acids from the protein or peptide. In one embodiment, a part of a protein or peptide relates according to the invention to one or a plurality of epitopes from the complete peptide or protein, where the plurality of epitopes may be present in their natural connection or may have an artificial, i.e. non-naturally occurring connection, i.e. the epitopes may be separated from one another for example by an artificial linker. A part of a protein or peptide preferably relates according to the invention to a sequence which is a target, in particular an epitope, for an immune response in a patient, for example in a patient with a neurological autoimmune disease. In preferred embodiments, the sequence is the target for an antibody- and/or T-cell-mediated immune response. A peptide, protein or derivative used according to the invention may also include a plurality of sequences which represent epitopes for antibodies or T cells.

A part, i.e. fragment, of a nucleic acid which codes for a protein or peptide relates according to the invention preferably to the part of the nucleic acid which codes at least for the protein or peptide and/or for a part of the protein or peptide as defined above. A part of a nucleic acid which codes for a protein or peptide preferably relates to the part of the nucleic acid which corresponds to the open reading frame. In a further embodiment, a part of a nucleic acid is the part of a nucleic acid which codes only for one or more epitopes of the protein or peptide which is encoded by the complete nucleic acid, in particular by the complete open reading frame.

The proteins, peptides or derivatives thereof which are employed for a therapeutic use are preferably those which inhibit a binding of the autoantibodies described herein to the autoantigens described herein, or compete therefor and/or inhibit the stimulation of T lymphocytes which recognize the autoantigens or parts thereof described herein, and thus protect a patient from an autoimmune disease of the nervous system such as multiple sclerosis. Proteins, peptides or derivatives which can be employed therapeutically are in particular those which interact with the binding of T cells via their T-cell receptor to the MHC/antigen complex which is necessary for initiating or propagating an immune recognition or an inflammatory course.

A protein or peptide which includes an antibody epitope and/or a T-cell epitope and is administered according to the invention to a patient may be able to modify the patient's response to an autoantigen, leading to inhibition of an autoimmune response. In particular, therefore, proteins, peptides or derivatives thereof able to compete with the autoantigens or fragments thereof for recognition by T lymphocytes or autoantibodies are used according to the invention. Peptides particularly preferred according to the invention are those which include or represent a modified version of the T-cell epitope from the naturally occurring autoantigen which can bind to MHC molecules but, in contrast to the naturally occurring epitope, does not activate specific T cells. The proteins, peptides or derivatives employed for a therapeutic use preferably compete for the binding of autoantigens to antibodies and/or MHC molecules and do not initiate proliferation and/or induction of a T cell which reacts with the autoantigen or parts thereof.

Candidate proteins, peptides, or derivatives can be screened in a test which measures a binding, in particular a competitive binding to antibodies and/or MHC molecules, and/or a test which measures a T-cell proliferation.

"MHC-binding peptides" relates according to the invention to peptides which bind to an MHC class I and/or an MHC class II molecule. In the case of class I MHC/peptide complexes, the binding peptides are typically 8-10 amino acids long, although longer or shorter peptides may be active. In the case of class II MHC/peptide complexes, the binding peptides are typically 10-25 amino acids long and in particular 13-18 amino acids long, although longer and shorter peptides may be active. It is possible according to the invention to administer an MHC-binding peptide for a direct binding to MHC molecules, or an MCH-binding peptide may result after suitable processing, especially in vivo after administration, from an administered protein, peptide or derivative thereof. It is also possible for an MHC-binding peptide to result through processing of an autoantigen. In particular embodiments, therefore, an MHC-binding peptide is a part of an administered protein, peptide or derivative thereof or of an autoantigen. Such cases are included when reference is made according to the invention to proteins, peptides or derivatives employed for a therapeutic use, or to T cells which react with an autoantigen.

The ability of a peptide to bind to an antibody can be determined for example with one of the immunoassays described herein.

The ability to bind competitively to MHC molecules can be determined according to the invention for example with known binding tests which measure the displacement of a labeled binding molecule.

Autoantigens described according to the invention can be employed in peptide libraries, including phage display libraries, in order for example to identify and select peptide binding partners of antibodies or MHC molecules. Such molecules can be used for example for screening assays, purification protocols, for interference with the function of the antibodies or MHC molecules and for other purposes known to the person skilled in the art.

Phage display may be particularly effective for identifying binding peptides. In this case, for example, a phage library which presents inserts of a length of from 4 to about 80 amino acid residues is prepared (by using for example the m13, fd or lambda phage). Phages which harbor inserts which bind to the target are then selected. This process can be repeated over a plurality of cycles of back-selection of phages which bind to the target. Repeated rounds lead to an enrichment of phages which harbor particular sequences. It is possible to analyze DNA sequences in order to identify the sequences of the expressed peptides. The smallest linear portion of the sequence which binds to the target can be determined.

The yeast "two-hybrid system" can also be employed for identifying peptides which bind to a target.

The ability to initiate a proliferation and/or induction of T cells can be determined simply by an in vitro test. Typically, T cells are provided for the tests by transformed T-cell lines, such as T-cell hybridomas or T cells which are isolated from a mammal such as a human or a rodent such as a mouse. Suitable T-cell hybridomas are freely available or can be prepared in a manner known per se. T cells can be isolated from a mammal in a manner known per se; cf., for example, Shimonkevitz, R. et al., 1983, J. Exp. Med. 158:303.

A suitable test for determining whether a peptide is capable of modulating the activity of T cells takes place as follows by steps 1-4 below. T cells express in a suitable manner a marker which can be tested and indicates T-cell activation or modulation of T-cell activity after activation. Thus, the mouse T-cell hybridoma DO11.10which expresses interleukin-2 (IL-2) on activation can be used. IL-2 concentrations can be measured in order to determine whether a specific presented peptide is capable of modulating the activity of this T-cell hybridoma. A suitable test of this type takes place by the following steps:
1. T cells are obtained for example from an interesting T-cell hybridoma or by isolation from a mammal.
2. The T cells are cultured under conditions permitting proliferation.
3. The growing T cells are contacted with antigen-presenting cells which in turn have been contacted with a peptide to be presented or with a nucleic acid coding therefor.
4. The T cells are tested for a marker, e.g. IL-2 production is measured.

The T cells used in the tests are incubated under conditions suitable for proliferation. For example, a DO11.10 T-cell hybridoma is suitably incubated at about 37° C. and 5% $CO_2$ in complete medium (RPMI 1640, supplemented with 10% FBS, penicillin/streptomycin, L-glutamine and $5 \times 10^{-5}$ M 2-mercaptoethanol). Serial dilutions of the investigated peptide can be tested. T-cell activation signals are provided by antigen-presenting cells which have been loaded with the peptide.

As an alternative to measuring an expressed protein such as IL-2, it is possible to determine the modulation of T-cell activation in a suitable manner through alterations in the proliferation of T cells as measured by known radiolabeling methods. For example, a labeled (such as tritiated) nucleotide can be introduced into a test culture medium. The introduction of such a labeled nucleotide into the DNA serves as quantity for measuring T-cell proliferation.

Identification of modified and substituted proteins or peptides which are suitable in the diagnostic and therapeutic methods of the invention can also easily be tested through their ability to inhibit proliferative responses in vitro of the patient's T cells or of T-cell lines or clones which are specific for an autoantigen, or a binding of the autoantigen to autoantibodies specific therefor. Epitopes in autoantigens against which antibodies and T cells in patients with multiple sclerosis are directed are identified by using truncated and/or mutagenized recombinant proteins and peptides. These peptide epitopes are tested for their antigenicity in generating a T-cell response or in binding to antibodies.

What has been stated above about therapeutically employed proteins, peptides or derivatives applies analogously to therapeutically employed nucleic acids which encode such proteins, peptides or derivatives.

Proteins, peptides or derivatives thereof described herein, where appropriate coupled to a polymer such as PEG which makes the protein, peptide or derivative tolerogenic, and/or in conjunction with an adjuvant, can also be employed therapeutically in order to generate tolerance. The proteins, peptides or derivatives are preferably employed in high doses in this embodiment. The method of tolerization is described for example in WO 94/06828. Thus, in one embodiment, a pharmaceutical composition of the invention is used to tolerize a patient to one or more autoantigens described herein. In this embodiment, the pharmaceutical composition preferably includes a peptide or protein which comprises an amino acid sequence which corresponds to a sequence motif of an autoantigen described herein, which is associated with a neurological autoimmune disease described herein, or is derived therefrom. Such peptides or proteins preferably bind to MHC molecules to form a complex which activates autoreactive T cells in patients with the autoimmune disease. The use of such a tolerization in relation to autoimmune diseases is known and need not therefore be explained in more detail.

Antibodies directed against the autoantigens described herein can be used to identify antigenic epitopes on the autoantigen. As soon as such epitopes have been identified, it is possible for synthetic peptides to be prepared and be employed for example as antigens in diagnostic tests or kits or for developing therapeutic agents.

Antisera containing antibodies which bind specifically to a target can be prepared by various standard methods; cf. for example "Monoclonal Antibodies: A Practical Approach" by Philip Shepherd, Christopher Dean ISBN 0-19-983722-9, "Antibodies: A Laboratory Manual" by Ed Harlow, David Lane ISBN: 0879893142 and "Using Antibodies: A Laboratory Manual: Portable protocol NO" by Edward Harlow, David Lane, Ed Harlow ISBN: 0879895447. It is also possible in this connection to generate antibodies which have affinity and specificity and which recognize complex membrane proteins in their native form (Azorsa et al., *J. Immunol. Methods* 229: 35-48, 1999; Anderson et al., *J. Immunol.* 143: 1899-1904, 1989; Gardsvoll, *J. Immunol. Methods*, 234: 107-116, 2000). This is important in particular for the production of antibodies which are to be employed therapeutically, but also for many diagnostic applications. It is possible for this purpose to use the complete protein, extracellular partial sequences as well as cells which express the target molecule in a physiologically folded form for immunization.

Monoclonal antibodies are traditionally produced with the aid of hybridoma technology (for technical details: see "Monoclonal Antibodies: A Practical Approach" by Philip Shepherd, Christopher Dean ISBN 0-19-963722-9, "Antibodies: A Laboratory Manual" by Ed Harlow, David Lane ISBN: 0879893142, "Using Antibodies: A Laboratory Manual: Portable protocol NO" by Edward Harlow, David Lane, Ed Harlow ISBN: 0879695447).

It is known that only a small part of an antibody molecule, the paratope, is involved in binding of the antibody to its epitope (cf. Clark, W. R. (1988), *The Experimental Foundations of Modern Immunology*, Wiley & Sons, Inc., New York; Roitt, I. (1991), *Essential Immunology*, 7$^{th}$ edition, Blackwell Scientific Publications, Oxford). The pFc' and Fc regions are for example effectors of the complement cascade, but are not involved in antigen binding. An antibody from which the pFc' region has been eliminated enzymatically or which has been prepared without the pFc' region, referred to as F(ab')$_2$ fragment, carries both antigen binding sites of a complete antibody. In a similar way, an antibody from which the Fc region has been eliminated enzymatically, or which has been produced without the Fc region, referred to as Fab fragment, carries one antigen binding site of an intact antibody molecule. In addition, Fab fragments consist of a covalently bonded light chain of an antibody and a part of the heavy chain of the antibody, referred as Fd. The Fd fragments are the principal determinants of antibody specificity (a single Fd fragment can be associated with up to ten different light chains without altering the specificity of the antibody) and Fd fragments retain on isolation the ability to bind to an epitope.

Within the antigen-binding part of an antibody there are complementarity-determining regions (CDRs) which interact directly with the epitope of the antigen, and framework regions (FRs) which maintain the tertiary structure of the paratope. Four framework regions (FR1 to FR4) are located both in the Fd fragment of the heavy chain and in the light chain of IgG immunoglobulins and are in each case separated by three complementarity-determining regions (CDR1 to CDR3). The CDRs and especially the CDRS regions, and even more the CDRS region of the heavy chain, are mostly responsible for antibody specificity.

It is known that the non-CDR regions of a mammalian antibody can be replaced by similar regions of antibodies with the same or a different specificity, with the specificity for the epitope of the original antibody being retained. This made it possible to develop so-called "humanized" antibodies in which non-human CDRs are covalently connected to human FR regions and/or Fc/pFc' regions to produce a functional antibody.

As another example, WO 92/04381 describes the preparation and use of humanized mouse RSV antibodies in which at least one part of the mouse FR regions have been replaced by FR regions of a human origin. Such antibodies, including fragments of intact antibodies with an antigen-binding capability, are often referred to as "chimeric" antibodies.

The term "antibody" includes according to the invention also F(ab')$_2$, Fab, Fv and Fd fragments of antibodies, chimeric antibodies in which the Fc and/or FR and/or CDR1 and/or CDR2 and/or light chain CDRS regions have been replaced by homologous human or non-human sequences, chimeric F(ab')$_2$ fragment antibodies in which the FR and/or CDR1 and/or CDR2 and/or light chain CDR3 regions have been replaced by homologous human or non-human sequences, chimeric Fab fragment antibodies in which the FR and/or CDR1 and/or CDR2 and/or light chain CDR3 regions have been replaced by homologous human or non-human sequences, and chimeric Fd fragment antibodies in which the FR and/or CDR1 and/or CDR2 regions have been replaced by homologous human or non-human sequences. The term "antibody" also includes according to the invention single-chain antibodies.

Antibodies can also be coupled to specific diagnostic agents in order for example to demonstrate cells and tissues which express particular proteins or peptides like the autoantigens described herein. They can further be coupled to therapeutic agents.

Diagnostic agents include any type of label which is suitable: (i) for providing a detectable signal, (ii) for interacting with a second label in order to modify the detectable signal provided by the first or second label, e.g. FRET (fluorescence resonance energy transfer), (iii) for influencing the mobility such as electrophoretic mobility through charge, hydrophobicity, shape or other physical parameters, or (iv) for providing a capture group, e.g. affinity, antibody/antigen or ionic complexation.

Suitable labels are structures such as fluorescent labels, luminescent labels, chromophore labels, radioisotope labels, isotope labels, preferably stable isotope labels, enzyme labels, particle labels, especially metal particle labels, magnetic particle labels, polymer particle labels, small organic molecules such as biotin, ligands of receptors or binding molecules such as cell adhesion proteins or lectins, and label sequences which include nucleic acid sequences and/or amino acid sequences. Diagnostic agents include in a non-limiting manner barium sulfate, iocetamic acid, iopanoic acid, calcium ipodate, sodium diatrizoate, meglumine diatrizoate, metrizamide, sodium tyropanoate and radiodiagnostic agents, including positron emitters such as fluorine-18 and carbon-11, gamma emitters such as iodine-123, technetium-99m, iodine-131 and indium-111, and nuclides for magnetic nuclear resonance such as fluorine and gadolinium.

The term "therapeutic agent" relates according to the invention to any substance which may have a therapeutic effect.

The term "major histocompatibility complex" or "MHC" relates to a complex of genes which is present in all vertebrates. MHC proteins or molecules are involved in the signaling between lymphocytes and antigen-presenting cells in normal immune responses, in which case they bind peptides and present them for recognition by T-cell receptors. MHC molecules bind peptides within an intracellular processing compartment and present these peptides on the surface of antigen-presenting cells for recognition by T cells. The human MHC region, also called HLA, is located on chromosome 6 and includes the class I and class II regions. In a preferred embodiment in all aspects of the invention, an MHC molecule is an HLA molecule.

The term "patient", "creature" or "organism" includes according to the invention humans, non-human primates or another animal, especially mammal such as cow, horse, pig, sheep, goat, dog, cat or rodent such as mouse and rat. In a particularly preferred embodiment, the patient is a human.

The term "disease" relates according to the invention to a pathological condition. The term "autoimmune disease" relates according to the invention to a disease caused by an excessive reaction of the immune system to endogenous tissue. The immune system erroneously recognizes endogenous tissue as a foreign body against which defence is necessary. This results in severe inflammatory reactions which lead to damage to the affected organs. The term "neurological autoimmune disease" relates according to the invention to an autoimmune disease of the nervous system. If the immune system in the CNS gets out of control in a neurological autoimmune disease it is possible for inflammatory cascades of damage to trigger nerve cell death and a neuropathological state associated therewith. Inflammatory processes and networks are involved in the development and progression of many neurodegenerative diseases such as multiple sclerosis, stroke, Parkinson's disease and Alzheimer's disease.

In a preferred embodiment, the term "neurological autoimmune disease" relates according to the invention to multiple sclerosis. Multiple sclerosis is an inflammatory, demyelinizing disease of the central nervous system which causes motor, sensory and cognitive deficits. Multiple sclerosis arises if T lymphocytes and other cells of the immune system infiltrate the white matter of the CNS. Inflammatory messengers block conduction at the Ranvier's nodes and soluble and cellular effectors bring about breakdown of the myelin layer. This results in so-called demyelinization or demyelination. This brings about progressive paralysis and other neurological symptoms such as, for example, muscle tremor, numbness, itching, color blindness, double vision, blindness, loss of coordination and balance, acute paralysis and a deterioration in cognitive abilities.

The term "increased amount" preferably relates to an increase of at least 10%, in particular at least 20%, at least 50% or at least 100%. The amount of a substance is also increased in a test object such as a biological sample in relation to a reference if it is detectable in the test object but not present and/or not detectable in the reference.

"Reduce" or "inhibit" relates here to the ability to bring about a decrease, such as a decrease of 20% or more, more preferably of 50% or more, most preferably of 75% or more.

A biological sample may according to the invention be a tissue sample, including body fluids, and/or a cellular sample and can be obtained in a conventional way, such as by tissue biopsy, including punch biopsy, and removal of blood, bronchial aspirate, sputum, urine, feces or other body fluids. The term "biological sample" also includes according to the invention fractions of biological samples.

The terms "T cell" and "T lymphocyte" are used here exchangeably and include T-helper cells and cytolytic T cells such as cytotoxic T cells.

The pharmaceutical compositions described according to the invention may also be employed preventively, i.e. as vaccines, in order to prevent the diseases described herein.

Proteins and peptides can be administered according to the invention in a manner known per se.

It is possible according to the invention to administer nucleic acids either as naked nucleic acid or in conjunction with an administration reagent. For example, the invention also provides for administration of nucleic acids in vivo by means of targeted liposomes.

It is possible to employ for administering nucleic acids vectors which are derived from adenovirus (AV), adeno-associated virus (AAV), retroviruses (such as Antiviruses (LV), rhabdoviruses, murine leukemia virus), or herpesvirus, and the like. The tropism of the viral vectors can be suitably modified by pseudotyping the vectors with envelope proteins or other surface antigens of other viruses or by replacing various viral capsid proteins.

Liposomes can assist delivery of the nucleic acid to a particular tissue and may also increase the half-life of the nucleic acid. Liposomes suitable according to the invention are formed from standard vesicle-forming lipids which generally include neutral or negatively charged phospholipids, and a sterol such as cholesterol. The selection of lipids is generally determined by factors such as the desired size of the liposomes and the half-life of the liposomes. A large number of methods for preparing liposomes is known; cf., for example, Szoka et al. (1980), Ann. Rev. Biophys. Bioeng. 9: 467; and U.S. Pat. Nos. 4,235,871, 4,501,728, 4,837,028 and 5,019,389.

In particular embodiments, direction of the nucleic acid to particular cells is preferred. In such embodiments, a carrier which is employed for administering a nucleic acid to a cell (e.g. a retrovirus or a liposome) may have a bound targeting molecule. For example, a molecule such as an antibody which is specific for a surface membrane protein on the target cell, or a ligand for a receptor on the target cell, can be incorporated in the nucleic acid carrier or bound thereto. If administration of a nucleic acid by liposomes is desired, it is possible to incorporate proteins which bind to a surface membrane protein which is associated with endocytosis into the liposome formulation in order to make targeting and/or uptake possible. Such proteins include capsid proteins or fragments thereof which are specific for a particular cell type, antibodies against proteins which are internalized, proteins which aim at an intracellular site, and the like.

The pharmaceutical compositions of the invention can be administered in pharmaceutically acceptable preparations. Such preparations may comprise usual pharmaceutically acceptable concentrations of salts, buffer substances, preservatives, carriers, supplementary immunity-enhancing substances such as adjuvants, CpG oligo-nucleotides, cytokines, chemokines, saponin, GM-CSF and/or RNA and, where appropriate, other therapeutic active ingredients.

The therapeutic active ingredients of the invention can be administered in any conventional way, including by injection or by infusion. Administration is possible for example orally, intravenously, intraperitoneally, intramuscularly, subcutaneously or transdermally.

Suitable methods for administering nucleic acids to cells include administration of the nucleic acid to a creature by means of a gene gun, electroporation, nanoparticles, microencapsulation and the like, or by parenteral and enteral delivery.

The compositions of the invention are administered in effective amounts. An "effective amount" relates to the amount which, alone or together with further doses, achieves a desired response or a desired effect. In the case of treatment of a particular disease or of a particular condition, the desired response preferably relates to inhibition of the course of the disease. This includes slowing the progression of the disease and in particular stopping or reversing progression of the disease. The desired response on treatment of a disease or of a condition may also be delaying the onset or preventing the onset of the disease or condition.

An effective amount of a composition of the invention will depend on the condition to be treated, the severity of the disease, the individual parameters of a patient, including age, physiological condition, height and weight, the duration of the treatment, the nature of a concomitant therapy (if present), the specific route of administration and similar factors.

The pharmaceutical compositions of the invention are preferably sterile and comprise an effective amount of the therapeutically effective substance for generating the desired response or the desired effect.

The doses of the compositions of the invention which are administered may depend on various parameters such as the mode of administration, the patient's condition, the desired period of administration etc. In the case where a response of a patient is inadequate with an initial dose, it is possible to employ higher doses (or effectively higher doses which are achieved by a different, more localized administration route).

The pharmaceutical compositions of the invention are generally administered in pharmaceutically acceptable amounts and in pharmaceutically acceptable compositions. The term "pharmaceutically acceptable" relates to a non-toxic material which does not interact with the effect of the active ingredient of the pharmaceutical composition. Such preparations may usually comprise salts, buffer substances, preservatives, carriers and, where appropriate, other therapeutic active ingredients. For use in medicine, the salts should be pharmaceutically acceptable. Non-pharmaceutically acceptable salts can, however, be used to prepare pharmaceutically acceptable salts and are included by the invention. Such pharmacologically and pharmaceutically acceptable salts include in a non-limiting manner those prepared from the following acids: hydrochloric, hydrobromic, sulfuric, nitric, phosphoric, maleic, acetic, salicylic, citric, formic, malonic, succinic acids and the like. Pharmaceutically suitable salts can also be prepared as alkali metal or alkaline earth metal salts such as sodium, potassium or calcium salts.

A pharmaceutical composition of the invention may include a pharmaceutically acceptable carrier. The term "pharmaceutically acceptable carrier" relates according to the invention to one or more compatible solid or liquid fillers, diluents, or capsule substances which are suitable for administration in particular to a human. The term "carrier" relates to an organic or inorganic ingredient, natural or synthetic in nature, in which the active ingredient is combined in order to facilitate use. The ingredients of the pharmaceutical composition of the invention are ordinarily of such a nature that no interaction which substantially impairs the desired pharmaceutical efficacy occurs.

The pharmaceutical compositions of the invention may comprise suitable buffer substances such as acetic acid in a salt, citric acid in a salt, boric acid in a salt and phosphoric acid in a salt.

The pharmaceutical compositions may also include where appropriate suitable preservatives such as benzalkonium chloride, chlorobutanol, parabens and thimerosal.

The pharmaceutical compositions are ordinarily supplied in a standard dose form and can be produced in a manner known per se. Pharmaceutical compositions of the invention may for example be in the form of capsules, tablets, pastilles, suspensions, syrups, elixirs or as emulsion.

Compositions suitable for parenteral administration include ordinarily a sterile aqueous or nonaqueous preparation of the active ingredient, which is preferably isotonic with the recipient's blood. Suitable carriers and solvents are for example Ringer's solution and isotonic sodium chloride solution. Ordinarily employed additionally as dissolving or suspending medium are sterile, fixed oils.

The present invention is described in detail by the following figures and examples which serve exclusively for illustration and are not to be understood as limiting. Further embodiments which are likewise encompassed by the invention are accessible to the person skilled in the art on the basis of the description and the examples.

EXAMPLES

Example 1

Production of a Brain-Specific cDNA Library

A brain-specific cDNA expression library was produced in lambda phages (FIG. 1). In this system, a complete pBluescript plasmid is present in a lambda phage genome and thus combines the properties of a phage and of a plasmid. Human mRNA isolated from brain tissue was transcribed into methylated cDNA in a first-strand synthesis using a reverse transcriptase and an oligo-dT linker on whose 5' end an XhoI cleavage site was attached. After targeted degradation of the mRNA, the DNA was made double-stranded in a second-strand synthesis. An EcoRI linker was ligated onto the double-stranded DNA, and the construct was then cleaved with the restriction endonuclease XhoI. The use of methylated dCTPs in the first-strand synthesis protects the cDNA first strand from XhoI cleavage. The cDNA fragments obtained in this way were cloned into vector previously cleaved with XhoI/EcoRI. Over $1\times10^6$ recombinant clones were obtained.

Example 2

Immunoscreening Methods and Antigen Identification

Figure 2:
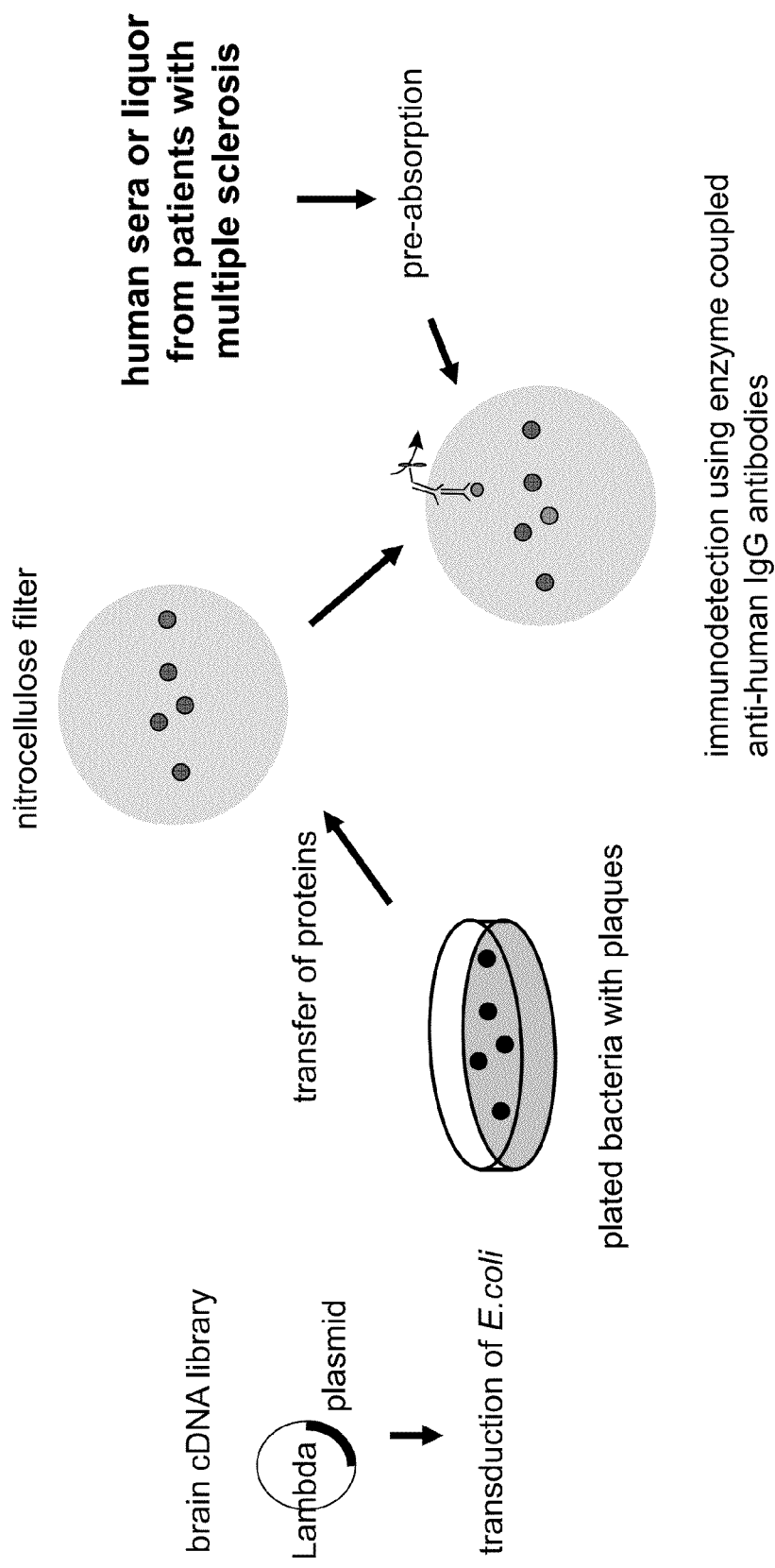
FIG. 2. Immunoscreening with sera from MS patients and identification of a reactive antigen.

The immunoscreening was carried out as described in Molecular Cloning: A Laboratory Manual, J. Sambrook et al., editors, 2$^{nd}$ edition, Cold Spring Harbor Laboratory Press, Cold Spring Harbor, N.Y., 1989 or Current Protocols in Molecular Biology, F. M. Ausubel et al., editors, John Wiley & Sons, Inc., New York. The method is depicted diagrammatically in FIG. 2. Bacteria of the strain XL1 MRF derived from *E. coli* K12 were harvested in the exponential phase of growth, adjusted to an $OD_{600}$ of 0.5 and infected with the lambda phages of the described expression library. The number of plaque-forming units (pfu) was adjusted so that the plaques were subconfluent (e.g. ~5000 pfu/145 mm Petri dish). With addition of TOP agar and IPTG, the infection mixture was plated out on agar plates with tetracycline. Phage plaques formed on the bacterial lawn in an overnight culture at 37° C. Each individual plaque represents a lambda phage clone with the nucleic acid inserted into this clone and simultaneously comprises the recombinantly expressed protein encoded by the nucleic acid.

Nitrocellulose membranes were put on in order to produce plaque-lift preparations of the recombinant proteins. Washing steps in TBS-Tween and blocking of nonspecific binding sites in TBS+10% milk powder were followed by incubation in serum overnight. Serum diluted 1:100-1:1000 was used for this purpose. After further washing steps, the nitrocellulose membranes were incubated with a secondary AP-conjugated antibody directed against human IgG. It was possible to visualize bindings of serum antibodies to proteins expressed recombinantly in phage plaques by a color reaction in this way. It was possible to trace clones identified as reacting with sera back to the culture plate and to isolate therefrom the corresponding phage construct monoclonally. Such positive clones were confirmed after renewed plating out. The lambda phage clone was recircularized to the phagemid by in vivo excision.

To analyze the brain-specific phage library, in total about 1 000 000 clones were analyzed, using a total of 17 different sera. Pooled sera were used in some cases, initially identified clones were firstly isolated oligoclonally augmented by adjacent non-reactive phage plaques and were monoclonalized after confirmation. The integrated human DNA was amplified from the monoclonal clones by PCR with the T7/T3 standard primers of the integrated plasmid vector, and the amplicon was then sequenced by standard methods. The sequences found in this way were compared with known sequences in the gene library by BLAST analysis. It was possible through the analysis to isolate in total 44 different clones which reacted with serum from MS patients. The antigens were assigned to different groups according to their properties (FIG. 3).

Example 3

Molecular Biological and Serological Validation of the Autoantigens

Validation of the antigens identified according to the invention is of central importance for utilization of the autoantigens for immunotherapeutic purposes (antibody therapy using monoclonal antibodies, vaccination to induce an improved autoantigen tolerance, T-cell receptor-mediated therapeutic approaches; cf. EP-B 0 879 282) or other targeted approaches (small compounds, siRNA etc.) in the treatment of autoimmune diseases and for diagnostic questions. In this case, validation takes place by expression analysis at the RNA level and by serological analyses.

1. Investigation of RNA Expression

The first validation of the identified autoantigens takes place with the aid of RNA obtained from various tissues or from tissue-specific cell lines. Brain-specific expression of the autoantigens associated with the neurological diseases is of decisive importance in this connection for the later therapeutic use. Isolation of total RNA from native tissue samples or from cell lines takes place with standard methods of molecular biology. For example, isolation is possible with the aid of the RNeasy Maxi Kit (Qiagen, cat. No. 75162) according to the manufacturer's instructions. This isolation method is based on the use of guanidinium isothiocyanate as chaotropic reagent. Isolation can be carried out alternatively with acidic phenol (Chomczynski & Sacchi, Anal. Biochem. 162: 156-159, 1987). After the tissue has been worked up with guanidinium isothiocyanate, the RNA is extracted with acidic phenol, and then the RNA is precipitated with isopropanol and taken up in DEPC-treated water.

2-4 μg of the RNA isolated in this way are then transcribed into cDNA, e.g. using Superscript II (Invitrogen) in accordance with the manufacturers protocol. The cDNA synthesis is in this case primed with the aid of random hexamers (e.g. Roche Diagnostics) according to the standard protocols of the respective manufacturer. For quality control, the cDNAs are amplified in 30 cycles with primers which are specific for the only slightly expressed p53 gene. Only p53-positive cDNA samples are used for further reaction steps.

For detailed analysis, the target candidates are investigated by PCR or quantitative PCR (qPCR) for their expression in a comprehensive set of normal tissues. For this purpose, 0.5 μl of cDNA from the above batch is amplified with a DNA polymerase (e.g. 1 U of HotStarTaq DNA polymerase, Qiagen) in analogy to the protocols of the respective manufacturer (total volume of the mixture: 25-50 μl). Besides the polymerase, the amplification mixture contains 0.3 mM dNTPs, reaction buffer (final concentration 1×, depending on the manufacturer of the DNA polymerase) and 0.3 mM each of the gene-specific forward and reverse primer.

The specific primers of the target gene are selected, where possible, so that they are located in two different exons and thus genomic contamination does not lead to any false-positive results. In a non-quantitative endpoint PCR, the cDNA is typically incubated at 95° C. for 15 minutes in order to denature the DNA and activate the Hot-Start enzyme. The DNA is then amplified in 35 cycles (1 min 95° C., 1 min primer-specific hybridization temperature (about 55-65° C.), 1 min 72° C. for elongation of the amplicons). 10 μl of the PCR mixture are then loaded onto agarose gels and fractionated in an electrical field. The DNA in the gels is visualized by staining with ethidium bromide, and the result of the PCR is documented by photograph.

As alternative to conventional PCR, the expression analysis of a target gene can also take place by quantitative real time PCR. Various analysis systems are now obtainable for this analysis, the best-known being the ABI PRISM sequence detection system (TaqMan, Applied Biosystems), the iCycler (Biorad) and the Light cycler (Roche Diagnostics). As described above, a specific PCR mixture is subjected to a run in the real time apparatuses. The newly synthesized DNA is visualized by addition of a DNA-intercalating dye (e.g. ethidium bromide, CybrGreen) by specific photoexcitation (according to information from the dye manufacturers). The complete process can be followed by a large number of measurement points during the amplification, and a quantitative determination of the nucleic acid concentration of the target gene can be carried out. Normalization of the PCR mixture takes place by measuring a housekeeping gene (e.g. 18S RNA, β-actin). Alternative strategies with fluorescence-labeled DNA probes likewise permit quantitative determination of the target gene from a specific tissue sample (see TaqMan applications of Applied Biosystems).

2. Cloning

The complete target gene is cloned, as is necessary for further characterization of the antigen, by conventional methods of molecular biology (e.g. in "Current Protocols in Molecular Biology", John Wiley & Sons Ltd., Wiley InterScience). For cloning and sequence analysis of the target gene, the latter is initially amplified with a DNA polymerase with proofreading function (e.g. pfu, Roche Diagnostics). The amplicon is then ligated into a cloning vector by standard methods. Positive clones are identified by sequence analysis and then characterized with the aid of prediction programs and known algorithms.

3. Expression and Purification

For detailed characterization and for product development it is necessary for the identified antigens to be synthesized in an expression system and then purified.

Very diverse systems are well established and commercially available for antigen expression, some examples of commercial suppliers are indicated, and detailed protocols are published by the suppliers. The commonest expression systems are in vitro transcription/translation (Roche Diagnostics, Invitrogen), antigen expression in *E. coli* (Qiagen, Invitrogen), in yeast (Invitrogen, Stratagene, RCT) and in eukaryotic cells after transfection of the cells or after infection with viral expression vectors such as, for example, with recombinant baculoviruses or vacciniaviruses (Invitrogen, Roche Diagnostics). Very diverse methods (e.g. electroporation, liposome-based transfection, calcium phosphate precipitation) are well established (e.g. Lemoine et al., *Methods Mol. Biol.* 75: 441-7, 1997) for transfecting cells with DNA for antigen expression.

Antigen expression is followed by purification of the antigen by commercially available methods. A wide selection of chromatographic methods in particular is established (Biorad, Amersham Biosciences). Affinity chromatography is particularly suitable for antigen purification. It is possible to employ for this purpose on the one hand short, universally employable protein anchors such as, for example, the His tag, the FLAG tag or glutatione S-transferase (GST) (Biorad, Amersham Biosciences, Qiagen). Purification then takes place via the specific properties of the anchor molecule. Affinity chromatography can, however, also take place using an antigen-specific antibody. A large number of protocols are to be found with the commercial suppliers or in the literature, e.g. in "Current Protocols of Proteinsciences" (John Wiley & Sons Ltd., Wiley InterScience).

4. Serological Analysis of the Identified Antigens

In order to detect disease-associated antigens, all the antigens found are investigated for the presence of specific immune responses (antibodies) in patients with MS, and in control groups without the disease. This allows antigens of clinical relevance to be determined. It is possible to employ for this purpose several detection and measurement methods such as protein arrays based on proteomic analyses or mostly immunological analytical methods such as, for example, ELISA, CrELISA or Western blotting. Direct serological detection with the aid of the expression system used in the immunoscreening is also possible.

The most widely used serological detection method is the enzyme-linked immune sorbent assay (ELiSA) which is published in very diverse embodiments. In principle, a protein (peptide, antigen or antibody) is bound to a surface for this purpose. The sample to be analyzed is analyzed with this bound protein. The next step is incubation, usually with a further antibody which is coupled to a dye (e.g. FITC, Cy3) or an enzyme (e.g. peroxidase, alkaline phosphatase). The antigen detection then takes place depending on the coupled substance, e.g. by a color reaction or by fluorescence. ELISA for detecting very diverse antigens are commercially available (Amersham Bioscience, Biorad etc), and detailed protocols are for example in the "Short Protocols in Molecular Biology" (Asubel, 2003; Wiley & Sons, ISBN: 047132938X) or in the "Current Protocols of Proteinsciences" (John Wiley & Sons Ltd., Wiley InterScience). In analogy to the ELISA, the crude lysate enzyme-linked immune sorbent assay (CrELISA) is based on the binding of lysates of the antigen-expressing bacteria on a surface (Türeci et al., 2004, J Imm Methods 289, 191). The sample to be analyzed is then analyzed with this bound protein. The next step is incubation, usually with a further antibody which is coupled to a dye (e.g. FITC, Cy3) or an enzyme (e.g. peroxidase, alkaline phosphatase). The antigen detection then takes place depending on the coupled substance, e.g. by a color reaction or by fluorescence. Direct detection using the expression system used for the antigen screening is possible with the SEROGRID method (Krause et al., 2003, J Imm Methods 283, 261). For this purpose, *E. coli* bacteria are harvested in the exponential growth phase and infected subconfluently with antigen-specific, monoclonal lambda phages. The infection mixture is plated out, with addition of TOP agar and IPTG, on large-area agar plates with tetracycline. The individual clones are in this case separated from one another with the aid of spacers. Phage plaques form on the bacterial lawn on overnight culture at 37° C., each individual plaque representing a specific lambda phage clone with the inserted nucleic acid of the antigen which is to be analyzed and which is expressed recombinantly. The antigens are then blotted as in a normal immunoscreening method onto a nitrocellulose membrane and then incubated with the human sera. The advantage of the SEROGRID method is the parallelized analysis of numerous identified antigens in one test mixture.

Further validation of the identified antigens permits the use of protein arrays which makes simultaneous analysis of a plurality of antigens in one mixture possible. In this case, the antigen molecules are bound at defined positions in wells or on planar surfaces such as, for example, on filter membranes such as nitrocellulose or modified glass surfaces. The antigens can be bound covalently through chemical linkers or non-covalently via hydrophobic van der Waals, ionic or other interactions. The directed binding of the antigens onto the surface can be facilitated for example via a tag (e.g. histidine tag). Spotting of the protein arrays mostly takes place by pin-based systems which transfer solutions in the nanoliter range. Antigen detection is frequently based on fluorescence. One application of protein arrays is investigation of antigen-antibody interactions. Protein array technology can also be employed as clinical diagnostic tests.

Example 4

Obtaining Antibodies

Antibodies can be used for example for characterizing the peptides and/or proteins of the invention and in the diagnostic and therapeutic methods of the invention. It is possible for antibodies to recognize proteins in native and/or denatured state (Anderson et al., *J. Immunol.* 143: 1899-1904, 1989: Gardsvoll, *J. Immunol. Methods* 234: 107-116, 2000; Kayyem et al., *Eur. J. Biochem.* 208: 1-8, 1992; Spiller et al., *J. Immunol. Methods* 224: 51-60, 1999).

Antisera containing specific antibodies which bind specifically to the target protein can be prepared by various standard methods; cf. for example "Monoclonal Antibodies: A Practical Approach" by Philip Shepherd, Christopher Dean ISBN 0-19-963722-9, "Antibodies: A Laboratory Manual" by Ed Harlow, David Lane ISBN: 0879893142 and "Using Antibodies: A Laboratory Manual: Portable protocol NO" by Edward Harlow, David Lane, Ed Harlow ISBN: 0879695447. It is also possible in this connection to generate antibodies which have affinity and specificity and which recognize complex membrane proteins in their native form (Azorsa et al., *J. Immunol. Methods* 229: 35-48, 1999; Anderson et al., *J. Immunol.* 143: 1899-1904, 1989; Gardsvoll, *J. Immunol. Methods*, 234: 107-118, 2000). This is important in particular for the production of antibodies which are to be employed therapeutically, but also for many diagnostic applications. It is possible for this purpose to use the complete protein as well as extracellular partial sequences for immunization.

Immunization and Obtaining Polyclonal Antibodies

A species (e.g. rabbits, mice) is immunized by a first injection of the desired target protein. The immune response of the animal to the immunogen can be enhanced by a second or third immunization within a defined period (e.g. about 2-4 weeks after the last immunization). Again after various defined time intervals (e.g. $1^{st}$ bleed after 4 weeks, subsequently every 2-3 weeks up to 5 removals) blood is taken from the animals, and immune serum is obtained. The immune sera taken in this way contain polyclonal antibodies with which the target protein can be detected and characterized in Western blotting, by flow cytometry, immunofluorescence or immunohistochemistry.

The animals are usually immunized by one of four well-established methods, although other methods exist. Immunization is possible in this connection with the peptides specific for the target protein, with the complete protein, with extracellular partial sequences of a protein which are identifiable by experiment or via prediction programs. Since the prediction programs do not always operate error-free, in some circumstances two domains separated from one another by a transmembrane domain are also used. One of the two domains must then be extracellular, which can then be demonstrated experimentally (see below).

(1) In the first case, peptides (with a length of, for example, 8-12 amino acids) are synthesized by in vitro methods (possible by a commercial service) and these peptides are used for the immunization. Usually 3 immunizations take place (e.g. with a concentration of 5-100 µg/immunization). The immunization can also be carried out as a service by service providers.

(2) Alternatively, immunization is possible with recombinant proteins. For this purpose, the cloned DNA of the target gene is cloned into an expression vector, and the target protein is synthesized in analogy to the conditions of the respective manufacturer (e.g. Roche Diagnostics, Invitrogen, Clontech, Qiagen), e.g. cell-free in vitro, in bacteria (e.g. *E. coli*), in yeast (e.g. *S. pombe*), in insect cells or in mammalian cells. It is also possible in this connection for the target protein to be synthesized with the aid of viral expression systems (e.g. baculovirus, vacciniavirus, adenovirus). After synthesis in one of the systems, the target protein is purified. The purification in this case usually takes place by chromatographic methods. It is also possible in this connection to use for the immunization proteins which have a molecular anchor as aid to purification (e.g. His tag, Qiagen; FLAG tag, Roche Diagnostics; GST fusion proteins). A large number of protocols are to be found for example in "Current Protocols in Molecular Biology", John Wiley & Sons Ltd., Wiley InterScience. Purification of the target protein is followed by immunization as described above.

(3) If a cell line which synthesizes the desired protein endogenously is available, this cell line can also be used directly for producing the specific antiserum. The immunization takes place in this case in 1-3 injections with in each case about $1-5 \times 10^7$ cells.

(4) The immunization can also take place by injecting DNA (DNA immunization). For this purpose, the target gene is initially cloned into an expression vector so that the target sequence is under the control of a strong eukaryotic promoter (e.g. CMV promoter). DNA (e.g. 1-10 µg per injection) is then transferred as immunogen using a gene gun into capillary regions with a strong blood flow in an organism (e.g. mouse, rabbit). The transferred DNA is taken up by the animal's cells, the target gene is expressed, and the animal finally develops an immune response to the target protein (Jung et al., *Mol. Cells* 12: 41-49, 2001; Kasinrerk et al., *Hybrid Hybridomics* 21: 287-293, 2002).

Obtaining Monoclonal Antibodies

Monoclonal antibodies are traditionally produced with the aid of hybridoma technology (for technical details: see "Monoclonal Antibodies: A Practical Approach" by Philip Shepherd, Christopher Dean ISBN 0-19-983722-9, "Antibodies: A Laboratory Manual" by Ed Harlow, David Lane ISBN: 0879893142 and "Using Antibodies: A Laboratory Manual: Portable protocol NO" by Edward Harlow, David Lane, Ed Harlow ISBN: 0879695447). A new method also employed is the so-called SLAM technology. This entails B cells being isolated from whole blood, and the cells being monoclonalized. The supernatant of the isolated B cell is then analyzed for its antibody specificity. In contrast to hybridoma technology, the variable region of the antibody gene is then amplified by a single-cell PCR and cloned into a suitable vector. The obtaining of monoclonal antibodies is expedited in this manner (de Wildt et al. *J. Immunol. Methods* 207: 81-67, 1997).

Example 5

Construction of a Test System for Diagnosing Autoimmune Diseases

The identified autoantigens form the basis for a diagnostic system which is specific for the diagnosis of autoimmune diseases and/or specific for the diagnosis or prognosis of multiple sclerosis. Diagnosis involves in this case the detection of the presence or quantification of one or more human autoantibodies which are specific for an epitope or specific for a plurality of epitopes of the identified autoantigens. The presence or the increased concentration of one or more of these autoantibodies in this case indicates a particular stage of the MS disease or a possible more aggressive stage of the disease.

A test system for diagnosis can in this case be based on the use of one or on the use of a combination of the identified autoantigens. This includes specific antigens as markers of autoimmune diseases and/or multiple sclerosis and/or polyclonal/monoclonal antibodies specific for antigens whose prevalence is associated with autoimmune diseases. The test system for diagnosis is based on the use of the antigens or antibodies for example immunoassays such as, for example, ELISA assays or protein arrays (see Example 3). Detection includes the removal of a biological sample such as, for example, serum or CSF from MS patients.

Example 6

Identification of CLSTN1 as Autoantigen

Calsyntenin 1 or CLSTN1 (SEQ ID NO: 1) is a gene which is located on chromosome 1 (1p36.22). The gene encodes a type I transmembrane protein with a size of about 110 kDa (SEQ ID NO: 2). The protein contains two cadherin domains and might, according to analyses of homology, be a calcium-dependent neurotransmitter.

Figure 4:
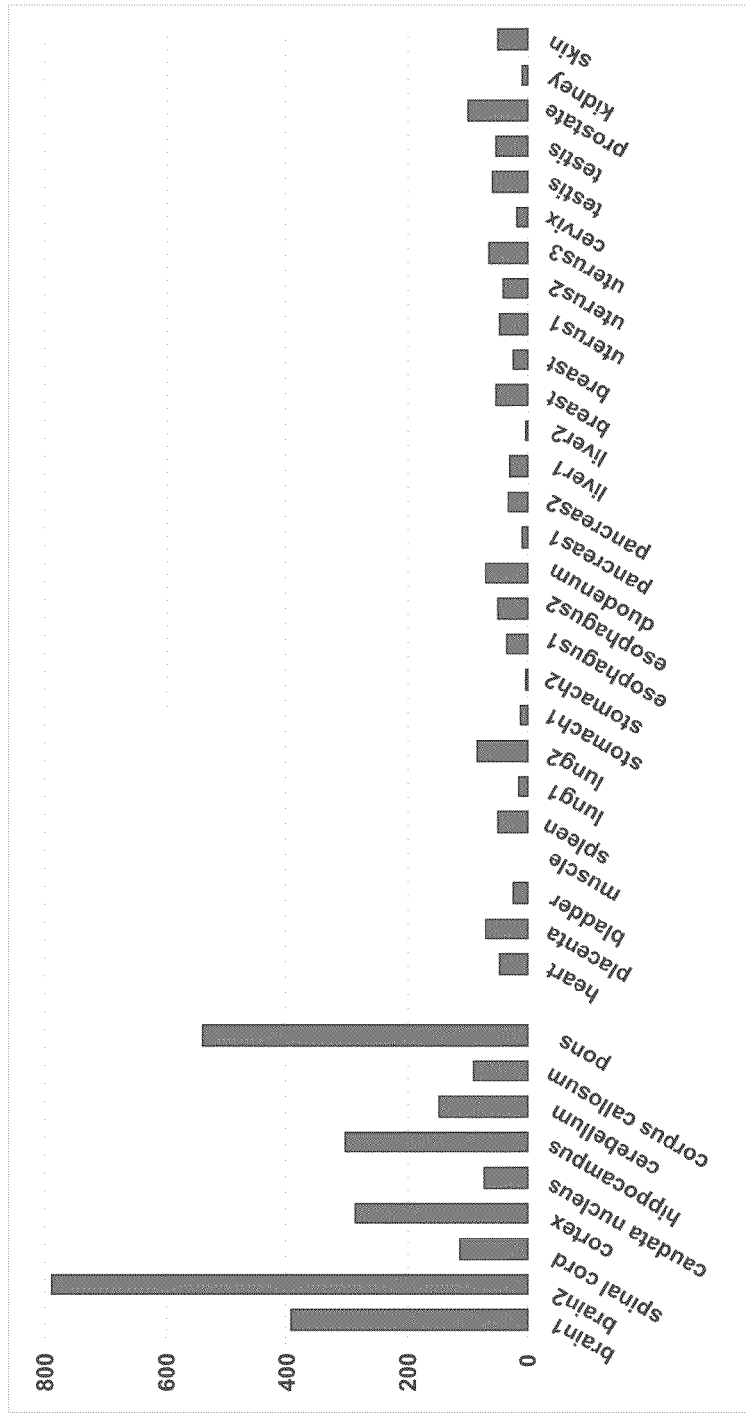
FIG. 4: Analysis of CLSTN1-specific expression. Quantitative analysis of CLSTN1-specific expression in healthy tissue samples. The relative expression (-fold activation) is shown.

It was possible according to the invention to identify CLSTN1 as an autoantigen in the autoimmunoscreening. To analyze the tissue-specific expression of CLSTN1, establishment of a gene-specific quantitative RT-PCR (primer pair SEQ ID NO: 89 and 90) was followed by analysis of the amount of the specific transcripts in various regions of the brain and in other healthy tissues. CLSTN1 is distinctly overexpressed in all the investigated regions of the brain by comparison with the other tissues investigated (FIG. 4) and can thus be regarded as brain-specific. Expression in the analyzed tissues might be attributable to expression in peripheral nerve tissue.

Example 7

Identification of ARPP-19 as Autoantigen

Cyclic AMP phosphoprotein 19 or ARPP-19 (SEQ ID NO: 3) is a gene located on chromosome 15 (15q21). The gene encodes a protein which is probably localized in the cytoplasm and has a size of about 12 kDa (SEQ ID NO: 4). Analyses of homology indicate that ARPP-19 is a phosphoprotein and belongs to the endosulfine family. ARPP-19 might thus be a substrate for a cAMP-dependent kinase.

Figure 5:
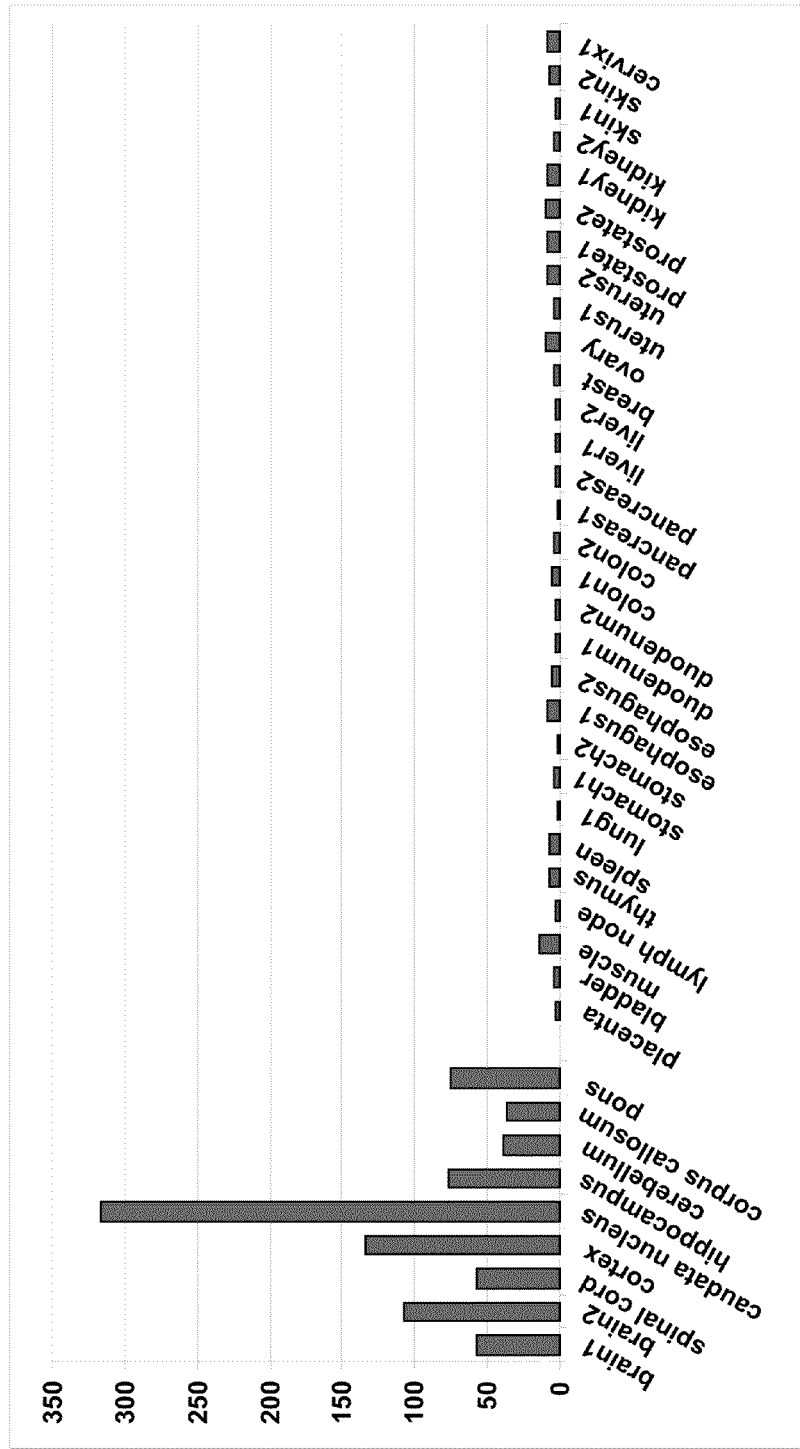
FIG. 5: Analysis of ARPP19-specific expression, Quantitative analysis of ARPP19-specific expression in healthy tissue samples. The relative expression (-fold activation) is shown.

It was possible according to the invention to identify ARPP-19 as an autoantigen in autoimmunoscreening. To analyze the tissue-specific expression of ARPP-19, establishment of a gene-specific quantitative RT-PCR (primer pair SEQ ID NO: 91 and 92) was followed by analysis of the amount of the specific transcripts in various regions of the brain and in other healthy tissues. ARPP-19 is at least 10-fold overexpressed in all the regions of the brain investigated by comparison with the other tissues investigated (FIG. 5) and is thus to be regarded as brain-specific. Expression in the analyzed tissues might be attributable to expression in peripheral nerve tissue.

Example 8

Identification of CMTM2 as Autoantigen

Figure 6:
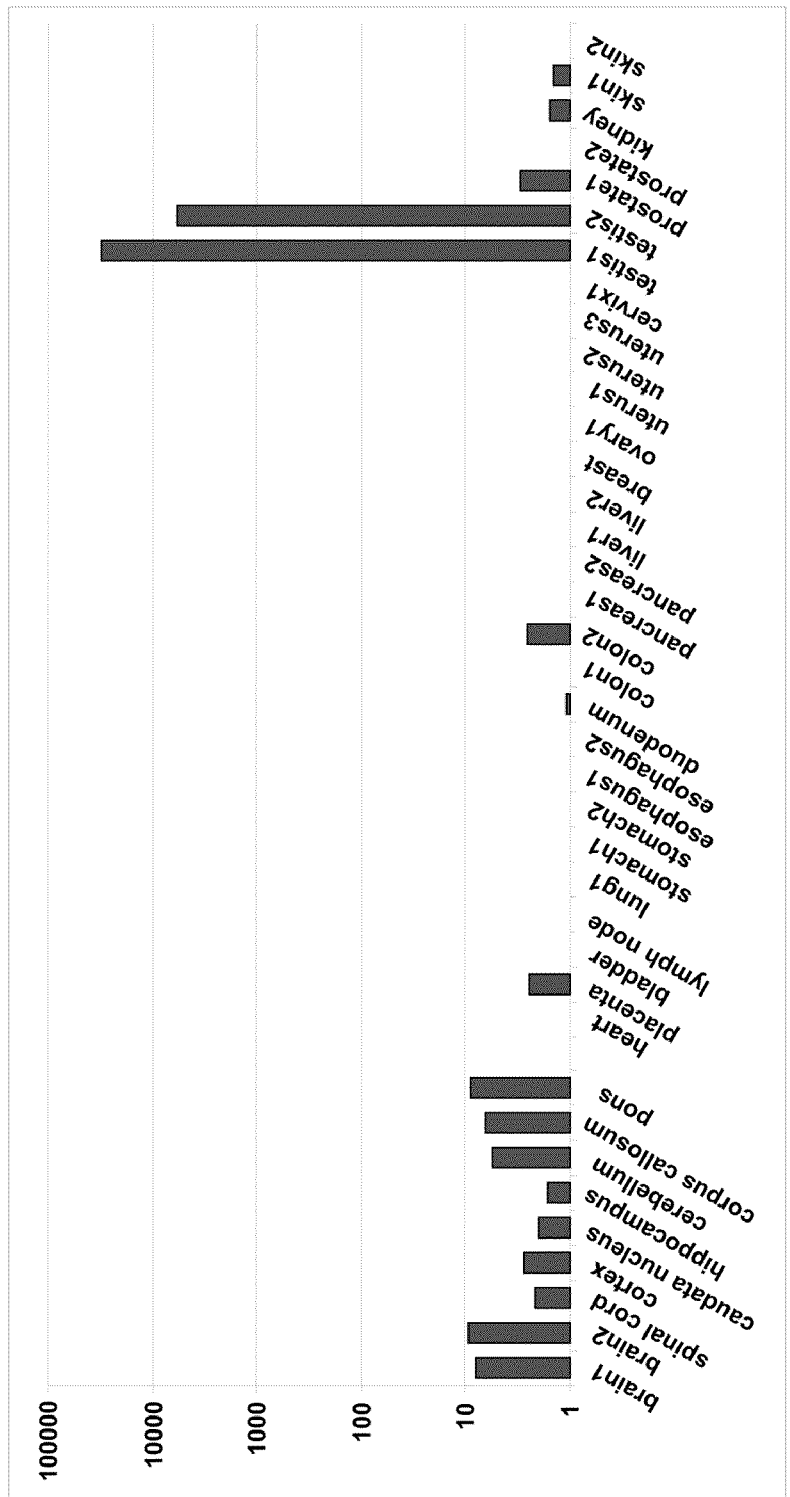
FIG. 6: Analysis of CMTM2-specific expression. Quantitative analysis of CMTM2-specific expression in healthy tissue samples. The relative expression (-fold activation) is shown.

CMTM2 (SEQ ID NO: 5) is a gene which is located on chromosome 16 (16q22.1). The gene encodes an integral membrane protein with a size of about 27 kDa (SEQ ID NO: 6). The protein belongs to the family of chemokine-like factors and has in addition significant homologies with the family of signal molecules with four transmembrane domains. CMTM2 might thus be an important molecule in cellular signal transduction. It was possible according to the invention to identify CMTM2 as an autoantigen in autoimmunoscreening. To analyze the tissue-specific expression of CMTM2, establishment of a gene-specific quantitative RT-PCR (primer pair SEQ ID NO: 93 and 94) was followed by analysis of the amount of the specific transcripts in various regions of the brain and in other healthy tissues. CMTM2 is highly overexpressed in the immunoprivileged testis (FIG. 6). In the other tissues investigated, CMTM2 was very selectively expressed especially in the various regions of the brain, so that the autoimmune response is to be regarded as brain-specific.

Example 9

Identification of CPE as Autoantigen

Carboxypeptidase E or CPE (SEQ ID NO: 7) is a gene which is located on chromosome 4 (4q32). The gene encodes a soluble protein with a size of about 53 kDa (SEQ ID NO: 8) which is localized in the cytoplasm. CPE is a carboxypeptidase which activates prohormones and neurotransmitters through its enzymatic function and is thus involved in the biosynthesis of these biological regulators.

Figure 7:
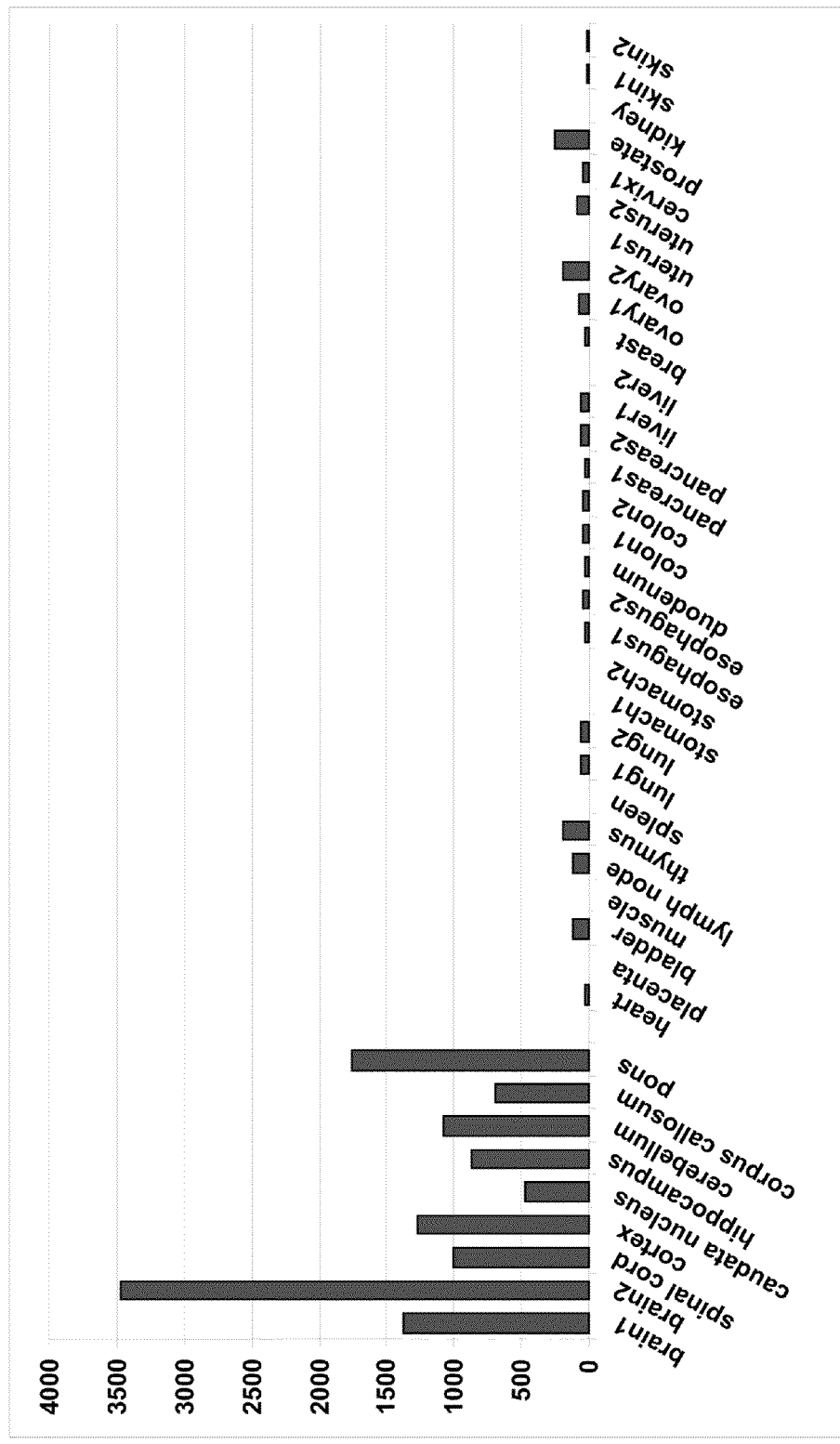
FIG. 7: Analysis of CPE-specific expression. Quantitative analysis of CPE-specific expression in healthy tissue samples. The relative expression (-fold activation) is shown.

It was possible according to the invention to identify CPE as an autoantigen in autoimmunoscreening. To analyze the tissue-specific expression of CPE, establishment of a gene-specific quantitative RT-PCR (primer pair SEQ ID NO: 95 and 96) was followed by analysis of the amount of the specific transcripts in various regions of the brain and in other healthy tissues. It was possible to detect in a quantitative RT-PCR an at least 5-fold overexpression in the brain by comparison with all the other tissues investigated (FIG. 7).

Example 10

Identification of LITAF as Autoantigen

LPS-induced TNF-alpha factor or LITAF (SEQ ID NO: 9) is a gene which is located on chromosome 16 (16p13). The gene encodes a soluble protein with a size of about 24 kDa (SEQ ID NO: 10) which is localized in the nucleus. LITAF has an important role in the regulation of transcription of the cytokine TNF-alpha and is thought to be associated with the neurological Charcot-Marie-tooth disease (Street, 2003. *Neurology* 60: 22-26).

Figure 8:
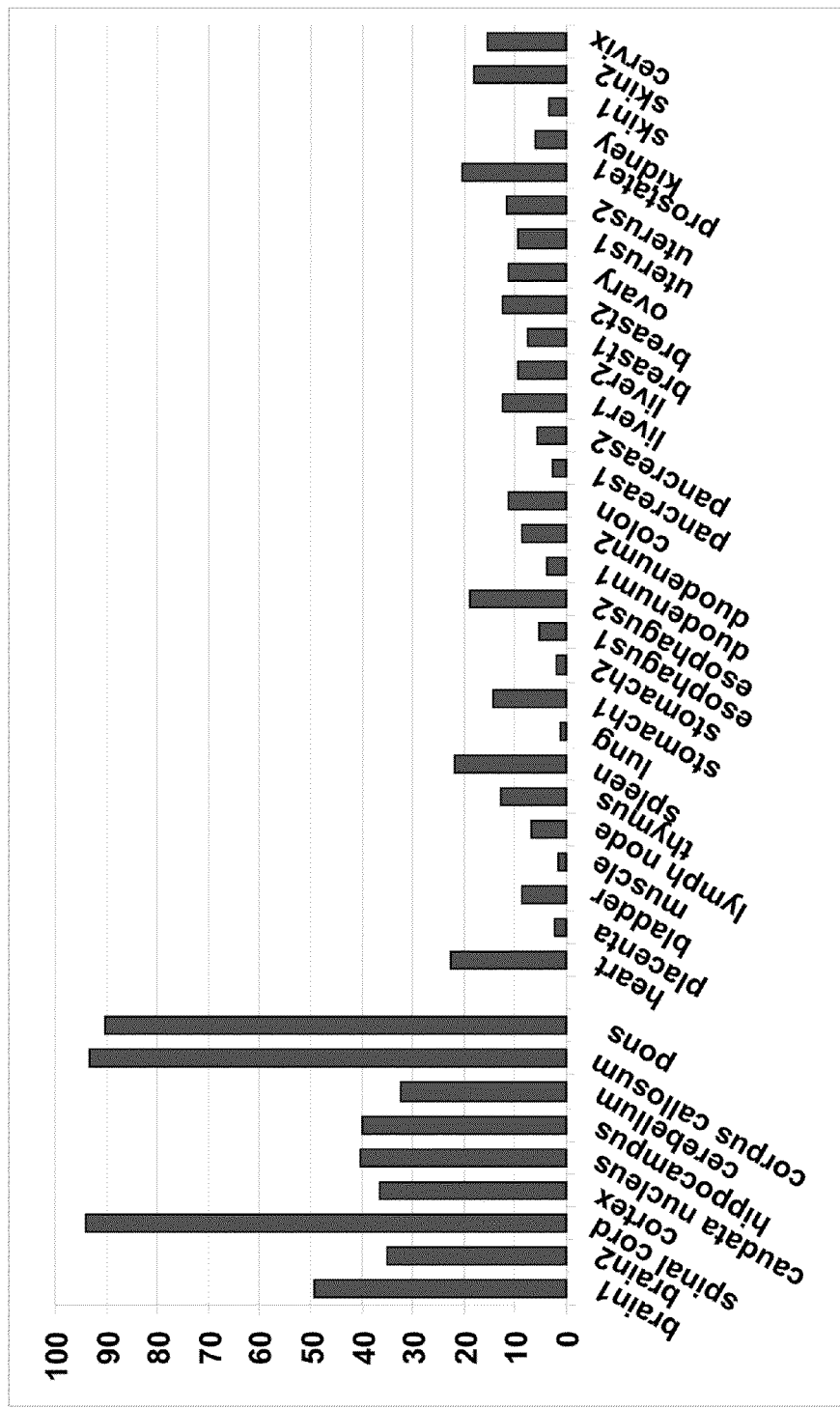
FIG. 8: Analysis of LITAF-specific expression. Quantitative analysis of LITAF-specific expression in healthy tissue samples. The relative expression (-fold activation) is shown.

It was possible according to the invention to identify LITAF as an autoantigen in autoimmunoscreening. To analyze the tissue-specific expression of LITAF, establishment of a gene-specific quantitative RT-PCR (primer pair SEQ ID NO: 97 and 98) was followed by analysis of the amount of the specific transcripts in various regions of the brain and in other healthy tissues. It was possible to detect an at least 2- to 5-fold overexpression in the brain by comparison with all the other tissues investigated (FIG. 8).

Example 11

Identification of TUBG1 as Autoantigen

Tubulin gamma 1 or TUBG1 (SEQ ID NO: 11) is a gene which is located on chromosome 17 (16q21). The gene encodes a soluble protein with a size of about 51 kDa (SEQ ID NO: 12) which is localized in the nucleus. TUBG1 is a member of the tubulin family and constituent of the microtubules in the cell nucleus. The protein plays an important part in regulating division of the cell nucleus.

Figure 9:
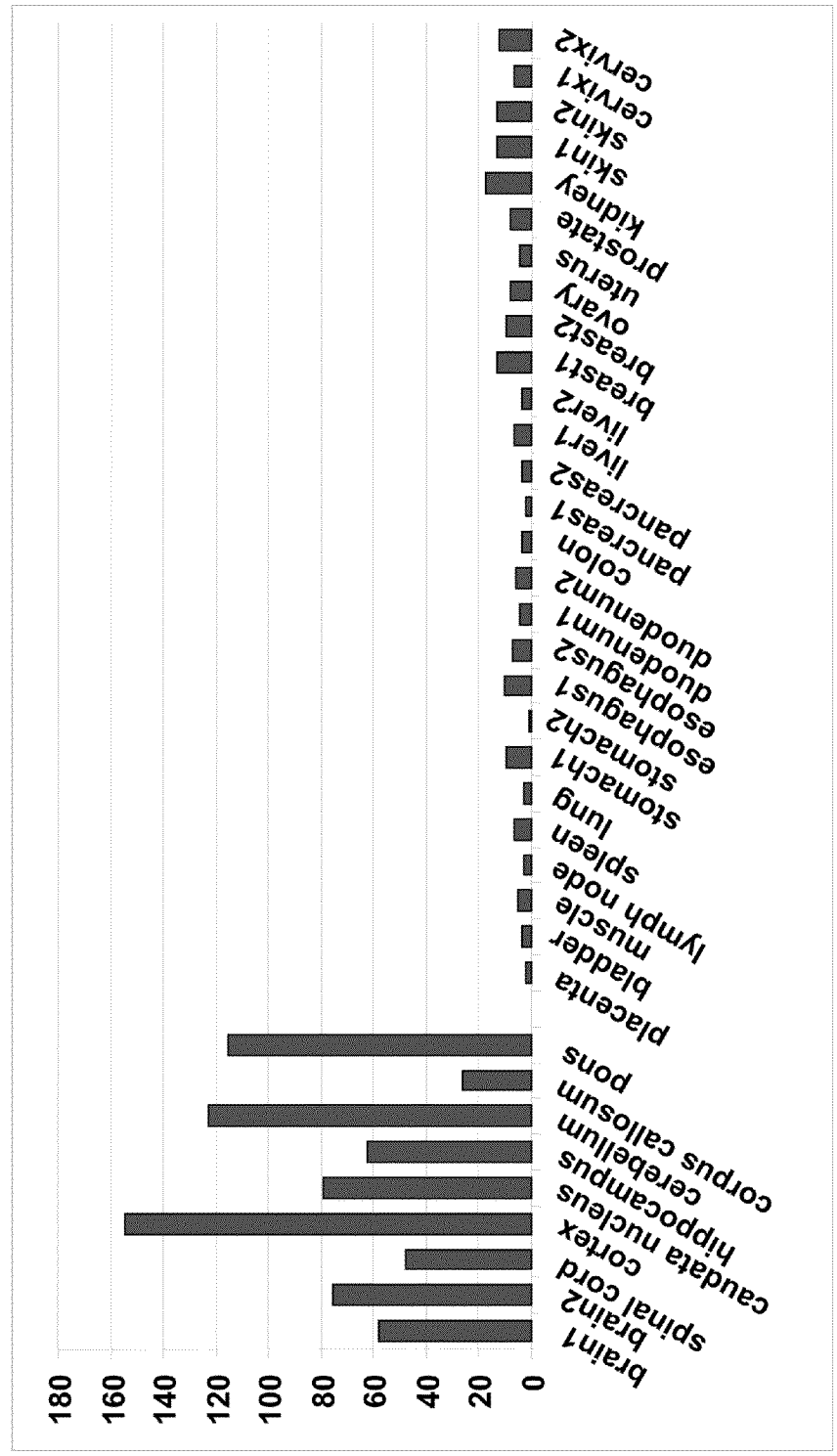
FIG. 9: Analysis of TUBG1-specific expression. Quantitative analysis of TUBG1-specific expression in healthy tissue samples. The relative expression (-fold activation) is shown.

It was possible according to the invention to identify TUBG1 as an autoantigen in autoimmunoscreening. To analyze the tissue-specific expression of TUBG1, establishment of a gene-specific quantative RT-PCR (primer pair SEQ ID NO: 99 and 100) was followed by analysis of the amount of the specific transcripts in various regions of the brain and in other healthy tissues. It was possible to detect an at least 2- to 5-fold overexpression in the brain by comparison with all the other tissues investigated (FIG. 9).

Example 12

Identification of NAP1L3 as Autoantigen

Nucleosome assembly protein 1-like 3 or NAP1L3 (SEQ ID NO: 13) is a gene which is located on chromosome X (Xq21-22). The gene encodes a soluble protein with a size of about 58 kDa (SEQ ID NO: 14) which is localized in the nucleus. NAP1L3 is a member of the nucleosome assembly family and plays an important role in regulating the cell nucleus.

Example 13

Identification of ENO2 as Autoantigen

Enolase 2 or ENO2 (SEQ ID NO: 15) is a gene which is located on chromosome 12 (12q13). The gene encodes a soluble protein with a size of about 47 kDa (SEQ ID NO: 16) which is localized in the cytoplasm. The ENO2 gene codes for an enzyme of the glycolytic metabolic pathway which is mainly expressed in neurons and cells of neuronal origin.

Example 14

Identification of Autoantigens Already Associated With Other Autoimmune Diseases It was surprisingly possible by the immunoscreening to identify a total of four autoantigens which have previously been described in connection with other autoimmune responses.

The gene SDCCAG8 (SEQ ID NO: 17) is located on chromosome 1 (1q43-44). The gene codes for a protein with a size of about 49 kDa (SEQ ID NO: 18) with as yet unknown function. SDCCAG8 has been described as a colon-specific tumor autoantigen.

The gene HSP90B1 (SEQ ID NO: 19) is located on chromosome 12 (12q24) and codes for a protein having a size of about 92 kDa (SEQ ID NO: 20). The gene belongs to the family of chaperones which have an important function in the genesis and transport of secreted proteins in the lumen of the ER. HSP90B1 is upregulated in myelomas.

The gene SAT (SEQ ID NO: 21) is located on the X chromosome (Xp22) and codes for a protein about 20 kDa in size (SEQ ID NO: 22). The soluble enzyme is present in the cytoplasm as a homotetramer and fulfills a catalytic function in the regulation of polyamines.

The gene EXOSC5 (SEQ ID NO: 23) is located on chromosome 19 (19q13) and codes for a nuclear protein about 25 kDa in size (SEQ ID NO: 24). The enzyme has exonuclease activity and is a constituent of the nuclear exosome. EXOSC5-specific autoantibodies were detectable in patients with myopathies and skin diseases.

Example 15

Identification of Autoantigens of as Yet Unknown Function

It was surprisingly possible to identify by the immunoscreening a total of ten novel, previously hypothetical genes and some chromosomal regions to which no gene has yet been assignable to date. Accordingly, the function and properties of their gene products are unknown. These genes and the relevant gene products are as follows: chromosome 20 sequence: SEQ ID NO: 25, 26; CEP63: SEQ ID NO: 27, 28; LOC115648: SEQ ID NO: 29, 30; chromsome 18 sequence: SEQ ID NO: 31, 32; chromosome 14 sequence 1: SEQ ID NO: 33, 34; chromosome 14 sequence 2: SEQ ID NO: 35, 36; IQWD1: SEQ ID NO: 37, 38; C60ORF199: SEQ ID NO: 39, 40; chromosome 22 sequence: SEQ ID NO: 41, 42; LOC400843: SEQ ID NO: 43, 44. The gene product with SEQ ID NO: 28 is a soluble centrosomally located protein of unknown function. IQWD1 codes for a nuclear protein with a size of about 96 kDa (SEQ ID NO: 38) with several WD40 domains and a nuclear translocation sequence. WD40 domains probably have a function in protein-protein interactions. The gene with SEQ ID NO: 39 codes for a protein with a size of about 48 kDa, which is possibly localized in mitochondria and has an adenylate kinase function.

Example 16

Identification of Further Human Autoantigens

It was surprisingly possible to identify by the immunoscreening a total of 17 cellular antigens not previously known to be involved in autoimmune responses.

Interferon regulatory factor 2 binding protein 2 or IRF2BP2 (SEQ ID NO: 45) is a gene which is located on chromosome 1 (1p42). The gene encodes a soluble protein with a size of about 61 kDa (SEQ ID NO: 46) which is probably localized in the nucleus. The exact function of IRF2BP2 is not yet known. The protein binds to the transcription factor IRF2 and influences IRF2-specific gene regulation.

Sterol regulatory element binding factor 1 or SREBF1 (SEQ ID NO: 47) is a gene which is located on chromosome 17 (17p11). The gene encodes a protein with a size of about 122 kDa (SEQ ID NO: 48). SREBF1 has a transmembrane domain and plays a role in the regulation of transcription and in sterol transport. In the unactivated state, SREBF1 is localized in the ER but, after activation, it is translocated into the nucleus where the protein regulates the transcription of various genes by direct DNA binding.

Exportin4 or XPO4 (SEQ ID NO: 49) is a gene which is located on chromosome 1 (13q11). The gene encodes a soluble protein with a size of about 130 kDa (SEQ ID NO: 50). XPO4 binds to the elongation factor eIF-5A and mediates the transport of the elongation factor from the nucleus into the cytoplasm.

Zinc finger protein 64 or ZFP64 (SEQ ID NO: 51) is a gene which is located on chromosome 1 (20q13). The gene encodes a soluble protein with a size of about 75 kDa (SEQ ID NO: 52) which is localized in the nucleus. ZFP64 probably binds to DNA and has the function of a transcription factor.

Formin binding protein 1 or FNBP1 (SEQ ID NO: 53) is a gene which is located on chromosome 9 (9q34). The gene encodes a soluble protein with a size of about 70 kDa (SEQ ID NO: 54) which is probably localized in the cytoplasm. The protein is assigned a function in cellular growth regulation.

CCL4 (SEQ ID NO: 55) is a gene which is located on chromosome 17 (17q24). The gene encodes a soluble protein with a size of about 10.5 kDa (SEQ ID NO: 56) which is secreted. The protein binds to cytokine receptors and belongs to the family of chemokines.

COPA (SEQ ID NO: 57) is a gene which is located on chromosome 1 (1q23-25). The gene encodes a soluble protein with a size of about 138 kDa (SEQ ID NO: 58) which is localized in the cytoplasm. The protein is involved in regulating secretory vesicles and is also secreted during this.

GHITM (SEQ ID NO: 59) is a gene which is located on chromosome 10 (10q23.1). The gene encodes an integral membrane protein with a size of about 34 kDa (SEQ ID NO: 60) whose expression is probably chemokine-dependent. The protein is assigned a function in the interferon signaling system and a potential receptor function.

NGLY1 (SEQ ID NO: 61) is a gene which is located on chromosome 3 (3q24.2). The gene encodes an integral membrane protein with a size of about 55 kDa (SEQ ID NO: 62). The protein is assigned a function in the degradation of incorrectly folded proteins.

KTN1 (SEQ ID NO: 63) is a gene which is located on chromosome 14 (14q22.1). The gene encodes a membrane protein with a size of about 156 kDa (SEQ ID NO: 64). The protein is assigned a function as kinesin receptor and thus in kinesin-driven vesicle motility.

SFRS11 (SEQ ID NO: 65) is a gene which is located on chromosome 1 (1q31). The gene encodes a soluble protein with a size of about 54 kDa (SEQ ID NO: 66) which is probably localized in the nucleus. The protein is assigned a function in pre-mRNA splicing.

NME1-NME2 (SEQ ID NO: 67) is a gene which is located on chromosome 17 (17q21.3). The gene encodes a soluble protein with a size of about 17 kDa (SEQ ID NO: 68) which is probably localized in the cytoplasm and nucleus. The protein has, as nucleoside-diphosphate kinase, a function in the synthesis of non-ATP nucleoside triphosphates.

RPS15 (SEQ ID NO: 69) is a gene which is located on chromsome 19 (19q13.3). The gene encodes a soluble protein with a size of about 17 kDa (SEQ ID NO: 70) which is probably localized in the cytoplasm. RPS15 is a member of the S19P family of ribosomal proteins and plays a part in protein synthesis.

APC2 (SEQ ID NO: 71) is a gene which is located on chromosome 19 (19q13.3). The gene encodes a soluble protein with a size of about 245 kDa (SEQ ID NO: 72) which is localized in the cytoplasm and possibly colocalized with tubular structures and the golgi apparatus. The protein is assigned a function as tumor suppressor.

GLS2 (SEQ ID NO: 73) is a gene which is located on chromosome 12 (12q13). The gene encodes a soluble protein with a size of about 68 kDa (SEQ ID NO: 74) which is localized in mitochondria. The protein is assigned an enzymatic function as glutaminase in the hydrolysis of glutamine.

TECAL8 (SEQ ID NO: 75) is a gene which is located on chromosome X (Xq22.1). The gene codes for a soluble protein with a size of about 14 kDa (SEQ ID NO: 76). The protein is assigned a function as transcription elongation factor.

PPIF (SEQ ID NO: 77) is a gene which is located on chromosome 10 (10q22-q23). The gene codes for a protein with a size of about 22 kDa (SEQ ID NO: 78) which is localized in the mitochondria. The protein is assigned an enzymatic function in protein folding and a possible function in the induction of apoptotic and necrotic cell death.

Example 17

Identification of Mitochondrial Autoantigens

It was possible by the immunoscreening to identify a total of five mitochondrial genes against whose gene products autoantibodies are formed in patients with multiple sclerosis. These genes and relevant gene products are as follows: ND4: SEQ ID NO: 79, 80; ATP5H: SEQ ID NO: 81, 82; COX1: SEQ ID NO: 83, 84; COX2: SEQ ID NO: 85, 88; COX3: SEQ ID NO: 87, 88.

Example 18

Serological Analysis of Selected Autoimmune Antigens

Figure 10:
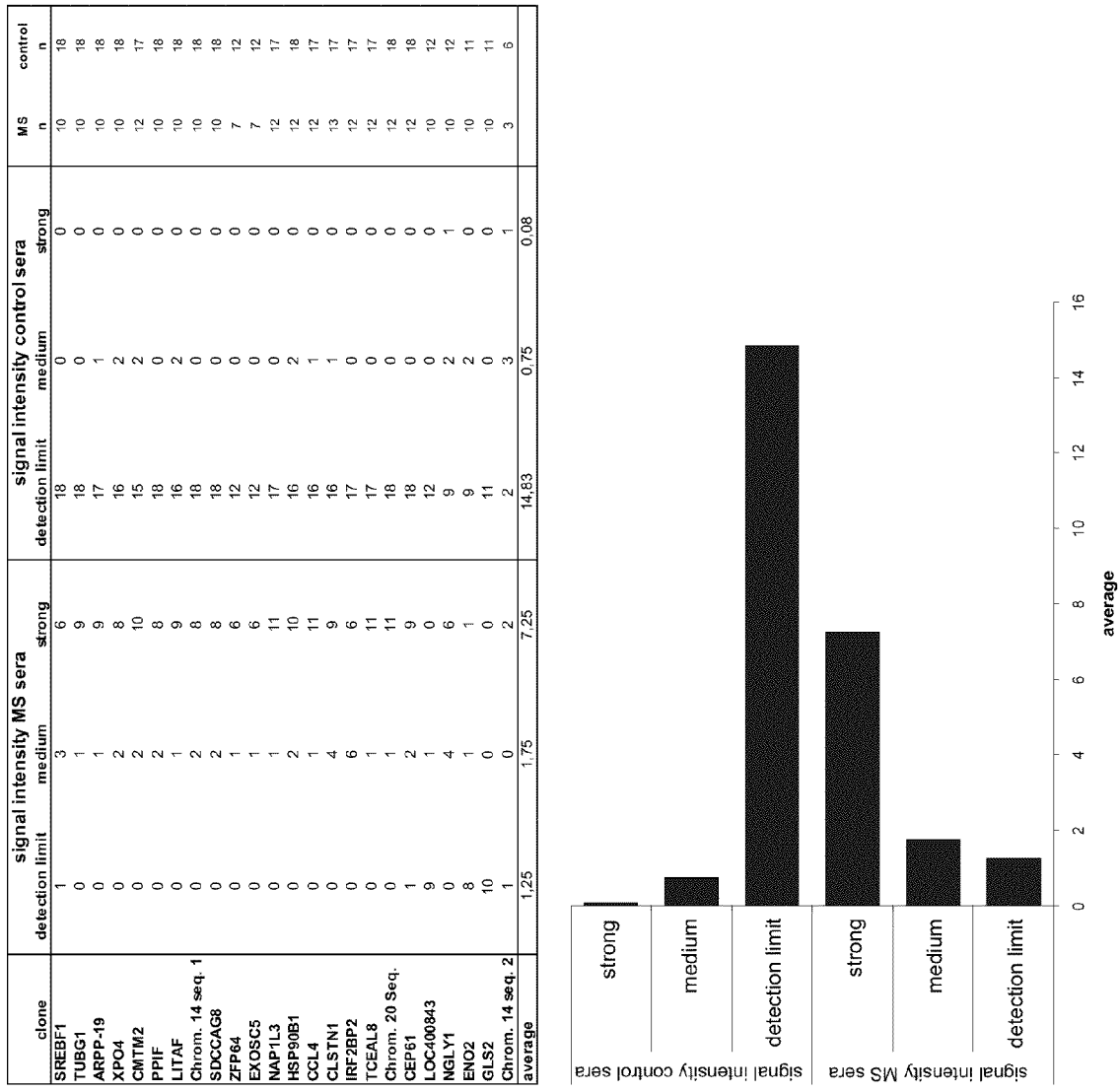
FIG. 10, Differential serology of selected antigens. A: Representation of the qualitative analysis of the signal intensity for selected antigens after incubation with sera from MS patients compared with healthy control sera.

In order to investigate the prevalence of the identified antigens in patients with multiple sclerosis, 24 of the 44 identified antigens were investigated with up to 12 sera from MS patients and up to 18 sera from control patients in a Serogrid analysis (Krause et al., 2003, *J Imm Methods* 283, 261) (see Example 3). The result of the analysis is depicted in FIG. 10. The identified antigens were moderately to strongly positive in almost all the samples investigated originating from patients with an MS disease and thus demonstrated a high prevalence of the identified autoantibodies in patients with multiple sclerosis. It was by contrast possible to identify at the most only a weak reactivity close to the limit of detection in the control samples (n=18) derived from healthy subjects.

The invention claimed is:

1. A method for the diagnosis of multiple sclerosis in a patient, comprising detection of moderately to strongly positive presence of autoantibodies, wherein the autoantibody is specific for a protein or peptide which is encoded by the nucleic acid sequence of SEQ ID NO: 1 in blood, serum or plasma isolated from a patient.

2. The method as claimed in claim 1, where the protein or peptide for which the autoantibody is specific comprises the sequence of SEQ ID NO: 2.

3. The method as claimed in claim 1 or 2, which further comprises detection of the autoantibody in blood, serum or plasma isolated from a patient without multiple sclerosis.

4. The method as claimed in claim 1 or 2, where the detection of the autoantibody takes place with an immunoassay.

5. The method as claimed in claim 1 or 2, where the detection of the autoantibody comprises
   (i) contacting the blood, serum or plasma with an agent which specifically binds to the autoantibody, and
   (ii) detecting the formation of a complex between the agent and the autoantibody.

6. The method as claimed in claim 5, where the agent which specifically binds to the autoantibody is immobilized on a support material.

7. The method as claimed in claim 5, where the agent which specifically binds to the autoantibody is a protein or peptide which specifically binds to the autoantibody.

8. The method as claimed in claim 7, where the protein or peptide which specifically binds to the autoantibody comprises an amino acid sequence which is encoded by the nucleic acid of SEQ ID NO: 1.

9. The method as claimed in claim 7, where the protein or peptide which specifically binds to the autoantibody comprises the sequence of SEQ ID NO: 2.

* * * * *

SEQUENCE LISTING

```
<160> NUMBER OF SEQ ID NOS: 106

<210> SEQ ID NO 1
<211> LENGTH: 5209
<212> TYPE: DNA
<213> ORGANISM: Homo sapiens

<400> SEQUENCE: 1
acctctactg gggagacgag gaccccgagg ttctgggggg cgacgcgacc tgcccgaagt      60
gacaagggtc ctgggccgca ctgctccgcc ggggtctgcg ctcctcggcg gagcgggtgg     120
gaaggatgag tcctcggggt ggagaaggag gagcgggtcc ccgggtaccg ctcacccggc     180
cttaggagcc cgggagcgcg cgtagggacg cggagttgag gctctccatc tgcggccagg     240
gaaagggata cagtcccccg ggcccctccc ggccgctcgg aacccacccc aggcgcgtcc     300
ccgcgggcgc gcgctccagg cggggccgac gggctcggag gcgcgcgccc gctgccgggt     360
ccgccgcgcg cgctccctcc gctcctctcc cccgcccctc ccgggcccgc gcgctcccag     420
ggtccgccgc gcgcgcgcct cgcgtcgctc cccatccccg cccctcccgc cgccacccccg     480 cccccggccg ggtaccctcg ccggacccga gagagagcgc cgccgccatc ttagttgctg     540
ccgctgcctt cagcaagacg ctgctctgag gcggggaggg cgccgcgtcc tgagcgcgcg     600
gcccagcgtc acgcggcgg cggcggcggc tcctccttgg accccggag ctcccgcgc     660 cgcggagcag ctggccccag gcccctagag ccccgagagc tccgagagct ccgctcggcg     720
```

```
tcccgcgcgc ctccctgccg ctcccgcccc gggctggcga tgctgcgccg ccccgctccc    780
gcgctggccc cggccgcccg gctgctgctg gccgggctgc tgtgcggcgg cggggtctgg    840
gccgcgcgag ttaacaagca caagccctgg ctggagccca cctaccacgg catagtcaca    900
gagaacgaca acaccgtgct cctcgacccc ccactgatcg cgctggataa agatgcgcct    960
ctgcgatttg cagagagttt tgaggtgaca gtcaccaaag aaggtgagat tgtggatttt   1020
aaaattcacg ggcagaatgt cccctttgat gcagtggtag tggataaatc cactggtgag   1080
ggagtcattc gctccaaaga gaaactggac tgtgagctgc agaaagacta ttcattcacc   1140
atccaggcct atgattgtgg aagggaccct gatggcacca acgtgaaaaa gtctcataaa   1200
gcaactgttc atattcaggt gaacgacgtg aatgagtacg cgcccgtgtt caaggagaag   1260
tcctacaaag ccacggtcat cgaggggaag cagtacgaca gcattttgag ggtggaggcc   1320
gtggatgccg actgctcccc tcagttcagc cagatttgca gctacgaaat catcactcca   1380
gacgtgccct ttactgttga caaagatggt tatataaaaa acacagagaa attaaactac   1440
gggaaagaac atcaatataa gctgaccgtc actgcctatg actgtgggaa gaaaagagcc   1500
acagaagatg ttttggtgaa gatcagcatt aagcccacct gcacccctgg gtggcaagga   1560
tggaacaaca ggattgagta tgagccgggc accggcgcgt tggccgtctt tccaaatatc   1620
cacctggaga catgtgacga gccagtcgcc tcagtacagg ccacagtgga gctagaaacc   1680
agccacatag ggaaaggctg cgaccgagac acctactcag agaagtccct ccaccggctc   1740
tgtggtgcgg ccgcgggcac tgccgagctg ctgccatccc cgagtggatc cctcaactgg   1800
accatgggcc tgcccaccga caatggccac gacagcgacc aggtgtttga gttcaacggc   1860
acccaggcag tgaggatccc ggatggcgtc gtgtcggtca gccccaaaga gccgttcacc   1920
atctcggtgt ggatgagaca tgggccattc ggcaggaaga aggagacaat tctttgcagt   1980
tctgataaaa cagatatgaa tcggcaccac tactccctct atgtccacgg gtgccggctg   2040
atcttcctct tccgtcagga tccttctgag gagaagaaat acagacctgc agagttccac   2100
tggaagttga atcaggtctg tgatgaggaa tggcaccact acgtcctcaa tgtagaattc   2160
ccgagtgtga ctctctatgt ggatggcacg tcccacgagc ccttctctgt gactgaggat   2220
tacccgctcc atccatccaa gatagaaact cagctcgtgg tgggggcttg ctggcaagag   2280
ttttcaggag ttgaaaatga caatgaaact gagcctgtga ctgtggcctc tgcaggtggc   2340
gacctgcaca tgacccagtt tttccgaggc aatctggctg gcttaactct ccgttccggg   2400
aaactcgcgc ataagaaggt gatcgactgt ctgtatacct gcaaggaggg gctggacctg   2460
caggtcctcg aagacagtgg cagaggcgtg cagatccaag cacaccccag ccagttggta   2520
ttgaccttgg agggagaaga cctcgggaa ttggataagg ccatgcagca catctcgtac   2580
ctgaactccc ggcagttccc cacgcccgga attcgcagac tcaaaatcac cagcacaatc   2640
aagtgtttta cgaggccac ctgcatttcg gtcccccgg tagatggcta cgtgatggtt   2700
ttacagcccg aggagcccaa gatcagcctg agtggcgtcc accattttgc ccgagcagct   2760
tctgaatttg aaagctcaga aggggtgttc ctttttccctg agcttcgcat catcagcacc   2820
atcacgagag aagtggagcc tgaaggggac ggggctgagg accccacagt tcaagaatca   2880
ctggtgtccg aggagatcgt gcacgacctg gatacctgtg aggtcacggt ggaggggagg   2940
gagctgaacc acgagcagga gagcctggag gtggacatgg cccgcctgca gcagaagggc   3000
attgaagtga gcagctctga actgggcatg accttcacag gcgtggacac catggccagc   3060
tacgaggagg ttttgcacct gctgcgctat cggaactggc atgccaggtc cttgcttgac   3120
```

-continued

```
cggaagttta agctcatctg ctcagagctg aatggccgct acatcagcaa cgaatttaag    3180
gtggaggtga atgtaatcca cacgccaac cccatggaac acgccaacca catggctgcc     3240
cagccacagt tcgtgcaccc ggaacaccgc tcctttgttg acctgtcagg ccacaacctg    3300
gccaaccccc acccgttcgc agtcgtcccc agcactgcga cagttgtgat cgtggtgtgc    3360
gtcagcttcc tggtgttcat gattatcctg ggggtatttc ggatccgggc cgcacatcgg    3420
cggaccatgc gggatcagga caccgggaag gagaacgaga tggactggga cgactctgcc    3480
ctgaccatca ccgtcaaccc catggagacc tatgaggacc agcacagcag tgaggaggag    3540
gaggaagagg aagaggaaga ggaaagcgag gacggcgaag aagaggatga catcaccagc    3600
gccgagtcgg agagcagcga ggaggaggag ggggagcagg gcgaccccca gaacgcaacc    3660
cggcagcagc agctggagtg ggatgactcc accctcagct actgaccgt  gcccccggcc    3720 acctcggttt ctgctttcga agactctgct gccatccgtt ctcccagtcc caagggtcca    3780
cgatgtacaa agtcatttcg gccagtaggt gtgcagaccc ctccccgcca cgatcgtcgc    3840
tgtgcttggt gtgtaggacc ctaggctccc cgcccaccct ctgcctggtc gcgctcttca    3900
gtcccacgag gagctgacac gtcctctctg gccgccatcc ggctcgcaca ggggcctccc    3960
agcgcctcag gccccgcgtt tgtgtctgga gtctccccccc ggggagagga cactggcccc    4020
tcgcactcca gaaaagccat gccagctggg ctcgttgaca aagggtaaaa catgctcact    4080
cccacccggt aatcattttt ttctttttt  aaaaaaagtt tttattttt  ccaaactagt    4140 gcatgtataa ataatggcag gatgggggt  actgtgtaga tgattaactg  actttttaat   4200
attttgtaaa taaatcggat tccttgtgtc ctttgtgcta gtgtaacccg ggactggaat    4260
gtaaagtgaa gttcggagct ctgagcacgg gctcttcccg ccgggtcctc cctccccaga    4320
ccccagaggg agaggcccac cccgcccagc ccgccccag  ccctgctca  ggtctgagta    4380 tggctgggag tcgggggcca caggcctcta gctgtgctgc tcaagagact ggatcagggt    4440
agctacaagt ggccgggcct tgccttttggg attctacctg ttcctaattt ggtgtggggt   4500
gcggggtccc tggcccctttt tccacactcc tcctccgaca gcagctccct gggcagtggc    4560
ctggtctcac cgtgtgcagc cttgtggttt atgcttaaat gtacattttc ctgctggtaa    4620
aaggagaaac tgagaggtgt cctgcagacc ggctgaccac tccttttgga dacggcagga   4680
ggcctgagcg atccgtactc agaacgtcca ggagagacgc atggcccgaa gtcaaagtgc    4740
tggaattttc caaaacagcc tgttctctcc tctctcctcc ccagagcacc cctgccatc    4800 agggggggttga aaatccctct ccccccaggag ccctgctgct ttgcttggtg gtagggcagg   4860
agagcaaaca aacagtcatg gtctaaaacc cacatagcac tttgctctta gttacatgta    4920
aaattttaga tttctaaaac aggtgggcaa tcatttgaa  tactgttctg tgaccctgac    4980
tgctagttct gaggacactg gtggctgtgc tatgtgtggc catcctccat gtcccgtccc    5040
tgtagctgct ctgtttagac agcggacaga cgctcacgcc caggggatgt cctcacgctg    5100
tcgccgcgcg gtttcccttc gcagatgtgt atactcatga taggtcagaa agtgtatccg    5160
ctacaataaa gttctggttc taactaactc caaaaaaaaa aaaaaaaaa               5209
```

<210> SEQ ID NO 2
<211> LENGTH: 981
<212> TYPE: PRT
<213> ORGANISM: Homo sapiens

<400> SEQUENCE: 2

Met Leu Arg Arg Pro Ala Pro Ala Leu Ala Pro Ala Ala Arg Leu Leu
1               5                   10                  15

```
Leu Ala Gly Leu Leu Cys Gly Gly Val Trp Ala Ala Arg Val Asn
            20              25              30
Lys His Lys Pro Trp Leu Glu Pro Thr Tyr His Gly Ile Val Thr Glu
        35              40              45
Asn Asp Asn Thr Val Leu Leu Asp Pro Pro Leu Ile Ala Leu Asp Lys
50              55              60
Asp Ala Pro Leu Arg Phe Ala Glu Ser Phe Glu Val Thr Val Thr Lys
65              70              75              80
Glu Gly Glu Ile Cys Gly Phe Lys Ile His Gly Gln Asn Val Pro Phe
                85              90              95
Asp Ala Val Val Val Asp Lys Ser Thr Gly Glu Gly Val Ile Arg Ser
            100             105             110
Lys Glu Lys Leu Asp Cys Glu Leu Gln Lys Asp Tyr Ser Phe Thr Ile
            115             120             125
Gln Ala Tyr Asp Cys Gly Lys Gly Pro Asp Gly Thr Asn Val Lys Lys
        130             135             140
Ser His Lys Ala Thr Val His Ile Gln Val Asn Asp Val Asn Glu Tyr
145             150             155             160
Ala Pro Val Phe Lys Glu Lys Ser Tyr Lys Ala Thr Val Ile Glu Gly
                165             170             175
Lys Gln Tyr Asp Ser Ile Leu Arg Val Glu Ala Val Asp Ala Asp Cys
            180             185             190
Ser Pro Gln Phe Ser Gln Ile Cys Ser Tyr Glu Ile Ile Thr Pro Asp
            195             200             205
Val Pro Phe Thr Val Asp Lys Asp Gly Tyr Ile Lys Asn Thr Glu Lys
        210             215             220
Leu Asn Tyr Gly Lys Glu His Gln Tyr Lys Leu Thr Val Thr Ala Tyr
225             230             235             240
Asp Cys Gly Lys Lys Arg Ala Thr Glu Asp Val Leu Val Lys Ile Ser
                245             250             255
Ile Lys Pro Thr Cys Thr Pro Gly Trp Gln Gly Trp Asn Asn Arg Ile
            260             265             270
Glu Tyr Glu Pro Gly Thr Gly Ala Leu Ala Val Phe Pro Asn Ile His
        275             280             285
Leu Glu Thr Cys Asp Glu Pro Val Ala Ser Val Gln Ala Thr Val Glu
        290             295             300
Leu Glu Thr Ser His Ile Gly Lys Gly Cys Asp Arg Asp Thr Tyr Ser
305             310             315             320
Glu Lys Ser Leu His Arg Leu Cys Gly Ala Ala Gly Thr Ala Glu
                325             330             335
Leu Leu Pro Ser Pro Ser Gly Ser Leu Asn Trp Thr Met Gly Leu Pro
        340             345             350
Thr Asp Asn Gly His Asp Ser Asp Gln Val Phe Glu Phe Asn Gly Thr
        355             360             365
Gln Ala Val Arg Ile Pro Asp Gly Val Val Ser Val Ser Pro Lys Glu
    370             375             380
Pro Phe Thr Ile Ser Val Trp Met Arg His Gly Pro Phe Gly Arg Lys
385             390             395             400
Lys Glu Thr Ile Leu Cys Ser Ser Asp Lys Thr Asp Met Asn Arg His
                405             410             415
His Tyr Ser Leu Tyr Val His Gly Cys Arg Leu Ile Phe Leu Phe Arg
            420             425             430
Gln Asp Pro Ser Glu Glu Lys Lys Tyr Arg Pro Ala Glu Phe His Trp
```

-continued

```
                435                 440                 445
Lys Leu Asn Gln Val Cys Asp Glu Glu Trp His His Tyr Val Leu Asn
    450                 455                 460
Val Glu Phe Pro Ser Val Thr Leu Tyr Val Asp Gly Thr Ser His Glu
465                 470                 475                 480
Pro Phe Ser Val Thr Glu Asp Tyr Pro Leu His Pro Ser Lys Ile Glu
                485                 490                 495
Thr Gln Leu Val Val Gly Ala Cys Trp Gln Glu Phe Ser Gly Val Glu
    500                 505                 510
Asn Asp Asn Glu Thr Glu Pro Val Thr Val Ala Ser Ala Gly Gly Asp
                515                 520                 525
Leu His Met Thr Gln Phe Phe Arg Gly Asn Leu Ala Gly Leu Thr Leu
    530                 535                 540
Arg Ser Gly Lys Leu Ala Asp Lys Lys Val Ile Asp Cys Leu Tyr Thr
545                 550                 555                 560
Cys Lys Glu Gly Leu Asp Leu Gln Val Leu Glu Asp Ser Gly Arg Gly
                565                 570                 575
Val Gln Ile Gln Ala His Pro Ser Gln Leu Val Leu Thr Leu Glu Gly
    580                 585                 590
Glu Asp Leu Gly Glu Leu Asp Lys Ala Met Gln His Ile Ser Tyr Leu
                595                 600                 605
Asn Ser Arg Gln Phe Pro Thr Pro Gly Ile Arg Arg Leu Lys Ile Thr
    610                 615                 620
Ser Thr Ile Lys Cys Phe Asn Glu Ala Thr Cys Ile Ser Val Pro Pro
625                 630                 635                 640
Val Asp Gly Tyr Val Met Val Leu Gln Pro Glu Glu Pro Lys Ile Ser
                645                 650                 655
Leu Ser Gly Val His His Phe Ala Arg Ala Ala Ser Glu Phe Glu Ser
    660                 665                 670
Ser Glu Gly Val Phe Leu Phe Pro Glu Leu Arg Ile Ile Ser Thr Ile
                675                 680                 685
Thr Arg Glu Val Glu Pro Glu Gly Asp Gly Ala Glu Asp Pro Thr Val
    690                 695                 700
Gln Glu Ser Leu Val Ser Glu Ile Val His Asp Leu Asp Thr Cys
705                 710                 715                 720
Glu Val Thr Val Glu Gly Glu Leu Asn His Glu Gln Glu Ser Leu
                725                 730                 735
Glu Val Asp Met Ala Arg Leu Gln Lys Gly Ile Val Ser Ser
    740                 745                 750
Ser Glu Leu Gly Met Thr Phe Thr Gly Val Asp Thr Met Ala Ser Tyr
    755                 760                 765
Glu Glu Val Leu His Leu Leu Arg Tyr Arg Asn Trp His Ala Arg Ser
    770                 775                 780
Leu Leu Asp Arg Lys Phe Lys Leu Ile Cys Ser Glu Leu Asn Gly Arg
785                 790                 795                 800
Tyr Ile Ser Asn Glu Phe Lys Val Glu Val Asn Val Ile His Thr Ala
                805                 810                 815
Asn Pro Met Glu His Ala Asn His Met Ala Ala Gln Pro Gln Phe Val
    820                 825                 830
His Pro Glu His Arg Ser Phe Val Asp Leu Ser Gly His Asn Leu Ala
    835                 840                 845
Asn Pro His Pro Phe Ala Val Val Pro Ser Thr Ala Thr Val Val Ile
    850                 855                 860
```

```
Val Val Cys Val Ser Phe Leu Val Phe Met Ile Ile Leu Gly Val Phe
865                 870                 875                 880

Arg Ile Arg Ala Ala His Arg Thr Met Arg Asp Gln Asp Thr Gly
                885                 890                 895

Lys Glu Asn Glu Met Asp Trp Asp Asp Ser Ala Leu Thr Ile Thr Val
                900                 905                 910

Asn Pro Met Glu Thr Tyr Glu Asp Gln His Ser Ser Glu Glu Glu
            915                 920                 925

Glu Glu Glu Glu Glu Glu Ser Glu Asp Gly Glu Glu Asp Asp
        930                 935                 940

Ile Thr Ser Ala Glu Ser Glu Ser Ser Glu Glu Glu Gly Glu Gln
945                 950                 955                 960

Gly Asp Pro Gln Asn Ala Thr Arg Gln Gln Gln Leu Glu Trp Asp Asp
                965                 970                 975

Ser Thr Leu Ser Tyr
            980

<210> SEQ ID NO 3
<211> LENGTH: 5162
<212> TYPE: DNA
<213> ORGANISM: Homo sapiens

<400> SEQUENCE: 3 gccatttcg  cgggcggagg  cggcccggcg  ggccctggga  gagctgggac  gggcggcggc       60
cgggtggcct  cggccacccg  ctaattgcat  cttttcccgg  cgtctcgtct  gcagagggag      120
cactatgtct  gcggaagtcc  ccgaggcagc  ctccgcggag  gagcagaagg  aaatggaaga      180
taaagtgact  agtccagaga  aagcagaaga  agcaaaatta  aaagcaagat  atcctcatct      240
gggacaaaag  cctggaggtt  cagatttctt  aaggaaacgg  ttgcagaaag  ggcaaaaata      300
ttttgattct  ggggattaca  acatggctaa  agcaaaatg   aagaacaagc  aacttcctac      360
tgcagctccg  gataagacgg  aggtcactgg  tgaccacatt  cccactccgc  aagaccttcc      420
tcaacggaag  ccgtcccttg  ttgctagcaa  gctggctggc  tgattaagag  gctgaactgc      480
atgaatctgc  taaatctcat  tatttctcct  taatatgtta  cttatctact  ttttatttcc      540
tttcattcac  tagtcatttg  agactgacag  ctttgcaggt  agcagtagtg  tgtgctgcta      600
ttgtggaata  tacgtgtgta  gagtttttga  ttagtttaac  agtgcactgg  tgaagaggac      660
atgttagagc  aacataagta  aactacttga  aaatagttgt  atatattacc  taacttctag      720
tgtagtactg  gttctaacaa  gtaacaagca  agttttaaaa  ttttaatgtt  ttggctttca      780
ttacttcatc  ttaattatag  ctttgtatgt  tactcttatt  taatataatc  tctattgtat      840
tgatttcttc  tgtattacc   ttttggattt  tgtaaaacag  aagttaaga   ccacaagtta      900 gaagaaaggt  cacatatttc  aaacacaact  agatgggct   ctgaaagatt  tgtatctctg      960
tgcttgaact  tgaatggcct  taaacctgtt  tcagctttaa  cagtagaatt  ttacttgggc     1020
aatatttgcc  cattctggtg  taacttatgt  gactctagtg  cttaacagct  gccgttgaag     1080
ctaatattca  gttctgtaga  gttagaatac  cttttgttgt  tgaagatgtg  aatgaagtat     1140
gcatgtgcat  taactgttga  attcactttt  gtgccatttt  tgtaaataca  gtagttttgc     1200
acaacctctc  acaaatgtct  gtattaattt  cacatactta  aaaagtagat  aatgtgccaa     1260
ccagaagcac  aagagttcct  acacaaaact  ctgtaaatca  ttatagcttt  tgtataataa     1320
gagtagttta  caatctcggg  cttatagaat  accaaactga  aatcttagtt  caatctgcca     1380
tagacttaag  cttttcattt  gttactaata  tccatgacat  tcagtggcct  tgtgcaaata     1440
```

```
cgatatgttg cttaggcata tcttttgtcc tatgcagaac ctttcatttt gattttttatg    1500 aaagttgcaa ttcatgtaat ttatataaac tttttaaatg tagaaacttt ttacttccac    1560
actcagtttt ggagaccccta gaataaaagg cttcaatact ctgcattcca tgccctctgc    1620
cacctgcttt ttttttcccct ttgttctttg actcaaatgg tattgagctg tttgttgtat    1680
atggaagcat aggtgtctat atccttactc ttttatataa cacaataatg gcgttttcct    1740
tctaatttct cagttgttaa cttctttctc tttttttttt aggatagggc cttgctctgt    1800
cacctgagct ctagtgcagt agtgcaatca cagctcactg caaccttact cctaggctca    1860
agttaactat tcttgatcct ttattattac taatattcta caattgttta aataaaagga    1920
actttataat gaaacggttc ggaatactgg ctcaagaacc tatgtcaaga tgagctgaat    1980
tttggtaaat tattttagga attatgacaa gctaattgaa ttaggcttgt gacaattaga    2040
gtaatttaca tgacaggtaa aactcctatt aaaaatgttt agatgtttgc ttctgtagat    2100
gtcactttag taaaatacca atttagtttt acttgtggct tatctagtta gaacttagca    2160
gactttactg ggacaagttt actgctcttg taggagctcc tctcacaagt agttgtaatg    2220
ctgtagcatg atactcagga tcagtagctt gagatgctac tatttttctc ttcatctttg    2280
acttgcagag agcctcccgt ttttggatcc aggcatcttt tctgaatcct ggttccatca    2340
gtatacctgc tctcctatga ccccaaatca tagtcaatgg tgcctcaaac atagcacctt    2400
aagttaaagg ctgcctagtg ctctgaggaa agcttgctga ttatcttcct gatctactca    2460
ccccaaaagg cagaaaagca acacagtcac tgctgtggtc atttgtaatg taaagatcag    2520
ttatatatat atatttgtaa tgagagcaag tatatactca ttatagaatc aatttaagaa    2580
gtttaaaata acccagagta gaatttctat atctagtctt ggttttttc atgaatattt    2640 gcaagtaatt accattaaat tcacacatga aagattaatc tgaaagatca gagaccatgt    2700
tattcctgac cacgatagaa ctgctcctgt ggtttgggac aagtaataaa acaactgctt    2760
gagttttgtt tgtaaaatac ataattaata tttgacctac ctcaaaatgt attgaggatc    2820
tgtgaaatgc taagtgccca aaataaaata ttgctgattg tctttttatt aaaagtaaat    2880
ttcctcatta agccaacctg ccttctgtaa gtcacagtgc ttaaatctca ggattttca    2940 ttaggagaga cctgtcgtta aggatttgta ggtataattg cttagcctcc attattggtg    3000
cttgggatag agaggtttta gattttttgtt tttttttttgt tctgcctcaa agctcagttt    3060
attgaagaca tttgtaagct attggatcat cacttgaatc aagattttga ctagtgagct    3120
taattgtcca tttcttacaa tttcaaagtt acagtctcag aaatggttaa ttttaataac    3180
tgtcctatca taaattaatg ttggaataaa ttgaagttgt tgataaatac ttcatgaaaa    3240
ctaaagtctg aaataaatta cttgttttat gtccaatagc tactacattt gatagaacag    3300
ttttgaggaa catttcattc ttgaacgcag catctgacat ggttctcagc aagttggaat    3360
agtaaggatt attggcttgt ttcgatgagt ggaagcggca tgtttgtagc atacaagtta    3420
ttcaataatc ttgtgctgat gacctaaaaa tatgtcttaa ctattcatca aggaaagcct    3480
ggtgaagcct ttacttgtta ctacttcaac agttggaatt agttgctctt tttacttgat    3540
gaaacaaaac tatacctctg aatatttatg gatacttttt actaaatcag gcttgtgttc    3600
ttaatccaaa ttagtaaagt tttatggaag ctgaaatgta atacagtagt ctcccccttat   3660 ctgtaagaga tacattccaa gacccctagt ggatgcctga aacctcagat agtactgaac    3720
cctttatcaa ctatgttttt tcagtctgac aaccaaggcg gctactaagt gactaagggg    3780
caggtagtat acagtgtgga taagcaggac aaagggggtga ttcacatccc aggcaggaca    3840
```

-continued

```
gagcaggaga tcatgagatt tcatcactca ggatggcttg tgatttattt tattttattc    3900
tttttttttt ttgagatgga gtctcactct tgcccaggct ggagtgcagt ggtgcgatct    3960
tggctcactg caacctctgc ctcctgggtt caagcagttc tcctgcctca gcctcccaag    4020
tagctgggat tacaggcgtc cgccaccatg cccagccaat ttttgtactt ttagtagaga    4080
tggggtttca ccatgttggc caggctggtc tcgaactcct gacctcaggt gatccactcg    4140
cctcggcctc ccaaagtgct gggattatag gcatgcgcca ccatgcccgg ccggcttatg    4200
atttaaaaca tgaattgttt atttctggaa ttttccacat aatattttg gaccaaggtt     4260 gcctcaggta acaaactaca gaaagtgaaa ttgcagataa agggattac tgctcctctg      4320 ctctaaaatt ggtgtttggg tgatcagaag caggtagcca atgggaagag cacttctgag    4380
tgataactaa agcagtttgg tggccttttc acattctcca atgttcaaac atattttcca    4440
ctttccattt tctctttcac ctcattttgc ctctctatcc cccatccctg cttatttctt    4500
aagcccattg atggcactca ttaaattgta tttagggcta atgagtcatt gttccttaat    4560
atcgttttca atatgccaca atttaggaca catttaaaat tttctaaaac aatatcctaa    4620
tcaatattga ctaatttgag ccacattccc aactctaact cagcacacac tgccagtctt    4680
ccccaatatc tgtctcctct caattcccca ccacaccta taaaattgta atcaaagata     4740
tctcactctg tcattgttaa tctaagaata aaaacactga ctttaatacg gttttactaa    4800
gtttcaacct tctaattagg taggcctcta ggtattctgc agatcactgc tggtcttgat    4860
agccattaat atatgtttgt attatgttat ttttcaacta atcgcagtt ggaaaaaaac      4920 atatttaata ttatgcccctt ggatctgtta ctgcatcact agcacttgtg atgcaataga   4980
acacttcgcc tgtactgaaa gggccaagag taaatgcctt gttttgtttt tttgttttgt    5040
tttgttttgc ttttgttaa aacatgtcta tagagttggc agttaatgct gaatttgtca     5100 aataccccctt ccaaaattat acttgtattt aaaaaataaa tggatctacc taatttctat   5160
tg                                                                   5162
```

<210> SEQ ID NO 4
<211> LENGTH: 112
<212> TYPE: PRT
<213> ORGANISM: Homo sapiens

<400> SEQUENCE: 4

```
Met Ser Ala Glu Val Pro Glu Ala Ala Ser Ala Glu Glu Gln Lys Glu
1               5                   10                  15

Met Glu Asp Lys Val Thr Ser Pro Glu Lys Ala Glu Glu Ala Lys Leu
            20                  25                  30

Lys Ala Arg Tyr Pro His Leu Gly Gln Lys Pro Gly Gly Ser Asp Phe
        35                  40                  45

Leu Arg Lys Arg Leu Gln Lys Gly Gln Lys Tyr Phe Asp Ser Gly Asp
    50                  55                  60

Tyr Asn Met Ala Lys Ala Lys Met Lys Asn Lys Gln Leu Pro Thr Ala
65                  70                  75                  80

Ala Pro Asp Lys Thr Glu Val Thr Gly Asp His Ile Pro Thr Pro Gln
                85                  90                  95

Asp Leu Pro Gln Arg Lys Pro Ser Leu Val Ala Ser Lys Leu Ala Gly
            100                 105                 110
```

<210> SEQ ID NO 5
<211> LENGTH: 1073
<212> TYPE: DNA
<213> ORGANISM: Homo sapiens

<400> SEQUENCE: 5

```
ggcgcgggag ttggcattcg gtggtcctgg cagttagctg agcacgccct ctgagccgct      60
cggtggacac caggcactct agtaggcctg gcctacccag aaacagcagg agagagaaga     120
aacaggccag ctgtgagaag ccaaggacac cgagtcagtc atggcaccta aggcggcaaa     180
gggggccaag ccagagccag caccagctcc acctccaccc ggggccaaac ccgaggaaga     240
caagaaggac ggtaaggagc catcggacaa acctcaaaag gcggtgcagg accataagga     300
gccatcggac aaacctcaaa aggcggtgca gcccaagcac gaagtgggca cgaggagggg     360
gtgtcgccgc taccggtggg aattaaaaga cagcaataaa gagttctggc tcttggggca     420
cgctgagatc aagattcgga gtttgggctg cctaatagct gcaatgatac tgttgtcctc     480
actcaccgtg cacccccatct tgaggcttat catcaccatg gagatatcct tcttcagctt     540
cttcatctta ctgtacagct ttgccattca tagatacata cccttcatcc tgtggcccat     600
ttctgacctc ttcaacgacc tgattgcttg tgcgttcctt gtgggagccg tggtctttgc     660
tgtgagaagt cggcgatcca tgaatctcca ctacttactt gctgtgatcc ttattggtgc     720
ggctggagtt tttgctttta tcgatgtgtg tcttcaaaga aaccacttca gaggcaagaa     780
ggccaaaaag catatgctgg ttcctcctcc aggaaaggaa aaaggacccc agcagggcaa     840
gggaccagaa cccgccaagc caccagaacc tggcaagcca ccagggccag caaagggaaa     900
gaaatgactt ggaggaggct cctggtgtct gaaacggcag tgtatttac agcaatatgt     960
ttccactctc ttccttgtct tctttctgga atggttttct tttccatttt cattaccacc    1020
tttgcttgga aagaatgga ttaatggatt ctaaaagcct aaaaaaaaaa aaa            1073
```

<210> SEQ ID NO 6
<211> LENGTH: 248
<212> TYPE: PRT
<213> ORGANISM: Homo sapiens

<400> SEQUENCE: 6

```
Met Ala Pro Lys Ala Ala Lys Gly Ala Lys Pro Glu Pro Ala Pro Ala
1               5                   10                  15

Pro Pro Pro Pro Gly Ala Lys Pro Glu Glu Asp Lys Lys Asp Gly Lys
                20                  25                  30

Glu Pro Ser Asp Lys Pro Gln Lys Ala Val Gln Asp His Lys Glu Pro
            35                  40                  45

Ser Asp Lys Pro Gln Lys Ala Val Gln Pro Lys His Glu Val Gly Thr
        50                  55                  60

Arg Arg Gly Cys Arg Arg Tyr Arg Trp Glu Leu Lys Asp Ser Asn Lys
65                  70                  75                  80

Glu Phe Trp Leu Leu Gly His Ala Glu Ile Lys Ile Arg Ser Leu Gly
                85                  90                  95

Cys Leu Ile Ala Ala Met Ile Leu Leu Ser Ser Leu Thr Val His Pro
            100                 105                 110

Ile Leu Arg Leu Ile Ile Thr Met Glu Ile Ser Phe Phe Ser Phe Phe
        115                 120                 125

Ile Leu Leu Tyr Ser Phe Ala Ile His Arg Tyr Ile Pro Phe Ile Leu
    130                 135                 140

Trp Pro Ile Ser Asp Leu Phe Asn Asp Leu Ile Ala Cys Ala Phe Leu
145                 150                 155                 160

Val Gly Ala Val Val Phe Ala Val Arg Ser Arg Arg Ser Met Asn Leu
                165                 170                 175
```

```
His Tyr Leu Leu Ala Val Ile Leu Ile Gly Ala Ala Gly Val Phe Ala
                180                 185                 190

Phe Ile Asp Val Cys Leu Gln Arg Asn His Phe Arg Gly Lys Lys Ala
            195                 200                 205

Lys Lys His Met Leu Val Pro Pro Gly Lys Glu Lys Gly Pro Gln
210                 215                 220

Gln Gly Lys Gly Pro Glu Pro Ala Lys Pro Pro Glu Pro Gly Lys Pro
225                 230                 235                 240

Pro Gly Pro Ala Lys Gly Lys Lys
                245

<210> SEQ ID NO 7
<211> LENGTH: 2443
<212> TYPE: DNA
<213> ORGANISM: Homo sapiens

<400> SEQUENCE: 7
aaatggcgtg cccgtctctc cgccggcccc ctgcctcgca gtggtttctc ctgcagctcc      60
cctgggctcc gcggccagta gtgcagcccg tggagccgcg gctttgcccg tctcctctgg     120
gtggccccag tgcgcgggct gacactcatt cagccgggga aggtgaggcg agtagaggct     180
ggtgcggaac ttgccgcccc cagcagcgcc ggcgggctaa gcccagggcc gggcagacaa     240
aagaggccgc ccgcgtagga aggcacggcc ggcggcggcg gagcgcagcg atggccgggc     300 gaggggcag cgcgctgctg gctctgtgcg gggcactggc tgcctgcggg tggctcctgg      360
gcgccgaagc ccaggagccc ggggcgcccg cggcgggcat gaggcggcgc cggcggctgc     420
agcaagagga cggcatctcc ttcgagtacc accgctaccc cgagctgcgc gaggcgctcg     480
tgtccgtgtg gctgcagtgc accgccatca gcaggattta cacggtgggg cgcagcttcg     540
agggccggga gctcctggtc atcgagctgt ccgacaaccc tggcgtccat gagcctggtg     600
agcctgaatt taaatacatt gggaatatgc atgggaatga gctgttggac gagaactgc      660 tcattttctt ggcccagtac ctatgcaacg ataccagaa ggggaacgag acaattgtca      720
acctgatcca cagtacccgc attcacatca tgccttccct gaacccagat ggctttgaga     780
aggcagcgtc tcagcctggt gaactcaagg actggtttgt gggtcgaagc aatgcccagg     840
gaatagatct gaaccggaac tttccagacc tggataggag agtgtacgtg aatgagaaag     900
aaggtggtcc aaataatcat ctgttgaaaa atatgaagaa aattgtggat caaaacacaa     960
agcttgctcc tgagaccaag gctgtcattc attggattat ggatattcct tttgtgcttt    1020
ctgccaatct ccatggagga gaccttgtgg ccaattatcc atatgatgag acgcggagtg    1080
gtagtgctca cgaatacagc tcctccccag atgacgccat tttccaaagc ttggcccggg    1140
catactcttc tttcaacccg gccatgtctg accccaatcg gccaccatgt cgcaagaatg    1200
atgatgacag cagctttgta gatggaacca ccaacggtgg tgcttggtac agcgtacctg    1260
gagggatgca agacttcaat taccttagca gcaactgttt tgagatcacc gtggagctta    1320
gctgtgagaa gttcccacct gaagagactc tgaagaccta ctgggaggat aacaaaaact    1380
ccctcattag ctaccttgag cagatacacc gaggagttaa aggatttgtc cgagaccttc    1440
aaggtaaccc aattgcgaat gccaccatct ccgtggaagg aatagaccac gatgttacat    1500
ccgcaaagga tggtgattac tggagattgc ttatacctgg aaactataaa cttcagcct     1560 cagctccagg ctatctggca ataacaaaga aagtggcagt tccttacagc cctgctgctg    1620
gggttgattt tgaactggag tcattttctg aaaggaaaga gaggagaag gaagaattga    1680 tggaatggtg gaaaatgatg tcagaaactt taaatttta aaaaggcttc tagttagctg     1740
```

-continued

```
ctttaaatct atctatataa tgtagtatga tgtaatgtgg tctttttttt agattttgtg    1800
cagttaatac ttaacattga tttattttt aatcatttaa atattaatca actttcctta    1860
aaataaatag cctcttaggt aaaaatataa gaacttgata tatttcattc tcttatatag    1920
tattcatttt cctacctata ttacacaaaa aagtatagaa aagatttaag taattttgcc    1980
atcctaggct taaatgcaat attcctggta ttatttacaa tgcagaattt tttgagtaat    2040
tctagctttc aaaattagt gaagttcttt tactgtaatt ggtgacaatg tcacataatg     2100
aatgctattg aaaaggttaa cagatacagc tcggagttgt gagcactcta ctgcaagact    2160
taaatagttc agtataaatt gtcgtttttt tcttgtgctg actaactata agcatgatct    2220
tgttaatgca tttttgatgg gaagaaaagg tacatgttta caaagaggtt ttatgaaaag    2280
aataaaaatt gacttcttgc ttgtacatat aggagcaata ctattatatt atgtagtccg    2340
ttaacactac ttaaaagttt agggttttct cttggttgta gagtggccca gaattgcatt    2400
ctgaatgaat aaaggttaaa aaaaaatccc cagtgaaaaa aaa                      2443
```

<210> SEQ ID NO 8
<211> LENGTH: 476
<212> TYPE: PRT
<213> ORGANISM: Homo sapiens

<400> SEQUENCE: 8

```
Met Ala Gly Arg Gly Gly Ser Ala Leu Leu Ala Leu Cys Gly Ala Leu
1               5                   10                  15

Ala Ala Cys Gly Trp Leu Leu Gly Ala Glu Ala Gln Glu Pro Gly Ala
            20                  25                  30

Pro Ala Ala Gly Met Arg Arg Arg Arg Leu Gln Gln Glu Asp Gly
        35                  40                  45

Ile Ser Phe Glu Tyr His Arg Tyr Pro Glu Leu Arg Glu Ala Leu Val
    50                  55                  60

Ser Val Trp Leu Gln Cys Thr Ala Ile Ser Arg Ile Tyr Thr Val Gly
65                  70                  75                  80

Arg Ser Phe Glu Gly Arg Glu Leu Leu Val Ile Glu Leu Ser Asp Asn
                85                  90                  95

Pro Gly Val His Glu Pro Gly Glu Pro Glu Phe Lys Tyr Ile Gly Asn
            100                 105                 110

Met His Gly Asn Glu Ala Val Gly Arg Glu Leu Leu Ile Phe Leu Ala
        115                 120                 125

Gln Tyr Leu Cys Asn Glu Tyr Gln Lys Gly Asn Glu Thr Ile Val Asn
    130                 135                 140

Leu Ile His Ser Thr Arg Ile His Ile Met Pro Ser Leu Asn Pro Asp
145                 150                 155                 160

Gly Phe Glu Lys Ala Ala Ser Gln Pro Gly Glu Leu Lys Asp Trp Phe
                165                 170                 175

Val Gly Arg Ser Asn Ala Gln Gly Ile Asp Leu Asn Arg Asn Phe Pro
            180                 185                 190

Asp Leu Asp Arg Ile Val Tyr Val Asn Glu Lys Glu Gly Gly Pro Asn
        195                 200                 205

Asn His Leu Leu Lys Asn Met Lys Lys Ile Val Asp Gln Asn Thr Lys
    210                 215                 220

Leu Ala Pro Glu Thr Lys Ala Val Ile His Trp Ile Met Asp Ile Pro
225                 230                 235                 240

Phe Val Leu Ser Ala Asn Leu His Gly Gly Asp Leu Val Ala Asn Tyr
                245                 250                 255
```

```
Pro Tyr Asp Glu Thr Arg Ser Gly Ser Ala His Glu Tyr Ser Ser Ser
            260                 265                 270

Pro Asp Asp Ala Ile Phe Gln Ser Leu Ala Arg Ala Tyr Ser Ser Phe
        275                 280                 285

Asn Pro Ala Met Ser Asp Pro Asn Arg Pro Pro Cys Arg Lys Asn Asp
    290                 295                 300

Asp Asp Ser Ser Phe Val Asp Gly Thr Thr Asn Gly Gly Ala Trp Tyr
305                 310                 315                 320

Ser Val Pro Gly Gly Met Gln Asp Phe Asn Tyr Leu Ser Ser Asn Cys
                325                 330                 335

Phe Glu Ile Thr Val Glu Leu Ser Cys Glu Lys Phe Pro Pro Glu Glu
            340                 345                 350

Thr Leu Lys Thr Tyr Trp Glu Asp Asn Lys Asn Ser Leu Ile Ser Tyr
        355                 360                 365

Leu Glu Gln Ile His Arg Gly Val Lys Gly Phe Val Arg Asp Leu Gln
    370                 375                 380

Gly Asn Pro Ile Ala Asn Ala Thr Ile Ser Val Glu Gly Ile Asp His
385                 390                 395                 400

Asp Val Thr Ser Ala Lys Asp Gly Asp Tyr Trp Arg Leu Leu Ile Pro
                405                 410                 415

Gly Asn Tyr Lys Leu Thr Ala Ser Ala Pro Gly Tyr Leu Ala Ile Thr
            420                 425                 430

Lys Lys Val Ala Val Pro Tyr Ser Pro Ala Ala Gly Val Asp Phe Glu
        435                 440                 445

Leu Glu Ser Phe Ser Glu Arg Lys Glu Glu Lys Glu Glu Leu Met
    450                 455                 460

Glu Trp Trp Lys Met Met Ser Glu Thr Leu Asn Phe
465                 470                 475

<210> SEQ ID NO 9
<211> LENGTH: 2368
<212> TYPE: DNA
<213> ORGANISM: Homo sapiens

<400> SEQUENCE: 9
gtttctctcc ctgcccccgc gacttcgcgc aagatccggg aaggacaccc gaggcccctg    60
ggagaccctg gggaggtgaa agtcagagag cgaagcgggc cgtggcccct aggcctgacc   120
cctccccgcg gggtaaggcg ggcacccccgc gagcgcaggg gtcctcttac tgctgatggc   180
acccagctct gggcccagac gccgctcacc gtccaccgcc ggtgctgggt aaaatgtcgg   240
ttccaggacc ttaccaggcg ccactgggc cttcctcagc accatccgca cctccatcct   300
atgaagagac agtggctgtt aacagttatt accccacacc tccagctccc atgcctgggc   360
caactacggg gcttgtgacg gggcctgatg gaagggcat gaatcctcct tcgtattata   420
cccagccagc gcccatcccc aataacaatc caattaccgt gcagacggtc tacgtgcagc   480 acccccatcac cttttggac cgccctatcc aaatgtgttg tccttcctgc aacaagatga   540
tcgtgagtca gctgtcctat aacgccggtg ctctgacctg gctgtcctgc gggagcctgt   600
gcctgctggg gtgcatagcg ggctgctgct tcatccctt ctgcgtggat gccctgcagg   660
acgtggacca ttactgtccc aactgcagag ctctcctggg cacctacaag cgtttgtagg   720
actcagccag acgtggaggg agccgggtgc cgcaggaagt cctttccacc tctcatccag   780
cttcacgcct ggtggaggtt ctgccctggt ggtctcacct ctccaggggg cccaccttca   840
tgtcttcttt tgggggaat acgtcgcaaa actaacaaat ctccaaaccc cagaaattgc   900
```

```
tgcttggagt cgtgcatagg acttgcaaag acattcccct tgagtgtcag ttccacggtt    960
tcctgcctcc ctgagaccct gagtcctgcc atctaactgt gatcattgcc ctatccgaat   1020
atcttcctgt gatctgccat cagtggctct ttttcctgc ttccatgggc ctttctggtg   1080
gcagtctcaa actgagaagc cacagttgcc ttattttga ggctgttctg cccagagctc   1140
ggctgaacca gcctttagtg cctaccatta tcttatccgt tcttcccgt ccctgatgac   1200
aaagatcttg ccttacagac tttacaggct tggctttgag attctgtaac tgcagacttc   1260
attagcacac agattcactt taatttctta attttttttt taaatacaag gaggggcta   1320
ttaacaccca gtacagacat atccacaagg tcgtaaatgc atgctagaaa aatagggctg   1380
gatcttatca ctgccctgtc tccccttgtt tctctgtgcc agatcttcag tgccccttc   1440
catacaggga ttttttctc atagagtaat tatatgaaca gttttatga cctccttttg   1500
gtctgaaata cttttgaaca gaatttcttt tttttaaaaa aaacagaga tggggtctta   1560
ctatgttgcc caggctggtg tcgaactcct gggctcaagc gatccttctg ccttggcctc   1620
ccgaagtgct gggattgcag gcataagcta ccatgctggg cctgaacata atttcaagag   1680
gaggatttat aaaaccattt tctgtaatca aatgattggt gtcatttcc catttgccaa   1740
tgtagtctca cttaaaaaaa aaaaaagaa aagaaatgg ataatttcat ctactgcctt   1800
tacttggggt taatgtgatt cttaaacacc ttcatcatgg aactctcaga gtggggtccg   1860
ttttggtttc ctggtggtgg gttttgaaag ataagggaaa gcacattttg agcatgtctg   1920
ggtaccatgg tgcggatgct tgggaaccag aactgtttca gaggaatcta aagtctgatt   1980
ttagttttca gagacacagc ttgttgtaaa acatgagaag acatgatttc taggactcaa   2040
gcagcaagcc aggattctag gttggctgct gtgtcatctt tgaagtcaag acaaagctgg   2100
gctcgacctt caagggtcct cgttttgata atacttcaga atagggaact catgtgaata   2160
ctactatgta gaaataaaac ctagaccttg agcgaacatc tgtatattgg ttgaaaacga   2220
tagtggtaac cattgatccc ccttcatttg atgtttggaa aattccagta attatcattt   2280
ttgcaacgaa tatggatacc acatagtact tggtgttac ctgctttttga aaaataaagt   2340
ctttggttca cccggtaaaa aaaaaaaa                                      2368
```

<210> SEQ ID NO 10
<211> LENGTH: 161
<212> TYPE: PRT
<213> ORGANISM: Homo sapiens

<400> SEQUENCE: 10

```
Met Ser Val Pro Gly Pro Tyr Gln Ala Ala Thr Gly Pro Ser Ala
1               5                   10                  15

Pro Ser Ala Pro Pro Ser Tyr Glu Glu Thr Val Ala Val Asn Ser Tyr
                20                  25                  30

Tyr Pro Thr Pro Ala Pro Met Pro Gly Pro Thr Thr Gly Leu Val
            35                  40                  45

Thr Gly Pro Asp Gly Lys Gly Met Asn Pro Ser Tyr Tyr Thr Gln
        50                  55                  60

Pro Ala Pro Ile Pro Asn Asn Asn Pro Ile Thr Val Gln Thr Val Tyr
65                  70                  75                  80

Val Gln His Pro Ile Thr Phe Leu Asp Arg Pro Ile Gln Met Cys Cys
                85                  90                  95

Pro Ser Cys Asn Lys Met Ile Val Ser Gln Leu Ser Tyr Asn Ala Gly
                100                 105                 110
```

```
Ala Leu Thr Trp Leu Ser Cys Gly Ser Leu Cys Leu Leu Gly Cys Ile
        115                 120                 125

Ala Gly Cys Cys Phe Ile Pro Phe Cys Val Asp Ala Leu Gln Asp Val
130                 135                 140

Asp His Tyr Cys Pro Asn Cys Arg Ala Leu Leu Gly Thr Tyr Lys Arg
145                 150                 155                 160

Leu

<210> SEQ ID NO 11
<211> LENGTH: 1645
<212> TYPE: DNA
<213> ORGANISM: Homo sapiens

<400> SEQUENCE: 11
gcgggctggc gtgcggcgcc gttgcgggcg ggagcggctg caacgccggt gcctgaggag      60
cgatgccgag ggaaatcatc accctacagt tgggccagtg cggcaatcag attgggttcg     120
agttctggaa acagctgtgc gccgagcatg gtatcagccc cgagggcatc gtggaggagt     180 cgccaccga gggcactgac cgcaaggacg tcttttttcta ccaggcagac gatgagcact     240
acatcccccg gccgtgctg ctggacttgg aaccccgggt gatccactcc atcctcaact     300 cccctatgc caagctctac aacccagaga acatctacct gtcggaacat ggaggaggag     360
ctggcaacaa ctgggccagc ggattctccc agggagaaaa gatccatgag acatttttg     420 acatcatga ccgggaggca gatggtagtg acagtctaga gggctttgtg ctgtgtcact     480
ccattgctgg ggggacaggc tctgactgg gttcctacct cttagaacgg ctgaatgaca     540
ggtatcctaa gaagctggtg cagacatact cagtgtttcc caaccaggac gagatgagcg     600
atgtggtggt ccagccttac aattcactcc tcacactcaa gaggctgacg cagaatgcag     660
actgtgtggt ggtgctggac aacacagccc tgaaccggat tgccacagac cgcctgcaca     720
tccagaaccc atccttctcc cagatcaacc agctggtgtc taccatcatg tcagccagca     780
ccaccaccct gcgctaccct ggctacatga caatgacct catcggcctc atcgcctcgc     840
tcattcccac cccacggctc cacttcctca tgaccggcta caccccctc actacggacc     900 agtcagtggc cagcgtgagg aagaccacgg tcctggatgt catgaggcgg ctgctgcagc     960
ccaagaacgt gatggtgtcc acaggccgag accgccagac caaccactgc tacatcgcca    1020
tcctcaacat catccaggga gaggtggacc ccacccaggt ccacaagagc ttgcagagga    1080
tccgggaacg caagttggcc aacttcatcc cgtggggccc cgccagcatc caggtggccc    1140
tgtcgaggaa gtctccctac ctgccctcgg cccacccggt cagcgggctc atgatggcca    1200
accacaccag catctcctcg ctcttcgaga aacctgtcg ccagtatgac aagctgcgta    1260
agcgggaggc cttcctggag cagttccgca aggaggacat gttcaaggac aactttgatg    1320
agatggacac atccagggag attgtgcagc agctcatcga tgagtaccat gcggccacac    1380
ggccagacta catctcctgg ggcacccagg agcagtgagt cccccaggac agggaccctc    1440
atctgcctta ctggttggcc caagccctgc ctgactgacc accccctcag agcacagatc    1500
agggacctca cgcatctctt tctcatatac atggactctc tgttggcctg caaacacatt    1560
tacttctcct cttatgagac tatttatctt taataaagca ctggatataa aaaaaaaaa     1620 aaaaaaaaaa aaaaaaaaa aaaa                                            1645

<210> SEQ ID NO 12
<211> LENGTH: 451
<212> TYPE: PRT
<213> ORGANISM: Homo sapiens
```

<400> SEQUENCE: 12

```
Met Pro Arg Glu Ile Ile Thr Leu Gln Leu Gly Gln Cys Gly Asn Gln
1               5                   10                  15

Ile Gly Phe Glu Phe Trp Lys Gln Leu Cys Ala Glu His Gly Ile Ser
            20                  25                  30

Pro Glu Gly Ile Val Glu Glu Phe Ala Thr Glu Gly Thr Asp Arg Lys
        35                  40                  45

Asp Val Phe Phe Tyr Gln Ala Asp Glu His Tyr Ile Pro Arg Ala
    50                  55                  60

Val Leu Leu Asp Leu Glu Pro Arg Val Ile His Ser Ile Leu Asn Ser
65                  70                  75                  80

Pro Tyr Ala Lys Leu Tyr Asn Pro Glu Asn Ile Tyr Leu Ser Glu His
                85                  90                  95

Gly Gly Gly Ala Gly Asn Asn Trp Ala Ser Gly Phe Ser Gln Gly Glu
            100                 105                 110

Lys Ile His Glu Asp Ile Phe Asp Ile Ile Asp Arg Glu Ala Asp Gly
            115                 120                 125

Ser Asp Ser Leu Glu Gly Phe Val Leu Cys His Ser Ile Ala Gly Gly
130                 135                 140

Thr Gly Ser Gly Leu Gly Ser Tyr Leu Leu Glu Arg Leu Asn Asp Arg
145                 150                 155                 160

Tyr Pro Lys Lys Leu Val Gln Thr Tyr Ser Val Phe Pro Asn Gln Asp
                165                 170                 175

Glu Met Ser Asp Val Val Gln Pro Tyr Asn Ser Leu Leu Thr Leu
            180                 185                 190

Lys Arg Leu Thr Gln Asn Ala Asp Cys Val Val Leu Asp Asn Thr
            195                 200                 205

Ala Leu Asn Arg Ile Ala Thr Asp Arg Leu His Ile Gln Asn Pro Ser
210                 215                 220

Phe Ser Gln Ile Asn Gln Leu Val Ser Thr Ile Met Ser Ala Ser Thr
225                 230                 235                 240

Thr Thr Leu Arg Tyr Pro Gly Tyr Met Asn Asn Asp Leu Ile Gly Leu
                245                 250                 255

Ile Ala Ser Leu Ile Pro Thr Pro Arg Leu His Phe Leu Met Thr Gly
            260                 265                 270

Tyr Thr Pro Leu Thr Thr Asp Gln Ser Val Ala Ser Val Arg Lys Thr
            275                 280                 285

Thr Val Leu Asp Val Met Arg Arg Leu Leu Gln Pro Lys Asn Val Met
290                 295                 300

Val Ser Thr Gly Arg Asp Arg Gln Thr Asn His Cys Tyr Ile Ala Ile
305                 310                 315                 320

Leu Asn Ile Ile Gln Gly Glu Val Asp Pro Thr Gln Val His Lys Ser
                325                 330                 335

Leu Gln Arg Ile Arg Glu Arg Lys Leu Ala Asn Phe Ile Pro Trp Gly
            340                 345                 350

Pro Ala Ser Ile Gln Val Ala Leu Ser Arg Lys Ser Pro Tyr Leu Pro
        355                 360                 365

Ser Ala His Arg Val Ser Gly Leu Met Met Ala Asn His Thr Ser Ile
370                 375                 380

Ser Ser Leu Phe Glu Arg Thr Cys Arg Gln Tyr Asp Lys Leu Arg Lys
385                 390                 395                 400

Arg Glu Ala Phe Leu Glu Gln Phe Arg Lys Glu Asp Met Phe Lys Asp
                405                 410                 415
```

```
Asn Phe Asp Glu Met Asp Thr Ser Arg Glu Ile Val Gln Gln Leu Ile
            420                 425                 430
Asp Glu Tyr His Ala Ala Thr Arg Pro Asp Tyr Ile Ser Trp Gly Thr
        435                 440                 445
Gln Glu Gln
    450

<210> SEQ ID NO 13
<211> LENGTH: 2687
<212> TYPE: DNA
<213> ORGANISM: Homo sapiens

<400> SEQUENCE: 13
```

| | | | | | |
|---|---|---|---|---|---|
| gatctaaaac | gagaagagat | ctcggggtct | catactgcgc | cattcggctg | cggtacatct     60 |
| cggcactcta | gctgcagccg | ggagaggcct | tgccgccacc | gctgtcgccc | aagcctccac    120 |
| tgccgctgcc | acctcagcgc | cggcctctgc | atccccagct | ccagctccgc | tctgcgccgc    180 |
| tgctgccatc | gccgctgcca | cctccgcagc | ccgggcctcc | gccgccgcca | ctcaagcatc    240 |
| cgtgagtcat | tttctgccca | tctctggtcg | cgcggtctcc | ctggtagagt | ttgtaggctt    300 |
| gcaagatggc | agaagcagat | tttaaaatgg | tctcggaacc | tgtcgcccat | ggggttgccg    360 |
| aagaggagat | ggctagctcg | actagtgatt | ctggggaaga | atctgacagc | agtagctcta    420 |
| gcagcagcac | tagtgacagc | agcagcagca | gcagcactag | tggcagcagc | agcggcagcg    480 |
| gcagcagcag | cagcagcagc | ggcagcacta | gcagccgcag | ccgcttgtat | agaaagaaga    540 |
| gggtacctga | gccttccaga | agggcgcggc | gggccccgtt | gggaacaaat | ttcgtggata    600 |
| ggctgcctca | ggcagttaga | aatcgtgtgc | aagcgcttag | aaacattcaa | gatgaatgtg    660 |
| acaaggtaga | taccctgttc | ttaaaagcaa | ttcatgatct | tgaaagaaaa | tatgctgaac    720 |
| tcaacaagcc | tctgtatgat | aggcggtttc | aaatcatcaa | tgcagaatac | gagcctacag    780 |
| aagaagaatg | tgaatggaat | tcagaggatg | aggagttcag | cagtgatgag | gaggtgcagg    840 |
| ataacacccc | tagtgaaatg | cctcccttag | agggtgagga | agaagaaaac | cctaaagaaa    900 |
| acccagaggt | gaaagctgaa | gagaaggaag | ttcctaaaga | aattcctgag | gtgaaggatg    960 |
| aagaaaagga | agttcctaaa | gaaattcctg | aggtaaaggc | tgaagaaaaa | gcagattcta   1020 |
| aagactgtat | ggaggcaacc | cctgaagtaa | agaagatcc  | taaagaagtc | ccccaggtaa   1080 |
| aggcagatga | taaagaacag | cctaaagcaa | cagaggctaa | ggcaagggct | gcagtaagag   1140 |
| agactcataa | aagagttcct | gaggaaaggc | ttcaggacag | tgtagatctt | aaaagagcta   1200 |
| ggaagggaaa | gcctaaaaga | gaagaccta  | aaggcattcc | tgactattgg | ctgattgttt   1260 |
| taaagaatgt | tgacaagctc | gggcctatga | ttcagaagta | tgatgagccc | attctgaagt   1320 |
| tcttgtcgga | tgttagcctg | aagttctcaa | aacctggcca | gcctgtaagt | tacacctttg   1380 |
| aatttcattt | tctacccaac | ccatacttca | gaaatgaggt | gctggtgaag | acatatataa   1440 |
| taaaggcaaa | accagatcac | aatgatccct | tcttttcttg | gggatgggaa | attgaagatt   1500 |
| gcaaaggctg | caagatagac | tggagaagag | gaaaagatgt | tactgtgaca | actacccaga   1560 |
| gtcgcacaac | tgctactgga | gaaattgaaa | tccagccaag | agtggttcct | aatgcatcat   1620 |
| tcttcaactt | ctttagtcct | cctgagattc | ctatgattgg | gaagctggaa | ccacgagaag   1680 |
| atgctatcct | ggatgaggac | tttgaaattg | gcagattttt | acatgataat | gtcatcctga   1740 |
| aatcaatcta | ttactatact | ggagaagtca | atggtaccta | ctatcaattt | ggcaaacatt   1800 |
| atggaaacaa | gaaatacaga | aaataagtca | atctgaaaga | ttttcaaga  | atcttaaaat   1860 |

```
ctcaagaagt gaagcagatt catacagcct tgaaaaaagt aaaaccctga cctgtaacct      1920
gaacactatt attccttata gtcaagtttt tgtggtttct tggtagtcta tattttaaaa      1980
atagtcctaa aaagtgtcta agtgccagtt tattctatct aggctgttgt agtataatat      2040
tcttcaaaat atgtaagctg ttgtcaatta tctaaagcat gttagtttgg tgctacacag      2100
tgttgatttt tgtgatgtcc tttggtcatg tttctgttag actgtagctg tgaaactgtc      2160
agaattgtta actgaaacaa atatttgctt gaaaaaaaaa gttcatgaag taccaatgca      2220
agtgttttat tttttctttt tttccagccc ataagactaa gggtttaaat ctgcttgcac      2280
tagctgtgcc ttcattagtt tgctatagaa atccagtact tatagtaaat aaaacagtgt      2340
attttgaagt ttgactgctt gaaaaagatt agcatacatc taatgtgaaa agaccacatt      2400
tgattcaact gagaccttgt gtatgtgaca tatagtggcc tataaattta atcataatga      2460
tgttattgtt taccactgag gtgttaatat aacatagtat ttttgaaaaa gtttcttcat      2520
cttatattgt gtaattgtaa actaaagata ccgtgttttc tttgtattgt gttctacctt      2580 cccttttcact gaaaatgatc acttcatttg atactgtttt tcatgttctt gtattgcaac      2640
ctaaaataaa taatattaa agtgtgttat actataaaaa aaaaaaa              2687

<210> SEQ ID NO 14
<211> LENGTH: 506
<212> TYPE: PRT
<213> ORGANISM: Homo sapiens

<400> SEQUENCE: 14

Met Ala Glu Ala Asp Phe Lys Met Val Ser Glu Pro Val Ala His Gly
1               5                   10                  15

Val Ala Glu Glu Glu Met Ala Ser Ser Thr Ser Asp Ser Gly Glu Glu
            20                  25                  30

Ser Asp Ser Ser Ser Ser Ser Ser Thr Ser Asp Ser Ser Ser Ser
        35                  40                  45

Ser Ser Thr Ser Gly Ser Ser Ser Gly Ser Gly Ser Ser Ser Ser Ser
    50                  55                  60

Ser Gly Ser Thr Ser Ser Arg Ser Arg Leu Tyr Arg Lys Lys Arg Val
65                  70                  75                  80

Pro Glu Pro Ser Arg Arg Ala Arg Arg Ala Pro Leu Gly Thr Asn Phe
                85                  90                  95

Val Asp Arg Leu Pro Gln Ala Val Arg Asn Arg Val Gln Ala Leu Arg
            100                 105                 110

Asn Ile Gln Asp Glu Cys Asp Lys Val Asp Thr Leu Phe Leu Lys Ala
        115                 120                 125

Ile His Asp Leu Glu Arg Lys Tyr Ala Glu Leu Asn Lys Pro Leu Tyr
    130                 135                 140

Asp Arg Arg Phe Gln Ile Ile Asn Ala Glu Tyr Glu Pro Thr Glu Glu
145                 150                 155                 160

Glu Cys Glu Trp Asn Ser Glu Asp Glu Phe Ser Asp Glu Glu
                165                 170                 175

Val Gln Asp Asn Thr Pro Ser Glu Met Pro Leu Glu Gly Glu Glu
            180                 185                 190

Glu Glu Asn Pro Lys Glu Asn Pro Glu Val Lys Ala Glu Lys Glu
        195                 200                 205

Val Pro Lys Glu Ile Pro Glu Val Lys Asp Glu Lys Glu Val Pro
    210                 215                 220

Lys Glu Ile Pro Glu Val Lys Ala Glu Glu Lys Ala Asp Ser Lys Asp
225                 230                 235                 240
```

Cys Met Glu Ala Thr Pro Glu Val Lys Glu Asp Pro Lys Glu Val Pro
            245                 250                 255

Gln Val Lys Ala Asp Asp Lys Glu Gln Pro Lys Ala Thr Glu Ala Lys
            260                 265                 270

Ala Arg Ala Ala Val Arg Glu Thr His Lys Arg Val Pro Glu Glu Arg
            275                 280                 285

Leu Gln Asp Ser Val Asp Leu Lys Arg Ala Arg Lys Gly Lys Pro Lys
            290                 295                 300

Arg Glu Asp Pro Lys Gly Ile Pro Asp Tyr Trp Leu Ile Val Leu Lys
305                 310                 315                 320

Asn Val Asp Lys Leu Gly Pro Met Ile Gln Lys Tyr Asp Glu Pro Ile
                325                 330                 335

Leu Lys Phe Leu Ser Asp Val Ser Leu Lys Phe Ser Lys Ser Pro Gly Gln
            340                 345                 350

Pro Val Ser Tyr Thr Phe Glu Phe His Phe Leu Pro Asn Pro Tyr Phe
            355                 360                 365

Arg Asn Glu Val Leu Val Lys Thr Tyr Ile Ile Lys Ala Lys Pro Asp
            370                 375                 380

His Asn Asp Pro Phe Phe Ser Trp Gly Trp Glu Ile Glu Asp Cys Lys
385                 390                 395                 400

Gly Cys Lys Ile Asp Trp Arg Arg Gly Lys Asp Val Thr Val Thr Thr
                405                 410                 415

Thr Gln Ser Arg Thr Thr Ala Thr Gly Glu Ile Glu Ile Gln Pro Arg
            420                 425                 430

Val Val Pro Asn Ala Ser Phe Phe Asn Phe Phe Ser Pro Pro Glu Ile
            435                 440                 445

Pro Met Ile Gly Lys Leu Glu Pro Arg Glu Asp Ala Ile Leu Asp Glu
            450                 455                 460

Asp Phe Glu Ile Gly Gln Ile Leu His Asp Asn Val Ile Leu Lys Ser
465                 470                 475                 480

Ile Tyr Tyr Tyr Thr Gly Glu Val Asn Gly Thr Tyr Gln Phe Gly
                485                 490                 495

Lys His Tyr Gly Asn Lys Lys Tyr Arg Lys
500                 505

<210> SEQ ID NO 15
<211> LENGTH: 2423
<212> TYPE: DNA
<213> ORGANISM: Homo sapiens

<400> SEQUENCE: 15

```
acccgcgctc gtacgtgcgc ctccgccggc agctcctgac tcatcggggg ctccgggtca      60
catgcgcccg cgcggcccta ggcgcctcc ctccgcccgc cgcccgggag ccgcagccgc     120
cgccgccact gccactcccg ctctctcagc gccgccgtcg ccaccgccac cgccaccgcc     180
actaccaccg tctgagtctg cagtcccgag atcccagcca tcatgtccat agagaagatc     240
tgggcccggg agatcctgga ctcccgcggg aaccccacag tggaggtgga tctctatact     300
gccaaaggtc ttttccgggc tgcagtgccc agtggagcct acgggcat ctatgaggcc      360 ctggagctga gggatggaga caaacagcgt tacttaggca aaggtgtcct gaaggcagtg     420
gaccacatca actccaccat cgcgccagcc ctcatcagct caggtctctc tgtggtggag     480
caagagaaac tggacaacct gatgctggag ttggatggga ctgagaacaa atccaagttt     540
ggggccaatg ccatcctggg tgtgtctctg gccgtgtgta aggcaggggc agctgagcgg     600
```

```
gaactgcccc tgtatcgcca cattgctcag ctggccggga actcagacct catcctgcct    660
gtgccggcct tcaacgtgat caatggtggc tctcatgctg caacaagct  ggccatgcag    720
gagttcatga tcctcccagt gggagctgag agctttcggg atgccatgcg actaggtgca    780
gaggtctacc atacactcaa gggagtcatc aaggacaaat acggcaagga tgccaccaat    840
gtggggatg  aaggtggctt tgcccccaat atcctggaga acagtgaagc cttggagctg    900
gtgaaggaag ccatcgacaa ggctggctac acggaaaaga tcgttattgg catggatgtt    960
gctgcctcag agttttatcg tgatggcaaa tatgacttgg acttcaagtc tcccactgat   1020
ccttcccgat acatcactgg ggaccagctg ggggcactct accaggactt tgtcagggac   1080
tatcctgtgg tctccattga ggacccattt gaccaggatg attgggctgc ctggtccaag   1140
ttcacagcca atgagggat  ccagattgtg ggtgatgacc tgacagtgac caacccaaaa   1200
cgtattgagc gggcagtgga agaaaaggcc tgcaactgtc tgctgctcaa ggtcaaccag   1260
atcggctcgg tcactgaagc catccaagcg tgcaagctgg cccaggagaa tggctggggg   1320
gtcatggtga gtcatcgctc aggagagact gaggacacat tcattgctga cctggtggtg   1380
gggctgtgca caggccagat caagactggt gccccgtgcc gttctgaacg tctggctaaa   1440
tacaaccagc tcatgagaat tgaggaagag ctggggatg  aagctcgctt tgccggacat   1500
aacttccgta atcccagtgt gctgtgattc tctgcttgc ctggagacgt ggaacctctg   1560
tctcatcctc ctggaacctt gctgtcctga tctgtgatag ttcacccct  gagatcccct   1620
gagcccagg  gtgcccagaa cttccctgat tgacctgctc cgctgctcct ggcttacct    1680
gacctcttgc tgtctctgct cgccctcctt tctgtgccct actcattggg gttccgcact   1740
ttccacttct tcctttctct ttctctcttc cctcagaaac tagaaatgtg aatgaggatt   1800
attataaaag ggggtccgtg aagaatgat  cagcatctgt gatgggagcg tcagggttgg   1860
tgtgctgagg tgttagagag ggaccatgtg tcacttgtgc tttgctcttg tcccacgtgt   1920
cttccacttt gcatatgagc cgtgaactgt gcatagtgct gggatggagg ggagtgttgg   1980
gcatgtgatc acgcctggct aataaggctt tagtgtattt atttatttat ttatttttatt  2040
tgtttttcat tcatcccatt aatcatttcc ccataactca atggcctaaa actggcctga   2100
cttgggggaa cgatgtgtct gtatttcatg tggctgtaga tcccaagatg actggggtgg   2160
gaggtcttgc tagaatggga agggtcatag aaagggcctt gacatcagtt cctttgtgtg   2220
tactcactga agcctgcgtt ggtccagagc ggaggctgtg tgcctggggg agttttcctc   2280
tatacatctc tccccaaccc taggttccct gttcttcctc cagctgcacc agagcaacct   2340
ctcactcccc atgccacgtt ccacagttgc caccacctct gtggcattga aatgagcacc   2400
tccattaaag tctgaatcag tgc                                            2423
```

<210> SEQ ID NO 16
<211> LENGTH: 434
<212> TYPE: PRT
<213> ORGANISM: Homo sapiens

<400> SEQUENCE: 16

Met Ser Ile Glu Lys Ile Trp Ala Arg Glu Ile Leu Asp Ser Arg Gly
1               5                   10                  15

Asn Pro Thr Val Glu Val Asp Leu Tyr Thr Ala Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Gln Arg Tyr Leu Gly Lys Gly Val Leu Lys 50                  55                  60
Ala Val Asp His Ile Asn Ser Thr Ile Ala Pro Ala Leu Ile Ser Ser
 65                  70                  75                  80

Gly Leu Ser Val Val Glu Gln Glu Lys Leu Asp Asn Leu Met Leu Glu
                 85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Arg Glu Leu
        115                 120                 125

Pro Leu Tyr Arg His Ile Ala Gln Leu Ala Gly Asn Ser Asp Leu Ile
130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
        195                 200                 205

Asp Glu Gly Gly Phe Ala Pro Asn Ile Leu Glu Asn Ser Glu Ala Leu
210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Thr Asp Pro Ser Arg Tyr Ile Thr
            260                 265                 270

Gly Asp Gln Leu Gly Ala Leu Tyr Gln Asp Phe Val Arg Asp Tyr Pro
        275                 280                 285

Val Val Ser Ile Glu Asp Pro Phe Asp Gln Asp Trp Ala Ala Trp
290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
            340                 345                 350

Ala Ile Gln Ala Cys Lys Leu Ala Gln Glu Asn Gly Trp Gly Val Met
        355                 360                 365

Val Ser His Arg Ser Gly Glu Thr Glu Asp Thr Phe Ile Ala Asp Leu
370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Glu Ala Arg Phe Ala Gly His Asn Phe Arg Asn Pro Ser
            420                 425                 430

Val Leu

<210> SEQ ID NO 17
<211> LENGTH: 2142
<212> TYPE: DNA
<213> ORGANISM: Homo sapiens

<400> SEQUENCE: 17

```
atggcgaagt ccccggagaa ctctaccctg gaggagattc tggggcagta tcaacggagt    60
ctccgggaac atgccagcag aagcattcac caactgacat gtgccctgaa agaaggcgat   120
gtcactattg gagaagatgc accaaatctt tcttttagca ccagtgtggg aaatgaggac   180
gccaggacag cctggcccga attacaacag agccatgctg ttaatcagct caaagatttg   240
ttgcgccaac aagcagataa ggaaagtgaa gtatctccgt caagaagaag aaaaatgtcc   300
cccttgaggt cattagaaca tgaggaaacc aatatgccta ctatgcacga ccttgttcat   360
actattaatg accagtctca atatattcat catttagagg cagaagttaa gttctgcaag   420
gaggaactct ctggaatgaa aaataaaata caagtagttg tgcttgaaaa cgaagggctc   480
cagcaacagc taaaatctca aagacaagag gagacactga gggaacaaac acttctggat   540
gcatccggaa acatgcacaa ttcttggatt acaacaggtg aagattctgg ggtgggcgaa   600
acctccaaaa gaccattttc ccatgacaat gcagattttg gcaaagctgc atctgctggt   660
gagcagctag aactggagaa gctaaaactt acttatgagg aaaagtgtga aattgaggaa   720
tcccaattga gttttttgag gaacgactta gctgaatatc agagaacttg tgaagatctt   780
aaagagcaac taaagcataa agaatttctt ctggctgcta atacttgtaa ccgtgttggt   840
ggtctttgtt tgaaatgtgc tcagcatgaa gctgttcttt cccaacccca tactaatgtt   900
catatgcaga ccatcgaaag actggttaaa gaaagagatg acttgatgtc tgcactagtt   960
tccgtaagga gcagcttggc agatacgcag caaagagaag caagtgctta tgaacaggtg  1020
aaacaagttt tgcaaatatc tgaggaagcc aattttgaaa aaaccaaggc tttaatccag  1080
tgtgaccagt tgaggaagga gctggagagg caggcggagc gacttgaaaa agaacttgca  1140
tctcagcaag agaaaagggc cattgagaaa gacatgatga aaaaggaaat aacgaaagaa  1200
agggagtaca tgggatcaaa gatgttgatc ttgtctcaga atattgccca actggaggcc  1260
caggtggaaa aggttacaaa ggaaaagatt tcagctatta tcaactggag gaaaattcaa  1320
agccagctgg cttctcggga aatggatgtc acaaggtgt gtggagaaat gcgctatcag  1380
ctgaataaaa ccaacatgga gaaggatgag gcagaaaagg agcacagaga gttcagagca  1440
aaaactaaca gggatcttga aattaaagat caggaaatag agaaattgag aatagaactg  1500
gatgaaagca acaacacttt ggaacaggag cagcagaagg cagccctggc cagagaggag  1560
tgcctgagac taacagaact gctgggcgaa tctgagcacc aactgcacct caccagacag  1620
gaaaaagata gcattcagca gagctttagc aaggaagcaa aggcccaagc ccttcaggcc  1680
cagcaaagag agcaggagct gacacagaag atacagcaaa tggaagccca gcatgacaaa  1740
actgaaaatg aacagtattt gttgctgacc tcccagaata cattttttgac aaagttaaag  1800
gaagaatgct gtacattagc caagaaactg gaacaaatct ctcaaaaaac cagatctgaa  1860
atagctcaac tcagtcaaga aaaaaggtat acatatgata aattgggaaa gttacagaga  1920
agaaatgaag aattggagga acagtgtgtc cagcatggga gagtacatga gacgatgaag  1980
caaaggctaa ggcagctgga taagcacagc caggccacag cccagcagct ggtgcagctc  2040
ctcagcaagc agaaccagct tctcctggag aggcagagcc tgtcggaaga ggtggaccgg  2100
ctgcggaccc agttacccag catgccacaa tctgattgct ga                     2142
```

<210> SEQ ID NO 18
<211> LENGTH: 713
<212> TYPE: PRT
<213> ORGANISM: Homo sapiens

<400> SEQUENCE: 18

-continued

```
Met Ala Lys Ser Pro Glu Asn Ser Thr Leu Glu Glu Ile Leu Gly Gln
1               5                   10                  15

Tyr Gln Arg Ser Leu Arg Glu His Ala Ser Arg Ser Ile His Gln Leu
            20                  25                  30

Thr Cys Ala Leu Lys Glu Gly Asp Val Thr Ile Gly Glu Asp Ala Pro
        35                  40                  45

Asn Leu Ser Phe Ser Thr Ser Val Gly Asn Glu Asp Ala Arg Thr Ala
    50                  55                  60

Trp Pro Glu Leu Gln Gln Ser His Ala Val Asn Gln Leu Lys Asp Leu
65                  70                  75                  80

Leu Arg Gln Gln Ala Asp Lys Glu Ser Glu Val Ser Pro Ser Arg Arg
                85                  90                  95

Arg Lys Met Ser Pro Leu Arg Ser Leu Glu His Glu Glu Thr Asn Met
            100                 105                 110

Pro Thr Met His Asp Leu Val His Thr Ile Asn Asp Gln Ser Gln Tyr
        115                 120                 125

Ile His His Leu Glu Ala Glu Val Lys Phe Cys Lys Glu Glu Leu Ser
    130                 135                 140

Gly Met Lys Asn Lys Ile Gln Val Val Leu Glu Asn Glu Gly Leu
145                 150                 155                 160

Gln Gln Gln Leu Lys Ser Gln Arg Gln Glu Glu Thr Leu Arg Glu Gln
                165                 170                 175

Thr Leu Leu Asp Ala Ser Gly Asn Met His Asn Ser Trp Ile Thr Thr
            180                 185                 190

Gly Glu Asp Ser Gly Val Gly Glu Thr Ser Lys Arg Pro Phe Ser His
        195                 200                 205

Asp Asn Ala Asp Phe Gly Lys Ala Ala Ser Ala Gly Glu Gln Leu Glu
    210                 215                 220

Leu Glu Lys Leu Lys Leu Thr Tyr Glu Glu Lys Cys Glu Ile Glu Glu
225                 230                 235                 240

Ser Gln Leu Lys Phe Leu Arg Asn Asp Leu Ala Glu Tyr Gln Arg Thr
                245                 250                 255

Cys Glu Asp Leu Lys Glu Gln Leu Lys His Lys Glu Phe Leu Leu Ala
            260                 265                 270

Ala Asn Thr Cys Asn Arg Val Gly Gly Leu Cys Leu Lys Cys Ala Gln
        275                 280                 285

His Glu Ala Val Leu Ser Gln Thr His Thr Asn Val His Met Gln Thr
    290                 295                 300

Ile Glu Arg Leu Val Lys Glu Arg Asp Asp Leu Met Ser Ala Leu Val
305                 310                 315                 320

Ser Val Arg Ser Ser Leu Ala Asp Thr Gln Gln Arg Glu Ala Ser Ala
                325                 330                 335

Tyr Glu Gln Val Lys Gln Val Leu Gln Ile Ser Glu Glu Ala Asn Phe
            340                 345                 350

Glu Lys Thr Lys Ala Leu Ile Gln Cys Asp Gln Leu Arg Lys Glu Leu
        355                 360                 365

Glu Arg Gln Ala Glu Arg Leu Glu Lys Glu Leu Ala Ser Gln Gln Glu
    370                 375                 380

Lys Arg Ala Ile Glu Lys Asp Met Met Lys Glu Ile Thr Lys Glu
385                 390                 395                 400

Arg Glu Tyr Met Gly Ser Lys Met Leu Ile Leu Ser Gln Asn Ile Ala
                405                 410                 415

Gln Leu Glu Ala Gln Val Glu Lys Val Thr Lys Glu Lys Ile Ser Ala
```

```
                420              425                430
Ile Asn Gln Leu Glu Glu Ile Gln Ser Gln Leu Ala Ser Arg Glu Met
            435                  440                 445
Asp Val Thr Lys Val Cys Gly Glu Met Arg Tyr Gln Leu Asn Lys Thr
        450                  455                 460
Asn Met Glu Lys Asp Glu Ala Glu Lys Glu His Arg Glu Phe Arg Ala
465                 470                  475                 480
Lys Thr Asn Arg Asp Leu Glu Ile Lys Asp Gln Glu Ile Glu Lys Leu
                485                  490                 495
Arg Ile Glu Leu Asp Glu Ser Lys Gln His Leu Glu Gln Gln Gln
            500                  505                 510
Lys Ala Ala Leu Ala Arg Glu Glu Cys Leu Arg Leu Thr Glu Leu Leu
        515                  520                 525
Gly Glu Ser Glu His Gln Leu His Leu Thr Arg Gln Glu Lys Asp Ser
        530                  535                 540
Ile Gln Gln Ser Phe Ser Lys Glu Ala Lys Ala Gln Ala Leu Gln Ala
545                 550                  555                 560
Gln Gln Arg Glu Gln Glu Leu Thr Gln Lys Ile Gln Gln Met Glu Ala
                565                  570                 575
Gln His Asp Lys Thr Glu Asn Glu Gln Tyr Leu Leu Leu Thr Ser Gln
            580                  585                 590
Asn Thr Phe Leu Thr Lys Leu Lys Glu Glu Cys Cys Thr Leu Ala Lys
        595                  600                 605
Lys Leu Glu Gln Ile Ser Gln Lys Thr Arg Ser Glu Ile Ala Gln Leu
        610                  615                 620
Ser Gln Glu Lys Arg Tyr Thr Tyr Asp Lys Leu Gly Lys Leu Gln Arg
625                 630                  635                 640
Arg Asn Glu Glu Leu Glu Gln Cys Val Gln His Gly Arg Val His
                645                  650                 655
Glu Thr Met Lys Gln Arg Leu Arg Gln Leu Asp Lys His Ser Gln Ala
            660                  665                 670
Thr Ala Gln Gln Leu Val Gln Leu Leu Ser Lys Gln Asn Gln Leu Leu
        675                  680                 685
Leu Glu Arg Gln Ser Leu Ser Glu Glu Val Asp Arg Leu Arg Thr Gln
        690                  695                 700
Leu Pro Ser Met Pro Gln Ser Asp Cys
705                  710

<210> SEQ ID NO 19
<211> LENGTH: 2780
<212> TYPE: DNA
<213> ORGANISM: Homo sapiens

<400> SEQUENCE: 19
gtgggcggac cgcgcggctg gaggtgtgag gatccgaacc caggggtggg gggtggaggc    60
ggctcctgcg atcgaagggg acttgagact caccggccgc acgccatgag ggccctgtgg   120
gtgctgggcc tctgctgcgt cctgctgacc ttcgggtcgg tcagagctga cgatgaagtt   180
gatgtggatg gtacagtaga agaggatctg ggtaaaagta gagaaggatc aaggacggat   240
gatgaagtag tacagagaga ggaagaagct attcagttgg atggattaaa tgcatcacaa   300
ataagagaac ttagagagaa gtcggaaaag ttgccttcc  aagccgaagt taacagaatg   360
atgaaactta tcatcaattc attgtataaa aataaagaga ttttcctgag agaactgatt   420
tcaaatgctt ctgatgcttt agataagata aggctaatat cactgactga tgaaaatgct   480
```

```
ctttctggaa atgaggaact aacagtcaaa attaagtgtg ataaggagaa gaacctgctg    540
catgtcacag acaccggtgt aggaatgacc agagaagagt tggttaaaaa ccttggtacc    600
atagccaaat ctgggacaag cgagttttta aacaaaatga ctgaagcaca ggaagatggc    660
cagtcaactt ctgaattgat tggccagttt ggtgtcggtt tctattccgc cttccttgta    720
gcagataagg ttattgtcac ttcaaaacac aacaacgata cccagcacat ctgggagtct    780
gactccaatg aattttctgt aattgctgac ccaagaggaa acactctagg acggggaacg    840
acaattaccc ttgtcttaaa agaagaagca tctgattacc ttgaattgga tacaattaaa    900
aatctcgtca aaaatattc acagttcata aactttccta tttatgtatg gagcagcaag    960
actgaaactg ttgaggagcc catggaggaa gaagaagcag ccaaagaaga gaaagaagaa   1020
tctgatgatg aagctgcagt agaggaagaa gaagaagaaa agaaaccaaa gactaaaaaa   1080
gttgaaaaaa ctgtctggga ctgggaactt atgaatgata tcaaaccaat atggcagaga   1140
ccatcaaaag aagtagaaga agatgaatac aaagctttct acaaatcatt ttcaaaggaa   1200
agtgatgacc ccatggctta tattcacttt actgctgaag gggaagttac cttcaaatca   1260
attttatttg tacccacatc tgctccacgt ggtctgtttg acgaatatgg atctaaaaag   1320
agcgattaca ttaagctcta tgtgcgccgt gtattcatca cagacgactt ccatgatatg   1380
atgcctaaat acctcaattt tgtcaagggt gtggtggact cagatgatct ccccttgaat   1440
gtttcccgcg agactcttca gcaacataaa ctgcttaagg tgattaggaa gaagcttgtt   1500
cgtaaaacgc tggacatgat caagaagatt gctgatgata aatacaatga tacttttgg   1560 aaagaatttg gtaccaacat caagcttggt gtgattgaag accactcgaa tcgaacacgt   1620
cttgctaaac ttcttaggtt ccagtcttct catcatccaa ctgacattac tagcctagac   1680
cagtatgtgg aaagaatgaa ggaaaaacaa gacaaaatct acttcatggc tgggtccagc   1740
agaaaagagg ctgaatcttc tccatttgtt gagcgacttc tgaaaaaggg ctatgaagtt   1800
atttacctca cagaacctgt ggatgaatac tgtattcagg cccttcccga atttgatggg   1860
aagaggttcc agaatgttgc caaggaagga gtgaagttcg atgaaagtga gaaaactaag   1920
gagagtcgtg aagcagttga gaaagaattt gagcctctgc tgaattggat gaaagataaa   1980
gcccttaagg acaagattga aaaggctgtg gtgtctcagc gcctgacaga atctccgtgt   2040
gctttggtgg ccagccagta cggatggtct ggcaacatgg agagaatcat gaaagcacaa   2100
gcgtaccaaa cgggcaagga catctctaca aattactatg cgagtcagaa gaaaacatt    2160 gaaattaatc ccagacaccc gctgatcaga gacatgcttc gacgaattaa ggaagatgaa   2220
gatgataaaa cagttttgga tcttgctgtg gttttgtttg aaacagcaac gcttcggtca   2280
gggtatcttt taccagacac taagcatat ggagatagaa tagaaagaat gcttcgcctc    2340
agtttgaaca ttgaccctga tgcaaaggtg gaagaagagc ccgaagaaga acctgaagag   2400
acagcagaag acacaacaga agacacagag caagacgaag atgaagaaat ggatgtggga   2460
acagatgaag aagaagaaac agcaaaggaa tctacagctg aaaaagatga attgtaaatt   2520
atactctcac catttggatc ctgtgtggag agggaatgtg aaatttacat catttctttt   2580
tgggagagac ttgttttgga tgcccccctaa tccccttctc ccctgcactg taaaatgtgg   2640
gattatgggt cacaggaaaa agtgggtttt ttagttgaat tttttttaac attcctcatg   2700
aatgtaaatt tgtactattt aactgactat tcttgatgta aaatcttgtc atgtgtataa   2760
aaataaaaaa gatcccaaat                                                2780
```

<210> SEQ ID NO 20

<211> LENGTH: 803
<212> TYPE: PRT
<213> ORGANISM: Homo sapiens

<400> SEQUENCE: 20

```
Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Ala Ile Gln Leu Asp Gly Leu Asn Ala Ser
50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
            260                 265                 270

Gln Phe Ile Asn Phe Pro Ile Tyr Val Trp Ser Ser Lys Thr Glu Thr
        275                 280                 285

Val Glu Glu Pro Met Glu Glu Glu Ala Ala Lys Glu Glu Lys Glu
290                 295                 300

Glu Ser Asp Asp Glu Ala Ala Val Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
            340                 345                 350

Asp Glu Tyr Lys Ala Phe Tyr Lys Ser Phe Ser Lys Glu Ser Asp Asp
        355                 360                 365

Pro Met Ala Tyr Ile His Phe Thr Ala Glu Gly Glu Val Thr Phe Lys
370                 375                 380

Ser Ile Leu Phe Val Pro Thr Ser Ala Pro Arg Gly Leu Phe Asp Glu
385                 390                 395                 400
```

```
Tyr Gly Ser Lys Lys Ser Asp Tyr Ile Lys Leu Tyr Val Arg Arg Val
                405                 410                 415
Phe Ile Thr Asp Asp Phe His Asp Met Met Pro Lys Tyr Leu Asn Phe
            420                 425                 430
Val Lys Gly Val Val Asp Ser Asp Leu Pro Leu Asn Val Ser Arg
                435                 440                 445
Glu Thr Leu Gln Gln His Lys Leu Leu Lys Val Ile Arg Lys Lys Leu
        450                 455                 460
Val Arg Lys Thr Leu Asp Met Ile Lys Lys Ile Ala Asp Asp Lys Tyr
465                 470                 475                 480
Asn Asp Thr Phe Trp Lys Glu Phe Gly Thr Asn Ile Lys Leu Gly Val
                    485                 490                 495
Ile Glu Asp His Ser Asn Arg Thr Arg Leu Ala Lys Leu Leu Arg Phe
                500                 505                 510
Gln Ser Ser His His Pro Thr Asp Ile Thr Ser Leu Asp Gln Tyr Val
            515                 520                 525
Glu Arg Met Lys Glu Lys Gln Asp Lys Ile Tyr Phe Met Ala Gly Ser
        530                 535                 540
Ser Arg Lys Glu Ala Glu Ser Ser Pro Phe Val Glu Arg Leu Leu Lys
545                 550                 555                 560
Lys Gly Tyr Glu Val Ile Tyr Leu Thr Glu Pro Val Asp Glu Tyr Cys
                    565                 570                 575
Ile Gln Ala Leu Pro Glu Phe Asp Gly Lys Arg Phe Gln Asn Val Ala
                580                 585                 590
Lys Glu Gly Val Lys Phe Asp Glu Ser Glu Lys Thr Lys Glu Ser Arg
            595                 600                 605
Glu Ala Val Glu Lys Glu Phe Glu Pro Leu Leu Asn Trp Met Lys Asp
        610                 615                 620
Lys Ala Leu Lys Asp Lys Ile Glu Lys Ala Val Val Ser Gln Arg Leu
625                 630                 635                 640
Thr Glu Ser Pro Cys Ala Leu Val Ala Ser Gln Tyr Gly Trp Ser Gly
                    645                 650                 655
Asn Met Glu Arg Ile Met Lys Ala Gln Ala Tyr Gln Thr Gly Lys Asp
                660                 665                 670
Ile Ser Thr Asn Tyr Tyr Ala Ser Gln Lys Lys Thr Phe Glu Ile Asn
            675                 680                 685
Pro Arg His Pro Leu Ile Arg Asp Met Leu Arg Arg Ile Lys Glu Asp
        690                 695                 700
Glu Asp Asp Lys Thr Val Leu Asp Leu Ala Val Val Leu Phe Glu Thr
705                 710                 715                 720
Ala Thr Leu Arg Ser Gly Tyr Leu Leu Pro Asp Thr Lys Ala Tyr Gly
                    725                 730                 735
Asp Arg Ile Glu Arg Met Leu Arg Leu Ser Leu Asn Ile Asp Pro Asp
                740                 745                 750
Ala Lys Val Glu Glu Glu Pro Glu Glu Glu Pro Glu Glu Thr Ala Glu
            755                 760                 765
Asp Thr Thr Glu Asp Thr Glu Gln Asp Glu Glu Glu Met Asp Val
        770                 775                 780
Gly Thr Asp Glu Glu Glu Glu Thr Ala Lys Glu Ser Thr Ala Glu Lys
785                 790                 795                 800
Asp Glu Leu

<210> SEQ ID NO 21
```

```
<211> LENGTH: 1060
<212> TYPE: DNA
<213> ORGANISM: Homo sapiens

<400> SEQUENCE: 21
cgcgggccga ctggtgttta tccgtcactc gccgaggttc cttgggtcat ggtgccagcc    60
tgactgagaa gaggacgctc ccgggagacg aatgaggaac cacctcctcc tactgttcaa   120
gtacaggggc ctggtccgca aagggaagaa aagcaaaaga cgaaaatggc taaattcgtg   180
atccgcccag ccactgccgc cgactgcagt gacatactgc ggctgatcaa ggagctggct   240
aaatatgaat acatggaaga caagtaatc ttaactgaaa agatctgct agaagatggt   300
tttggagagc acccctttta ccactgcctg gttgcagaag tgccgaaaga gcactggact   360
ccggaaggac acagcattgt tggttttgcc atgtactatt ttacctatga cccgtggatt   420
ggcaagttat tgtatcttga ggacttcttc gtgatgagtg attatagagg ctttggcata   480
ggatcagaaa ttctgaagaa tctaagccag gttgcaatga ggtgtcgctg cagcagcatg   540
cacttcttgg tagcagaatg gaatgaacca tccatcaact tctataaaag aagaggtgct   600
tctgatctgt ccagtgaaga gggttggaga ctgttcaaga tcgacaagga gtacttgcta   660
aaaatggcaa cagaggagtg aggagtgctg ctgtagatga caacctccat tctatttag   720
aataaattcc caacttctct tgctttctat gctgtttgta gtgaaataat agaatgagca   780
cccattccaa agctttatta ccagtggcgt tgttgcatgt ttgaaatgag gtctgtttaa   840
agtggcaatc tcagatgcag tttggagagt cagatctttc tccttgaata tctttcgata   900
aacaacaagg tggtgtgatc ttaatatatt tgaaaaaaac ttcattctcg tgagtcattt   960
aaatgtgtac aatgtacaca ctggtactta gagtttctgt ttgattcttt tttaataaac  1020
tactctttga tttaaaaaaa aaaaaaaaaa aaaaaaaaa                         1060

<210> SEQ ID NO 22
<211> LENGTH: 171
<212> TYPE: PRT
<213> ORGANISM: Homo sapiens

<400> SEQUENCE: 22

Met Ala Lys Phe Val Ile Arg Pro Ala Thr Ala Ala Asp Cys Ser Asp
1               5                   10                  15

Ile Leu Arg Leu Ile Lys Glu Leu Ala Lys Tyr Glu Tyr Met Glu Glu
            20                  25                  30

Gln Val Ile Leu Thr Glu Lys Asp Leu Leu Glu Asp Gly Phe Gly Glu
        35                  40                  45

His Pro Phe Tyr His Cys Leu Val Ala Glu Val Pro Lys Glu His Trp
    50                  55                  60

Thr Pro Glu Gly His Ser Ile Val Gly Phe Ala Met Tyr Tyr Phe Thr
65                  70                  75                  80

Tyr Asp Pro Trp Ile Gly Lys Leu Leu Tyr Leu Glu Asp Phe Phe Val
                85                  90                  95

Met Ser Asp Tyr Arg Gly Phe Gly Ile Gly Ser Glu Ile Leu Lys Asn
            100                 105                 110

Leu Ser Gln Val Ala Met Arg Cys Arg Cys Ser Ser Met His Phe Leu
        115                 120                 125

Val Ala Glu Trp Asn Glu Pro Ser Ile Asn Phe Tyr Lys Arg Arg Gly
    130                 135                 140

Ala Ser Asp Leu Ser Ser Glu Glu Gly Trp Arg Leu Phe Lys Ile Asp
145                 150                 155                 160
```

Lys Glu Tyr Leu Leu Lys Met Ala Thr Glu Glu
            165                 170

<210> SEQ ID NO 23
<211> LENGTH: 1006
<212> TYPE: DNA
<213> ORGANISM: Homo sapiens

<400> SEQUENCE: 23
cagccgcacg tgggctcggc gcgatggagg aggagacgca tactgacgcc aaaatccgtg      60
ctgaaaatgg aacagggtcc agccctcggg gtcctggctg cagcctccgg cactttgcct     120
gcgaacagaa cctgctgtcg cggccagatg gctctgcttc cttcctgcaa ggtgacacct     180
ctgtcctggc gggtgtgtac gggccggccg aggtgaaggt cagcaaagag attttcaaca     240
aggccacact cgaagtgatc ctgaggccga agattgggct gcctggtgtt gcagagaaga     300
gccgggagcg gctgatcagg aacacgtgcg aggcggtggt gctgggcacg ttgcaccccc     360
gcacctccat caccgtggtg ctgcaggttg tcagcgatgc cggctctctc ctggcctgtt     420
gtctgaatgc cgcctgcatg gcattggtgg atgcaggtgt gcccatgcgg gctctcttct     480
gtggggtcgc ctgcgccctg gactctgatg ggaccctcgt gctggatcct acatccaagc     540
aagaaaagga ggcccgggca gtcctgacct ttgccctgga cagcgtggaa cggaagctgc     600
tgatgtccag caccaagggg ctctactcag acactgagct ccagcagtgc ctggctgcgg     660
cccaggccgc ttcgcaacac gtcttccgtt ctaccgggga atcgctgcag aggcgttact     720
ccaagagctg aggcaagctg gggcaagggg ccgctcccat gcctccacc cactcacccc     780
ctacagcctg aagcaaacca gcagcccagc cttgcctctc tgacccatgg gctccttgag     840
cctgcagctc tgtaaccaca gggctcctgt ggggaggcct tggcctgtga cagccccag     900
gcctggggc acagatcccc ccagcaagga taacattcaa aggagctcac atttatggaa     960
tggatgaatc aataaattaa ttcactttaa caaaaaaaaa aaaaaa                    1006

<210> SEQ ID NO 24
<211> LENGTH: 235
<212> TYPE: PRT
<213> ORGANISM: Homo sapiens

<400> SEQUENCE: 24

Met Glu Glu Glu Thr His Thr Asp Ala Lys Ile Arg Ala Glu Asn Gly
1               5                   10                  15

Thr Gly Ser Ser Pro Arg Gly Pro Gly Cys Ser Leu Arg His Phe Ala
            20                  25                  30

Cys Glu Gln Asn Leu Leu Ser Arg Pro Asp Gly Ser Ala Ser Phe Leu
        35                  40                  45

Gln Gly Asp Thr Ser Val Leu Ala Gly Val Tyr Gly Pro Ala Glu Val
    50                  55                  60

Lys Val Ser Lys Glu Ile Phe Asn Lys Ala Thr Leu Glu Val Ile Leu
65                  70                  75                  80

Arg Pro Lys Ile Gly Leu Pro Gly Val Ala Glu Lys Ser Arg Glu Arg
                85                  90                  95

Leu Ile Arg Asn Thr Cys Glu Ala Val Val Leu Gly Thr Leu His Pro
            100                 105                 110

Arg Thr Ser Ile Thr Val Val Leu Gln Val Val Ser Asp Ala Gly Ser
        115                 120                 125

Leu Leu Ala Cys Cys Leu Asn Ala Ala Cys Met Ala Leu Val Asp Ala
    130                 135                 140

```
Gly Val Pro Met Arg Ala Leu Phe Cys Gly Val Ala Cys Ala Leu Asp
145                 150                 155                 160

Ser Asp Gly Thr Leu Val Leu Asp Pro Thr Ser Lys Gln Glu Lys Glu
            165                 170                 175

Ala Arg Ala Val Leu Thr Phe Ala Leu Asp Ser Val Glu Arg Lys Leu
        180                 185                 190

Leu Met Ser Ser Thr Lys Gly Leu Tyr Ser Asp Thr Glu Leu Gln Gln
    195                 200                 205

Cys Leu Ala Ala Ala Gln Ala Ala Ser Gln His Val Phe Arg Phe Tyr
210                 215                 220

Arg Glu Ser Leu Gln Arg Arg Tyr Ser Lys Ser
225                 230                 235
```

```
<210> SEQ ID NO 25
<211> LENGTH: 315
<212> TYPE: DNA
<213> ORGANISM: Homo sapiens

<400> SEQUENCE: 25
gctctctata aaaattattt gtgttctata tagtgagttt taccagtaaa tgtggcttaa      60
tattttaatt cttagaatgt gtcttctcta cgtgatgtga ctaaattctg ttttgtttgt     120
ggaatgacta gcacaggccg actccctctc tccctcactt aacaaaagac caatgagctg     180
ttaatcgagc tgttatctcc atggtattac ttgctaaatg cactgatttc ataagtatgt     240
ggaatccttt ccttttgaa tctgtatatc atatataaga ctgaatctac ttaataaaca      300
ctgaacaaca aaccg                                                      315

<210> SEQ ID NO 26
<211> LENGTH: 10
<212> TYPE: PRT
<213> ORGANISM: Homo sapiens

<400> SEQUENCE: 26

Ala Leu Tyr Lys Asn Tyr Leu Cys Ser Ile
1               5                   10

<210> SEQ ID NO 27
<211> LENGTH: 1970
<212> TYPE: DNA
<213> ORGANISM: Homo sapiens

<400> SEQUENCE: 27
caaacgcgcc gactacagag gctggacgta agcttagcgg tggcgcgcgt gcgcagcgcc      60
ggcccgagtt gccaaaacaa agggatttg tgatggagg ctttgttaga aggaatacaa       120
aatcgagggc atggtggggg atttttgaca tcttgtgaag cagaactaca ggagctcatg     180
aaacagattg acataatggt ggctcataaa aaatctgaat gggaaggacg tacacatgct     240
ctagaaactt gcttgaaaat ccgtgaacag gaacttaaga gtcttaggag tcagttggat     300
gtgacacata aggaggttgg aatgttgcat cagcaggtag aagaacatga aaaaatcaag     360
caagagatga ccatggaata taagcaggag ttgaagaaac tacatgaaga attatgcata     420
ctgaagagaa gctatgaaaa gcttcagaaa aagcaaatga gggaattcag aggaaatacc     480
aaaaatcaca gggaagatcg gtctgaaatt gagaggttaa ctgcaaaaat agaggaattc     540
cgtcagaaat cgctggactg ggagaagcaa cgcttgattt atcagcaaca ggtatcttca     600
ctggaggcac aaaggaaggc tctggctgaa caatcagaga taattcaggc tcagcttgtc     660
aatcggaaac agaaattaga gtctgtggaa ctttctagcc aatcagaaat tcaacactta     720
```

```
agcagtaaac tggagcgggc taatgacact atctgtgcca atgagttgga aatagagcgc     780
ctcaccatga gggtcaatga cttggttgga accagtatga ctgtcctaca ggagcagcag     840
caaaaagaag aaaaattgag ggaatctgaa aaactattag aggctctgca ggaagaaaag     900
agagaattga aggcagctct tcagtctcaa gaaaatctca tacatgaggc cagaatacaa     960
aaggagaagt acaagaaaaa agtaaaggca actaacactc aacatgctgt agaagctata    1020
aggccacggg aagaatctct ggcagaaaag aagtacacct ctcaagggca ggggdactta    1080
gacagtgtgc tctcccagtt gaattttacc catactagtg aggaccttct gcaggcagag    1140
gtgacttgtc ttgaaggcag tttggaatct gtgagtgcaa cgtgtaaaca gctgagccaa    1200
gaactaatgg aaaatatga agaactgaag aggatggaag cacataacaa tgaatacaaa    1260
gcagagatta agaagttgaa agaacagatt ttacagggtg aacaaagtta cagttctgca    1320
ctagaaggaa tgaagatgga aatctcccat ctaactcagg agttacatca gcgagatatc    1380
actattgctt ccaccaaagg ttcttcctca gacatggaaa agcgactcag agcagagatg    1440
caaaaggcag aagacaaagc agtagagcat aaggagattt tggatcagct ggagtcactc    1500
aaattagaaa atcgtcatct ttctgaaatg gtgatgaaat ggaattggg tttacatgag    1560 tgttccttgc ctgtatctcc ccttggttca atagctacca gattttgga agaggaggaa    1620 ctgaggtctc atcacattct agagcgcttg gatgcccata ttgaagaact aaaaagagag    1680
agtgaaaaga cagtgagaca attcacagcc ttaaagtagc ctcttaaaaa aatcacaatc    1740
ttggaaataa aaataaacac caaagagtta ctgtcatctg aagtagcagc tctttaaaaa    1800
catgaagaga taaaattata aaaatgatac atctaaagca gtggtgaaga aagctgaaaa    1860
actgatactt ttgataggca ttttctctgc actggtttgt ttaaaggact tcttccagca    1920
ataagttgaa agaataaacc actttgctag acaaaaaaaa aaaaaaaaaa                1970
```

<210> SEQ ID NO 28
<211> LENGTH: 541
<212> TYPE: PRT
<213> ORGANISM: Homo sapiens

<400> SEQUENCE: 28

```
Met Glu Ala Leu Leu Glu Gly Ile Gln Asn Arg Gly His Gly Gly Gly
1               5                   10                  15

Phe Leu Thr Ser Cys Glu Ala Glu Leu Gln Glu Leu Met Lys Gln Ile
            20                  25                  30

Asp Ile Met Val Ala His Lys Lys Ser Glu Trp Glu Gly Arg Thr His
        35                  40                  45

Ala Leu Glu Thr Cys Leu Lys Ile Arg Glu Gln Glu Leu Lys Ser Leu
    50                  55                  60

Arg Ser Gln Leu Asp Val Thr His Lys Glu Val Gly Met Leu His Gln
65                  70                  75                  80

Gln Val Glu Glu His Glu Lys Ile Lys Gln Glu Met Thr Met Glu Tyr
                85                  90                  95

Lys Gln Glu Leu Lys Lys Leu His Glu Glu Leu Cys Ile Leu Lys Arg
            100                 105                 110

Ser Tyr Glu Lys Leu Gln Lys Lys Gln Met Arg Glu Phe Arg Gly Asn
        115                 120                 125

Thr Lys Asn His Arg Glu Asp Arg Ser Glu Ile Glu Arg Leu Thr Ala
    130                 135                 140

Lys Ile Glu Glu Phe Arg Gln Ser Leu Asp Trp Glu Lys Gln Arg
145                 150                 155                 160
```

Leu Ile Tyr Gln Gln Gln Val Ser Ser Leu Glu Ala Gln Arg Lys Ala
            165                 170                 175

Leu Ala Glu Gln Ser Glu Ile Ile Gln Ala Gln Leu Val Asn Arg Lys
        180                 185                 190

Gln Lys Leu Glu Ser Val Glu Leu Ser Ser Gln Ser Glu Ile Gln His
            195                 200                 205

Leu Ser Ser Lys Leu Glu Arg Ala Asn Asp Thr Ile Cys Ala Asn Glu
210                 215                 220

Leu Glu Ile Glu Arg Leu Thr Met Arg Val Asn Asp Leu Val Gly Thr
225                 230                 235                 240

Ser Met Thr Val Leu Gln Gln Gln Lys Glu Lys Leu Arg
                245                 250                 255

Glu Ser Glu Lys Leu Leu Glu Ala Leu Gln Glu Lys Arg Glu Leu
            260                 265                 270

Lys Ala Ala Leu Gln Ser Gln Glu Asn Leu Ile His Glu Ala Arg Ile
            275                 280                 285

Gln Lys Glu Lys Leu Gln Glu Lys Val Lys Ala Thr Asn Thr Gln His
            290                 295                 300

Ala Val Glu Ala Ile Arg Pro Arg Glu Glu Ser Leu Ala Glu Lys Lys
305                 310                 315                 320

Tyr Thr Ser Gln Gly Gln Gly Asp Leu Asp Ser Val Leu Ser Gln Leu
                325                 330                 335

Asn Phe Thr His Thr Ser Glu Asp Leu Leu Gln Ala Glu Val Thr Cys
            340                 345                 350

Leu Glu Gly Ser Leu Glu Ser Val Ser Ala Thr Cys Lys Gln Leu Ser
            355                 360                 365

Gln Glu Leu Met Glu Lys Tyr Glu Glu Leu Lys Arg Met Glu Ala His
            370                 375                 380

Asn Asn Glu Tyr Lys Ala Glu Ile Lys Lys Leu Lys Glu Gln Ile Leu
385                 390                 395                 400

Gln Gly Glu Gln Ser Tyr Ser Ala Leu Glu Gly Met Lys Met Glu
                405                 410                 415

Ile Ser His Leu Thr Gln Glu Leu His Gln Arg Asp Ile Thr Ile Ala
            420                 425                 430

Ser Thr Lys Gly Ser Ser Asp Met Glu Lys Arg Leu Arg Ala Glu
                435                 440                 445

Met Gln Lys Ala Glu Asp Lys Ala Val Glu His Lys Glu Ile Leu Asp
450                 455                 460

Gln Leu Glu Ser Leu Lys Leu Glu Asn Arg His Leu Ser Glu Met Val
465                 470                 475                 480

Met Lys Leu Glu Leu Gly Leu His Glu Cys Ser Leu Pro Val Ser Pro
                485                 490                 495

Leu Gly Ser Ile Ala Thr Arg Phe Leu Glu Glu Glu Leu Arg Ser
            500                 505                 510

His His Ile Leu Glu Arg Leu Asp Ala His Ile Glu Glu Leu Lys Arg
            515                 520                 525

Glu Ser Glu Lys Thr Val Arg Gln Phe Thr Ala Leu Lys
530                 535                 540

<210> SEQ ID NO 29
<211> LENGTH: 1733
<212> TYPE: DNA
<213> ORGANISM: Homo sapiens

<400> SEQUENCE: 29

-continued

```
ctccaggtct acccttcact gctctgtgtc ctcagcgtgt gtggcttcgt gacctgaaga     60
tactgggaaa tccatagcta agatgccagg accccctgaa agcctagaca tggggccgtt    120
gacatttagg gatgtggcca tagaattctc tctggaggag tggcaatgcc tggacactgc    180
tcagcaggat ttgtatagga aagtgatgtt agagaactac agaaacctgg tcttcttggc    240
aggtattgct gtctctaagc cagatctggt cacctgtctg gagcaaggaa aagatccctg    300
gaatatgaag ggacacagta cggtagtcaa acccccagta gagacggggt ttcaccgttt    360
tggccaggat ggtctctatc tcctgacctc gtgatccgcc cgcctcagtc tcccaaagtg    420
ctggtattac aggcgtgagc caccatgccc agcctaataa aaattttttt atttctattg    480
tatccaatag cttgttttaa gtgtgtagaa caataactta cacttttatg ttaattttat    540
attttgttaa tttactgact gtattattag tttagacaaa tttcaatgta ctgtggtttt    600
ttatgtgtaa gattatatat tcctcaaaca gcaacttttt acttatttgt cttcagtttc    660
aatggcttta aaaagaattc ttttttcatt attctgccac atgcttccag tgctatgtta    720
aaatagaaac attgacaaag ggcacaatag agtttactat tggtgtctgt gaatttgaaa    780
tggcaaacaa ctccttaagt ttttataagc tgatttcagg aggtaaagat cttcttttct    840
tgtgttcccc agggttttgg gatgccctct gggtttgtag tggagtgggg ttgtaacttg    900
gttgcaaggc tgctggttct acattagggt ccatatttag ttgtcatgtt acaagaggct    960
tgggtagttg tacttcccaa tttttttttt tttttttttt tttttttgag acaggagtct   1020
cgctctgtcg cctggctgga gtgcagtggt gtgatctcag ctcatcaaaa cctttgcctc   1080
cctagttcaa gcgattttcc tacctcagcc tcctgagtag ctgggattac aggtgcccac   1140
cagcacgccc agctaatttt ttgtgtgttt ttagtggaga cggggtttca ccatgttggc   1200
taagctgggt ctcgaactcc tgacctcagg tgatccaccc gccttggcct cctgggtgct   1260
gggattacag acgtgagcca ccacccccgg ccacttgttt cttttaaatg cttattaaaa   1320
gtttctcatc agaatatttt atttataatt atactgcata ttctctgaaa ttttactgcc   1380
aatttttcaa aatacctgct tttgatgagt acagttacag tcaaatactg tagttagaca   1440
aattcttttt taatggtata ttaatgttgc ataccaaatt gtatgagtta aacgtctctt   1500
cctgtgcagt ttcatattag tggtgttttc agtgtaggta tcttaatatc agcttatcgt   1560
ggtttttggt tatgtattat aattttagtc aatttgcaat tctgtctgta tactttatgt   1620
caatgtgagg ttgaattaaa agatagccat atgtctatca caaaaaaaaa aaaaaaaaaa   1680
aaaaaaaaaa aaaaaaaaaa aaaaaaaaaa aaaaaaaaaa aaaaaacctc ggg          1733
```

```

<210> SEQ ID NO 30
<211> LENGTH: 103
<212> TYPE: PRT
<213> ORGANISM: Homo sapiens

<400> SEQUENCE: 30

Met Pro Gly Pro Pro Glu Ser Leu Asp Met Gly Pro Leu Thr Phe Arg
1               5                   10                  15

Asp Val Ala Ile Glu Phe Ser Leu Glu Glu Trp Gln Cys Leu Asp Thr
            20                  25                  30

Ala Gln Gln Asp Leu Tyr Arg Lys Val Met Leu Glu Asn Tyr Arg Asn
        35                  40                  45

Leu Val Phe Leu Ala Gly Ile Ala Val Ser Lys Pro Asp Leu Val Thr
    50                  55                  60

Cys Leu Glu Gln Gly Lys Asp Pro Trp Asn Met Lys Gly His Ser Thr
```

```
                65                  70                  75                  80
Val Val Lys Pro Pro Val Glu Thr Gly Phe His Arg Phe Gly Gln Asp
                        85                  90                  95

Gly Leu Tyr Leu Leu Thr Ser
            100

<210> SEQ ID NO 31
<211> LENGTH: 285
<212> TYPE: DNA
<213> ORGANISM: Homo sapiens

<400> SEQUENCE: 31
cttctgtctc agcctcctga gtagctggga ctacaggcat gcccgtgccc agctaatttt      60 tttttatt  ttagtggaga cggggtttca caatgttggc caggctggtc tcgaactcct     120
tacctcaagt gatctgcctg cctcagcctc ctaaagtgct agcattacca ctgtggctag     180
cgtgagccac tgtgctgggt ctgtagaata tatttggatt attatgatca caaaactagt     240
tttttgttgt tgagaaatgg gctttgaaaa gatccgagga ccaga                     285

<210> SEQ ID NO 32
<211> LENGTH: 50
<212> TYPE: PRT
<213> ORGANISM: Homo sapiens

<400> SEQUENCE: 32

Phe Cys Leu Ser Leu Leu Ser Ser Trp Asp Tyr Arg His Ala Arg Ala
1               5                  10                  15

Gln Leu Ile Phe Phe Leu Phe Leu Val Glu Thr Gly Phe His Asn Val
            20                  25                  30

Gly Gln Ala Gly Leu Glu Leu Leu Thr Ser Ser Asp Leu Pro Ala Ser
        35                  40                  45

Ala Ser
    50

<210> SEQ ID NO 33
<211> LENGTH: 369
<212> TYPE: DNA
<213> ORGANISM: Homo sapiens

<400> SEQUENCE: 33
ttgattgttt aactcttatt ctgaaatgca ctggttactg gcataaagta aattatatta      60
gtaaatatta tgacaaaaat tttcgaatat gtatttatag tgtaaaaatt tttgagcagt     120
tgcctcttat tttctcaact attaaaaata acaaattatt gaagaataat aagacctgtt     180
catatctttt gacatagtaa tcttttatca tagaatctat cataataaaa ttttaaaaat     240
taaaagtatt atttgcatag agctgtttat tgcagcatta ttataactct ggaaaaatta     300
aaaccaacct gaatgatcat tcaggttaac tctacaaaag atattaaaca cctgtgcatc     360
agatacact                                                             369

<210> SEQ ID NO 34
<211> LENGTH: 64
<212> TYPE: PRT
<213> ORGANISM: Homo sapiens

<400> SEQUENCE: 34

Asp Cys Leu Thr Leu Ile Leu Lys Cys Thr Gly Tyr Trp His Lys Val
1               5                  10                  15

Asn Tyr Ile Ser Lys Tyr Tyr Asp Lys Asn Phe Arg Ile Cys Ile Tyr
```

```
                    20                  25                  30
Ser Val Lys Ile Phe Glu Gln Leu Pro Leu Ile Phe Ser Thr Ile Lys
        35                  40                  45

Asn Asn Lys Leu Leu Lys Asn Asn Lys Thr Cys Ser Tyr Leu Leu Thr
    50                  55                  60

<210> SEQ ID NO 35
<211> LENGTH: 799
<212> TYPE: DNA
<213> ORGANISM: Homo sapiens

<400> SEQUENCE: 35
cctctgatca acagcccgga agaaagagat atcttttctc agcaagtagc agttctttc      60 tacagtcaag cctcagttca tcctatttcc aactgtctgg aagaatggtc cacaaaggag    120
ccacgataag atgactgaaa agaaacctcc agtgatcatc cccccacagg gggaaaacaa    180
aattgaacaa ctattcatgc aagaaagcac cttcataaga actaaaaatc aggtggagtc    240
tcactctgtc gcccaagctg gaatgcaggg gcgtgatctt ggctcactgc aagctccacc    300
tcctgggttc acgcggtttt tctgcttcgg catcccgagt agctgggatt acaggatttt    360
ttgctgtttt tccaatgaga agatgagcgg ggagcagagc aggtgacaga gttatcttgg    420
aagtcccact gaaactcagt ctgtactagc ggtctctggg agccctagct ttggaccaga    480
tgtattgccc acaggaggcc tcttgtgcct tgctgctctc agcttgcaga gttgctacct    540
gtgaggtttc atctatgtaa ccagatcacc tttgctagct atgcctcctc ttccccctct    600
cccatcacct gccttgccat taaagcctga tataccacta taacctgttt gtagccatac    660
tttgagcctg cattctttct gtagcctcaa gatggtatgt tagtttccta ttggggggtcg   720 ggctttcttt ctaaaggctc ttatgtataa gaattaaata aatttatgtg ccttttctcc    780
tgttaaaaaa aaaaaaaaa                                                  799

<210> SEQ ID NO 36
<211> LENGTH: 91
<212> TYPE: PRT
<213> ORGANISM: Homo sapiens

<400> SEQUENCE: 36

Met Thr Glu Lys Lys Pro Pro Val Ile Ile Pro Pro Gln Gly Glu Asn
1               5                   10                  15

Lys Ile Glu Gln Leu Phe Met Gln Glu Ser Thr Phe Ile Arg Thr Lys
            20                  25                  30

Asn Gln Val Glu Ser His Ser Val Ala Gln Ala Gly Met Gln Gly Arg
        35                  40                  45

Asp Leu Gly Ser Leu Gln Ala Pro Pro Gly Phe Thr Arg Phe Phe
    50                  55                  60

Cys Phe Gly Ile Pro Ser Ser Trp Asp Tyr Arg Ile Phe Cys Cys Phe
65                  70                  75                  80

Ser Asn Glu Lys Met Ser Gly Glu Gln Ser Arg
                85                  90

<210> SEQ ID NO 37
<211> LENGTH: 3243
<212> TYPE: DNA
<213> ORGANISM: Homo sapiens

<400> SEQUENCE: 37
gttgctgatc tttggatgtt ctggttagtc taagaaggag agtatgaggc gagctccggc      60
```

-continued

```
ccgggtgcgg ccgggcttca ggggcccagg cgccgctgct gccaccgcca tctaacgctg      120
cgccctggag gccggcgcg cggatggtgc cggtgcggct cgggtgttga acgggtgtc       180 ccctcccct cctccctcc cccacgcggt ggtctcccct cccacccggc tcaggcagag       240
ccatgtctcg gggtggctcc tacccacacc tgttgtggga cgtgaggaaa aggtccctcg     300
ggctggagga cccgtcccgg ctgcggagtc gctacctggg aagaagagaa tttatccaaa     360
gattaaaact tgaagcaacc cttaatgtgc atgatggttg tgttaataca atctgttgga     420
atgacactgg agaatatatt ttatctggct cagatgacac caaattagta attagtaatc     480
cttacagcag aaaggttttg acaacaattc gttcagggca ccgagcaaac atatttagtg     540
caaagttctt accttgtaca atgataaac agattgtatc ctgctctgga gatggagtaa     600
tattttatac caacgttgag caagatgcag aaaccaacag acaatgccaa tttacgtgtc     660
attatggaac tacttatgag attatgactg tacccaatga cccttacact tttctctctt     720
gtggtgaaga tggaactgtt aggtggtttg atacacgcat caaaactagc tgcacaaaag     780
aagattgtaa agatgatatt ttaattaact gtcgacgtgc tgccacgtct gttgctattt     840
gcccaccaat accatattac cttgctgttg gttgttctga cagctcagta cgaatatatg     900
atcggcgaat gctgggcaca agagctacag ggaattatgc aggtcgaggg actactggaa     960
tggttgcccg tttattcct tcccatctta ataataagtc ctgcagagtg acatctctgt     1020
gttacagtga agatggtcaa gagattctcg ttagttactc ttcagattac atatatcttt    1080
ttgacccgaa agatgataca gcacgagaac ttaaaactcc ttctgcggaa gagagaagag    1140
aagagttgcg acaaccacca gttaagcgtt tgagacttcg tggtgattgg tcagatactg    1200
gacccagagc aaggccggag agtgaacgag aacgagatgg agagcagagt cccaatgtgt    1260
cattgatgca gagaatgtct gatatgttat caagatggtt tgaagaagca agtgaggttg    1320
cacaaagcaa tagaggacga ggaagatctc gacccagagg tggaacaagt caatcagata    1380
tttcaactct tcctacggtc ccatcaagtc ctgatttgga agtgagtgaa actgcaatgg    1440
aagtagatac tccagctgaa caatttcttc agccttctac atcctctaca atgtcagctc    1500
aggctcattc gacatcatct cccacagaaa gccctcattc tactcctttg ctatcttctc    1560
cagacagtga acaaaggcag tctgttgagg catctggaca ccacacacat catcagtctg    1620
ataacaataa tgaaaagctg agccccaaac cagggacagg tgaaccagtt ttaagtttgc    1680
actacagcac agaaggaaca actacaagca caataaaact gaactttaca gatgaatgga    1740
gcagtatagc atcaagttct agaggaattg ggagccattg caaatctgag ggtcaggagg    1800
aatctttcgt cccacagagc tcagtgcaac caccagaagg agacagtgaa acaaaagctc    1860
ctgaagaatc atcagaggat gtgacaaaat atcaggaagg agtatctgca gaaaacccag    1920
ttgagaacca tatcaatata acacaatcag ataagttcac agccaagcca ttggattcca    1980
actcaggaga agaaatgac ctcaatcttg atcgctcttg tggggttcca gaagaatctg     2040
cttcatctga aaaagccaag gaaccagaaa cttcagatca gactagcact gagagtgcta    2100
ccaatgaaaa taacaccaat cctgagcctc agttccaaac agaagccact gggccttcag    2160
ctcatgaaga aacatccacc agggactctg ctcttcagga cacagatgac agtgatgatg    2220
acccagtcct gatcccaggt gcaaggtatc gagcaggacc tggtgataga cgctctgctg    2280
ttgcccgtat tcaggagttc ttcagacgga gaaaagaaag gaagaaatg gaagaattgg     2340 atactttgaa cattagaagg ccgctagtaa aaatggttta taaggccat cgcaactcca     2400 ggacaatgat aaaagaagcc aatttctggg gtgctaactt tgtaatgagt ggttctgact    2460
```

-continued

```
gtggccacat tttcatctgg gatcggcaca ctgctgagca tttgatgctt ctggaagctg   2520
ataatcatgt ggtaaactgc ctgcagccac atccgtttga cccaatttta gcctcatctg   2580
gcatagatta tgacataaag atctggtcac cattagaaga gtcaaggatt tttaaccgaa   2640
aacttgctga tgaagttata actcgaaacg aactcatgct ggaagaaact agaaacacca   2700
ttacagttcc agcctctttc atgttgagga tgttggcttc acttaatcat atccgagctg   2760
accggttgga gggtgacaga tcagaaggct ctggtcaaga gaatgaaaat gaggatgagg   2820
aataataaac tctttttggc aagcacttaa atgttctgaa atttgtataa gacatttatt   2880 atatttttt ctttacagag ctttagtgca atttttaaggt tatggttttt ggagtttttc   2940
cctttttttg ggataaccta acattggttt ggaatgattg tgtgcatgaa tttgggagat   3000
tgtataaaac aaaactagca gaatgttttt aaaactttt gccgtgtatg aggagtgcta   3060
gaaaatgcaa agtgcaatat tttccctaac cttcaaatgt gggagcttgg atcaatgttg   3120
aagaataatt ttcatcatag tgaaaatgtt ggttcaaata aatttctaca cttgccattt   3180
gcatgtttgt tgctttctaa ttaaagaaac tggttgtttt aagatacct gaaaaaaaaa   3240 aaa                                                                 3243
```

<210> SEQ ID NO 38
<211> LENGTH: 860
<212> TYPE: PRT
<213> ORGANISM: Homo sapiens

<400> SEQUENCE: 38

```
Met Ser Arg Gly Gly Ser Tyr Pro His Leu Leu Trp Asp Val Arg Lys
1               5                   10                  15

Arg Ser Leu Gly Leu Glu Asp Pro Ser Arg Leu Arg Ser Arg Tyr Leu
            20                  25                  30

Gly Arg Arg Glu Phe Ile Gln Arg Leu Lys Leu Glu Ala Thr Leu Asn
        35                  40                  45

Val His Asp Gly Cys Val Asn Thr Ile Cys Trp Asn Asp Thr Gly Glu
    50                  55                  60

Tyr Ile Leu Ser Gly Ser Asp Asp Thr Lys Leu Val Ile Ser Asn Pro
65                  70                  75                  80

Tyr Ser Arg Lys Val Leu Thr Thr Ile Arg Ser Gly His Arg Ala Asn
                85                  90                  95

Ile Phe Ser Ala Lys Phe Leu Pro Cys Thr Asn Asp Lys Gln Ile Val
            100                 105                 110

Ser Cys Ser Gly Asp Gly Val Ile Phe Tyr Thr Asn Val Glu Gln Asp
        115                 120                 125

Ala Glu Thr Asn Arg Gln Cys Gln Phe Thr Cys His Tyr Gly Thr Thr
    130                 135                 140

Tyr Glu Ile Met Thr Val Pro Asn Asp Pro Tyr Thr Phe Leu Ser Cys
145                 150                 155                 160

Gly Glu Asp Gly Thr Val Arg Trp Phe Asp Thr Arg Ile Lys Thr Ser
                165                 170                 175

Cys Thr Lys Glu Asp Cys Lys Asp Asp Ile Leu Ile Asn Cys Arg Arg
            180                 185                 190

Ala Ala Thr Ser Val Ala Ile Cys Pro Pro Ile Pro Tyr Tyr Leu Ala
        195                 200                 205

Val Gly Cys Ser Asp Ser Ser Val Arg Ile Tyr Asp Arg Arg Met Leu
    210                 215                 220

Gly Thr Arg Ala Thr Gly Asn Tyr Ala Gly Arg Gly Thr Thr Gly Met
225                 230                 235                 240
```

```
Val Ala Arg Phe Ile Pro Ser His Leu Asn Asn Lys Ser Cys Arg Val
            245                 250                 255

Thr Ser Leu Cys Tyr Ser Glu Asp Gly Gln Glu Ile Leu Val Ser Tyr
            260                 265                 270

Ser Ser Asp Tyr Ile Tyr Leu Phe Asp Pro Lys Asp Asp Thr Ala Arg
            275                 280                 285

Glu Leu Lys Thr Pro Ser Ala Glu Glu Arg Arg Glu Glu Leu Arg Gln
            290                 295                 300

Pro Pro Val Lys Arg Leu Arg Leu Arg Gly Asp Trp Ser Asp Thr Gly
305                 310                 315                 320

Pro Arg Ala Arg Pro Glu Ser Glu Arg Glu Arg Asp Gly Glu Gln Ser
            325                 330                 335

Pro Asn Val Ser Leu Met Gln Arg Met Ser Asp Met Leu Ser Arg Trp
            340                 345                 350

Phe Glu Glu Ala Ser Glu Val Ala Gln Ser Asn Arg Gly Arg Gly Arg
            355                 360                 365

Ser Arg Pro Arg Gly Gly Thr Ser Gln Ser Asp Ile Ser Thr Leu Pro
            370                 375                 380

Thr Val Pro Ser Ser Pro Asp Leu Glu Val Ser Glu Thr Ala Met Glu
385                 390                 395                 400

Val Asp Thr Pro Ala Glu Gln Phe Leu Gln Pro Ser Thr Ser Ser Thr
            405                 410                 415

Met Ser Ala Gln Ala His Ser Thr Ser Ser Pro Thr Glu Ser Pro His
            420                 425                 430

Ser Thr Pro Leu Leu Ser Ser Pro Asp Ser Glu Gln Arg Gln Ser Val
            435                 440                 445

Glu Ala Ser Gly His His Thr His His Gln Ser Asp Asn Asn Asn Glu
            450                 455                 460

Lys Leu Ser Pro Lys Pro Gly Thr Gly Glu Pro Val Leu Ser Leu His
465                 470                 475                 480

Tyr Ser Thr Glu Gly Thr Thr Thr Ser Thr Ile Lys Leu Asn Phe Thr
            485                 490                 495

Asp Glu Trp Ser Ser Ile Ala Ser Ser Ser Arg Gly Ile Gly Ser His
            500                 505                 510

Cys Lys Ser Glu Gly Gln Glu Glu Ser Phe Val Pro Gln Ser Ser Val
            515                 520                 525

Gln Pro Pro Glu Gly Asp Ser Glu Thr Lys Ala Pro Glu Glu Ser Ser
            530                 535                 540

Glu Asp Val Thr Lys Tyr Gln Glu Gly Val Ser Ala Glu Asn Pro Val
545                 550                 555                 560

Glu Asn His Ile Asn Ile Thr Gln Ser Asp Lys Phe Thr Ala Lys Pro
            565                 570                 575

Leu Asp Ser Asn Ser Gly Glu Arg Asn Asp Leu Asn Leu Asp Arg Ser
            580                 585                 590

Cys Gly Val Pro Glu Glu Ser Ala Ser Ser Glu Lys Ala Lys Glu Pro
            595                 600                 605

Glu Thr Ser Asp Gln Thr Ser Thr Glu Ser Ala Thr Asn Glu Asn Asn
            610                 615                 620

Thr Asn Pro Glu Pro Gln Phe Gln Thr Glu Ala Thr Gly Pro Ser Ala
625                 630                 635                 640

His Glu Glu Thr Ser Thr Arg Asp Ser Ala Leu Gln Asp Thr Asp Asp
            645                 650                 655

Ser Asp Asp Asp Pro Val Leu Ile Pro Gly Ala Arg Tyr Arg Ala Gly
```

-continued

```
                       660              665             670
Pro Gly Asp Arg Arg Ser Ala Val Ala Arg Ile Gln Glu Phe Phe Arg
               675                 680                 685
Arg Arg Lys Glu Arg Lys Glu Met Glu Glu Leu Asp Thr Leu Asn Ile
           690                 695                 700
Arg Arg Pro Leu Val Lys Met Val Tyr Lys Gly His Arg Asn Ser Arg
705                 710                 715                 720
Thr Met Ile Lys Glu Ala Asn Phe Trp Gly Ala Asn Phe Val Met Ser
                   725                 730                 735
Gly Ser Asp Cys Gly His Ile Phe Ile Trp Asp Arg His Thr Ala Glu
               740                 745                 750
His Leu Met Leu Leu Glu Ala Asp Asn His Val Val Asn Cys Leu Gln
           755                 760                 765
Pro His Pro Phe Asp Pro Ile Leu Ala Ser Ser Gly Ile Asp Tyr Asp
       770                 775                 780
Ile Lys Ile Trp Ser Pro Leu Glu Glu Ser Arg Ile Phe Asn Arg Lys
785                 790                 795                 800
Leu Ala Asp Glu Val Ile Thr Arg Asn Glu Leu Met Leu Glu Glu Thr
                   805                 810                 815
Arg Asn Thr Ile Thr Val Pro Ala Ser Phe Met Leu Arg Met Leu Ala
               820                 825                 830
Ser Leu Asn His Ile Arg Ala Asp Arg Leu Glu Gly Asp Arg Ser Glu
           835                 840                 845
Gly Ser Gly Gln Glu Asn Glu Asn Glu Asp Glu Glu
       850                 855                 860

<210> SEQ ID NO 39
<211> LENGTH: 2584
<212> TYPE: DNA
<213> ORGANISM: Homo sapiens

<400> SEQUENCE: 39
atagggaggt cgggtagagg ctcccgggac ctgcgtgctg ccgagagagg aagcgaaggg     60
caccatcttt gtattttgtg tcatgacttc tcaagagaag acagaagagt atccttttgc    120
agatatattt gatgaagatg aaactgaaag gaattttttg ttgtccaaac ctgtttgctt    180
tgttgtattt gggaaaccag gtgttgggaa acaacatta gcccgttaca taacacaggc     240
atggaaatgt attcgtgttg aagctttgcc aattttagaa gaacagattg ctgctgaaac    300
cgaatcagga gttatgttgc aatcaatgtt gatcagcggt caaagcattc agatgaactg    360
tgtcataaag ctaatgttgg agaagctcaa ctccccagaa gtctgtcact tggttatat     420 tatcactgaa ataccatcac tttcacagga tgccatgact accttacagc aaatagaatt    480
aattaaaaac ttaaacctga acctgatgt tataatcaat ataaagtgtc ctgactatga    540
tttgtgccag agaatttctg gcaaagaca gcacaatat acgggataca tatacagtag     600
agaccagtgg gatcctgaag tcattgagaa tcataggaaa agaagaaag aagcccaaaa    660 ggacggaaaa ggagaagagg aagaagagga agaagagcaa gaagaagaag aggcatttat    720
tgccgaaatg cagatggtgg ctgaaattct tcatcatcta gtccagaggc ctgaagatta    780
tttggaaaat gttgaaaaca ttgttaagct ttataaggaa acaattctcc aaactttaga    840
agaagtaatg gctgaacaca tcccccagta tctcattgag ctaaatggaa ataaaccagc    900
agaggagctc tttatgattg ttatggatcg acttaaatat ctgaacctaa aaagagcagc    960
tattctaacc aaacttcagg gtgcagagga agaaattaat gacacaatgg aaaatgatga   1020
```

-continued

```
gctatttcgt actcttgcat cttataaact tattgcacca agatacagat ggcaaagaag   1080
taaatgggga cgtacatgtc ctgtgaattt aaaagatggt aacatttatt caggattacc   1140
agattattct gtgagttttc taggtaaaat ctactgtctt tcatcagaag aagcattaaa   1200 accattttg ttgaacccac gtccctatct gcttccacct atgccaggac caccatgtaa    1260
agtattcata cttggacctc aatattcagg gaaaacaaca ctttgcaata tgcttgcaga   1320
aaattacaaa ggaaaggtga ctaactaact atctgtctat ctatctatct atctatctat   1380
ctatctatct atctatctat gtctatctgt catgtatcta tactcgatta aatttgtag    1440 gatttatttt gtactcagtt tttaaaattt catgttttaa ttgaataatt gttccactgg   1500
gcttggggta gggtaggcat tcttttttgtt gtttattgct gcttccagac cagagtccct   1560
ccctgcttcc caaaagctcc cacatgtgaa atcgtgtca ttcagactct gccacctatt    1620
agctttcttg gttctactca tcttctgtcc cctgggtttc acttctcctg gctcactctc   1680
actctcccca tataatcact cctgtcctaa ttcttggtga tttcagtatt acaaagatga   1740
tcctcccaac accttgacac ctccctcagt aatcttgttc tccactctca gtaaatgaaa   1800
ttatttttag cttagacaag agtgatagca gtaaagtgg tatgaaacaa gcatatttgg    1860
gatataattt gaagacaaag ctgaaagatt tgatgaggga ttggaatgtg gaggaattct   1920
agaaggggca atgtggcttg aggattgcct atgcaagaag gaatggcaca agatcatggc   1980
taaagacaga gcaattcagg ccacagaaag gtgttagaag ttgttcaaag tgctgttgca   2040
ttcttttaag cgccggagta tcattttcta tttgctttta actttttcat tgtgaaacat   2100
gacaaacata cagaaaagtg aagcccactg agttaccgca aaatgaaccc ccatgtaacc   2160
accaaccagg tcaaatctgg aatgttgcca gcacccagac gccctctcat gtttcttctc   2220
aataccagtc tcctcactct ccacacaaag gtaaccactc cccagaattt tatggcattc   2280
acttccatac ttctcctatg gttttgccgt ggaagcatac atccaaatac ataggctag    2340 ttttgcatgg tttttttgaa ttttatagac ctaaacaatt tatcttcttt gtgcctggct   2400
tctttcactt aacattataa ttatgatatt tgtccagact attgaatgta gctgtagttt   2460
attcattttt attgttttat tgtattctgt tgattgactt ataccataat gtatttatcc   2520
acatttgagc actaataaaa cttggattga ttccagattg gagtaaacaa aaaaaaaaa    2580 aaaa                                                                2584
```

<210> SEQ ID NO 40
<211> LENGTH: 421
<212> TYPE: PRT
<213> ORGANISM: Homo sapiens

<400> SEQUENCE: 40

```
Met Thr Ser Gln Glu Lys Thr Glu Glu Tyr Pro Phe Ala Asp Ile Phe
1               5                   10                  15

Asp Glu Asp Glu Thr Glu Arg Asn Phe Leu Leu Ser Lys Pro Val Cys
            20                  25                  30

Phe Val Val Phe Gly Lys Pro Gly Val Gly Lys Thr Thr Leu Ala Arg
        35                  40                  45

Tyr Ile Thr Gln Ala Trp Lys Cys Ile Arg Val Glu Ala Leu Pro Ile
    50                  55                  60

Leu Glu Glu Gln Ile Ala Ala Glu Thr Glu Ser Gly Val Met Leu Gln
65                  70                  75                  80

Ser Met Leu Ile Ser Gly Gln Ser Ile Pro Asp Glu Leu Val Ile Lys
                85                  90                  95
```

| | | | | | | | | | | | | | |
|---|---|---|---|---|---|---|---|---|---|---|---|---|---|
|Leu|Met|Leu|Glu|Lys|Leu|Asn|Ser|Pro|Glu|Val|Cys|His|Phe|Gly|Tyr|
| | | |100| | | |105| | | |110| | | |

Ile Ile Thr Glu Ile Pro Ser Leu Ser Gln Asp Ala Met Thr Thr Leu
            115                 120                 125

Gln Gln Ile Glu Leu Ile Lys Asn Leu Asn Leu Lys Pro Asp Val Ile
130                 135                 140

Ile Asn Ile Lys Cys Pro Asp Tyr Asp Leu Cys Gln Arg Ile Ser Gly
145                 150                 155                 160

Gln Arg Gln His Asn Asn Thr Gly Tyr Ile Tyr Ser Arg Asp Gln Trp
                165                 170                 175

Asp Pro Glu Val Ile Glu Asn His Arg Lys Lys Lys Glu Ala Gln
            180                 185                 190

Lys Asp Gly Lys Gly Glu Glu Glu Glu Glu Glu Glu Gln Glu Glu
            195                 200                 205

Glu Glu Ala Phe Ile Ala Glu Met Gln Met Val Ala Glu Ile Leu His
210                 215                 220

His Leu Val Gln Arg Pro Glu Asp Tyr Leu Glu Asn Val Glu Asn Ile
225                 230                 235                 240

Val Lys Leu Tyr Lys Glu Thr Ile Leu Gln Thr Leu Glu Glu Val Met
            245                 250                 255

Ala Glu His Asn Pro Gln Tyr Leu Ile Glu Leu Asn Gly Asn Lys Pro
            260                 265                 270

Ala Glu Glu Leu Phe Met Ile Val Met Asp Arg Leu Lys Tyr Leu Asn
            275                 280                 285

Leu Lys Arg Ala Ala Ile Leu Thr Lys Leu Gln Gly Ala Glu Glu
            290                 295                 300

Ile Asn Asp Thr Met Glu Asn Asp Glu Leu Phe Arg Thr Leu Ala Ser
305                 310                 315                 320

Tyr Lys Leu Ile Ala Pro Arg Tyr Arg Trp Gln Arg Ser Lys Trp Gly
            325                 330                 335

Arg Thr Cys Pro Val Asn Leu Lys Asp Gly Asn Ile Tyr Ser Gly Leu
            340                 345                 350

Pro Asp Tyr Ser Val Ser Phe Leu Gly Lys Ile Tyr Cys Leu Ser Ser
            355                 360                 365

Glu Glu Ala Leu Lys Pro Phe Leu Leu Asn Pro Arg Pro Tyr Leu Leu
370                 375                 380

Pro Pro Met Pro Gly Pro Pro Cys Lys Val Phe Ile Leu Gly Pro Gln
385                 390                 395                 400

Tyr Ser Gly Lys Thr Thr Leu Cys Asn Met Leu Ala Glu Asn Tyr Lys
            405                 410                 415

Gly Lys Val Thr Asn
            420

<210> SEQ ID NO 41
<211> LENGTH: 212
<212> TYPE: DNA
<213> ORGANISM: Homo sapiens

<400> SEQUENCE: 41
tgcccctccc cctgtggaga agacgcttag ttgggggtgt gggtttgggc tccattctgg     60
attcggcggt tccgggggag gggtgggtct gtgccgatta ctctgtcttg tacgtttgtt    120
ctgctgctct tcaatattgt atcaacgcca ggaaggggg gtgaaaagcc tcttttaccc    180
cccaaataaa ttgtcacatt ccgaagctga aa                                 212

```
<210> SEQ ID NO 42
<211> LENGTH: 71
<212> TYPE: PRT
<213> ORGANISM: Homo sapiens
<220> FEATURE:
<221> NAME/KEY: misc_feature
<222> LOCATION: (71)..(71)
<223> OTHER INFORMATION: Xaa can be any naturally occurring amino acid

<400> SEQUENCE: 42

Ala Pro Pro Val Glu Lys Thr Leu Ser Trp Gly Cys Gly Phe Gly
1               5                   10                  15

Leu His Ser Gly Phe Gly Gly Ser Gly Gly Val Gly Leu Cys Arg
            20                  25                  30

Leu Leu Cys Leu Val Arg Leu Phe Cys Cys Ser Ser Ile Leu Tyr Gln
                35                  40                  45

Arg Gln Glu Arg Gly Val Lys Ser Leu Phe Tyr Pro Pro Asn Lys Leu
        50                  55                  60

Ser His Ser Glu Ala Glu Xaa
65                  70

<210> SEQ ID NO 43
<211> LENGTH: 1882
<212> TYPE: DNA
<213> ORGANISM: Homo sapiens

<400> SEQUENCE: 43
atggaggttg caggtctttt cctgggtggg cgtggggcgg ggcagcgggt tcccagcgtc      60
ctcctggcct gggcgtcttg gaggctgttg gggtgcattc cgtcccttg cgcggggcgg      120 ggccttgagg cgctggggcg ggattggcgg ggacggtcg cggagccccg ccccgaagca      180
cagggtcgag tcccttcttt ccgctccaac gcacggaggg tgaggtcggt acgcggtggt      240
ggcgtcacgg cgccagctcc tcccgacgcc gaggtgggtt ccgggagacc cgcgggtctg      300
gctgcgagag accatggggg ctcagctaag cggcggccgc ggcgcccgg agcctgcgca      360 aacccagccc cagccccagc ccagcctgc ggcgccggag ggcccggaac agccccggca      420
tccgccccag cccagccccc agccccagcc ccagccccag cccgagccca gcccgtgggg      480
gccgctggac gacgtgcgct tcctcatcgc ctgcacttcc tggtactgac ggcgtcctcc      540
gcaggatgtc gcccgtctgt ccgccgtccc ctgtggttct tgcctgcctt gtctcctctc      600
cccacgtccc tgcgtctctt acacccccctc ccacccgagg ctccccagag atagcagaga      660
attcgaagag gtcgccgggg actggaaaga agtcccggca gggccgcctt cgcagtctac      720 acccccagcct gcttcccagc ctacacccag acccagctca gaccttcgtg accaccccat      780
ccctttctcc ggctggctgg gtcggggggca tccctctctg tcgctggctt ccagaggcag      840
gacaggcctc ctggtaagcc cgcaaagttg ctgacctcct gacttcgtct gccttttatt      900
aatatctgta ttgctgataa ccgtgctctt gactatgtgt cccaggtcat gtcccaggtc      960
atggagaagc ccgtgccaca gtgaccctcc ccatactcct ggggggggctg ctctccatcc     1020 tggatcgtaa ggaggcatca tcaggctgtg ttcctggaac cccaataacc ctgggccccc     1080
agggccagcc tgttgtagag ggaggctatc tgaccgccgg tctggcagag gagatgggtg     1140
ggcagctccc agacacccca aaggaccgg ttctcttccc agagcgtcct aaggttactc     1200
ttggaacctg atctttgttc cctcatccca gggaaatgac acactctgta tttctgtttt     1260
atttagaaat gatttaaaaa acattataca aaggctgatc agtttaaaat gtgactgaca     1320
ctgaaatgct gtgatgtccc ccaggctgag gggaagctag gctctggggc ccccagtgct     1380
```

```
ttgcccctct gtctgccctg tcctggggtg atggacaaac agatgaccac aggcaggaga    1440
atctgagatt ggaagcctct aggctgagcc ctctgggcct ggccccacat ccctcacctc    1500
tgcagcctgg gctgcctgcc tccatctcct gttcattctc agctggcctg ccaggagcca    1560
atggggagcc tggcgggagg cggggtgcc tagagctttc aagaagtgag agcaccaacc     1620
tgaggagtgg acagggacca ggaagtgggg gaagggaggc caggaagagg tggatacagg    1680
agacacttct catctcatct cagaccctag aggggtccac agatggggac acaagaccca    1740
gccagcccac tggatggccc gggcaagtaa caacctctct gtgcttcatc tgagggcacg    1800
gtgagagtta ccgtcggcct cccagggcct aacacgagtt tcatgtgagt ggacaggtgt    1860
gagctaataa agtgctttgc aa                                             1882
```

<210> SEQ ID NO 44
<211> LENGTH: 217
<212> TYPE: PRT
<213> ORGANISM: Homo sapiens

<400> SEQUENCE: 44

```
Met Glu Val Ala Gly Leu Phe Leu Gly Gly Arg Gly Ala Gly Gln Arg
1               5                   10                  15

Val Pro Ser Val Leu Leu Ala Trp Ala Ser Trp Arg Leu Leu Gly Cys
            20                  25                  30

Ile Pro Ser Pro Cys Ala Gly Arg Gly Leu Glu Ala Leu Gly Arg Asp
        35                  40                  45

Trp Arg Gly Thr Val Ala Glu Pro Arg Pro Glu Ala Gln Gly Arg Val
    50                  55                  60

Pro Ser Phe Arg Ser Asn Ala Arg Arg Val Arg Ser Val Arg Gly Gly
65                  70                  75                  80

Gly Val Thr Ala Pro Ala Pro Pro Asp Ala Glu Val Gly Ser Gly Arg
                85                  90                  95

Pro Ala Gly Leu Ala Ala Arg Asp His Gly Gly Ser Ala Lys Arg Arg
            100                 105                 110

Pro Arg Arg Pro Gly Ala Cys Ala Asn Pro Ala Pro Ala Pro Ala Pro
        115                 120                 125

Ala Cys Gly Ala Gly Gly Pro Gly Thr Ala Pro Ala Ser Ala Pro Ala
    130                 135                 140

Pro Ala Pro Ala Pro Ala Pro Ala Arg Ala Gln Pro Val Gly
145                 150                 155                 160

Ala Ala Gly Arg Arg Ala Leu Pro His Arg Leu His Phe Leu Val Leu
                165                 170                 175

Thr Ala Ser Ser Ala Gly Cys Arg Pro Ser Val Arg Arg Pro Leu Trp
            180                 185                 190

Phe Leu Pro Ala Leu Ser Pro Leu Pro Thr Ser Leu Arg Leu Leu His
        195                 200                 205

Pro Leu Pro Pro Glu Ala Pro Gln Arg
    210                 215
```

<210> SEQ ID NO 45
<211> LENGTH: 1900
<212> TYPE: DNA
<213> ORGANISM: Homo sapiens

<400> SEQUENCE: 45

```
ctcctcctcc ggcgtcgcgg gctcctcgga catggccgcg gcgtggcgg tggcggccgc      60 gtcccggcgg cagtcgtgct acctgtgtga cctgccccgc atgccctggg ccatgatctg    120
```

-continued

```
ggacttcacc gaacccgtct gccgcggctg cgtcaactac gagggcgccg accgcgtcga     180
gttcgtcatc gagacggcgc ggcagctcaa gcgggcgcac ggctgcttcc cggagggtcg     240
ctccccaccc ggcgccgcgg cctcggccgc cgccaagccg ccgccgctct ccgccaagga     300
catccttttg cagcagcagc agcagcttgg ccacggcggc cccgaggcgg ccccgcgcgc     360
gccgcaggcc ttggagcgct acccgttggc ggccgcggcc gagaggcccc cgcgcctcgg     420
ctctgacttc ggcagcagcc gcccggcagc gagcctggcc cagccgccga cgccgcagcc     480
gccgcccgtg aacggcatcc tggtgcccaa cggcttctcc aagctagagg aaccgcccga     540
gctgaatcgc cagagcccga aaccacggcg cggccacacg gtgccgccca ccctggtgcc     600
gctcatgaac ggctcggcca cgccgctgcc caccgcgctc ggcctcggcg ccgcgctgc     660
cgcctcctta gccgcggtgt ccggaaccgc ggccgccagc ctgggctccg cgcagcccac     720
cgatctgggc gcccacaagc ggccggcatc cgtgtcgagc agcgctaccg tggagcacga     780
gcagcgtgag gcggcagcca aggagaaaca accgccgccg cctgcgcacc ggggcccggc     840
cgacagcctg tccaccgcgg ccggggccgc cgagctgagc gcggaaggtg cgggcaagag     900
ccgcgggtct ggagagcagg actgggtcaa caggcccaag accgtgcgcg acacgctgct     960
ggcgctgcac cagcacggcc actcggggcc cttcgagagc aagtttaaga aggagccggc    1020
cctgactgca gcaggttgt tgggtttcga ggccaacggg gccaacgggt ctaaagcagt    1080
tgcaagaaca gcaggaaaaa ggaagccctc tccagaacca aaggtgaag tcgggccccc    1140
taagatcaac ggagaggccc agccgtggct gtccacatcc acagaggggc tcaagatccc    1200
catgactcct acatcctctt ttgtgtctcc gccaccaccc actgcctcac ctcattccaa    1260
ccggaccaca ccgcctgaag cggcccagaa tggccagtcc cccatggcag ccctgatctt    1320
agtagcagac aatgcagggg gcagtcatgc ctcaaaagat gccaaccagg ttcactccac    1380
taccaggagg aatagcaaca gtccgccctc tccgtcctct atgaaccaaa gaaggctggg    1440
cccagagag gtgggggcc agggagcagg caacacagga ggactggagc cagtgcaccc    1500
tgccagcctc ccggactcct ctctggcaac cagtgccccg ctgtgctgca ccctctgcca    1560
cgagcggctg gaggacaccc attttgtgca gtgcccgtcc gtcccttcgc acaagttctg    1620
cttcccttgc tccagacaaa gcatcaaaca gcagggagct agtggagagg tctattgtcc    1680
cagtggggaa aaatgccctc ttgtgggctc caatgtcccc tgggccttta tgcaaggga    1740
aattgcaacc atccttgctg gagatgtgaa agtgaaaaaa gagagagact cgtgactttt    1800
ccggttcag aaaacccaa tgattaccct taattaaaac tgcttgaatt gtatatatat    1860
ctccatatat atatatatcc aagacaaggg aaatgtagac                          1900
```

<210> SEQ ID NO 46
<211> LENGTH: 587
<212> TYPE: PRT
<213> ORGANISM: Homo sapiens

<400> SEQUENCE: 46

```
Met Ala Ala Val Ala Val Ala Ala Ser Arg Arg Gln Ser Cys
1               5                   10                  15

Tyr Leu Cys Asp Leu Pro Arg Met Pro Trp Ala Met Ile Trp Asp Phe
            20                  25                  30

Thr Glu Pro Val Cys Arg Gly Cys Val Asn Tyr Glu Gly Ala Asp Arg
        35                  40                  45

Val Glu Phe Val Ile Glu Thr Ala Arg Gln Leu Lys Arg Ala His Gly
    50                  55                  60
```

```
Cys Phe Pro Glu Gly Arg Ser Pro Gly Ala Ala Ser Ala Ala
 65                  70                  75                  80

Ala Lys Pro Pro Leu Ser Ala Lys Asp Ile Leu Leu Gln Gln Gln
             85                  90                  95

Gln Gln Leu Gly His Gly Gly Pro Glu Ala Ala Pro Arg Ala Pro Gln
        100                 105                 110

Ala Leu Glu Arg Tyr Pro Leu Ala Ala Ala Glu Arg Pro Pro Arg
        115                 120                 125

Leu Gly Ser Asp Phe Gly Ser Ser Arg Pro Ala Ala Ser Leu Ala Gln
130                 135                 140

Pro Pro Thr Pro Gln Pro Pro Val Asn Gly Ile Leu Val Pro Asn
145                 150                 155                 160

Gly Phe Ser Lys Leu Glu Glu Pro Pro Glu Leu Asn Arg Gln Ser Pro
                165                 170                 175

Lys Pro Arg Arg Gly His Thr Val Pro Pro Thr Leu Val Pro Leu Met
                180                 185                 190

Asn Gly Ser Ala Thr Pro Leu Pro Thr Ala Leu Gly Leu Gly Gly Arg
        195                 200                 205

Ala Ala Ala Ser Leu Ala Ala Val Ser Gly Thr Ala Ala Ser Leu
210                 215                 220

Gly Ser Ala Gln Pro Thr Asp Leu Gly Ala His Lys Arg Pro Ala Ser
225                 230                 235                 240

Val Ser Ser Ser Ala Thr Val Glu His Glu Gln Arg Glu Ala Ala Ala
                245                 250                 255

Lys Glu Lys Gln Pro Pro Pro Ala His Arg Gly Pro Ala Asp Ser
        260                 265                 270

Leu Ser Thr Ala Ala Gly Ala Ala Glu Leu Ser Ala Glu Gly Ala Gly
        275                 280                 285

Lys Ser Arg Gly Ser Gly Glu Gln Asp Trp Val Asn Arg Pro Lys Thr
        290                 295                 300

Val Arg Asp Thr Leu Leu Ala Leu His Gln His Gly His Ser Gly Pro
305                 310                 315                 320

Phe Glu Ser Lys Phe Lys Lys Glu Pro Ala Leu Thr Ala Gly Arg Leu
                325                 330                 335

Leu Gly Phe Glu Ala Asn Gly Ala Asn Gly Ser Lys Ala Val Ala Arg
        340                 345                 350

Thr Ala Arg Lys Arg Lys Pro Ser Pro Glu Pro Glu Gly Glu Val Gly
        355                 360                 365

Pro Pro Lys Ile Asn Gly Glu Ala Gln Pro Trp Leu Ser Thr Ser Thr
370                 375                 380

Glu Gly Leu Lys Ile Pro Met Thr Pro Thr Ser Ser Phe Val Ser Pro
385                 390                 395                 400

Pro Pro Pro Thr Ala Ser Pro His Ser Asn Arg Thr Thr Pro Pro Glu
                405                 410                 415

Ala Ala Gln Asn Gly Gln Ser Pro Met Ala Ala Leu Ile Leu Val Ala
        420                 425                 430

Asp Asn Ala Gly Gly Ser His Ala Ser Lys Asp Ala Asn Gln Val His
        435                 440                 445

Ser Thr Thr Arg Arg Asn Ser Asn Ser Pro Pro Ser Pro Ser Ser Met
450                 455                 460

Asn Gln Arg Arg Leu Gly Pro Arg Glu Val Gly Gly Gln Gly Ala Gly
465                 470                 475                 480

Asn Thr Gly Gly Leu Glu Pro Val His Pro Ala Ser Leu Pro Asp Ser
                485                 490                 495
```

```
Ser Leu Ala Thr Ser Ala Pro Leu Cys Cys Thr Leu Cys His Glu Arg
            500                 505                 510
Leu Glu Asp Thr His Phe Val Gln Cys Pro Ser Val Pro Ser His Lys
        515                 520                 525
Phe Cys Phe Pro Cys Ser Arg Gln Ser Ile Lys Gln Gln Gly Ala Ser
    530                 535                 540
Gly Glu Val Tyr Cys Pro Ser Gly Glu Lys Cys Pro Leu Val Gly Ser
545                 550                 555                 560
Asn Val Pro Trp Ala Phe Met Gln Gly Glu Ile Ala Thr Ile Leu Ala
            565                 570                 575
Gly Asp Val Lys Val Lys Lys Glu Arg Asp Ser
            580                 585

<210> SEQ ID NO 47
<211> LENGTH: 4284
<212> TYPE: DNA
<213> ORGANISM: Homo sapiens

<400> SEQUENCE: 47
agcagagctg cggccggggg aacccagttt ccgaggaact tttcgccggc gccgggccgc      60
ctctgaggcc agggcaggac acgaacgcgc ggagcggcgg cggcgactga gagccggggc     120
cgcggcggcg ctccctagga agggccgtac gaggcggcgg gcccggcggg cctcccggag     180
gaggcggctg cgccatggac gagccaccct tcagcgaggc ggctttggag caggcgctgg     240
gcgagccgtg cgatctggac gcggcgctgc tgaccgacat cgaaggtgaa gtcggcgcgg     300
ggagggggtag ggccaacggc ctggacgccc aagggcggg cgcagatcgc ggagccatgg     360
attgcacttt cgaagacatg cttcagctta tcaacaacca agacagtgac ttccctggcc     420
tatttgaccc accctatgct gggagtgggg caggggcac agaccctgcc agccccgata     480
ccagctcccc aggcagcttg tctccacctc ctgccacatt gagctcctct cttgaagcct     540
tcctgagcgg gccgcaggca gcgccctcac ccctgtcccc tccccagcct gcacccactc     600
cattgaagat gtacccgtcc atgcccgctt tctcccctgg gctggtatc aaggaagagt     660
cagtgccact gagcatcctg cagaccccca ccccacagcc cctgccaggg gccctcctgc     720
cacagagctt cccagcccca gccccaccgc agttcagctc cacccctgtg ttaggctacc     780
ccagccctcc gggaggcttc tctacaggaa gccctcccgg gaacacccag cagccgctgc     840
ctggcctgcc actggcttcc ccgcaggggg tcccgcccgt ctccttgcac acccaggtcc     900
agagtgtggt cccccagcag ctactgacag tcacagctgc cccacggca gcccctgtaa     960
cgaccactgt gacctcgcag atccagcagg tcccggtcct gctgcagccc cacttcatca    1020
aggcagactc gctgcttctg acagccatga agacagacgg agccactgtg aaggcggcag    1080
gtctcagtcc cctggtctct ggcaccactg tgcagacagg cctttgccg acctggtga    1140
gtggcggaac catcttggca acagtcccac tggtcgtaga tgcggagaag ctgcctatca    1200
accggctcgc agctggcagc aaggcccgg cctctgccca gagccgtgga gagaagcgca    1260
cagcccacaa cgccattgag aagcgctacc gctcctccat caatgacaaa atcattgagc    1320
tcaaggatct ggtggtgggc actgaggcaa agctgaataa atctgctgtc ttgcgcaagg    1380
ccatcgacta cattcgctcc ttctgcaacac agcaaccaga actcaagcag agaaacctaa    1440
gtctgcgcac tgctgtccac aaaagcaaat ctctgaagga tctggtgtcg gcctgtggca    1500
gtggagggaa cacagacgtg ctcatggagg gcgtgaagac tgaggtggag acacactga    1560
ccccaccccc ctcggatgct ggctcacctt tccagagcag cccccttgtcc cttggcagca    1620
```

| | |
|---|---|
| ggggcagtgg cagcggtggc agtggcagtg actcggagcc tgacagccca gtctttgagg | 1680 |
| acagcaaggc aaagccagag cagcggccgt ctctgcacag ccggggcatg ctggaccgct | 1740 |
| cccgcctggc cctgtgcacg ctcgtcttcc tctgcctgtc ctgcaacccc ttggcctcct | 1800 |
| tgctgggggc ccgggggctt cccagcccct cagataccac cagcgtctac catagccctg | 1860 |
| ggcgcaacgt gctgggcacc gagagcagag atggccctgg ctgggcccag tggctgctgc | 1920 |
| ccccagtggt ctggctgctc aatgggctgt tggtgctcgt ctccttggtg cttctctttg | 1980 |
| tctacggtga gccagtcaca cggccccact caggccccgc cgtgtacttc tggaggcatc | 2040 |
| gcaagcaggc tgacctggac ctggcccggg gagactttgc ccaggctgcc cagcagctgt | 2100 |
| ggctggccct gcgggcactg ggccggcccc tgcccacctc ccacctggac ctggcttgta | 2160 |
| gcctcctctg gaacctcatc cgtcacctgc tgcagcgtct ctggggtgggc cgctggctgg | 2220 |
| caggccgggc aggggggcctg cagcaggact gtgctctgcg agtggatgct agcgccagcg | 2280 |
| cccgagacgc agccctggtc taccataagc tgcaccagct gcacaccatg gggaagcaca | 2340 |
| caggcgggca cctcactgcc accaacctgg cgctgagtgc cctgaacctg gcagagtgtg | 2400 |
| caggggatgc cgtgtctgtg gcgacgctgg ccgagatcta tgtggcggct gcattgagag | 2460 |
| tgaagaccag tctcccacgg gccttgcatt ttctgacacg cttcttcctg agcagtgccc | 2520 |
| gccaggcctg cctggcacag agtggctcag tgcctcctgc catgcagtgg ctctgccacc | 2580 |
| ccgtgggcca ccgtttcttc gtggatgggg actggtccgt gctcagtacc ccatgggaga | 2640 |
| gcctgtacag cttggcccggg aacccagtgg accccctggc ccaggtgact cagctattcc | 2700 |
| gggaacatct cttagagcga gcactgaact gtgtgaccca gcccaacccc agccctgggt | 2760 |
| cagctgatgg ggacaaggaa ttctcggatg ccctcgggta cctgcagctg ctgaacagct | 2820 |
| gttctgatgc tgcgggggct cctgcctaca gcttctccat cagttccagc atggccacca | 2880 |
| ccaccggcgt agacccggtg gccaagtggt gggcctctct gacagctgtg gtgatccact | 2940 |
| ggctgcggcg ggatgaggag gcggctgagc ggctgtgccc gctggtggag cacctgcccc | 3000 |
| gggtgctgca ggagtctgag agaccccctgc ccagggcagc tctgcactcc ttcaaggctg | 3060 |
| cccgggccct gctgggctgt gccaaggcag agtctggtcc agccagcctg accatctgtg | 3120 |
| agaaggccag tgggtacctg caggacagcc tggctaccac accagccagc agctccattg | 3180 |
| acaaggccgt gcagctgttc ctgtgtgacc tgcttcttgt ggtgcgcacc agcctgtggc | 3240 |
| ggcagcagca gccccggcc ccggcccag cagcccaggg caccagcagc aggccccagg | 3300 |
| cttccgccct tgagctgcgt ggcttccaac gggacctgag cagcctgagg cggctggcac | 3360 |
| agagcttccg gcccgccatg cggagggtgt tcctacatga ggccacggcc cggctgatgg | 3420 |
| cgggggccag ccccacacgg acacaccagc tcctcgaccg cagtctgagg cggcgggcag | 3480 |
| gccccgtgg caaaggaggc gcggtggcgg agctggagcc gcggcccacg cggcgggagc | 3540 |
| acgcggaggc cttgctgctg gcctcctgct acctgccccc cggcttcctg tcggcgcccg | 3600 |
| ggcagcgcgt gggcatgctg gctgaggcgg cgcgcacact cgagaagctt ggcgatcgcc | 3660 |
| ggctgctgca cgactgtcag cagatgctca tgcgcctggg cggtgggacc actgtcactt | 3720 |
| ccagctagac cccgtgtccc cggcctcagc acccctgtct ctagccactt tggtcccgtg | 3780 |
| cagcttctgt cctgcgtcga agctttgaag gccgaaggca gtgcaagaga ctctggcctc | 3840 |
| cacagttcga cctgcggctg ctgtgtgcct tcgcggtgga aggcccgagg ggcgcgatct | 3900 |
| tgaccctaag accggcggcc atgatggtgc tgacctctgg tggccgatcg gggcactgca | 3960 |
| ggggccgagc cattttgggg ggccccctc cttgctctgc aggcaccttca gtggcttttt | 4020 |

-continued

```
tcctcctgtg tacagggaag agagggtac atttccctgt gctgacggaa gccaacttgg    4080
ctttcccgga ctgcaagcag ggctctgccc cagaggcctc tctctccgtc gtgggagaga    4140
gacgtgtaca tagtgtaggt cagcgtgctt agcctcctga cctgaggctc ctgtgctact    4200 ttgcctttg caaactttat tttcatagat tgagaagttt tgtacagaga attaaaatg    4260 aaattattta taatctggaa aaaa    4284
```

<210> SEQ ID NO 48
<211> LENGTH: 1177
<212> TYPE: PRT
<213> ORGANISM: Homo sapiens

<400> SEQUENCE: 48

```
Met Asp Glu Pro Pro Phe Ser Glu Ala Ala Leu Glu Gln Ala Leu Gly
1               5                   10                  15

Glu Pro Cys Asp Leu Asp Ala Ala Leu Leu Thr Asp Ile Glu Gly Glu
            20                  25                  30

Val Gly Ala Gly Arg Gly Arg Ala Asn Gly Leu Asp Ala Pro Arg Ala
        35                  40                  45

Gly Ala Asp Arg Gly Ala Met Asp Cys Thr Phe Glu Asp Met Leu Gln
    50                  55                  60

Leu Ile Asn Asn Gln Asp Ser Asp Phe Pro Gly Leu Phe Asp Pro Pro
65                  70                  75                  80

Tyr Ala Gly Ser Gly Ala Gly Gly Thr Asp Pro Ala Ser Pro Asp Thr
                85                  90                  95

Ser Ser Pro Gly Ser Leu Ser Pro Pro Ala Thr Leu Ser Ser Ser
            100                 105                 110

Leu Glu Ala Phe Leu Ser Gly Pro Gln Ala Ala Pro Ser Pro Leu Ser
        115                 120                 125

Pro Pro Gln Pro Ala Pro Thr Pro Leu Lys Met Tyr Pro Ser Met Pro
    130                 135                 140

Ala Phe Ser Pro Gly Pro Gly Ile Lys Glu Glu Ser Val Pro Leu Ser
145                 150                 155                 160

Ile Leu Gln Thr Pro Thr Pro Gln Pro Leu Pro Gly Ala Leu Leu Pro
                165                 170                 175

Gln Ser Phe Pro Ala Pro Ala Pro Pro Gln Phe Ser Ser Thr Pro Val
            180                 185                 190

Leu Gly Tyr Pro Ser Pro Pro Gly Gly Phe Ser Thr Gly Ser Pro Pro
        195                 200                 205

Gly Asn Thr Gln Gln Pro Leu Pro Gly Leu Pro Leu Ala Ser Pro Pro
    210                 215                 220

Gly Val Pro Pro Val Ser Leu His Thr Gln Val Gln Ser Val Val Pro
225                 230                 235                 240

Gln Gln Leu Leu Thr Val Thr Ala Ala Pro Thr Ala Ala Pro Val Thr
                245                 250                 255

Thr Thr Val Thr Ser Gln Ile Gln Gln Val Pro Val Leu Leu Gln Pro
            260                 265                 270

His Phe Ile Lys Ala Asp Ser Leu Leu Leu Thr Ala Met Lys Thr Asp
        275                 280                 285

Gly Ala Thr Val Lys Ala Ala Gly Leu Ser Pro Leu Val Ser Gly Thr
    290                 295                 300

Thr Val Gln Thr Gly Pro Leu Pro Thr Leu Val Ser Gly Gly Thr Ile
305                 310                 315                 320

Leu Ala Thr Val Pro Leu Val Val Asp Ala Glu Lys Leu Pro Ile Asn
```

```
                325                 330                 335
Arg Leu Ala Ala Gly Ser Lys Ala Pro Ala Ser Ala Gln Ser Arg Gly
                340                 345                 350
Glu Lys Arg Thr Ala His Asn Ala Ile Glu Lys Arg Tyr Arg Ser Ser
                355                 360                 365
Ile Asn Asp Lys Ile Ile Glu Leu Lys Asp Leu Val Val Gly Thr Glu
                370                 375                 380
Ala Lys Leu Asn Lys Ser Ala Val Leu Arg Lys Ala Ile Asp Tyr Ile
385                 390                 395                 400
Arg Phe Leu Gln His Ser Asn Gln Lys Leu Lys Gln Glu Asn Leu Ser
                405                 410                 415
Leu Arg Thr Ala Val His Lys Ser Lys Ser Leu Lys Asp Leu Val Ser
                420                 425                 430
Ala Cys Gly Ser Gly Asn Thr Asp Val Leu Met Glu Gly Val Lys
                435                 440                 445
Thr Glu Val Glu Asp Thr Leu Thr Pro Pro Ser Asp Ala Gly Ser
                450                 455                 460
Pro Phe Gln Ser Ser Pro Leu Ser Leu Gly Ser Arg Gly Ser Gly Ser
465                 470                 475                 480
Gly Gly Ser Gly Ser Asp Ser Glu Pro Asp Ser Pro Val Phe Glu Asp
                485                 490                 495
Ser Lys Ala Lys Pro Glu Gln Arg Pro Ser Leu His Ser Arg Gly Met
                500                 505                 510
Leu Asp Arg Ser Arg Leu Ala Leu Cys Thr Leu Val Phe Leu Cys Leu
                515                 520                 525
Ser Cys Asn Pro Leu Ala Ser Leu Leu Gly Ala Arg Gly Leu Pro Ser
                530                 535                 540
Pro Ser Asp Thr Thr Ser Val Tyr His Ser Pro Gly Arg Asn Val Leu
545                 550                 555                 560
Gly Thr Glu Ser Arg Asp Gly Pro Gly Trp Ala Gln Trp Leu Leu Pro
                565                 570                 575
Pro Val Val Trp Leu Leu Asn Gly Leu Leu Val Leu Val Ser Leu Val
                580                 585                 590
Leu Leu Phe Val Tyr Gly Glu Pro Val Thr Arg Pro His Ser Gly Pro
                595                 600                 605
Ala Val Tyr Phe Trp Arg His Arg Lys Gln Ala Asp Leu Asp Leu Ala
                610                 615                 620
Arg Gly Asp Phe Ala Gln Ala Ala Gln Leu Trp Leu Ala Leu Arg
625                 630                 635                 640
Ala Leu Gly Arg Pro Leu Pro Thr Ser His Leu Asp Leu Ala Cys Ser
                645                 650                 655
Leu Leu Trp Asn Leu Ile Arg His Leu Leu Gln Arg Leu Trp Val Gly
                660                 665                 670
Arg Trp Leu Ala Gly Arg Ala Gly Gly Leu Gln Gln Asp Cys Ala Leu
                675                 680                 685
Arg Val Asp Ala Ser Ala Ser Ala Arg Asp Ala Ala Leu Val Tyr His
                690                 695                 700
Lys Leu His Gln Leu His Thr Met Gly Lys His Thr Gly Gly His Leu
705                 710                 715                 720
Thr Ala Thr Asn Leu Ala Leu Ser Ala Leu Asn Leu Ala Glu Cys Ala
                725                 730                 735
Gly Asp Ala Val Ser Val Ala Thr Leu Ala Glu Ile Tyr Val Ala Ala
                740                 745                 750
```

-continued

```
Ala Leu Arg Val Lys Thr Ser Leu Pro Arg Ala Leu His Phe Leu Thr
        755                 760                 765

Arg Phe Phe Leu Ser Ser Ala Arg Gln Ala Cys Leu Ala Gln Ser Gly
    770                 775                 780

Ser Val Pro Pro Ala Met Gln Trp Leu Cys His Pro Val Gly His Arg
785                 790                 795                 800

Phe Phe Val Asp Gly Asp Trp Ser Val Leu Ser Thr Pro Trp Glu Ser
                805                 810                 815

Leu Tyr Ser Leu Ala Gly Asn Pro Val Asp Pro Leu Ala Gln Val Thr
                820                 825                 830

Gln Leu Phe Arg Glu His Leu Leu Glu Arg Ala Leu Asn Cys Val Thr
                835                 840                 845

Gln Pro Asn Pro Ser Pro Gly Ser Ala Asp Gly Asp Lys Glu Phe Ser
850                 855                 860

Asp Ala Leu Gly Tyr Leu Gln Leu Leu Asn Ser Cys Ser Asp Ala Ala
865                 870                 875                 880

Gly Ala Pro Ala Tyr Ser Phe Ser Ile Ser Ser Met Ala Thr Thr
                885                 890                 895

Thr Gly Val Asp Pro Val Ala Lys Trp Trp Ala Ser Leu Thr Ala Val
                900                 905                 910

Val Ile His Trp Leu Arg Arg Asp Glu Glu Ala Ala Glu Arg Leu Cys
        915                 920                 925

Pro Leu Val Glu His Leu Pro Arg Val Leu Gln Ser Glu Arg Pro
930                 935                 940

Leu Pro Arg Ala Ala Leu His Ser Phe Lys Ala Arg Ala Leu Leu
945                 950                 955                 960

Gly Cys Ala Lys Ala Glu Ser Gly Pro Ala Ser Leu Thr Ile Cys Glu
                965                 970                 975

Lys Ala Ser Gly Tyr Leu Gln Asp Ser Leu Ala Thr Thr Pro Ala Ser
                980                 985                 990

Ser Ser Ile Asp Lys Ala Val Gln Leu Phe Leu Cys Asp Leu Leu Leu
        995                 1000                1005

Val Val Arg Thr Ser Leu Trp Arg Gln Gln Gln Pro Pro Ala Pro
    1010                1015                1020

Ala Pro Ala Ala Gln Gly Thr Ser Ser Arg Pro Gln Ala Ser Ala
    1025                1030                1035

Leu Glu Leu Arg Gly Phe Gln Arg Asp Leu Ser Ser Leu Arg Arg
    1040                1045                1050

Leu Ala Gln Ser Phe Arg Pro Ala Met Arg Arg Val Phe Leu His
    1055                1060                1065

Glu Ala Thr Ala Arg Leu Met Ala Gly Ala Ser Pro Thr Arg Thr
    1070                1075                1080

His Gln Leu Leu Asp Arg Ser Leu Arg Arg Arg Ala Gly Pro Gly
    1085                1090                1095

Gly Lys Gly Gly Ala Val Ala Glu Leu Glu Pro Arg Pro Thr Arg
    1100                1105                1110

Arg Glu His Ala Glu Ala Leu Leu Leu Ala Ser Cys Tyr Leu Pro
    1115                1120                1125

Pro Gly Phe Leu Ser Ala Pro Gly Gln Arg Val Gly Met Leu Ala
    1130                1135                1140

Glu Ala Ala Arg Thr Leu Glu Lys Leu Gly Asp Arg Arg Leu Leu
    1145                1150                1155

His Asp Cys Gln Gln Met Leu Met Arg Leu Gly Gly Gly Thr Thr
    1160                1165                1170
```

Val Thr Ser Ser
   1175

<210> SEQ ID NO 49
<211> LENGTH: 8256
<212> TYPE: DNA
<213> ORGANISM: Homo sapiens

<400> SEQUENCE: 49

| | | | | | |
|---|---|---|---|---|---|
| gcaccacctt | ccatggtcaa | taatgaacaa | cgccagcatg | cagagcacat | attcttatca | 60 |
| tttaggaaat | caaaatcacc | atttgcagtt | tgcaagcata | ttttggaaac | tagtaaagtg | 120 |
| gactatgtcc | tctttcaagc | tgccacagcc | ataatggaag | cagttgtccg | agagtggatt | 180 |
| ctcttggaaa | aaggtagcat | cgagtctctg | cgaacattcc | ttttaaccta | tgtcttacaa | 240 |
| aggcccaacc | ttcaaaagta | tgttcgggaa | cagattctac | tagcagtagc | agtaattgta | 300 |
| aaaagaggat | cattagataa | atcaattgac | tgcaaaagca | ttttcatga | agtcagccag | 360 |
| ttgattagta | gtggcaatcc | cactgtgcaa | actctggcct | gttctattct | gactgcgcta | 420 |
| ttgagtgaat | tttcaagttc | aagtaaaact | agcaacattg | gattgagcat | ggaattccat | 480 |
| ggtaactgca | aaagagtttt | tcaggaagaa | gaccttcgtc | agatcttcat | gttaactgtt | 540 |
| gaagttctgc | aggagttcag | caggcgggaa | aacctcaatg | ctcagatgtc | ttcagtattt | 600 |
| cagcgttacc | ttgcactcgc | caatcaagtc | ttgagctgga | actttcttcc | tccaaatttg | 660 |
| ggcagacatt | atatagctat | gtttgaatcc | tcgcaaaatg | tgctgttgaa | gccaacagag | 720 |
| tcctggcggg | agactcttct | ggacagcaga | gttatggagc | ttttcttcac | agtacatcga | 780 |
| aaaatcagag | aagattcaga | tatggcacaa | gattctctgc | agtgccttgc | ccagttagct | 840 |
| tctcttcatg | gacccatctt | cccagatgaa | ggatcacaag | ttgattatct | agcacacttc | 900 |
| attgagggat | tactgaatac | tatcaatgga | attgaaatag | aagattctga | agctgtgggg | 960 |
| atctccagca | ttatcagcaa | cctgataacc | gtgttcccac | gaaatgtttt | aactgccatt | 1020 |
| ccaagtgaac | ttttctcctc | ctttgttaac | tgcctcacac | acctcacttg | ttcttttggg | 1080 |
| cgaagtgctg | cattggaaga | agtgcttgat | aaagatgaca | tggtatacat | ggaagcatat | 1140 |
| gataaattgt | tggagtcctg | gttaactttg | gttcaagatg | acaaacattt | ccataaaggc | 1200 |
| ttttttaccc | aacatgcagt | tcaagttttc | aattcctata | ttcagtgcca | cctagctgct | 1260 |
| ccagatggca | caagaaattt | gactgccaat | ggtgtggcct | ctcgtgagga | ggaagaaata | 1320 |
| agtgaacttc | aagaggatga | tcgagaccag | ttttctgatc | aactggccag | tgtaggaatg | 1380 |
| ctaggaagaa | ttgctgcaga | acactgtata | cctcttctga | caagtttatt | agaagaaaga | 1440 |
| gtaacaagac | tccatggtca | gttacaacga | catcagcaac | agttacttgc | ttcaccgggt | 1500 |
| tcaagcactg | ttgacaacaa | aatgcttgat | gatctctatg | aagatattca | ctggcttatt | 1560 |
| ttagttacag | gctacctctt | agctgatgat | actcagggag | agactccgct | aatacctcca | 1620 |
| gaaataatgg | aatattccat | taagcattca | tctgaagttg | acattaatac | aacacttcaa | 1680 |
| attttgggat | ctccaggaga | aaaggcttct | tccatcccag | gtacaacag | aacagattct | 1740 |
| gtgattaggc | tgttgtctgc | cattctcaga | gtttcagaag | ttgaatctcg | agcaataaga | 1800 |
| gcagatctca | ctcatctact | aagtcccag | atgggcaaag | atattgtttg | gttttaaaa | 1860 |
| cgctgggcaa | agacttatct | cctggtggat | gaaaaactgt | atgatcagat | aagtctgcca | 1920 |
| ttcagtacag | cgttcggagc | agatacagag | ggttctcagt | ggataattgg | ctacctctta | 1980 |
| caaaaagtca | tcagtaacct | ctcagtctgg | agtagtgagc | aggaccttgc | aaatgacact | 2040 |

```
gtgcagctcc ttgtcacttt ggtggaaaga agagaaaggg caaacttagt aattcaatgt    2100
gagaactggt ggaatttagc taagcagttt gcaagccgaa gcccacctct taatttcttg    2160
tcaagtcctg tgcagaggac attgatgaag gctctagtct taggaggttt tgcacatatg    2220
gacacagaaa ccaaacagca gtattggaca gaggttcttc agccacttca gcagcgattc    2280
ttaagagtga taaaccaaga aaacttccag cagatgtgtc agcaagagga agtcaagcag    2340
gaaatcactg ccacactaga ggccctgtgt ggcattgctg aggctaccca gattgacaac    2400
gtagcaatcc tgtttaattt tttaatggac ttccttacca attgcattgg attgatggaa    2460
gtttacaaga atacccccaga gactgtcaat ctcattatag aagttttgt tgaagttgca    2520 cataaacaga tatgctatct tggagagtcc aaagctatga acttatatga agcctgcctt    2580
actttgttgc aagtgtattc taagaataat ttagggcggc aaagaataga tgttacagca    2640
gaagaagagc aataccaaga cctgcttctc attatggaac ttcttactaa cctgctgtca    2700
aaagaattca tagatttcag tgatacagat gaagtgttta gaggacatga gccaggtcaa    2760
gcagcaaaca gatctgtgtc agcagcggat gttgtgttgt atggagtaaa cctaattctg    2820
cccttgatgt cacaggatct cttgaagttt ccaacccttt gtaatcagta ctacaaatta    2880
atcacattta tctgtgagat ttttcctgaa aaaataccac agcttcctga ggatctgttt    2940
aaaagtctga tgtactccct agaattagga atgacatcaa tgagttcgga ggtttgccag    3000 cttttgcctgg aggccttgac accgttagct gaacagtgtg caaaagcaca agaaacagac    3060
tcaccacttt ttctagcaac acggcacttt cttaagctgg ttttttgatat gctggttttg    3120 caaaagcaca acacagagat gaccactgcg gctggcgaag cttttctacac gttggtgtgt    3180 ttgcaccagg ctgaatattc tgaactggtc gaaacattac tatcaagtca gcaagaccca    3240
gttatttacc agagattagc agatgccttc aacaagctca ctgcaagcag cactcctcct    3300
acgctggatc ggaagcagaa gatggccttc ttaaagagtt tagaagaatt tatggcaaat    3360
gttggtggtc tcctttgtgt aaaataaaca acagaacttt atgcttaatt tagatccttt    3420
ctgcaaagtg cactgaattg ctgaaagttg acttgagtct tgtcctattc ctcagttcat    3480
ttggccattt tggattttgg agagcctgaa actttgatat gtatgtaata cagtgaaaca    3540
ggagaggtca acttggcatc agcttctgct gttaagtgtt agccacaatc tgtcatatat    3600
atgtctttta gattctgaat ggtgatttaa aattttcaaa atgaaattcc atatatgtgc    3660
aaacagatat gggcaccacg aaatacatat gcagtgcctt ttttcctttt aacataggtg    3720
gctagccaaa gttagaatt tttgtcatta aatatgaaat ggatatatgc taggcagtgt    3780
ttctcaaaat ctccatagat cgcctgcatc acttgaggag ctggtgaaaa ggcagattct    3840
taggcccaac tgtagacctt cagagtcaga atgtctggtt gttgggccca ggagtcttca    3900
tgttaataag cttctcccct tcgtcacccc aaaagttttg aatcaatgaa agagacattg    3960
aaaactctta agaggttttg tgcttttctag cttttcctcc ctttgatgat tgggttttat    4020
aattcagcag gaaggggaaa catcaccagg ggtttgttgg cttttttctta gcttgctttc    4080 ttgcttgctt gctttcttgc ttttcttgct ttctgtctct ctctttcttt tctctctctc    4140
tctcacatca acccagtgct gcaggttttg tgtaatacaa gtcactaatc atactctgat    4200
gcctgaactt gaggaggaaa atacatgtat attttttgttc cgtaaaaata acctaggaa    4260 ctgtagccat ttcattgcct taattttaag aggaaaatac aaaaacagct gatttgtttt    4320
agtaagaaac cacgtcttga tgcttcgagag ttggtttagg gtgttagctg ctatgaacct    4380 gttgccccttt tcgatcgtgt atttatgtag gtttatcagt gaaatgaaag gcttgtttcc    4440
```

```
gtctagtcta actttttgag tgtgtttcta tccagccaca tagcccatat ctactctaaa    4500
tggcttgctt aagcaataat tattttaaag gatgtgaatc actgattcac acagactatt    4560
gcacgttggg gcattagggg caataattct tatccagaca tgggagccag tgaatttaat    4620
ttcagagatt aaaaattcac tttagatcct ctagtttgat ctcttaatca ggatttttat    4680
acagctgcca ggctcccta attcagtgtg ccagcttaca atgtggaaat gaaagctaat    4740
ttatacacag caggcatatg aaactccact cattgcagta ctttcacagc acagtgacag    4800
gtagaggact ctggcacagg tgcactcatg aaactctgct tccaccatgt tcctgacacc    4860
tatctattaa accattctgc aaatacggtt tttctacctg attgcatata gcatatgtgt    4920
cattacatgt gatgctgtgc aaaactttgt ataattctgt gttattaaca gttaacaaaa    4980
ctggagcatc tgaattacat ccaacctgtg catgtgatgt taggtagatg tgaatgcagg    5040
gccttgggcc ataacttaca tttctctcaa tttgattagc tttgagtcac aattaagggg    5100
aagcaaaaac atcttgaaaa gactgctagg aaggaaatta atatcagtca tccagaagta    5160
cacgtttctg tattttaaaa aatactttga tgcatttatt tttaggtgtt ttttttttcc    5220
ccttaaaaaa cttgaagtga tatgcagcag taatctattt gttttgcatt gttcttggtg    5280
ttttgtgttt cccagatccc tcaagctttc tcagctgttg cgaattatgt gtatctgtgt    5340
gtgtgctaag tacagtctct ttaccaaagg gcactgaaac acacaattga ctggacaggt    5400
ccacgcgcca tgacaaaact ataatcaagt tattaaaact aaagaggagt gggaaaggaa    5460
tgccttggta agtaaaaagg catctatatt taataacttt tatccagatg gcaacatatt    5520
tgcaaaattt gcccagatcc tattacaata ctaaaaatag aaaatttcac ctccatattc    5580
ctgaggtgta atttcattag actagtttta gtttaaaaag accttcttca gattggacca    5640
aataatactt ataagatcag cagaatgttg aatattagct cactggggtg gggagaagcc    5700
actaccattt tttaggtgat ggggatgcca ctgagttgca acggctagac cttttcaggg    5760
tggttgtgtc catgtttgcc tgattggatg cttattcact ttgtgttttc ttttgtttta    5820
ttttgtccaa ttttgtcttt agctgtgttt attaacttct ccggtcttgt tttgttttaa    5880
tgctcttggc ccagtgggtg tcaagaacac tggcttaatt caagtcagtt gattttttt    5940 ctattaaaac tgttgttaaa atatttttta aaacaaaaac attatttgtg ccctctttta    6000
tatatgtcaa agggacactg tcaagtattt catttttaga ttttttgtttt ataaaatttc    6060 tgttgttcat atagtatcct ttaacctcta gttttccata catcctttgt ttgtttctca    6120
ttttattttc cttgacccat ttatttccca aggcacaatc actaaagact ttgtactttc    6180
acagtctgtt aatgtggtag cacctgtaac tgtgttcttg ttctgttaaa aggattgatt    6240
tgcttttata gtccttgtgc tggatgagtg gctgcctcag tagcaaaact acctgacagt    6300
atttgacagt gtcctttcca gcaccattat ttgggtcttt cagggtggcc atctctgtta    6360
gaagacagta gcatgttaac atcactgcat tgagttttg tctggtgtaa agtatgactt    6420
ttaatgtaaa caaactgcag gttttttca aactaatttt aagaatttag tcttatttcg    6480
ttgtaaactg tgtatctaat tatattacat tactctgttc agatgggatg ttactacca    6540 cttgtccatg attttcattt gaaaagcaag tatctatatc atttccccc agtcagcatt    6600 atttaacact cccttaact gtctttgaac tttctctttt aacaaaaatg tcaagtcttt    6660
atagttgtaa tatcaccatg tttcccattt ctgttaatac ttctatgaac ccctaaagta    6720
ttgaagggaa ctagctgtca gtttcaagga ttacaagttt gagtctccta gtattcaaca    6780
tcattctgaa ccctgaaata atattttct ctgttaaaca attttatct gtttgccacc    6840
```

-continued

```
tctgttgtta gaggtggttg tcaattgacc ttactaagtt agctgtcttt gatgaggaat    6900
tattgttatt ggttcctgaa taaaacatta accttttaag tcagaaggaa cctcggtact    6960
tcttaaggtt tgtttgtgtt ttctaaaacc agagaataag gaactgattt ggctatgagg    7020
tttaacatta taattttctg taagctttcc cacaaaaaaa cattgttgat ttgaggatat    7080
aataatgttt taatctttt aaaatataag tggttattct ctgacttggt aactatgttc     7140
tgaaaacact gcatttaaga attttaaaa attggttttc taaaattaaa atgtccaaat     7200
taggcatatt gctgagctca aattgatgtg aaatgccatg gttccagttg aattttaagc    7260
atattttcat ttagatataa aatatatgaa gtatgctttg ttgattatag tgagaaccca    7320
tgacatagtt aaccaaagaa tatgtttggt tcaaataaaa atagaagctt aatactgggc    7380
attcatactt tttaaagaga atgaatgaag aaatcggttt cctgctgtag ttctctatgg    7440
gtaagtctta gtaaagacga gaatgctgaa gtcggccgtg gcgattccct cctaggaact    7500
gggaggtgtg gcttgcccat tacccgcttg aagctcacat ctttaccctc ctctcccact    7560
gtggtttgat cttcacctat tcccaggccc tcccagcaat tggagaggtg tcttttttt     7620 tggttttggt tttttttctc cccgtctgca ttccttaggcc tcttagctat taggaactgt    7680
cagatacata ctagtagcta atttcctag cctgaaatta tatactgcat ctgcactatg     7740
tacctactag ggatctgacc tcaagtgttt tctgagccca ggcttcctgg tgtggtgtct    7800
tttaccacat aaaattatta caaattgcaa atgttggtat tgtgatttga ttatctgtac    7860
aaagaaagaa gctctatgca gtgagtttgt ggtttaatgg tcacaaaaat gttagcactg    7920
ctaccactca gcacgtgtaa aatttttaa atttataaat attaaaattt taaacttaca     7980
ctaagacttt tcagttttat ttaaagaccc agggatgagt gtactgttta aatatttacc    8040
tctattaaca taactaatga aggtataaaa ttgcatttag ttttcagaa gatgctgcaa     8100 tatgatttta ggaaataagg ctatgtattg agccagttat aggctgaata tcaggttgat    8160
aaaattttat ttgtatttt aaaattcata aatgggagtt aaaatgtgtc ttttcactaa     8220
atatttttat tacaaaaaaa aaaaaaaaaa aaaaaa                              8256
```

<210> SEQ ID NO 50
<211> LENGTH: 1124
<212> TYPE: PRT
<213> ORGANISM: Homo sapiens

<400> SEQUENCE: 50

```
Met Val Asn Asn Glu Gln Arg Gln His Ala Glu His Ile Phe Leu Ser
1               5                   10                  15

Phe Arg Lys Ser Lys Ser Pro Phe Ala Val Cys Lys His Ile Leu Glu
            20                  25                  30

Thr Ser Lys Val Asp Tyr Val Leu Phe Gln Ala Ala Thr Ala Ile Met
        35                  40                  45

Glu Ala Val Val Arg Glu Trp Ile Leu Leu Glu Lys Gly Ser Ile Glu
    50                  55                  60

Ser Leu Arg Thr Phe Leu Leu Thr Tyr Val Leu Gln Arg Pro Asn Leu
65                  70                  75                  80

Gln Lys Tyr Val Arg Glu Gln Ile Leu Leu Ala Val Ala Val Ile Val
                85                  90                  95

Lys Arg Gly Ser Leu Asp Lys Ser Ile Asp Cys Lys Ser Ile Phe His
            100                 105                 110

Glu Val Ser Gln Leu Ile Ser Ser Gly Asn Pro Thr Val Gln Thr Leu
        115                 120                 125
```

-continued

```
Ala Cys Ser Ile Leu Thr Ala Leu Leu Ser Glu Phe Ser Ser Ser
    130                 135                 140

Lys Thr Ser Asn Ile Gly Leu Ser Met Glu Phe His Gly Asn Cys Lys
145                 150                 155                 160

Arg Val Phe Gln Glu Glu Asp Leu Arg Gln Ile Phe Met Leu Thr Val
                165                 170                 175

Glu Val Leu Gln Glu Phe Ser Arg Arg Glu Asn Leu Asn Ala Gln Met
            180                 185                 190

Ser Ser Val Phe Gln Arg Tyr Leu Ala Leu Ala Asn Gln Val Leu Ser
        195                 200                 205

Trp Asn Phe Leu Pro Pro Asn Leu Gly Arg His Tyr Ile Ala Met Phe
    210                 215                 220

Glu Ser Ser Gln Asn Val Leu Leu Lys Pro Thr Glu Ser Trp Arg Glu
225                 230                 235                 240

Thr Leu Leu Asp Ser Arg Val Met Glu Leu Phe Phe Thr Val His Arg
                245                 250                 255

Lys Ile Arg Glu Asp Ser Asp Met Ala Gln Asp Ser Leu Gln Cys Leu
            260                 265                 270

Ala Gln Leu Ala Ser Leu His Gly Pro Ile Phe Pro Asp Gly Ser
        275                 280                 285

Gln Val Asp Tyr Leu Ala His Phe Ile Glu Gly Leu Leu Asn Thr Ile
    290                 295                 300

Asn Gly Ile Glu Ile Glu Asp Ser Glu Ala Val Gly Ile Ser Ser Ile
305                 310                 315                 320

Ile Ser Asn Leu Ile Thr Val Phe Pro Arg Asn Val Leu Thr Ala Ile
                325                 330                 335

Pro Ser Glu Leu Phe Ser Ser Phe Val Asn Cys Leu Thr His Leu Thr
            340                 345                 350

Cys Ser Phe Gly Arg Ser Ala Ala Leu Glu Glu Val Leu Asp Lys Asp
        355                 360                 365

Asp Met Val Tyr Met Glu Ala Tyr Asp Lys Leu Leu Glu Ser Trp Leu
    370                 375                 380

Thr Leu Val Gln Asp Asp Lys His Phe His Lys Gly Phe Phe Thr Gln
385                 390                 395                 400

His Ala Val Gln Val Phe Asn Ser Tyr Ile Gln Cys His Leu Ala Ala
                405                 410                 415

Pro Asp Gly Thr Arg Asn Leu Thr Ala Asn Gly Val Ala Ser Arg Glu
            420                 425                 430

Glu Glu Glu Ile Ser Glu Leu Gln Glu Asp Asp Arg Asp Gln Phe Ser
        435                 440                 445

Asp Gln Leu Ala Ser Val Gly Met Leu Gly Arg Ile Ala Ala Glu His
    450                 455                 460

Cys Ile Pro Leu Leu Thr Ser Leu Leu Glu Glu Arg Val Thr Arg Leu
465                 470                 475                 480

His Gly Gln Leu Gln Arg His Gln Gln Leu Leu Ala Ser Pro Gly
                485                 490                 495

Ser Ser Thr Val Asp Asn Lys Met Leu Asp Asp Leu Tyr Glu Asp Ile
            500                 505                 510

His Trp Leu Ile Leu Val Thr Gly Tyr Leu Leu Ala Asp Asp Thr Gln
        515                 520                 525

Gly Glu Thr Pro Leu Ile Pro Pro Glu Ile Met Glu Tyr Ser Ile Lys
    530                 535                 540

His Ser Ser Glu Val Asp Ile Asn Thr Thr Leu Gln Ile Leu Gly Ser
545                 550                 555                 560
```

```
Pro Gly Glu Lys Ala Ser Ser Ile Pro Gly Tyr Asn Arg Thr Asp Ser
            565                 570                 575

Val Ile Arg Leu Leu Ser Ala Ile Leu Arg Val Ser Glu Val Glu Ser
        580                 585                 590

Arg Ala Ile Arg Ala Asp Leu Thr His Leu Leu Ser Pro Gln Met Gly
    595                 600                 605

Lys Asp Ile Val Trp Phe Leu Lys Arg Trp Ala Lys Thr Tyr Leu Leu
610                 615                 620

Val Asp Glu Lys Leu Tyr Asp Gln Ile Ser Leu Pro Phe Ser Thr Ala
625                 630                 635                 640

Phe Gly Ala Asp Thr Glu Gly Ser Gln Trp Ile Ile Gly Tyr Leu Leu
            645                 650                 655

Gln Lys Val Ile Ser Asn Leu Ser Val Trp Ser Ser Glu Gln Asp Leu
                660                 665                 670

Ala Asn Asp Thr Val Gln Leu Leu Val Thr Leu Val Glu Arg Arg Glu
        675                 680                 685

Arg Ala Asn Leu Val Ile Gln Cys Glu Asn Trp Trp Asn Leu Ala Lys
    690                 695                 700

Gln Phe Ala Ser Arg Ser Pro Pro Leu Asn Phe Leu Ser Ser Pro Val
705                 710                 715                 720

Gln Arg Thr Leu Met Lys Ala Leu Val Leu Gly Gly Phe Ala His Met
            725                 730                 735

Asp Thr Glu Thr Lys Gln Gln Tyr Trp Thr Glu Val Leu Gln Pro Leu
                740                 745                 750

Gln Gln Arg Phe Leu Arg Val Ile Asn Gln Glu Asn Phe Gln Gln Met
        755                 760                 765

Cys Gln Gln Glu Val Lys Gln Glu Ile Thr Ala Thr Leu Glu Ala
    770                 775                 780

Leu Cys Gly Ile Ala Glu Ala Thr Gln Ile Asp Asn Val Ala Ile Leu
785                 790                 795                 800

Phe Asn Phe Leu Met Asp Phe Leu Thr Asn Cys Ile Gly Leu Met Glu
            805                 810                 815

Val Tyr Lys Asn Thr Pro Glu Thr Val Asn Leu Ile Ile Glu Val Phe
                820                 825                 830

Val Glu Val Ala His Lys Gln Ile Cys Tyr Leu Gly Glu Ser Lys Ala
        835                 840                 845

Met Asn Leu Tyr Glu Ala Cys Leu Thr Leu Leu Gln Val Tyr Ser Lys
    850                 855                 860

Asn Asn Leu Gly Arg Gln Arg Ile Asp Val Thr Ala Glu Glu Glu Gln
865                 870                 875                 880

Tyr Gln Asp Leu Leu Ile Met Glu Leu Leu Thr Asn Leu Leu Ser
            885                 890                 895

Lys Glu Phe Ile Asp Phe Ser Asp Thr Asp Glu Val Phe Arg Gly His
                900                 905                 910

Glu Pro Gly Gln Ala Ala Asn Arg Ser Val Ser Ala Ala Asp Val Val
        915                 920                 925

Leu Tyr Gly Val Asn Leu Ile Leu Pro Leu Met Ser Gln Asp Leu Leu
    930                 935                 940

Lys Phe Pro Thr Leu Cys Asn Gln Tyr Tyr Lys Leu Ile Thr Phe Ile
945                 950                 955                 960

Cys Glu Ile Phe Pro Glu Lys Ile Pro Gln Leu Pro Glu Asp Leu Phe
            965                 970                 975

Lys Ser Leu Met Tyr Ser Leu Glu Leu Gly Met Thr Ser Met Ser Ser
```

```
                 980             985              990
Glu Val Cys Gln Leu Cys Leu Glu  Ala Leu Thr Pro Leu Ala Glu Gln
                995              1000              1005

Cys Ala Lys Ala Gln Glu Thr Asp  Ser Pro Leu Phe Leu Ala Thr
       1010             1015              1020

Arg His Phe Leu Lys Leu Val Phe  Asp Met Leu Val Leu Gln Lys
       1025             1030              1035

His Asn Thr Glu Met Thr Thr Ala  Ala Gly Glu Ala Phe Tyr Thr
       1040             1045              1050

Leu Val Cys Leu His Gln Ala Glu  Tyr Ser Glu Leu Val Glu Thr
       1055             1060              1065

Leu Leu Ser Ser Gln Gln Asp Pro  Val Ile Tyr Gln Arg Leu Ala
       1070             1075              1080

Asp Ala Phe Asn Lys Leu Thr Ala  Ser Ser Thr Pro Pro Thr Leu
       1085             1090              1095

Asp Arg Lys Gln Lys Met Ala Phe  Leu Lys Ser Leu Glu Glu Phe
       1100             1105              1110

Met Ala Asn Val Gly Gly Leu Leu  Cys Val Lys
       1115             1120

<210> SEQ ID NO 51
<211> LENGTH: 3281
<212> TYPE: DNA
<213> ORGANISM: Homo sapiens

<400> SEQUENCE: 51
ggcaggggcg catccctcgc cacccgcggt cgcccagcac gccgggacgc gcgtggccat    60
ccagctcccc gggggcgttg gggggctccg cgggcctggg cctcgggatt cgcccgccgc   120
ttccccgggg agccgctgct gcaaagccag gttgggcgc cgggcccggc cagcgccctc    180
taggcagcgg aagtgcagct tgctttacat ccgtcctccc cgcctcgcag agttgggaga   240
aggcagggtg gggggtgtgg aaaaataaaa ggaaaagtcc ttgcaccatg tagatcagcg   300
tcccccactt tggcatcccg gccggccggg gacctcccag tctgcggcca tgaacgcgag   360
cagcgagggc gagagcttcg cgggctcggt gcaaattcca ggtggcacaa cggtgctggt   420
ggagctgact cccgacatcc atatctgcgg catctgcaag cagcagttta caaacctgga   480
tgcctttgta gctcacaagc aaagtggctg ccagctgaca ggcacatccg cagcagcccc   540
cagcacggtc cagtttgtat cggaggaaac agtgcctgcc acccgactc agaccaccac    600 cagaaccatc acctcggaga cccagacaat cacagtttca gctccagaat tgttttttga   660
acatggctat caaacttacc tgcccacgga aagtaatgaa aaccagacag ccactgtcat   720
ctctctccct gccaagtcac gcaccaaaaa gcccacaaca ccacctgctc agaaaaggct   780
taactgttgc tatccaggtt gccaattcaa gactgcttat ggcatgaagg acatggagcg   840
gcatttaaaa attcacacgg gagacaaacc ccataagtgt gaagtctgtg caagtgctt    900 tagccggaaa gacaagctga aaactcacat gcggtgccac acgggcgtga agccctacaa   960
gtgtaagacg tgtgactacg ccgctgccga cagcagcagc ctcaacaagc acctgaggat  1020
ccactcggac gagcggccct tcaaatgcca gatctgcccc tacgccagcc gcaactccag  1080
ccagctcact gtccacctgc gatcccacac ggggacgcc ccttccagt gctggctctg    1140 tagcgccaag ttcaaaatca gctcggactt gaaaaggcac atgcgggtgc actcggggga  1200
gaagcctttc aagtgcgagt tctgcaatgt ccgctgcacc atgaagggga acctcaagtc  1260
gcacatccgt atcaagcaca gcgggaataa cttcaagtgt cctcattgcg acttcctggg  1320
```

```
tgacagcaaa gccaccctcc ggaagcacag ccgcgtgcac cagtcggagc atcctgagaa   1380
gtgctcggaa tgcagctact cctgctccag caaggccgcc ctgcgcatcc acgagcgtat   1440
ccactgcacc gaccgccctt tcaagtgcaa ctactgcagc ttcgacacca acagcccag    1500
caacctgagc aagcacatga agaagttcca tggggacatg gttaagactg aggctctaga   1560
gaggaaggac accggcaggc agagcagccg gcaggtggcc aagctggatg ccaagaagag   1620
tttccactgc gatatatgcg atgcctcctt catgcgggag gactcgctcc gcagccacaa   1680
gagacagcac agtgagtaca gtgagagtaa gaactcggac gtgaccgttc tccagtttca   1740
gatcgacccc agcaagcagc ccgccacgcc cctcactgtg ggacacctcc aggtgcccct   1800
ccagcccagc caagtgcccc agttcagcga gggaagagtc aaaatcatcg ttgggcatca   1860
ggtgccccag gcgaacacca tcgtccaggc tgccgccgct gcagtgaaca tcgtcccgcc   1920
tgccttggtg gcccagaacc cagaggaact cccaggggaac agccggctgc agatcctgcg   1980
ccaggtcagt ctgatcgccc ccctcagtc ctcgcggtgt ccgagcgagg cgggcgcaat    2040
gacccagccg gctgtcctgc tgaccaccca cgagcagacg gacggagcca ctctgcacca   2100
gactctcatc cccacggcct caggtggccc ccaggaaggc tctggcaatc aaactttcat   2160
taccagttcg ggtattactt gcactgactt tgaaggccta aacgccttga ttcaggaggg   2220
gacagcagaa gtgacagtgg tgagcgatgg aggccagaac atcgcagtgg ccaccacagc   2280
gccaccggtc ttctcctcct cttcccagca agaactaccc aagcagacct actccatcat   2340
tcaaggggca gccatccag ctttgctctg tcccgccgac tccattccag attagtgctt    2400
aaaaaaacaa aaggagtggg ggaaaggaat tgagaaaaag aaatcttaag tagaattctc   2460
taaaaggttt gctcttaatg ttttctttgt tttgttttgt ttttgagacg gagtctcgct   2520
ctgtttccca ggctggagtg cagtggcgct atcttggctc actgcaacgt ccgcctccca   2580
ggttcaagcg attctcatgc ctcagccctc cgagtagctg ggaccacagg tgtacgacat   2640
catgactggc taattttgt atatttagta gagacggggt ttcatcatgt tgaactcctg    2700
acctcaagtg atctgcccac ctcagcctcc caaagtgctg ggattacagg tgtgagccac   2760
catgcctggc cgtggtttgc tcttaatgtt tttaaggatg gttgtgaatc ccctggccc    2820
cataataaat tgtaattta tactgcttac tataatttt ttaacactgt aacaactttg     2880
agaccacctc tgaatcgtcg cattataact gttgtagaat cttaaatgtt accaagatga   2940
ttccaatgag gggttggaat taaatgcatt aagtagtgaa ttcatgtgtt tgtttccaac   3000
ttgattttcc aactctaata aaggtttctg tccatcttat tacatttgtg tagtaaatgg   3060
tacttcccag cctctctttt gcccattcct ggaatactcc ccagagtttg ggggtgttca   3120
tgttttatac atgtaagtct gttggcatga aggaccattt tctacataat atgacatgga   3180
tacttgaccc aaaaaaaaat gtttagtgct aatgagcaga aaatgaatgg ttccataata   3240
aattgatatc tgattaaaat ataaaaaaaa aaaaaaaaa a                        3281
```

<210> SEQ ID NO 52
<211> LENGTH: 681
<212> TYPE: PRT
<213> ORGANISM: Homo sapiens

<400> SEQUENCE: 52

```
Met Asn Ala Ser Ser Glu Gly Glu Ser Phe Ala Gly Ser Val Gln Ile
1               5                   10                  15

Pro Gly Gly Thr Thr Val Leu Val Glu Leu Thr Pro Asp Ile His Ile
            20                  25                  30
```

```
Cys Gly Ile Cys Lys Gln Gln Phe Asn Asn Leu Asp Ala Phe Val Ala
         35                  40                  45

His Lys Gln Ser Gly Cys Gln Leu Thr Gly Thr Ser Ala Ala Ala Pro
 50                  55                  60

Ser Thr Val Gln Phe Val Ser Glu Glu Thr Val Pro Ala Thr Gln Thr
 65                  70                  75                  80

Gln Thr Thr Thr Arg Thr Ile Thr Ser Glu Thr Gln Thr Ile Thr Val
                 85                  90                  95

Ser Ala Pro Glu Phe Val Phe Glu His Gly Tyr Gln Thr Tyr Leu Pro
            100                 105                 110

Thr Glu Ser Asn Glu Asn Gln Thr Ala Thr Val Ile Ser Leu Pro Ala
            115                 120                 125

Lys Ser Arg Thr Lys Lys Pro Thr Thr Pro Pro Ala Gln Lys Arg Leu
130                 135                 140

Asn Cys Cys Tyr Pro Gly Cys Gln Phe Lys Thr Ala Tyr Gly Met Lys
145                 150                 155                 160

Asp Met Glu Arg His Leu Lys Ile His Thr Gly Asp Lys Pro His Lys
                165                 170                 175

Cys Glu Val Cys Gly Lys Cys Phe Ser Arg Lys Asp Lys Leu Lys Thr
            180                 185                 190

His Met Arg Cys His Thr Gly Val Lys Pro Tyr Lys Cys Lys Thr Cys
            195                 200                 205

Asp Tyr Ala Ala Ala Asp Ser Ser Ser Leu Asn Lys His Leu Arg Ile
            210                 215                 220

His Ser Asp Glu Arg Pro Phe Lys Cys Gln Ile Cys Pro Tyr Ala Ser
225                 230                 235                 240

Arg Asn Ser Ser Gln Leu Thr Val His Leu Arg Ser His Thr Gly Asp
                245                 250                 255

Ala Pro Phe Gln Cys Trp Leu Cys Ser Ala Lys Phe Lys Ile Ser Ser
            260                 265                 270

Asp Leu Lys Arg His Met Arg Val His Ser Gly Glu Lys Pro Phe Lys
            275                 280                 285

Cys Glu Phe Cys Asn Val Arg Cys Thr Met Lys Gly Asn Leu Lys Ser
290                 295                 300

His Ile Arg Ile Lys His Ser Gly Asn Asn Phe Lys Cys Pro His Cys
305                 310                 315                 320

Asp Phe Leu Gly Asp Ser Lys Ala Thr Leu Arg Lys His Ser Arg Val
                325                 330                 335

His Gln Ser Glu His Pro Glu Lys Cys Ser Glu Cys Ser Tyr Ser Cys
            340                 345                 350

Ser Ser Lys Ala Ala Leu Arg Ile His Glu Arg Ile His Cys Thr Asp
            355                 360                 365

Arg Pro Phe Lys Cys Asn Tyr Cys Ser Phe Asp Thr Lys Gln Pro Ser
370                 375                 380

Asn Leu Ser Lys His Met Lys Lys Phe His Gly Asp Met Val Lys Thr
385                 390                 395                 400

Glu Ala Leu Glu Arg Lys Asp Thr Gly Arg Gln Ser Ser Arg Gln Val
                405                 410                 415

Ala Lys Leu Asp Ala Lys Lys Ser Phe His Cys Asp Ile Cys Asp Ala
            420                 425                 430

Ser Phe Met Arg Glu Asp Ser Leu Arg Ser His Lys Arg Gln His Ser
            435                 440                 445

Glu Tyr Ser Glu Ser Lys Asn Ser Asp Val Thr Val Leu Gln Phe Gln
```

```
                  450                 455                 460
Ile Asp Pro Ser Lys Gln Pro Ala Thr Pro Leu Thr Val Gly His Leu
465                 470                 475                 480

Gln Val Pro Leu Gln Pro Ser Gln Val Pro Gln Phe Ser Glu Gly Arg
                    485                 490                 495

Val Lys Ile Ile Val Gly His Gln Val Pro Gln Ala Asn Thr Ile Val
                500                 505                 510

Gln Ala Ala Ala Ala Val Asn Ile Val Pro Pro Ala Leu Val Ala
            515                 520                 525

Gln Asn Pro Glu Glu Leu Pro Gly Asn Ser Arg Leu Gln Ile Leu Arg
            530                 535                 540

Gln Val Ser Leu Ile Ala Pro Pro Gln Ser Ser Arg Cys Pro Ser Glu
545                 550                 555                 560

Ala Gly Ala Met Thr Gln Pro Ala Val Leu Leu Thr Thr His Glu Gln
                565                 570                 575

Thr Asp Gly Ala Thr Leu His Gln Thr Leu Ile Pro Thr Ala Ser Gly
                580                 585                 590

Gly Pro Gln Glu Gly Ser Gly Asn Gln Thr Phe Ile Thr Ser Ser Gly
                595                 600                 605

Ile Thr Cys Thr Asp Phe Glu Gly Leu Asn Ala Leu Ile Gln Glu Gly
610                 615                 620

Thr Ala Glu Val Thr Val Ser Asp Gly Gly Gln Asn Ile Ala Val
625                 630                 635                 640

Ala Thr Thr Ala Pro Pro Val Phe Ser Ser Ser Gln Gln Glu Leu
                645                 650                 655

Pro Lys Gln Thr Tyr Ser Ile Ile Gln Gly Ala Ala His Pro Ala Leu
                660                 665                 670

Leu Cys Pro Ala Asp Ser Ile Pro Asp
                675                 680

<210> SEQ ID NO 53
<211> LENGTH: 5457
<212> TYPE: DNA
<213> ORGANISM: Homo sapiens

<400> SEQUENCE: 53
cggccgcggc tgctgcttcc tcgggccatt ttgctgtgga gcggcgggga ggaggagccg      60
ccgaggagac cccgggcgag gagctgcgag ccggaggagg ccgcgcggac tccgggcttt     120
ccgccgtcgc ggggatctcg gggggcaaag ggatcgccgg ggaggggggac cagagagccg    180 cgcccgccgc gcggagcgcc ccttcgcgtc cctgcacca tgagctgggg caccgagctc    240
tgggatcagt ttgacaactt agaaaaacac acacagtggg gaattgatat tcttgagaaa    300
tatatcaagt ttgtgaaaga aggacagag attgaactca gctatgcaaa gcaactcagg    360
aatctttcaa agaagtacca acctaaaaag aactcgaagg aggaagaaga atacaagtat    420
acgtcatgta aagctttcat ttccaacctg aacgaaatga atgattacgc agggcagcat    480
gaagttatct ccgagaacat ggcatcacag atcattgtgg acttggcacg ctatgttcag    540
gaactgaaac aggagaggaa atcaaacttt cacgatggcc gtaaagcaca gcagcacatc    600
gagacttgct ggaagcagct tgaatctagt aaaaggcgat ttgaacgcga ttgcaaagag    660
gcggacaggg cgcagcagta ctttgagaaa atggacgctg acatcaatgt cacaaaagcg    720
gatgttgaaa aggcccgaca acaagctcaa atacgtcacc aaatggcaga ggacagcaaa    780
gcagattact catccattct ccagaaattc aaccatgagc agcatgaata ttaccatact    840
```

```
cacatcccca acatcttcca gaaaatacaa gagatggagg aaaggaggat tgtgagaatg    900
ggagagtcca tgaagacata tgcagaggtt gatcggcagg tgatcccaat cattgggaag    960
tgcctggatg gaatagtaaa agcagccgaa tcaattgatc agaaaaatga ttcacagctg   1020
gtaatagaag cttataaatc agggtttgag cctcctggag acattgaatt tgaggattac   1080
actcagccaa tgaagcgcac tgtgtcagat aacagccttt caaattccag aggagaaggc   1140
aaaccagacc tcaaatttgg tggcaaatcc aaaggaaagt tatggccgtt catcaaaaaa   1200
aataagctta tgtccctttt aacatccccc catcagcctc cccctccccc tcctgcctct   1260
gcctcaccct ctgctgttcc caacggcccc cagtctccca agcagcaaaa ggaaccectc   1320 tcccatcgct tcaacgagtt catgacctcc aaacccaaaa tccactgctt caggagccta   1380
aagcgtgggc tttctctcaa gctgggtgca acaccggagg atttcagcaa cctcccacct   1440
gaacaaagaa ggaaaaagct gcagcagaaa gtcgatgagt taaataaaga aattcagaag   1500
gagatggatc aaagagatgc cataacaaaa atgaaagatg tctacctaaa gaatcctcag   1560
atgggagacc cagccagttt ggatcacaaa ttagcagaag tcagccaaaa tatagagaaa   1620
ctgcgagtag agacccagaa atttgaggcc tggctggctg aggttgaagg ccggctccca   1680
gcacgcagcg agcaggcgcg ccggcagagc ggactgtacg acagccagaa cccacccaca   1740
gtcaacaact gcgcccagga ccgtgagagc ccagatggca gttacacaga ggagcagagt   1800
caggagagtg agatgaaggt gctggccacg gattttgacg acgagtttga tgatgaggag   1860
cccctccctg ccatagggac gtgcaaagct ctctacacat ttgaaggtca gaatgaagga   1920
acgatttccg tagttgaagg agaaacattg tatgtcatag aggaagacaa aggcgatggc   1980 tggaccegca ttcggagaaa tgaagatgaa gagggttatg tccccacttc atatgtcgaa   2040
gtctgtttgg acaaaaatgc caaagattcc tagagggag tgcctgcgag cctcgggtga   2100
gccttcctgg aggagcctcc gtctgcttgt cccacaggc ctccagcgcc ctgccctgtg   2160
gacagcccac ccctccgcag ccccatccct gcgggcggt ctctctctct ctccagcatg   2220
ctccctgcgg ccctgccctc ccgcccagcc cgggccacct cgtggggac aagtctcgcc   2280 agcgcccacc cccatggctc gggtcagtcc tcatcgctcc ccctcccac cccgcgcagg   2340 ccactgagac ggtgggacac acgcccctac ctgctccttc ctgggccctc agtccacccg   2400
ggctcgtcct ggcagccctt ccgcgcttca cacagtgcct tttgtgaaag tgtcatcacg   2460
ggtcccctga ggagacaagg caggtccagc gcacatcagg cggactgagc actcgatgtc   2520
atccgtgtcg atgtcatccg tgtgtcccag actgtctgct gtagaaaaca cttcctcctc   2580
tcctgagtct gtgaagtcct cagtggtcct tttgattc taggcttgca cctcatacta   2640
aacattgacc ctttcactat gccctcaacc tgggagcatc tggcaggcag gggggcaggt   2700
acacacacac ccacaggcac acccaccagt acacacgcgt gcgcatacac acattttggt   2760
ttgacgccct gttttcagtg gcctggggag gtccacactg gaagtcgaat tccagctcgc   2820
cttgttgact cgcctgtgtc caccggccat gaggagccca cgcctgtcct ccccatcact   2880
ttcctgtccc tgagaactgt agatcatgcg cttgtgagcg aggccctccc ctctgccacca   2940 gctcattgca aagcgaacat cctctcctt ccaggagccc caggattagc atctgaaaag   3000
ggtagcactt ccttttttgt tgttgttttt ttttttttt tgagacggga gtctcgctct   3060
attgttcaga ctggagtgca gtggcatgat ctcggctcac tacaacctcc acctcctggg   3120
ttccagcgat tctcctgcct cagcctccca aatagctgtg attacaggcg tgcaccacca   3180
cgcccggcta atgtttgtat ttttagtaga cagggtttt caccgtgttg gtcaggctgg   3240
```

```
tctcaaactc ctgacctcag gtgatccgcc cgcctcagcc tcccaaagtg ctgagattac    3300
aggtgtgagc taccgcaccc cgccgaggtt agcactttca tcaccaaaga ccccgtgcct    3360
ctcgtggtcc tttgagggat cccgccgcca ccacccttgt attttatcac gtgctcttca    3420
gggcatgtgg aattcgttga gtttgctttt agagccaagt tctttccct gtgtgggttt    3480
ttgaggaaaa cctgaggtcc cctaatctgt ggccaccacc cccccccc gccacgcctt    3540
agagcagagc agcccctcct ctcatttggt gcagaaacag tcaagaggaa ccattggcct    3600
agagctcctg tgaccgagag cgccacggaa gcctggggat gacgtcgggc agctttattc    3660
tttgcttggc tttggtaact aggtggtccc ctcaagcatc ctcagttcct cttgctgttt    3720
atgaatctaa gacaaggaag tcctatagaa gccaaggga cagggacgga aaggacaggt    3780
cccaagggat ggggctgtct ttacttgtgg aaaccaggaa attgctcctc tcagccaacc    3840
aaggttgacc acacaccacc cttccggagc agctcagtca gccctcgggg acgagaaacc    3900
acaagcgcag agacgctgag gcccaggcag gtgaagagga agtggctttg ggttttaaa    3960
gtaggtgagc gtgagcctct ctgactgctt cttccccggg ggggactgca aaccgctcag    4020
ggttgcggca gagccatgga cttccggtcc ctgcaacggg tgacctaagc gtggtgcacc    4080
catcagtcac gcaggaggac tgacttgaca gacgaaagac aagcccggat gacacagggt    4140
gagaagagtc agggccgcac ctctgtccct gcaaaccaac aggtgcatgg tgagtgtggc    4200
agtccccaca gctccacaat gggctccccc gccaacgggg acgacaggga tcttcaggaa    4260
cttctgacct caccaagtca gtggaccac tctccactcc acgaggatgt gaaacggttc    4320
tttaaaatgg gatttagag cctcgggaat gcatgtgcgt cacatctttc atattatggg    4380
tcaggataga ttcatttctt gcaacatagt ggaaaagata taagctgcag taatttgctc    4440
tttgaatgac cgtcaccccc agtataggat atgcttgtat ccccccgtca ctcctccgcc    4500
tgtttttaa acttttccac cacctgcgtc caaaaagaat gttatagcga gtgctcttaa    4560
atgttgaacc tgggtgttgc ttccgggcca gtctgcgtgg ctccatgaaa agctcactgc    4620
tgccccagcc gggcttctta gaggaggtca gttgtcctat gtatcatcat ttactctggg    4680
aatcctactg tgaaatcatg tctgtatttt tctggagcag ttcacataga gtagaatgtg    4740
gaatttcccg tgaacgtctc cttcctcccc cgtatctgcc gcctgtcact tcgccaccgt    4800
gctagaatac tgttgtgttg taagatgact aattttaaaa gaacctgccc tgaaaagttc    4860
ttagaaacgc agtgaaaggg aggaacttgt cctttaccca gttttttcctt tgtaggatgg    4920
gaaagtataa aaaggcacag aaggttgtca tgggctgttc cttgggggtt tttatcctgc    4980
tcaccgtgga gataagcctg cggcttgtct aaccagcgca gcgcaaaggt ctcgatgcct    5040
tttggtaaca tccgtcattg cagaagaaag tttacgcgac gtcaaaaagt gacgttcatg    5100
ctaagtgttt ttccagaaat attggtttca tgtttcttat tggctctgcc tcctgtgctt    5160
atatcatcca aaaactttt aaaaaggtcc agaattctat tttaacctga tgttgagcac    5220
ctttaaaatg ttcgtatgtg tgttgcacta attctaaact ttggaggcat tttgctgtgt    5280
gaggccgatc gccactgtaa aggtcctaga gttgcctgtt tgtctctgga gatggaatta    5340
aaccaaataa agagcttcca ctggaggctt gtattgacct tgtaactata tgttaatctc    5400
gtgttaaaat aaaatataac ttgtgaaaaa aaaaaaaaa aaaaaaaaa aaaaaaa       5457
```

<210> SEQ ID NO 54
<211> LENGTH: 617
<212> TYPE: PRT
<213> ORGANISM: Homo sapiens -continued

```
<400> SEQUENCE: 54

Met Ser Trp Gly Thr Glu Leu Trp Asp Gln Phe Asp Asn Leu Glu Lys
  1               5                  10                  15

His Thr Gln Trp Gly Ile Asp Ile Leu Glu Lys Tyr Ile Lys Phe Val
             20                  25                  30

Lys Glu Arg Thr Glu Ile Glu Leu Ser Tyr Ala Lys Gln Leu Arg Asn
         35                  40                  45

Leu Ser Lys Lys Tyr Gln Pro Lys Lys Asn Ser Lys Glu Glu Glu Glu
 50                  55                  60

Tyr Lys Tyr Thr Ser Cys Lys Ala Phe Ile Ser Asn Leu Asn Glu Met
 65                  70                  75                  80

Asn Asp Tyr Ala Gly Gln His Glu Val Ile Ser Glu Asn Met Ala Ser
                 85                  90                  95

Gln Ile Ile Val Asp Leu Ala Arg Tyr Val Gln Glu Leu Lys Gln Glu
             100                 105                 110

Arg Lys Ser Asn Phe His Asp Gly Arg Lys Ala Gln Gln His Ile Glu
         115                 120                 125

Thr Cys Trp Lys Gln Leu Glu Ser Ser Lys Arg Arg Phe Glu Arg Asp
130                 135                 140

Cys Lys Glu Ala Asp Arg Ala Gln Gln Tyr Phe Glu Lys Met Asp Ala
145                 150                 155                 160

Asp Ile Asn Val Thr Lys Ala Asp Val Glu Lys Ala Arg Gln Gln Ala
                165                 170                 175

Gln Ile Arg His Gln Met Ala Glu Asp Ser Lys Ala Asp Tyr Ser Ser
            180                 185                 190

Ile Leu Gln Lys Phe Asn His Glu Gln His Glu Tyr Tyr His Thr His
        195                 200                 205

Ile Pro Asn Ile Phe Gln Lys Ile Gln Glu Met Glu Glu Arg Arg Ile
    210                 215                 220

Val Arg Met Gly Glu Ser Met Lys Thr Tyr Ala Glu Val Asp Arg Gln
225                 230                 235                 240

Val Ile Pro Ile Ile Gly Lys Cys Leu Asp Gly Ile Val Lys Ala Ala
                245                 250                 255

Glu Ser Ile Asp Gln Lys Asn Asp Ser Gln Leu Val Ile Glu Ala Tyr
            260                 265                 270

Lys Ser Gly Phe Glu Pro Pro Gly Asp Ile Glu Phe Glu Asp Tyr Thr
        275                 280                 285

Gln Pro Met Lys Arg Thr Val Ser Asp Asn Ser Leu Ser Asn Ser Arg
    290                 295                 300

Gly Glu Gly Lys Pro Asp Leu Lys Phe Gly Gly Lys Ser Lys Gly Lys
305                 310                 315                 320

Leu Trp Pro Phe Ile Lys Lys Asn Lys Leu Met Ser Leu Leu Thr Ser
                325                 330                 335

Pro His Gln Pro Pro Pro Pro Ala Ser Ala Ser Pro Ser Ala
            340                 345                 350

Val Pro Asn Gly Pro Gln Ser Pro Lys Gln Lys Glu Pro Leu Ser
        355                 360                 365

His Arg Phe Asn Glu Phe Met Thr Ser Lys Pro Lys Ile His Cys Phe
    370                 375                 380

Arg Ser Leu Lys Arg Gly Leu Ser Leu Lys Leu Gly Ala Thr Pro Glu
385                 390                 395                 400

Asp Phe Ser Asn Leu Pro Pro Glu Gln Arg Arg Lys Lys Leu Gln Gln
                405                 410                 415
```

| | | | | | | | | | | | |
|---|---|---|---|---|---|---|---|---|---|---|---|
|Lys|Val|Asp|Glu|Leu|Asn|Lys|Glu|Ile|Gln|Lys|Glu|Met|Asp|Gln|Arg|
| | |420| | | |425| | | |430| |

Asp Ala Ile Thr Lys Met Lys Asp Val Tyr Leu Lys Asn Pro Gln Met
            435                 440                 445

Gly Asp Pro Ala Ser Leu Asp His Lys Leu Ala Glu Val Ser Gln Asn
    450                 455                 460

Ile Glu Lys Leu Arg Val Glu Thr Gln Lys Phe Glu Ala Trp Leu Ala
465             470                 475                 480

Glu Val Glu Gly Arg Leu Pro Ala Arg Ser Glu Gln Ala Arg Arg Gln
                485                 490                 495

Ser Gly Leu Tyr Asp Ser Gln Asn Pro Pro Thr Val Asn Asn Cys Ala
            500                 505                 510

Gln Asp Arg Glu Ser Pro Asp Gly Ser Tyr Thr Glu Glu Gln Ser Gln
            515                 520                 525

Glu Ser Glu Met Lys Val Leu Ala Thr Asp Phe Asp Asp Glu Phe Asp
530                 535                 540

Asp Glu Glu Pro Leu Pro Ala Ile Gly Thr Cys Lys Ala Leu Tyr Thr
545                 550                 555                 560

Phe Glu Gly Gln Asn Glu Gly Thr Ile Ser Val Val Glu Gly Glu Thr
                565                 570                 575

Leu Tyr Val Ile Glu Glu Asp Lys Gly Asp Gly Trp Thr Arg Ile Arg
            580                 585                 590

Arg Asn Glu Asp Glu Glu Gly Tyr Val Pro Thr Ser Tyr Val Glu Val
            595                 600                 605

Cys Leu Asp Lys Asn Ala Lys Asp Ser
610                 615

<210> SEQ ID NO 55
<211> LENGTH: 696
<212> TYPE: DNA
<213> ORGANISM: Homo sapiens

<400> SEQUENCE: 55 ttccccccc ccccccccc ccccgcccga gcacaggaca cagctgggtt ctgaagcttc      60
tgagttctgc agcctcacct ctgagaaaac ctctttttcca ccaataccat gaagctctgc     120
gtgactgtcc tgtctctcct catgctagta gctgccttct gctctccagc gctctcagca     180
ccaatgggct cagaccctcc caccgcctgc tgcttttctt acaccgcgag gaagcttcct     240
cgcaactttg tggtagatta ctatgagacc agcagcctct gctcccagcc agctgtggta     300
ttccaaacca aaagaagcaa gcaagtctgt gctgatccca gtgaatcctg ggtccaggag     360
tacgtgtatg acctggaact gaactgagct gctcagagac aggaagtctt cagggaaggt     420
cacctgagcc cggatgcttc tccatgagac acatctcctc catactcagg actcctctcc     480
gcagttcctg tcccttctct taatttaatc ttttttatgt gccgtgttat tgtattaggt     540
gtcatttcca ttatttatat tagtttagcc aaaggataag tgtcctatgg ggatggtcca     600
ctgtcactgt ttctctgctg ttgcaaatac atggataaca catttgattc tgtgtgtttt     660
ccataataaa actttaaaat aaaatgcaga cagtta                               696

<210> SEQ ID NO 56
<211> LENGTH: 92
<212> TYPE: PRT
<213> ORGANISM: Homo sapiens

<400> SEQUENCE: 56

Met Lys Leu Cys Val Thr Val Leu Ser Leu Leu Met Leu Val Ala Ala

```
              1               5              10              15
Phe Cys Ser Pro Ala Leu Ser Ala Pro Met Gly Ser Asp Pro Pro Thr
             20                  25                  30
Ala Cys Cys Phe Ser Tyr Thr Ala Arg Lys Leu Pro Arg Asn Phe Val
         35                  40                  45
Val Asp Tyr Tyr Glu Thr Ser Ser Leu Cys Ser Gln Pro Ala Val Val
     50                  55                  60
Phe Gln Thr Lys Arg Ser Lys Gln Val Cys Ala Asp Pro Ser Glu Ser
 65                  70                  75                  80
Trp Val Gln Glu Tyr Val Tyr Asp Leu Glu Leu Asn
                 85                  90

<210> SEQ ID NO 57
<211> LENGTH: 5064
<212> TYPE: DNA
<213> ORGANISM: Homo sapiens

<400> SEQUENCE: 57
gagaagggga ccttcaggtc caggcaaagg gggaacttct gtcgtgggaa cgaaaaagaa      60
agaggattta cagggtgggg ggacagaggg gcagcaggaa ccagaaggga gacagtggcg     120
gtcgcaccgg ggccgatccg agagttcccc ttagagaacg gagctcacgg gcggggaggc     180
ctcacctgct agtaggacgc agaaagacag aaggcgaagg agaccccctg ccgtagccat     240
cttgcctctc tgctgagcgg aagcccccgt tcggctcctg tctgttagcg gcctctctag     300
gctaccactg acaccgtctc tgtggcccgg agcctaagag accggaagtt cgtgtttcca     360
ggcgcttccg gaaaccgcgg gagagggtcg ctgacgtgga ggcgtccgaa gggcagcagg     420
gtgtgtcggg gctcggatta agacatcgga gtcggagacc tgagagatgt taaccaaatt     480
cgagaccaag agcgcgcggg tcaaagggct cagctttcac cccaaaagac cttggatcct     540
gactagttta cataatgggg tcatccagtt atgggactat cggatgtgca ctctcattga     600
caagtttgat gaacatgatg gtccagtgcg aggcattgac ttccataagc agcagccact     660
gttcgtctct ggaggagatg actataagat taaggtttgg aattacaagc ttcggcgctg     720
tcttttcaca ttgcttgggc acttagatta tattcgcacc acgttttttc atcatgaata     780
tccctggatt ctgagtgcct ccgatgatca gaccatccga gtgtggaatt ggcaatctag     840
aacctgtgtt tgtgtgttaa cagggcacaa ccattatgtg atgtgtgctc agttccaccc     900
cacagaagac ttggtagtat cagccagcct ggaccagact gtgcgcgttt gggatatttc     960
tggtctgagg aaaaaaaacc tgtcccctgg tgcggtggaa tcggatgtga gaggaataac    1020
tggggttgat ctatttggaa ctacagatgc agtggtgaag catgtactag agggtcacga    1080
tcgtggagta aactgggctg ccttccaccc cactatgccc cttattgtat ctggggcaga    1140
tgatcgtcaa gtgaagatct ggcgcatgaa tgaatcaaag gcatgggagg ttgatacctg    1200
ccgggggcat tacaacaatg tatcttgtgc cgtcttccac cctcgccaag agttgatcct    1260
cagcaattct gaggacaaga gtattcgagt ctgggatatg tctaagcgga ctggggttca    1320
gactttccgc agagaccatg atcgtttctg ggtcctagct gctcacccta accttaacct    1380
ctttgcagca ggccatgatg gtggtatgat tgtgtttaag ctggaacggg aacggccagc    1440
ctatgctgtt catggcaata tgctacacta tgtcaaggac cgattcttac gacagctgga    1500
tttcaacagc tccaaagatg tagctgtgat gcagttgcgg agtggttcca gtttccagt    1560
attcaatatg tcatacaatc cagcagaaaa tgcagtcctg ctttgtacaa gagctagcaa    1620
tctagagaat agtacctatg acctgtacac catccctaaa gatgctgact cccagaatcc    1680
```

```
tgatgcgcct gaagggaaac gatcctcagg cctgacagcc gtttgggtcg ctcgaaatcg   1740
gtttgctgtc ctagatcgga tgcattcgct tctgatcaag aatctgaaga atgagatcac   1800
caaaaaggta caggtgccca actgtgatga gatcttctat gctggacag  gcaatctcct   1860 gcttcgagat gcggactcta tcacactctt tgacgtacag cagaagcgga ctctggcatc   1920
tgtgaagatt tctaaagtga aatacgttat ctggtcagca gacatgtcac atgtagcact   1980
actagccaaa cacgccattg tgatctgtaa ccgcaaactg gatgctttat gtaacattca   2040
tgagaacatt cgtgtcaaga gtggggcctg ggatgagagt ggggtattta tctataccac   2100
aagcaaccac atcaaatatg ctgtcaccac tggggaccac gggatcattc gaactctgga   2160
tttacccatc tatgtcacac gggtgaaggg caacaatgta tactgcctag acagggagtg   2220
tcgtccccgg gtactcacca ttgatcccac tgagttcaaa ttcaagctgg ccctgatcaa   2280
cagaaaatat gatgaggtac tgcacatggt gaggaatgcc aaactagttg gccagtctat   2340
tattgcttat ctccagaaga agggctatcc tgaagtggca ctgcattttg tcaaggatga   2400
gaaaactcgc tttagtctgg cactggagtg tggaaacatt gagattgctc tggaagcagc   2460
caaagcactg gatgacaaga actgctggga aaagctggga gaagtggccc tgctgcaggg   2520
gaaccaccag attgtggaaa tgtgctatca gcgtaccaaa aactttgaca aagtttcctt   2580
cctgtatctt atcactggca acttagaaaa acttcgcaag atgatgaaga ttgctgagat   2640
cagaaaggac atgagtggcc actatcagaa tgccctatac ctgggtgatg tgtcagagcg   2700
tgtgcggatc ctgaagaact gtggacagaa gtccctggcc tatctcacag ctgctaccca   2760
tggcttagat gaagaagctg agagcctaaa ggagacattt gacccagaga aggagacaat   2820
cccagacatt gaccctaatg ccaagctgct ccagccacct gcacctatca tgccattgga   2880
taccaattgg cctttattga ctgtatccaa aggattttt  gaaggcacca ttgccagcaa   2940
agggaaggga ggagcactgg ctgctgacat tgacattgac actgttggta cagagggctg   3000
gggagaggat gcagagctgc agttggatga agatgggttt gtggaggcta cagaaggttt   3060
gggggatgat gctcttggca agggacagga agaaggaggt ggctgggatg tagaagaaga   3120
tctggagctc cctcctgagc tggatatatc ccctggggca gctggtgggg ctgaagatgg   3180
tttctttgtg cccccaacca agggaacaag tccaactcag atctggtgta ataactctca   3240
gcttccagtt gatcacatcc tggcaggctc tttcgaaaca gccatgcggc tccttcatga   3300
ccaagtaggg gtaatccagt ttggccccta caagcaactg ttcctacaga catacgcccg   3360
aggccgcaca acctatcagg ctctgccctg cctaccctcc atgtatggct atcctaatcg   3420
caactggaag gatgcagggc tgaagaatgg tgtaccagct gtgggcctga gcttaatga   3480 cctcatccaa cggttgcagc tgtgctacca gctcaccaca gttggcaaat tgaggaggc   3540 tgtggaaaaa ttccgttcca tccttctcag tgtgccactt cttgttgtgg acaataaaca   3600
agagattgca gaggcccagc agctcatcac catttgccgt gagtacattg tgggtttgtc   3660
cgtggagaca gaaaggaaga agctgcccaa agagactcta aacagcaga  agcgcatctg   3720 tgagatggca gcctatttca cccactcaaa cctgcagcct gtgcacatga tcctggtgct   3780
gcgtacagcc tcaatctgt  tcttcaagct caagaacttc aagacagctg ccacctttgc   3840
tcggcgccta ctagaactcg ggcccaagcc tgaggtggcc caacagaccc gaaaaatcct   3900
gtctgcctgt gagaagaatc ccacagatgc ctaccagctc aattatgaca tgcacaaccc   3960 cttttgacatt tgtgctgcat catatcgcc  catctaccgt ggaaagccag tagaaaagtg   4020
tccactcagt ggggcctgct attcccctga gttcaaaggt caaatctgca gggtcaccac   4080
```

```
agtgacagag attggcaaag atgtgattgg tttaaggatc agtcctctgc agtttcgcta    4140
aggccccctt tgtgtgcatg ggtcagtcac catatgttcc ccccagagaa tgtgtctata    4200
tcctccttct aacagcacct tcccctgca gctactcttc agatctggct ctctgtaccc     4260
taaaacctag tatcttttc tcttctatgg aaaatccgaa ggtctaaact tgactttttt    4320
gaggtcttct caacttgact acagttgtgc tcataattgt ccttgccttt ccagcttaat    4380
tattttaagg aacaaatgaa aactctgggc tgggtggagt ggctcatacc tgtaatccca    4440
gcactttggg aggctacggt gggcagatca tctgaggcca ggagttcgag acctgcctgg    4500
ccaacatggc aacaccccgt ctctaataaa aatataaaaa ttagcctggc atggtagcat    4560
gcgcctatag tcccagctgc tcaggaggct gaggcatgag aatcgcttga acctaggagg    4620
tggaggttgc attcaactga gatcatacca cttcattcca gcctgggtga cagagcaaga    4680
ctctgtctca aaaaaaaaaa aaaaaaaaaa aaaaaaaaaa aaaggaaaac tctgtgatgg    4740
acatttgttt agtaaatccc ttcagtattt atccctcctt tccccacagc agctttcttt    4800
cctgtcaact agaaggagc aggatgtaat aaatacattt tggtgtgact aggccacacc     4860
aactcttaat catctcccat tttccttaga catttaaatt tcaaggcagg taccctctgt    4920
gtactcagaa atttgaagaa gttatttggt tttccaaaat gcacactgcg ggttattgat    4980
ttgttcttta caactattgt tctcatattt ctcacactaa ataaatctct atgagagctt    5040
cttgaaaaaa aaaaaaaaaa agcg                                           5064

<210> SEQ ID NO 58
<211> LENGTH: 1224
<212> TYPE: PRT
<213> ORGANISM: Homo sapiens

<400> SEQUENCE: 58

Met Leu Thr Lys Phe Glu Thr Lys Ser Ala Arg Val Lys Gly Leu Ser
1               5                   10                  15

Phe His Pro Lys Arg Pro Trp Ile Leu Thr Ser Leu His Asn Gly Val
            20                  25                  30

Ile Gln Leu Trp Asp Tyr Arg Met Cys Thr Leu Ile Asp Lys Phe Asp
        35                  40                  45

Glu His Asp Gly Pro Val Arg Gly Ile Asp Phe His Lys Gln Gln Pro
    50                  55                  60

Leu Phe Val Ser Gly Gly Asp Asp Tyr Lys Ile Lys Val Trp Asn Tyr
65                  70                  75                  80

Lys Leu Arg Arg Cys Leu Phe Thr Leu Leu Gly His Leu Asp Tyr Ile
                85                  90                  95

Arg Thr Thr Phe Phe His His Glu Tyr Pro Trp Ile Leu Ser Ala Ser
            100                 105                 110

Asp Asp Gln Thr Ile Arg Val Trp Asn Trp Gln Ser Arg Thr Cys Val
        115                 120                 125

Cys Val Leu Thr Gly His Asn His Tyr Val Met Cys Ala Gln Phe His
    130                 135                 140

Pro Thr Glu Asp Leu Val Val Ser Ala Ser Leu Asp Gln Thr Val Arg
145                 150                 155                 160

Val Trp Asp Ile Ser Gly Leu Arg Lys Lys Asn Leu Pro Gly Ala
                165                 170                 175

Val Glu Ser Asp Val Arg Gly Ile Thr Gly Val Asp Leu Phe Gly Thr
            180                 185                 190

Thr Asp Ala Val Val Lys His Val Leu Glu Gly His Asp Arg Gly Val
```

```
                195                 200                 205
Asn Trp Ala Ala Phe His Pro Thr Met Pro Leu Ile Val Ser Gly Ala
210                 215                 220

Asp Asp Arg Gln Val Lys Ile Trp Arg Met Asn Glu Ser Lys Ala Trp
225                 230                 235                 240

Glu Val Asp Thr Cys Arg Gly His Tyr Asn Asn Val Ser Cys Ala Val
                245                 250                 255

Phe His Pro Arg Gln Glu Leu Ile Leu Ser Asn Ser Glu Asp Lys Ser
                260                 265                 270

Ile Arg Val Trp Asp Met Ser Lys Arg Thr Gly Val Gln Thr Phe Arg
            275                 280                 285

Arg Asp His Asp Arg Phe Trp Val Leu Ala Ala His Pro Asn Leu Asn
            290                 295                 300

Leu Phe Ala Ala Gly His Asp Gly Gly Met Ile Val Phe Lys Leu Glu
305                 310                 315                 320

Arg Glu Arg Pro Ala Tyr Ala Val His Gly Asn Met Leu His Tyr Val
                325                 330                 335

Lys Asp Arg Phe Leu Arg Gln Leu Asp Phe Asn Ser Ser Lys Asp Val
                340                 345                 350

Ala Val Met Gln Leu Arg Ser Gly Ser Lys Phe Pro Val Phe Asn Met
            355                 360                 365

Ser Tyr Asn Pro Ala Glu Asn Ala Val Leu Leu Cys Thr Arg Ala Ser
370                 375                 380

Asn Leu Glu Asn Ser Thr Tyr Asp Leu Tyr Thr Ile Pro Lys Asp Ala
385                 390                 395                 400

Asp Ser Gln Asn Pro Asp Ala Pro Glu Gly Lys Arg Ser Ser Gly Leu
                405                 410                 415

Thr Ala Val Trp Val Ala Arg Asn Arg Phe Ala Val Leu Asp Arg Met
            420                 425                 430

His Ser Leu Leu Ile Lys Asn Leu Lys Asn Glu Ile Thr Lys Lys Val
            435                 440                 445

Gln Val Pro Asn Cys Asp Glu Ile Phe Tyr Ala Gly Thr Gly Asn Leu
450                 455                 460

Leu Leu Arg Asp Ala Asp Ser Ile Thr Leu Phe Asp Val Gln Gln Lys
465                 470                 475                 480

Arg Thr Leu Ala Ser Val Lys Ile Ser Lys Val Lys Tyr Val Ile Trp
                485                 490                 495

Ser Ala Asp Met Ser His Val Ala Leu Leu Ala Lys His Ala Ile Val
            500                 505                 510

Ile Cys Asn Arg Lys Leu Asp Ala Leu Cys Asn Ile His Glu Asn Ile
            515                 520                 525

Arg Val Lys Ser Gly Ala Trp Asp Glu Ser Gly Val Phe Ile Tyr Thr
530                 535                 540

Thr Ser Asn His Ile Lys Tyr Ala Val Thr Thr Gly Asp His Gly Ile
545                 550                 555                 560

Ile Arg Thr Leu Asp Leu Pro Ile Tyr Val Thr Arg Val Lys Gly Asn
                565                 570                 575

Asn Val Tyr Cys Leu Asp Arg Glu Cys Arg Pro Arg Val Leu Thr Ile
                580                 585                 590

Asp Pro Thr Glu Phe Lys Phe Lys Leu Ala Leu Ile Asn Arg Lys Tyr
            595                 600                 605

Asp Glu Val Leu His Met Val Arg Asn Ala Lys Leu Val Gly Gln Ser
610                 615                 620
```

```
Ile Ile Ala Tyr Leu Gln Lys Lys Gly Tyr Pro Glu Val Ala Leu His
625                 630                 635                 640

Phe Val Lys Asp Glu Lys Thr Arg Phe Ser Leu Ala Leu Glu Cys Gly
            645                 650                 655

Asn Ile Glu Ile Ala Leu Glu Ala Ala Lys Ala Leu Asp Asp Lys Asn
                660                 665                 670

Cys Trp Glu Lys Leu Gly Glu Val Ala Leu Leu Gln Gly Asn His Gln
        675                 680                 685

Ile Val Glu Met Cys Tyr Gln Arg Thr Lys Asn Phe Asp Lys Val Ser
690                 695                 700

Phe Leu Tyr Leu Ile Thr Gly Asn Leu Glu Lys Leu Arg Lys Met Met
705                 710                 715                 720

Lys Ile Ala Glu Ile Arg Lys Asp Met Ser Gly His Tyr Gln Asn Ala
            725                 730                 735

Leu Tyr Leu Gly Asp Val Ser Glu Arg Val Arg Ile Leu Lys Asn Cys
                740                 745                 750

Gly Gln Lys Ser Leu Ala Tyr Leu Thr Ala Thr His Gly Leu Asp
        755                 760                 765

Glu Glu Ala Glu Ser Leu Lys Glu Thr Phe Asp Pro Glu Lys Glu Thr
770                 775                 780

Ile Pro Asp Ile Asp Pro Asn Ala Lys Leu Leu Gln Pro Pro Ala Pro
785                 790                 795                 800

Ile Met Pro Leu Asp Thr Asn Trp Pro Leu Leu Thr Val Ser Lys Gly
            805                 810                 815

Phe Phe Glu Gly Thr Ile Ala Ser Lys Gly Lys Gly Gly Ala Leu Ala
                820                 825                 830

Ala Asp Ile Asp Ile Asp Thr Val Gly Thr Glu Gly Trp Gly Glu Asp
        835                 840                 845

Ala Glu Leu Gln Leu Asp Glu Asp Gly Phe Val Glu Ala Thr Glu Gly
850                 855                 860

Leu Gly Asp Asp Ala Leu Gly Lys Gly Gln Glu Gly Gly Gly Trp
865                 870                 875                 880

Asp Val Glu Glu Asp Leu Glu Leu Pro Pro Glu Leu Asp Ile Ser Pro
            885                 890                 895

Gly Ala Ala Gly Gly Ala Glu Asp Gly Phe Phe Val Pro Pro Thr Lys
                900                 905                 910

Gly Thr Ser Pro Thr Gln Ile Trp Cys Asn Asn Ser Gln Leu Pro Val
        915                 920                 925

Asp His Ile Leu Ala Gly Ser Phe Glu Thr Ala Met Arg Leu Leu His
930                 935                 940

Asp Gln Val Gly Val Ile Gln Phe Gly Pro Tyr Lys Gln Leu Phe Leu
945                 950                 955                 960

Gln Thr Tyr Ala Arg Gly Arg Thr Thr Tyr Gln Ala Leu Pro Cys Leu
            965                 970                 975

Pro Ser Met Tyr Gly Tyr Pro Asn Arg Asn Trp Lys Asp Ala Gly Leu
                980                 985                 990

Lys Asn Gly Val Pro Ala Val Gly  Leu Lys Leu Asn Asp  Leu Ile Gln
        995                 1000                1005

Arg Leu  Gln Leu Cys Tyr Gln  Leu Thr Thr Val Gly  Lys Phe Glu
    1010                1015                1020

Glu Ala  Val Glu Lys Phe Arg  Ser Ile Leu Leu Ser  Val Pro Leu
    1025                1030                1035

Leu Val  Val Asp Asn Lys Gln  Glu Ile Ala Glu Ala  Gln Gln Leu
    1040                1045                1050
```

| Ile | Thr | Ile | Cys | Arg | Glu | Tyr | Ile | Val | Gly | Leu | Ser | Val | Glu | Thr |
| | 1055 | | | | 1060 | | | | | 1065 | | | | |

| Glu | Arg | Lys | Lys | Leu | Pro | Lys | Glu | Thr | Leu | Glu | Gln | Gln | Lys | Arg |
| 1070 | | | | | 1075 | | | | | 1080 | | | | |

Ile Cys Glu Met Ala Ala Tyr Phe Thr His Ser Asn Leu Gln Pro
   1085                1090                1095

Val His Met Ile Leu Val Leu Arg Thr Ala Leu Asn Leu Phe Phe
   1100                1105                1110

Lys Leu Lys Asn Phe Lys Thr Ala Ala Thr Phe Ala Arg Arg Leu
   1115                1120                1125

Leu Glu Leu Gly Pro Lys Pro Glu Val Ala Gln Gln Thr Arg Lys
   1130                1135                1140

Ile Leu Ser Ala Cys Glu Lys Asn Pro Thr Asp Ala Tyr Gln Leu
   1145                1150                1155

Asn Tyr Asp Met His Asn Pro Phe Asp Ile Cys Ala Ala Ser Tyr
   1160                1165                1170

Arg Pro Ile Tyr Arg Gly Lys Pro Val Glu Lys Cys Pro Leu Ser
   1175                1180                1185

Gly Ala Cys Tyr Ser Pro Glu Phe Lys Gly Gln Ile Cys Arg Val
   1190                1195                1200

Thr Thr Val Thr Glu Ile Gly Lys Asp Val Ile Gly Leu Arg Ile
   1205                1210                1215

Ser Pro Leu Gln Phe Arg
   1220

<210> SEQ ID NO 59
<211> LENGTH: 2374
<212> TYPE: DNA
<213> ORGANISM: Homo sapiens

<400> SEQUENCE: 59

```
gtcatgcagt gcgccggaga actgtgctct ttgaggccga cgctaggggc ccggaaggaa      60
actgcgaggc gaaggtgacc ggggaccgag catttcagat ctgctcggta gacctggtgc     120
accaccacca tgttggctgc aaggctggtg tgtctccgga cactaccttc tagggttttc     180
cacccagctt tcaccaaggc ctcccctgtt gtgaagaatt ccatcacgaa gaatcaatgg     240
ctgttaacac ctagcaggga atatgccacc aaaacaagaa ttgggatccg gcgtgggaga     300
actggccaag aactcaaaga ggcagcattg aaccatcga tggaaaaaat atttaaaatt     360
gatcagatgg gaagatggtt tgttgctgga ggggctgctg ttggtcttgg agcattgtgc     420
tactatggct tgggactgtc taatgagatt ggagctattg aaaaggctgt aatttggcct     480
cagtatgtca aggatagaat tcattccacc tatatgtact tagcagggag tattggttta     540
acagctttgt ctgccatagc aatcagcaga acgcctgttc tcatgaactt catgatgaga     600
ggctcttggg tgacaattgg tgtgaccttt gcagccatgg ttggagctgg aatgctggta     660
cgatcaatac catatgacca gagcccaggc ccaaagcatc ttgcttggtt gctacattct     720
ggtgtgatgg gtgcagtggt ggctcctctg acaatattag ggggtcctct tctcatcaga     780
gctgcatggt acacagctgg cattgtggga ggcctctcca ctgtggccat gtgtgcgccc     840
agtgaaaagt ttctgaacat gggtgcaccc ctggagtgg gcctgggtct cgtctttgtg     900
tcctcattgg gatctatgtt tcttccacct accaccgtgg ctggtgccac tctttactca     960
gtggcaatgt acgtggatt agttcttttc agcatgttcc ttctgtatga tacccagaaa    1020
gtatcaagcg tgcagaagta tcaccaatgt atggagttca aaaatatgat cccattaact    1080
```

```
cgatgctgag tatctacatg gatacattaa atatatttat gcgagttgca actatgctgg   1140
caactggagg caacagaaag aaatgaagtg actcagcttc tggcttctct gctacatcaa   1200
atatcttgtt taatggggca gatatgcatt aaatagtttg tacaagcagc tttcgttgaa   1260
gtttagaaga taagaaacat gtcatcatat ttaaatgttc cggtaatgtg atgcctcagg   1320
tctgcctttt tttctggaga ataaatgcag taatcctctc ccaaataagc acacacattt   1380
tcaattctca tgtttgagtg attttaaaat gttttggtga atgtgaaaac taaagtttgt   1440
gtcatgagaa tgtaagtctt ttttctactt taaaatttag taggttcact gagtaactaa   1500
aatttagcaa acctgtgttt gcatattttt ttggagtgca gaatattgta attaatgtca   1560
taagtgattt ggagctttgg taaagggacc agagagaagg agtcacctgc agtcttttgt   1620 tttttaaat acttagaact tagcacttgt gttattgatt agtgaggagc cagtaagaaa    1680
catctgggta tttggaaaca agtggtcatt gttacattca tctgctgaac ttaacaaaac   1740
tgttcatcct gaaacaggca caggtgatgc attctcctgc tgttgcttct cagtgctctc   1800
tttccaatat agatgtggtc atgtttgact tgtacagaat gttaatcata cagagaatcc   1860
ttgatggaat tatatatgtg tgttttactt ttgaatgtta caaaaggaaa taactttaaa   1920
actattctca agagaaaata ttcaaagcat gaaatatgtt gcttttttcca gaatacaaac  1980 agtatactca tgaattgcta agtgtttttt tattttgca tatttattga actgtctaat    2040
tgaatacagc ttgctcttgt cacctcttca agctttcaag cctttataga aaagcttctt   2100
tgtggcttac actggaaatt atgaaagcag ttttctcct aagacttttg gtttctcgca    2160
ttgcctctca gactaagcac taaaaagcaa agcaaaacag aactagttct gtcttaatga   2220
aatatatcaa cccaaaagtg taatgaggaa aatgcttcat tagtttcccc tagcagactt   2280
ttacttctct tacactgcta caccattact ttcttgagac atttgtaagt cctttgatac   2340
agaagagtta tatttaggag gctttaatga aggg                               2374
```

<210> SEQ ID NO 60
<211> LENGTH: 319
<212> TYPE: PRT
<213> ORGANISM: Homo sapiens

<400> SEQUENCE: 60

```
Met Leu Ala Ala Arg Leu Val Cys Leu Arg Thr Leu Pro Ser Arg Val
1               5                   10                  15

Phe His Pro Ala Phe Thr Lys Ala Ser Pro Val Val Lys Asn Ser Ile
            20                  25                  30

Thr Lys Asn Gln Trp Leu Leu Thr Pro Ser Arg Glu Tyr Ala Thr Lys
        35                  40                  45

Thr Arg Ile Gly Ile Arg Arg Gly Arg Thr Gly Gln Glu Leu Lys Glu
    50                  55                  60

Ala Ala Leu Glu Pro Ser Met Glu Lys Ile Phe Lys Ile Asp Gln Met
65                  70                  75                  80

Gly Arg Trp Phe Val Ala Gly Ala Ala Val Gly Leu Gly Ala Leu
                85                  90                  95

Cys Tyr Tyr Gly Leu Gly Leu Ser Asn Glu Ile Gly Ala Ile Glu Lys
            100                 105                 110

Ala Val Ile Trp Pro Gln Tyr Val Lys Asp Arg Ile His Ser Thr Tyr
        115                 120                 125

Met Tyr Leu Ala Gly Ser Ile Gly Leu Thr Ala Leu Ser Ala Ile Ala
    130                 135                 140
```

```
Ile Ser Arg Thr Pro Val Leu Met Asn Phe Met Arg Gly Ser Trp
145                 150                 155                 160

Val Thr Ile Gly Val Thr Phe Ala Ala Met Val Gly Ala Gly Met Leu
            165                 170                 175

Val Arg Ser Ile Pro Tyr Asp Gln Ser Pro Gly Pro Lys His Leu Ala
            180                 185                 190

Trp Leu Leu His Ser Gly Val Met Gly Ala Val Val Ala Pro Leu Thr
            195                 200                 205

Ile Leu Gly Gly Pro Leu Leu Ile Arg Ala Ala Trp Tyr Thr Ala Gly
        210                 215                 220

Ile Val Gly Gly Leu Ser Thr Val Ala Met Cys Ala Pro Ser Glu Lys
225                 230                 235                 240

Phe Leu Asn Met Gly Ala Pro Leu Gly Val Gly Leu Gly Leu Val Phe
                245                 250                 255

Val Ser Ser Leu Gly Ser Met Phe Leu Pro Pro Thr Thr Val Ala Gly
                260                 265                 270

Ala Thr Leu Tyr Ser Val Ala Met Tyr Gly Gly Leu Val Leu Phe Ser
            275                 280                 285

Met Phe Leu Leu Tyr Asp Thr Gln Lys Val Ser Ser Val Gln Lys Tyr
290                 295                 300

His Gln Cys Met Glu Phe Lys Asn Met Ile Pro Leu Thr Arg Cys
305                 310                 315

<210> SEQ ID NO 61
<211> LENGTH: 2182
<212> TYPE: DNA
<213> ORGANISM: Homo sapiens

<400> SEQUENCE: 61
ggagagcgag gggcggcggc ggcgcccgct ggcgctcaag catggcggcg gcggcattgg      60
gcagctcctc aggctcggcg tccccggccg tggctgagct ctgccagaac accccggaga     120
cctttttgga ggcctccaag ctgctgctca cctatgctga acatcctca gaaacccta      180 atgatgaaaa atatagatcc atccggattg gaaacacagc cttttctact agactcttgc    240
ctgtcagagg agctgttgaa tgtttatttg aaatgggctt tgaagaggga gaaacacatc   300
tcatctttcc taaaaaagct tcagtggagc agctgcaaaa aattcgtgac ctgattgcca    360
tagagagaag tagcagactg gatggctcaa ataagagcca caagtaaag tcatctcagc    420 aacctgcagc cagtacccag cttcctacaa caccatcttc aaatcccagt gggttaaacc    480
agcacacaag gaaccgtcaa gggcagtcat cagatccacc atctgcttca acggttgctg    540
ctgactcagc cattctagaa gttcttcagt ccaacattca gcatgtgctg gtctatgaaa    600
atcctgctct tcaggagaaa gcgttggctt gtattccggt ccaagaacta aaaaggaaat   660
cacaagaaaa gttatcgaga gctagaaaat tggataaagg tatcaatata agtgatgagg    720
atttttcttt gctggagctt tgcactggt ttaaggaaga ttttttcac tgggtgaata    780 acgttttgtg cagcaaatgt ggtggacaga ctaggtctag agatagatca ttactgccca   840
gtgatgatga gctgaagtgg ggtgcaaagg aagtggaaga tcattactgt gatgcctgcc   900
agttcagcaa tcgattccca agatataata accctgagaa acttttggaa caagatgtg   960 gacggtgtgg cgagtgggcc aattgtttta cactgtgctg ccgagctgta gggtttgaag   1020
ctcgctatgt ttgggattac acagaccatg tctggacaga agtctattct ccttctcagc   1080
agcggtggct gcactgtgat gcatgtgaag atgtctgtga caagccactc ctttatgaaa   1140
taggatgggg caagaagctt tcctatgtca tagcattttc aaaagatgag gtagttgatg    1200
```

-continued

```
tcacttggcg atattcctgc aaacatgaag aggtgattgc cagaagaact aaggttaaag    1260
aagcattact tcgagacact attaatgggc ttaataagca gaggcaactg tttttgtcag    1320
aaaacagaag gaaagaactt ctccagagga taattgtgga gcttgttgaa tttatatctc    1380
ccaaaacccc taaacctgga gaacttgggg gaagaatatc tgggtcagtg gcttggagag    1440
tagcccgagg tgaaatgggt ctacagagaa aagaaacctt gtttattccc tgtgaaaatg    1500
agaagatttc taaacagctc cacctttgtt acaatattgt gaaagatcgt tatgttcgag    1560
tttcaaataa caatcaaacc atttctggat gggagaatgg cgtgtggaaa atggaatcta    1620
tattcagaaa agttgaaaca gactggcaca tggtatattt ggcccgaaag gaaggatcat    1680
cttttgctta tatttcctgg aagtttgagt gtgggtcagt tggcctaaaa gtagatagca    1740
tttctattag aacaagtagt caaacttttc agactggaac agtagaatgg aaattgcgat    1800
ctgatacagc acaagtagaa ctgacaggcg ataacagtct tcactcctat gctgattttt    1860
ctggtgccac tgaagttatt ttggaagcag aattaagcag aggagatggt gatgtcgctt    1920
ggcaacacac ccagctgttt agacaaagct taaatgacca tgaagaaaat tgtttggaga    1980
taattataaa attcagtgac ctttgagaac ctgaacatta tagaaaagct ggcaataatc    2040
aaggacttac tgaagtagtc tgttggttca gtgcatgctt agttggcagt taccaccctg    2100
tgctagcata tttcttttgc tagctatcca tcatgtaacc ctcatgaaaa ttatctttat    2160
acgtggacta taataaaata tt                                             2182
```

<210> SEQ ID NO 62
<211> LENGTH: 654
<212> TYPE: PRT
<213> ORGANISM: Homo sapiens

<400> SEQUENCE: 62

```
Met Ala Ala Ala Leu Gly Ser Ser Gly Ser Ala Ser Pro Ala
1               5                   10                  15

Val Ala Glu Leu Cys Gln Asn Thr Pro Glu Thr Phe Leu Glu Ala Ser
            20                  25                  30

Lys Leu Leu Leu Thr Tyr Ala Asp Asn Ile Leu Arg Asn Pro Asn Asp
        35                  40                  45

Glu Lys Tyr Arg Ser Ile Arg Ile Gly Asn Thr Ala Phe Ser Thr Arg
    50                  55                  60

Leu Leu Pro Val Arg Gly Ala Val Glu Cys Leu Phe Glu Met Gly Phe
65                  70                  75                  80

Glu Glu Gly Glu Thr His Leu Ile Phe Pro Lys Lys Ala Ser Val Glu
                85                  90                  95

Gln Leu Gln Lys Ile Arg Asp Leu Ile Ala Ile Glu Arg Ser Ser Arg
            100                 105                 110

Leu Asp Gly Ser Asn Lys Ser His Lys Val Lys Ser Ser Gln Gln Pro
        115                 120                 125

Ala Ala Ser Thr Gln Leu Pro Thr Thr Pro Ser Ser Asn Pro Ser Gly
    130                 135                 140

Leu Asn Gln His Thr Arg Asn Arg Gln Gly Gln Ser Ser Asp Pro Pro
145                 150                 155                 160

Ser Ala Ser Thr Val Ala Ala Asp Ser Ala Ile Leu Glu Val Leu Gln
                165                 170                 175

Ser Asn Ile Gln His Val Leu Val Tyr Glu Asn Pro Ala Leu Gln Glu
            180                 185                 190

Lys Ala Leu Ala Cys Ile Pro Val Gln Glu Leu Lys Arg Lys Ser Gln
```

```
                195                 200                 205
  Glu Lys Leu Ser Arg Ala Arg Lys Leu Asp Lys Gly Ile Asn Ile Ser
      210                 215                 220
  Asp Glu Asp Phe Leu Leu Leu Glu Leu Leu His Trp Phe Lys Glu Glu
  225                 230                 235                 240
  Phe Phe His Trp Val Asn Asn Val Leu Cys Ser Lys Cys Gly Gly Gln
                      245                 250                 255
  Thr Arg Ser Arg Asp Arg Ser Leu Leu Pro Ser Asp Glu Leu Lys
                  260                 265                 270
  Trp Gly Ala Lys Glu Val Glu Asp His Tyr Cys Asp Ala Cys Gln Phe
              275                 280                 285
  Ser Asn Arg Phe Pro Arg Tyr Asn Asn Pro Glu Lys Leu Leu Glu Thr
          290                 295                 300
  Arg Cys Gly Arg Cys Gly Glu Trp Ala Asn Cys Phe Thr Leu Cys Cys
  305                 310                 315                 320
  Arg Ala Val Gly Phe Glu Ala Arg Tyr Val Trp Asp Tyr Thr Asp His
                      325                 330                 335
  Val Trp Thr Glu Val Tyr Ser Pro Ser Gln Gln Arg Trp Leu His Cys
                  340                 345                 350
  Asp Ala Cys Glu Asp Val Cys Asp Lys Pro Leu Leu Tyr Glu Ile Gly
              355                 360                 365
  Trp Gly Lys Lys Leu Ser Tyr Val Ile Ala Phe Ser Lys Asp Glu Val
          370                 375                 380
  Val Asp Val Thr Trp Arg Tyr Ser Cys Lys His Glu Glu Val Ile Ala
  385                 390                 395                 400
  Arg Arg Thr Lys Val Lys Glu Ala Leu Leu Arg Asp Thr Ile Asn Gly
                      405                 410                 415
  Leu Asn Lys Gln Arg Gln Leu Phe Leu Ser Glu Asn Arg Arg Lys Glu
                  420                 425                 430
  Leu Leu Gln Arg Ile Ile Val Glu Leu Val Glu Phe Ile Ser Pro Lys
              435                 440                 445
  Thr Pro Lys Pro Gly Glu Leu Gly Gly Arg Ile Ser Gly Ser Val Ala
          450                 455                 460
  Trp Arg Val Ala Arg Gly Glu Met Gly Leu Gln Arg Lys Glu Thr Leu
  465                 470                 475                 480
  Phe Ile Pro Cys Glu Asn Glu Lys Ile Ser Lys Gln Leu His Leu Cys
                      485                 490                 495
  Tyr Asn Ile Val Lys Asp Arg Tyr Val Arg Val Ser Asn Asn Asn Gln
                  500                 505                 510
  Thr Ile Ser Gly Trp Glu Asn Gly Val Trp Lys Met Glu Ser Ile Phe
              515                 520                 525
  Arg Lys Val Glu Thr Asp Trp His Met Val Tyr Leu Ala Arg Lys Glu
          530                 535                 540
  Gly Ser Ser Phe Ala Tyr Ile Ser Trp Lys Phe Glu Cys Gly Ser Val
  545                 550                 555                 560
  Gly Leu Lys Val Asp Ser Ile Ser Ile Arg Thr Ser Ser Gln Thr Phe
                      565                 570                 575
  Gln Thr Gly Thr Val Glu Trp Lys Leu Arg Ser Asp Thr Ala Gln Val
                  580                 585                 590
  Glu Leu Thr Gly Asp Asn Ser Leu His Ser Tyr Ala Asp Phe Ser Gly
              595                 600                 605
  Ala Thr Glu Val Ile Leu Glu Ala Glu Leu Ser Arg Gly Asp Gly Asp
          610                 615                 620
```

```
Val Ala Trp Gln His Thr Gln Leu Phe Arg Gln Ser Leu Asn Asp His
625                 630                 635                 640

Glu Glu Asn Cys Leu Glu Ile Ile Ile Lys Phe Ser Asp Leu
            645                 650
```

<210> SEQ ID NO 63
<211> LENGTH: 4816
<212> TYPE: DNA
<213> ORGANISM: Homo sapiens

<400> SEQUENCE: 63

| | | | | | |
|---|---|---|---|---|---|
| cgtcttcccg | gtctcctttc | ccggccgcac | agggtagatt | ttcgttccgt | cacccaggct | 60 |
| ggagtgcagt | ggtgtgacct | tggcttgctg | caaccctttg | cctcctgggt | tcaagtgatt | 120 |
| ctcattgcct | cagcctccta | agtagctggg | attacaggtt | ttataggatc | acattgacaa | 180 |
| aagtaccatg | gagttttatg | agtcagcata | ttttattgtt | cttattcctt | caatagttat | 240 |
| tacagtaatt | ttcctcttct | tctggctttt | catgaaagaa | acattatatg | atgaagttct | 300 |
| tgcaaaacag | aaaagagaac | aaaagcttat | tcctaccaaa | acagataaaa | agaaagcaga | 360 |
| aaagaaaaag | aataaaaaga | aagaaatcca | gaatggaaac | ctccatgaat | ccgactctga | 420 |
| gagtgtacct | cgagacttta | aattatcaga | tgctttggca | gtagaagatg | atcaagttgc | 480 |
| acctgttcca | ttgaatgtcg | ttgaaacttc | aagtagtgtt | agggaaagaa | aaagaaggaa | 540 |
| aaagaaacaa | agcctgtgc | ttgaagagca | ggtcatcaaa | gaaagtgacg | catcaaagat | 600 |
| tcctggcaaa | aaagtagaac | ctgtcccagt | tactaaacag | cccaccccc | cctctgaagc | 660 |
| agctgcctcg | aagaagaaac | agggcagaa | gaagtctaaa | aatggaagcg | atgaccagga | 720 |
| taaaaaggtg | gaaactctca | tggtaccatc | aaaaaggcaa | gaagcattgc | cctccacca | 780 |
| agagactaaa | caagaaagtg | gatcaggaa | gaagaaagct | tcatcaaaga | aacaaaagac | 840 |
| agaaaatgtc | ttcgtagatg | aacccttat | tcatgcaact | acttatattc | ctttgatgga | 900 |
| taatgctgac | tcaagtcctg | tggtagataa | gagagaggtt | attgatttgc | ttaaacctga | 960 |
| ccaagtagaa | gggatccaga | aatctgggac | taaaaaactg | aagaccgaaa | ctgacaaaga | 1020 |
| aaatgctgaa | gtgaagttta | agatttttct | tctgtccttg | aagactatga | tgttttctga | 1080 |
| agatgaggct | ctttgtgttg | tagacttgct | aaaggagaag | tctggtgtaa | tacaagatgc | 1140 |
| tttaaagaag | tcaagtaagg | gagaattgac | tacgcttata | catcagcttc | aagaaaagga | 1200 |
| caagttactc | gctgctgtga | aggaagatgc | tgctgctaca | aaggatcggt | gtaagcagtt | 1260 |
| aacccaggaa | atgatgacag | agaaagaaag | aagcaatgtg | ttataacaa | ggatgaaaga | 1320 |
| tcgaattgga | acattagaaa | aggaacataa | tgtatttcaa | acaaaatac | atgtcagtta | 1380 |
| tcaagagact | caacgatgc | agatgaagtt | tcagcaagtt | cgtgagcaga | tggaggcaga | 1440 |
| gatagctcac | ttgaagcagg | aaaatggtat | actgagagat | gcagtcagca | acactacaaa | 1500 |
| tcaactggaa | agcaagcagt | ctgcagaact | aaataaacta | cgccaggatt | atgctaggtt | 1560 |
| ggtgaatgag | ctgactgaga | aaacaggaaa | gctacagcaa | gaggaagtcc | aaaagaagaa | 1620 |
| tgctgagcaa | gcagctactc | agttgaaggt | tcaactacaa | gaagctgaga | aaggtggga | 1680 |
| agaagttcag | agctacatca | ggaagagaac | agcggaacat | gaggcagcac | agcaagattt | 1740 |
| acagagtaaa | tttgtggcca | agaaaaatga | agtacagagt | ctgcatagta | agcttacaga | 1800 |
| taccttggta | tcaaaacaac | agttggagca | agactaatg | cagttaatgg | aatcagagca | 1860 |
| gaaaagggtg | aacaagaag | agtctctaca | aatgcaggtt | caggatattt | tggagcagaa | 1920 |
| tgaggctttg | aaagctcaaa | ttcagcagtt | ccattcccag | atagcagccc | agacctccgc | 1980 |

```
ttcagttcta gcagaagaat tacataaagt gattgcagaa aaggataagc agataaaaca    2040
gactgaagat tctttagcaa gtgaacgtga tcgtttaaca agtaaagaag aggaacttaa    2100
ggatatacag aatatgaatt tcttattaaa agctgaagtg cagaaattac aggccctggc    2160
aaatgagcag gctgctgctg cacatgaatt ggagaagatg caacaaagtg tttatgttaa    2220
agatgataaa ataagattgc tggaagagca actacaacat gaaatttcaa acaaaatgga    2280
agaatttaag attctaaatg accaaaacaa agcattaaaa tcagaagttc agaagctaca    2340
gactcttgtt tctgaacagc taataagga tgttgtggaa caaatggaaa atgcattca     2400 agaaaaagat gagaagttaa agactgtgga agaattactt gaaactggac ttattcaggt    2460
ggcaactaaa gaagaggagc tgaatgcaat aagaacagaa aattcatctc tgacaaaaga    2520
agttcaagac ttaaaagcta agcaaaatga tcaggtttct tttgcctctc tagttgaaga    2580
acttaagaaa gtgatccatg agaaagatgg aaagatcaag tctgtagaag agcttctgga    2640
ggcagaactt ctcaaagttg ctaacaagga gaaaactgtt caggatttga acaggaaat    2700 aaaggctcta aagaagaaa taggaaatgt ccagcttgaa aaggctcaac agttatctat    2760
cacttccaaa gttcaggagc ttcagaactt attaaaagga aaagaggaac agatgaatac    2820
catgaaggct gttttggaag agaaagagaa agacctagcc aatacaggga gtggttaca    2880 ggatcttcaa gaagaaaatg aatctttaaa agcacatgtt caggaagtag cacaacataa    2940
cttgaaagag gcctcttctg catcacagtt tgaagaactt gagattgtgt tgaaagaaaa    3000
ggaaaatgaa ttgaagaggt tagaagccat gctaaaagag agggagagtg atctttctag    3060
caaaacacag ctgttacagg atgtacaaga tgaaaacaaa ttgtttaagt cccaaattga    3120
gcagcttaaa caacaaaact accaacaggc atcttctttt cccctcatg aagaattatt    3180 aaaagtaatt tcagaaagag agaaagaaat aagtggtctc tggaatgagt tagattcttt    3240
gaaggatgca gttgaacacc agaggaagaa aaacaatgac cttcgggaga aaaactggga    3300
agcaatggaa gcattggcat caactgaaaa aatgctgcag acaaagtga acaagacttc    3360 caaggaaagg cagcaacagg tggaagctgt tgagttggag gctaagaag ttctcaaaaa    3420 attatttcca aaggtgtctg tcccttctaa tttgagttat ggtgaatggt tgcatggatt    3480
tgaaaaaaag gcaaagaat gtatggctgg aacttcaggg tcagaggagg ttaaggttct    3540
agagcacaag ttgaaagaag ctgatgaaat gcacacattg ttacagctag agtgtgaaaa    3600
atacaaatcc gtccttgcag aaacagaagg aatttttcag aagctacaga gaagtgttga    3660
gcaagaagaa aataaatgga aagttaaggt cgatgaatca cacaagacta ttaaacagat    3720
gcagtcatca tttacatctt cagaacaaga gctagagcga ttaagaagcg aaaataagga    3780
tattgaaaat ctgagaagag aacgagaaca tttggaaatg gaactagaaa aggcagagat    3840
ggaacgatct acctatgtta cagaagtcag agagctgaaa gatctgttga ctgaattgca    3900
gaaaaaactt gatgattcat attctgaagc agtaagacag aatgaagagc taaatttgtt    3960
gaaggcacag ttaaatgaaa cactcacaaa acttagaact gaacaaaatg aaagacagaa    4020
ggtagctggt gatttgcata aggctcaaca gtcactggag cttatccagt caaaaatagt    4080
aaaagctgct ggagacacta ctgttattga aaatagtgat gtttccccag aaacggagtc    4140
ttctgagaag gagacaatgt ctgtaagtct aaatcagact gtaacacagt tacagcagtt    4200
gcttcaggcg gtaaaccaac agctcacaaa ggagaaagag cactaccagg tgttagagtg    4260
atcatcctct ggcctacctt gacacatgct ctccttcaaa atgctaattc agagtgaagt    4320
aattgggaaa ctgttcattt gaggataaaa aaggcattgt attatatttt gccaaattaa    4380
```

```
agccttattt atgttttcac cctttctact ttgtcagaaa cactgaacag agttttgtct    4440
tttctaatcc ttgttagact actgatttaa agaaggaaaa aaaaaagcca actctgtaga    4500
caccttcaga gtttagtttt ataataaaaa ctgtttgaat aattagacct ttacattcct    4560
gaagataaac atgtaatctt ttatcttatt ttgctcaata aaattgttca gaagatcaaa    4620
gtggtaaaga caatgtaaaa tttaacattt taatactgat gttgtacact gttttactta    4680
acattttggg aagtaactgc ctctgacttc aactcaagaa aacactttt tgttgctaat    4740 gtaatcggtt tttgtaatgg cgtcagcaaa taaaaggatg cttattattc aaaaaaaaaa    4800
aaaaaaaaaa aaaaa                                                    4816
```

<210> SEQ ID NO 64
<211> LENGTH: 1357
<212> TYPE: PRT
<213> ORGANISM: Homo sapiens

<400> SEQUENCE: 64

```
Met Glu Phe Tyr Glu Ser Ala Tyr Phe Ile Val Leu Ile Pro Ser Ile
1               5                   10                  15

Val Ile Thr Val Ile Phe Leu Phe Phe Trp Leu Phe Met Lys Glu Thr
            20                  25                  30

Leu Tyr Asp Glu Val Leu Ala Lys Gln Lys Arg Glu Gln Lys Leu Ile
        35                  40                  45

Pro Thr Lys Thr Asp Lys Lys Ala Glu Lys Lys Asn Lys Lys
    50                  55                  60

Lys Glu Ile Gln Asn Gly Asn Leu His Glu Ser Asp Ser Glu Ser Val
65                  70                  75                  80

Pro Arg Asp Phe Lys Leu Ser Asp Ala Leu Ala Val Glu Asp Asp Gln
                85                  90                  95

Val Ala Pro Val Pro Leu Asn Val Val Glu Thr Ser Ser Ser Val Arg
            100                 105                 110

Glu Arg Lys Lys Glu Lys Lys Gln Lys Pro Val Leu Glu Glu Gln
        115                 120                 125

Val Ile Lys Glu Ser Asp Ala Ser Lys Ile Pro Gly Lys Lys Val Glu
    130                 135                 140

Pro Val Pro Val Thr Lys Gln Pro Thr Pro Ser Glu Ala Ala Ala
145                 150                 155                 160

Ser Lys Lys Lys Pro Gly Gln Lys Lys Ser Lys Asn Gly Ser Asp Asp
                165                 170                 175

Gln Asp Lys Lys Val Glu Thr Leu Met Val Pro Ser Lys Arg Gln Glu
            180                 185                 190

Ala Leu Pro Leu His Gln Glu Thr Lys Gln Glu Ser Gly Ser Gly Lys
        195                 200                 205

Lys Lys Ala Ser Ser Lys Lys Gln Lys Thr Glu Asn Val Phe Val Asp
    210                 215                 220

Glu Pro Leu Ile His Ala Thr Thr Tyr Ile Pro Leu Met Asp Asn Ala
225                 230                 235                 240

Asp Ser Ser Pro Val Val Asp Lys Arg Glu Val Ile Asp Leu Leu Lys
                245                 250                 255

Pro Asp Gln Val Glu Gly Ile Gln Lys Ser Gly Thr Lys Lys Leu Lys
            260                 265                 270

Thr Glu Thr Asp Lys Glu Asn Ala Glu Val Lys Phe Lys Asp Phe Leu
        275                 280                 285

Leu Ser Leu Lys Thr Met Met Phe Ser Glu Asp Glu Ala Leu Cys Val
    290                 295                 300
```

```
Val Asp Leu Leu Lys Glu Lys Ser Gly Val Ile Gln Asp Ala Leu Lys
305                 310                 315                 320

Lys Ser Ser Lys Gly Glu Leu Thr Thr Leu Ile His Gln Leu Gln Glu
            325                 330                 335

Lys Asp Lys Leu Leu Ala Ala Val Lys Glu Asp Ala Ala Thr Lys
                340                 345                 350

Asp Arg Cys Lys Gln Leu Thr Gln Glu Met Met Thr Glu Lys Glu Arg
            355                 360                 365

Ser Asn Val Val Ile Thr Arg Met Lys Asp Arg Ile Gly Thr Leu Glu
    370                 375                 380

Lys Glu His Asn Val Phe Gln Asn Lys Ile His Val Ser Tyr Gln Glu
385                 390                 395                 400

Thr Gln Gln Met Gln Met Lys Phe Gln Gln Val Arg Glu Gln Met Glu
                405                 410                 415

Ala Glu Ile Ala His Leu Lys Gln Glu Asn Gly Ile Leu Arg Asp Ala
                420                 425                 430

Val Ser Asn Thr Thr Asn Gln Leu Glu Ser Lys Gln Ser Ala Glu Leu
            435                 440                 445

Asn Lys Leu Arg Gln Asp Tyr Ala Arg Leu Val Asn Glu Leu Thr Glu
450                 455                 460

Lys Thr Gly Lys Leu Gln Gln Glu Glu Val Gln Lys Lys Asn Ala Glu
465                 470                 475                 480

Gln Ala Ala Thr Gln Leu Lys Val Gln Leu Gln Glu Ala Glu Arg Arg
            485                 490                 495

Trp Glu Glu Val Gln Ser Tyr Ile Arg Lys Arg Thr Ala Glu His Glu
                500                 505                 510

Ala Ala Gln Gln Asp Leu Gln Ser Lys Phe Val Ala Lys Glu Asn Glu
                515                 520                 525

Val Gln Ser Leu His Ser Lys Leu Thr Asp Thr Leu Val Ser Lys Gln
            530                 535                 540

Gln Leu Glu Gln Arg Leu Met Gln Leu Met Glu Ser Glu Gln Lys Arg
545                 550                 555                 560

Val Asn Lys Glu Glu Ser Leu Gln Met Gln Val Gln Asp Ile Leu Glu
                565                 570                 575

Gln Asn Glu Ala Leu Lys Ala Gln Ile Gln Gln Phe His Ser Gln Ile
            580                 585                 590

Ala Ala Gln Thr Ser Ala Ser Val Leu Ala Glu Glu Leu His Lys Val
            595                 600                 605

Ile Ala Glu Lys Asp Lys Gln Ile Lys Gln Thr Glu Asp Ser Leu Ala
610                 615                 620

Ser Glu Arg Asp Arg Leu Thr Ser Lys Glu Glu Glu Leu Lys Asp Ile
625                 630                 635                 640

Gln Asn Met Asn Phe Leu Leu Lys Ala Glu Val Gln Lys Leu Gln Ala
            645                 650                 655

Leu Ala Asn Glu Gln Ala Ala Ala His Glu Leu Glu Lys Met Gln
            660                 665                 670

Gln Ser Val Tyr Val Lys Asp Asp Lys Ile Arg Leu Leu Glu Glu Gln
            675                 680                 685

Leu Gln His Glu Ile Ser Asn Lys Met Glu Glu Phe Lys Ile Leu Asn
            690                 695                 700

Asp Gln Asn Lys Ala Leu Lys Ser Glu Val Gln Lys Leu Gln Thr Leu
705                 710                 715                 720

Val Ser Glu Gln Pro Asn Lys Asp Val Val Glu Gln Met Glu Lys Cys
```

```
                    725                 730                 735
Ile Gln Glu Lys Asp Glu Lys Leu Lys Thr Val Glu Glu Leu Leu Glu
                740                 745                 750

Thr Gly Leu Ile Gln Val Ala Thr Lys Glu Glu Leu Asn Ala Ile
            755                 760                 765

Arg Thr Glu Asn Ser Ser Leu Thr Lys Glu Val Gln Asp Leu Lys Ala
            770                 775                 780

Lys Gln Asn Asp Gln Val Ser Phe Ala Ser Leu Val Glu Glu Leu Lys
785                 790                 795                 800

Lys Val Ile His Glu Lys Asp Gly Lys Ile Lys Ser Val Glu Glu Leu
                805                 810                 815

Leu Glu Ala Glu Leu Leu Lys Val Ala Asn Lys Glu Lys Thr Val Gln
                820                 825                 830

Asp Leu Lys Gln Glu Ile Lys Ala Leu Lys Glu Glu Ile Gly Asn Val
                835                 840                 845

Gln Leu Glu Lys Ala Gln Gln Leu Ser Ile Thr Ser Lys Val Gln Glu
                850                 855                 860

Leu Gln Asn Leu Leu Lys Gly Lys Glu Glu Gln Met Asn Thr Met Lys
865                 870                 875                 880

Ala Val Leu Glu Glu Lys Glu Lys Asp Leu Ala Asn Thr Gly Lys Trp
                885                 890                 895

Leu Gln Asp Leu Gln Glu Glu Asn Glu Ser Leu Lys Ala His Val Gln
                900                 905                 910

Glu Val Ala Gln His Asn Leu Lys Glu Ala Ser Ser Ala Ser Gln Phe
                915                 920                 925

Glu Glu Leu Glu Ile Val Leu Lys Glu Lys Glu Asn Glu Leu Lys Arg
                930                 935                 940

Leu Glu Ala Met Leu Lys Glu Arg Glu Ser Asp Leu Ser Ser Lys Thr
945                 950                 955                 960

Gln Leu Leu Gln Asp Val Gln Asp Glu Asn Lys Leu Phe Lys Ser Gln
                965                 970                 975

Ile Glu Gln Leu Lys Gln Gln Asn Tyr Gln Gln Ala Ser Ser Phe Pro
                980                 985                 990

Pro His Glu Glu Leu Leu Lys Val  Ile Ser Glu Arg Glu  Lys Glu Ile
                995                 1000                1005

Ser Gly  Leu Trp Asn Glu Leu  Asp Ser Leu Lys Asp  Ala Val Glu
     1010                 1015                1020

His Gln Arg Lys Lys Asn Asn  Asp Leu Arg Glu Lys  Asn Trp Glu
     1025                 1030                1035

Ala Met  Glu Ala Leu Ala Ser  Thr Glu Lys Met Leu  Gln Asp Lys
     1040                 1045                1050

Val Asn  Lys Thr Ser Lys Glu  Arg Gln Gln Gln Val  Glu Ala Val
     1055                 1060                1065

Glu Leu  Glu Ala Lys Glu Val  Leu Lys Lys Leu Phe  Pro Lys Val
     1070                 1075                1080

Ser Val  Pro Ser Asn Leu Ser  Tyr Gly Glu Trp Leu  His Gly Phe
     1085                 1090                1095

Glu Lys  Lys Ala Lys Glu Cys  Met Ala Gly Thr Ser  Gly Ser Glu
     1100                 1105                1110

Glu Val  Lys Val Leu Glu His  Lys Leu Lys Glu Ala  Asp Glu Met
     1115                 1120                1125

His Thr  Leu Leu Gln Leu Glu  Cys Glu Lys Tyr Lys  Ser Val Leu
     1130                 1135                1140
```

| | | | | | | | | | | |
|---|---|---|---|---|---|---|---|---|---|---|
| Ala | Glu | Thr | Glu | Gly | Ile | Leu | Gln | Lys | Leu | Gln | Arg | Ser | Val | Glu |
| | 1145 | | | | 1150 | | | | | 1155 | | | | |

Ala Glu Thr Glu Gly Ile Leu Gln Lys Leu Gln Arg Ser Val Glu
    1145                1150                1155

Gln Glu Glu Asn Lys Trp Lys Val Lys Val Asp Glu Ser His Lys
    1160                1165                1170

Thr Ile Lys Gln Met Gln Ser Ser Phe Thr Ser Ser Glu Gln Glu
    1175                1180                1185

Leu Glu Arg Leu Arg Ser Glu Asn Lys Asp Ile Glu Asn Leu Arg
    1190                1195                1200

Arg Glu Arg Glu His Leu Glu Met Glu Leu Glu Lys Ala Glu Met
    1205                1210                1215

Glu Arg Ser Thr Tyr Val Thr Glu Val Arg Glu Leu Lys Asp Leu
    1220                1225                1230

Leu Thr Glu Leu Gln Lys Lys Leu Asp Asp Ser Tyr Ser Glu Ala
    1235                1240                1245

Val Arg Gln Asn Glu Glu Leu Asn Leu Leu Lys Ala Gln Leu Asn
    1250                1255                1260

Glu Thr Leu Thr Lys Leu Arg Thr Glu Gln Asn Glu Arg Gln Lys
    1265                1270                1275

Val Ala Gly Asp Leu His Lys Ala Gln Gln Ser Leu Glu Leu Ile
    1280                1285                1290

Gln Ser Lys Ile Val Lys Ala Ala Gly Asp Thr Thr Val Ile Glu
    1295                1300                1305

Asn Ser Asp Val Ser Pro Glu Thr Glu Ser Ser Glu Lys Glu Thr
    1310                1315                1320

Met Ser Val Ser Leu Asn Gln Thr Val Thr Gln Leu Gln Gln Leu
    1325                1330                1335

Leu Gln Ala Val Asn Gln Gln Leu Thr Lys Glu Lys Glu His Tyr
    1340                1345                1350

Gln Val Leu Glu
    1355

<210> SEQ ID NO 65
<211> LENGTH: 2775
<212> TYPE: DNA
<213> ORGANISM: Homo sapiens

<400> SEQUENCE: 65

```
gcagtccaga tgtcgtcagc accagcgcct gggctggagg acagagaagc cttttccgtt      60
gccggtgccg cctagcgtc  ctggaattac ttcaatcaac aggagcgaga acccgagcag     120
cgccatgagc aacactaccg tcgtcccag  cactgcaggt ccgggcccca gcggcgggcc     180
cggtggcgga ggtggtggtg gcggcggagg cggcggcacc gaggtaatcc aggtgactaa     240
tgtctccccg agcgctagct ctgagcagat gcggactctc ttcggtttcc taggcaagat     300
cgacgaactg cgcctcttcc cgccggatga ttcgcctttg ccagtctcat tcgtgtctg      360 ctttgttaag ttccatgatc cagactcagc agttgtggca cagcatctga caaacactgt     420
attcgttgac agagctttga tagtcgtacc atatgcagaa ggagttattc ctgatgaagc     480
taaagctttg tctctgttgg caccagctaa tgcagtggca ggtcttctgc tggtggtgg      540 actcctgcct actcctaacc cacttaccca gattggcgct gttccactgg ctgctttggg     600
ggctcctact cttgatcctg cccttgctgc acttgggctt cctggagcaa acttgaactc     660
tcagtctctt gctgcagatc agttgctgaa gcttatgagt actgttgatc ccaagttgaa     720
tcatgtagct gctggtctcg tttcaccaag tctgaaatcg gatacctcta gtaaagaaat     780
agaggaagct atgaaaagag tacgagaagc acagtcccta atttctgctg ctatagaacc     840
```

```
agataagaaa gaagaaaaaa gaaggcattc aagatcaaga tcacgttcta ggaggaggag    900
gactccctca tcttctagac acaggcggtc aagaagcaga tcgagacggc ggtcacattc    960
taagtctagg agtcggcgac gatccaaaag cccaaggcgg agaagatctc attccagaga   1020
aagaggtaga aggtcaagga gcacatcaaa acaagagac aaaagaaag aagacaaaga    1080
aaagaaacgt tctaaaacac caccaaaaag ttacagcaca gccagacgtt ctagaagtgc   1140
aagcagagag agacgacgac gaagaagcag gagtggcaca agatctccta aaaagcctcg   1200
gtctcctaaa agaaaattgt cccgctcacc atccctagg agacataaaa aggagaagaa   1260
gaaagataaa gacaaagaaa gaagtaggga tgaaagagaa cgatcaacaa gcaagaagaa   1320
gaagagtaaa gataaggaaa aggaccggga aagaaaatca gagagtgata aagatgtaaa   1380
acaggttaca cgggattatg atgaagagga acagggtat gacagtgaga aagagaaaaa   1440
agaagagaag aaaccaatag aaacaggttc ccctaaaaca aaggaatgtt ctgtggaaaa   1500
gggaactggt gattcactaa gagaatccaa agtgaatggg gatgatcatc atgaagaaga   1560
catggatatg agtgactgaa tattgcctct gagggagtcc aactgtatac ctgcatcagt   1620
gtcattcctt tgtgtgattt cttaatgctg tatttgttca tctcaaacct agatgtatac   1680
agctctgagt tataaatggt tataaagctc ctgttactca tattagttat ttacatcaaa   1740
aagcttttag aaaatggtac gaggtaacca attcttgtca tggtgaaatc tgattgagta   1800
accaagcagt tttactattc tggtgctgct tcataacaaa aatgaaaagc tgcatgcatc   1860
tacagcaggc atggattgtt tatgtcgtat gatatccttt attaagtaag ttcacttata   1920
gtatttctat aatttgattc attgccgtaa tagagccatg taggaaatgc actgattgca   1980
tgttattgtg gcaagaatat cctaaatgtc attaaaatcc tccaacatga tggatctact   2040
tatggtcttg tttgttgaca tgacaaatta acattcttat agttacatct ggaaatgagc   2100
atttgaaata gataatcctt taagccttgt ggcaaaattt ttgtggcttt tgtttaactt   2160
tgaaaggtta ttatgcacta acctttttg gtggctaatt agggtttaaa tacagaaaca   2220
agatttcaaa taaaactgtc tttggcagtg agtaaatagc atattttgaa gtagagttgt   2280
atactttttc ataagatgtt tgggaatttt tttcctgaag taataattta ttccacatct   2340
acatcagtga aagctatcta cctatcctga gtctatctta aaggaaaaaa agaaaaaaac   2400
cttatctctt gcccttattt tgaattttcc actctttcat taatttgttt taagctccgt   2460
gttggaaaaa aggggtagtg cattttaaat tgaccttcat acgcttttaa aataagacaa   2520
atctacttga taatgtacct ttatttgatc tcaagttgta taaaaccaat aaatttgtgt   2580
tactgcagta gtaatcttat gcacacggtg atttcatgtt atatatgcaa agtaggcaac   2640
tgttttctta gttacagaag tttcaagctt cacttttgtg cagtagaaac aaaagtaggc   2700
tacagtctgt gccatgttga tgtacagttt ctgaaattgt tttacaagac tttgataata   2760
aaacccttaa actta                                                   2775
```

<210> SEQ ID NO 66
<211> LENGTH: 484
<212> TYPE: PRT
<213> ORGANISM: Homo sapiens

<400> SEQUENCE: 66

Met Ser Asn Thr Thr Val Val Pro Ser Thr Ala Gly Pro Gly Pro Ser
1               5                   10                  15

Gly Gly Pro Gly Gly Gly Gly Gly Gly Gly Gly Gly Gly Gly Thr
            20                  25                  30

```
Glu Val Ile Gln Val Thr Asn Val Ser Pro Ser Ala Ser Glu Gln
             35                  40                  45

Met Arg Thr Leu Phe Gly Phe Leu Gly Lys Ile Asp Glu Leu Arg Leu
 50                  55                  60

Phe Pro Pro Asp Asp Ser Pro Leu Pro Val Ser Ser Arg Val Cys Phe
 65                  70                  75                  80

Val Lys Phe His Asp Pro Asp Ser Ala Val Val Ala Gln His Leu Thr
                 85                  90                  95

Asn Thr Val Phe Val Asp Arg Ala Leu Ile Val Val Pro Tyr Ala Glu
                100                 105                 110

Gly Val Ile Pro Asp Glu Ala Lys Ala Leu Ser Leu Leu Ala Pro Ala
            115                 120                 125

Asn Ala Val Ala Gly Leu Leu Pro Gly Gly Leu Leu Pro Thr Pro
            130                 135                 140

Asn Pro Leu Thr Gln Ile Gly Ala Val Pro Leu Ala Ala Leu Gly Ala
145                 150                 155                 160

Pro Thr Leu Asp Pro Ala Leu Ala Ala Leu Gly Leu Pro Gly Ala Asn
                165                 170                 175

Leu Asn Ser Gln Ser Leu Ala Ala Asp Gln Leu Leu Lys Leu Met Ser
                180                 185                 190

Thr Val Asp Pro Lys Leu Asn His Val Ala Ala Gly Leu Val Ser Pro
                195                 200                 205

Ser Leu Lys Ser Asp Thr Ser Ser Lys Glu Ile Glu Glu Ala Met Lys
            210                 215                 220

Arg Val Arg Glu Ala Gln Ser Leu Ile Ser Ala Ala Ile Glu Pro Asp
225                 230                 235                 240

Lys Lys Glu Glu Lys Arg Arg His Ser Arg Ser Arg Ser Arg Ser Arg
                245                 250                 255

Arg Arg Arg Thr Pro Ser Ser Ser Arg His Arg Arg Ser Arg Ser Arg
                260                 265                 270

Ser Arg Arg Arg Ser His Ser Lys Ser Arg Ser Arg Arg Arg Ser Lys
            275                 280                 285

Ser Pro Arg Arg Arg Ser His Ser Arg Glu Arg Gly Arg Arg Ser
            290                 295                 300

Arg Ser Thr Ser Lys Thr Arg Asp Lys Lys Glu Asp Lys Glu Lys
305                 310                 315                 320

Lys Arg Ser Lys Thr Pro Pro Lys Ser Tyr Ser Thr Ala Arg Arg Ser
                325                 330                 335

Arg Ser Ala Ser Arg Glu Arg Arg Arg Arg Ser Arg Ser Gly Thr
            340                 345                 350

Arg Ser Pro Lys Lys Pro Arg Ser Pro Lys Arg Lys Leu Ser Arg Ser
            355                 360                 365

Pro Ser Pro Arg Arg His Lys Lys Glu Lys Lys Asp Lys Asp Lys
370                 375                 380

Glu Arg Ser Arg Asp Glu Arg Glu Arg Ser Thr Ser Lys Lys Lys Lys
385                 390                 395                 400

Ser Lys Asp Lys Glu Lys Asp Arg Glu Arg Lys Ser Glu Ser Asp Lys
                405                 410                 415

Asp Val Lys Gln Val Thr Arg Asp Tyr Asp Glu Glu Gln Gly Tyr
                420                 425                 430

Asp Ser Glu Lys Glu Lys Lys Glu Glu Lys Lys Pro Ile Glu Thr Gly
            435                 440                 445

Ser Pro Lys Thr Lys Glu Cys Ser Val Glu Lys Gly Thr Gly Asp Ser
```

Leu Arg Glu Ser Lys Val Asn Gly Asp Asp His His Glu Glu Asp Met
465                 470                 475                 480

Asp Met Ser Asp

<210> SEQ ID NO 67
<211> LENGTH: 1107
<212> TYPE: DNA
<213> ORGANISM: Homo sapiens

<400> SEQUENCE: 67
gcagaagcgt tccgtgcgtg caagtgctgc gaaccacgtg ggtcccgggc gcgtttcggg        60
tgctggcggc tgcagccgga gttcaaacct aagcagctgg aaggaaccat ggccaactgt       120
gagcgtacct tcattgcgat caaaccagat ggggtccagc ggggtcttgt gggagagatt       180
atcaagcgtt ttgagcagaa aggattccgc cttgttggtc tgaaattcat gcaagcttcc       240
gaagatcttc tcaaggaaca ctacgttgac ctgaaggacc gtccattctt tgccggcctg       300
gtgaaataca tgcactcagg gccggtagtt gccatggtct gggaggggct gaatgtggtg       360
aagacgggcc gagtcatgct cggggagacc aaccctgcag actccaagcc tgggaccatc       420
cgtggagact tctgcataca agttggcagg accatggcca acctggagcg caccttcatc       480
gccatcaagc cggacggcgt gcagcgcggc ctggtgggcg agatcatcaa gcgcttcgag       540
cagaagggat tccgcctcgt ggccatgaag ttcctccggg cctctgaaga cacctgaag        600 cagcactaca ttgacctgaa agaccgacca ttcttccctg gctggtgaa gtacatgaac        660 tcagggccgg ttgtggccat ggtctgggag gggctgaacg tggtgaagac aggccgagtg       720
atgcttgggg agaccaatcc agcagattca aagccaggca ccattcgtgg ggacttctgc       780
attcaggttg gcaggaacat cattcatggc agtgattcag taaaaagtgc tgaaaaagaa       840
atcagcctat ggtttaagcc tgaagaactg gttgactaca gtcttgtgc tcatgactgg       900 gtctatgaat aagaggtgga cacaacagca gtctccttca gcacggcgtg gtgtgtccct       960
ggacacagct cttcattcca ttgacttaga ggcaacagga ttgatcattc ttttatagag      1020
catatttgcc aataaagctt ttggaagccg aaaaaaaaa aaaaaaaaa aaaaaaaaa        1080 aaaaaaaaa aaaaaaaaa aaaaaaa                                          1107

<210> SEQ ID NO 68
<211> LENGTH: 267
<212> TYPE: PRT
<213> ORGANISM: Homo sapiens

<400> SEQUENCE: 68

Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
                20                  25                  30

Phe Arg Leu Val Gly Leu Lys Phe Met Gln Ala Ser Glu Asp Leu Leu
            35                  40                  45

Lys Glu His Tyr Val Asp Leu Lys Asp Arg Pro Phe Phe Ala Gly Leu
    50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val

```
              100                 105                 110
Gly Arg Thr Met Ala Asn Leu Glu Arg Thr Phe Ile Ala Ile Lys Pro
            115                 120                 125

Asp Gly Val Gln Arg Gly Leu Val Gly Glu Ile Ile Lys Arg Phe Glu
130                 135                 140

Gln Lys Gly Phe Arg Leu Val Ala Met Lys Phe Leu Arg Ala Ser Glu
145                 150                 155                 160

Glu His Leu Lys Gln His Tyr Ile Asp Leu Lys Asp Arg Pro Phe Phe
                165                 170                 175

Pro Gly Leu Val Lys Tyr Met Asn Ser Gly Pro Val Val Ala Met Val
            180                 185                 190

Trp Glu Gly Leu Asn Val Val Lys Thr Gly Arg Val Met Leu Gly Glu
            195                 200                 205

Thr Asn Pro Ala Asp Ser Lys Pro Gly Thr Ile Arg Gly Asp Phe Cys
            210                 215                 220

Ile Gln Val Gly Arg Asn Ile Ile His Gly Ser Asp Ser Val Lys Ser
225                 230                 235                 240

Ala Glu Lys Glu Ile Ser Leu Trp Phe Lys Pro Glu Glu Leu Val Asp
                245                 250                 255

Tyr Lys Ser Cys Ala His Asp Trp Val Tyr Glu
            260                 265

<210> SEQ ID NO 69
<211> LENGTH: 531
<212> TYPE: DNA
<213> ORGANISM: Homo sapiens

<400> SEQUENCE: 69
ggcagtctcg cgataactgc gcaggcgcgg accaaagcga tctcttctga ggatccggca      60
agatggcaga agtagagcag aagaagaagc ggaccttccg caagttcacc taccgcggcg     120
tggacctcga ccagctgctg gacatgtcct acgagcagct gatgcagctg tacagtgcgc     180
gccagcggcg gcggctgaac cggggcctgc ggcggaagca gcactccctg ctgaagcgcc     240
tgcgcaaggc caagaaggag gcgccgccca tggagaagcc ggaagtggtg aagacgcacc     300
tgcgggacat gatcatccta cccgagatgg tgggcagcat ggtgggcgtc tacaacggca     360
agaccttcaa ccaggtggag atcaagcccg agatgatcgg ccactacctg gcgagttct      420 ccatcaccta caagcccgta aagcatggcc ggcccggcat cggggccacc cactcctccc     480
gcttcatccc tctcaagtaa tggctcagct aataaaggcg cacatgactc c              531

<210> SEQ ID NO 70
<211> LENGTH: 145
<212> TYPE: PRT
<213> ORGANISM: Homo sapiens

<400> SEQUENCE: 70

Met Ala Glu Val Glu Gln Lys Lys Lys Arg Thr Phe Arg Lys Phe Thr
1               5                   10                  15

Tyr Arg Gly Val Asp Leu Asp Gln Leu Leu Asp Met Ser Tyr Glu Gln
            20                  25                  30

Leu Met Gln Leu Tyr Ser Ala Arg Gln Arg Arg Arg Leu Asn Arg Gly
        35                  40                  45

Leu Arg Arg Lys Gln His Ser Leu Leu Lys Arg Leu Arg Lys Ala Lys
    50                  55                  60

Lys Glu Ala Pro Pro Met Glu Lys Pro Glu Val Val Lys Thr His Leu
65                  70                  75                  80
```

Arg Asp Met Ile Ile Leu Pro Glu Met Val Gly Ser Met Val Gly Val
                    85                  90                  95

Tyr Asn Gly Lys Thr Phe Asn Gln Val Glu Ile Lys Pro Glu Met Ile
                100                 105                 110

Gly His Tyr Leu Gly Glu Phe Ser Ile Thr Tyr Lys Pro Val Lys His
                115                 120                 125

Gly Arg Pro Gly Ile Gly Ala Thr His Ser Ser Arg Phe Ile Pro Leu
            130                 135                 140

Lys
145

<210> SEQ ID NO 71
<211> LENGTH: 10151
<212> TYPE: DNA
<213> ORGANISM: Homo sapiens

<400> SEQUENCE: 71

| | | | | |
|---|---|---|---|---|
| gcagcgccgc | ctgcccaggc | ccggaccggg | ctttgtccgc | cccggagccc | ctgcccgcgc | 60 |
| cgcggagacc | ccggagcccg | cgcgctccga | ggccaccccg | ggcgggatt | tccggtgggg | 120 |
| cccgcggagc | cgcgcagagg | gaggaggccc | cagacccagg | cgccccgcca | gcccagctgc | 180 |
| acgtaagcgg | acgctgcagg | agctgaagat | ggcgagctcc | gtggcgccct | acgagcagct | 240 |
| ggtgaggcag | gtggaggcct | tgaaggctga | gaacagccac | ctgaggcagg | agctaaggga | 300 |
| caactccagc | cacctgtcca | gctgggacag | agagacgtcg | ggcatgaagg | aggtcctgaa | 360 |
| gcacctacag | ggaaaactgg | agcaggaggc | ccgagtgctg | gtgtcctcgg | ggcagacgga | 420 |
| ggtgctggag | cagctgaagg | ccctacagat | ggacatcacc | agcctgtaca | acctcaagtt | 480 |
| ccagccgccc | accctgggcc | cggagcctgc | cgcccggacc | ccgagggca | gcccagtaca | 540 |
| cggctccggg | ccctccaagg | acagctttgg | ggagctgagc | cgggccacca | tccggctgct | 600 |
| ggaggaactg | gaccgggaac | ggtgtttcct | gctgaatgag | attgagaagg | aggagaagga | 660 |
| gaagctctgg | tactactctc | agctgcaggg | cctgtccaag | cgcctggacg | agctgccgca | 720 |
| cgtggagacg | cagttctcga | tgcagatgga | cctgatccgg | cagcagcttg | agttcgaggc | 780 |
| ccagcacatc | cgctcgctga | tggaggagcg | cttcggcacc | tcggacgaga | tggtgcagcg | 840 |
| ggcacagatc | cgcgcctcgc | gcctggagca | gattgacaag | gagctgctgg | aggcgcagga | 900 |
| ccgagtgcag | cagacggagc | cccaggcctt | gctggcggtg | aagtcggtgc | cggtggacga | 960 |
| ggaccccgag | acagaggtcc | ccacacaccc | tgaggatggc | accctcagc | cgggcaacag | 1020 |
| caaggtggag | gtggtcttct | ggctgttgtc | catgttggcg | acgcgcgacc | aggaggatac | 1080 |
| agcgcgcacg | ctgctggcca | tgtccagctc | gcccgagagc | tgcgtggcca | tgcgccgctc | 1140 |
| gggctgtctg | cctctgctgc | tgcaaatcct | ccacggcacc | gaggccgcgg | ccgggggtcg | 1200 |
| cgccggggcc | ccagggcac | cgggcgccaa | ggacgcacgc | atgcgcgcca | acgcggcgct | 1260 |
| gcacaacatc | gtcttctcgc | agccggacca | gggcctggcg | cgcaaggaga | tgcgcgtcct | 1320 |
| gcacgtgctg | gagcagatcc | gggcctactg | cgagacctgc | tgggactggc | tgcaggcccg | 1380 |
| agacggcggg | cccgagggag | gtggcgccgg | cagcgccccg | atccccatcg | agccgcagat | 1440 |
| ctgccaggcc | acctgtgctg | ttatgaagct | gtccttgat | gaggagtacc | gccgtgccat | 1500 |
| gaacgagcta | ggtgggctgc | aggccgtggc | agagctgctg | caggttgact | atgagatgca | 1560 |
| caagatgacc | cggacccgc | tgaacctggc | gctgcgccgc | tacgcgggca | tgaccctcac | 1620 |
| caacctcacc | tttggggacg | ttgccaacaa | ggccaccctg | tgtgcgcgcc | gcggctgcat | 1680 |

```
ggaggccatc gtggcccagc tggcctccga cagtgaggag ctccaccagg tggtgtccag    1740
catccttcgg aacttgtcct ggagggccga catcaacagc aagaaggtgc tgagggaggc    1800
gggcagcgtg actgccctgg tgcagtgtgt cctgcgggcc accaaggagt ccaccctgaa    1860
gagcgtgctg agcgccctgt ggaatctgtc tgcacacagc acagagaaca aggcggccat    1920
ctgccaggtg gatggcgccc tgggcttcct ggtgagcacc ctgacctaca agtgtcagag    1980
caactcgctg gccatcatcg agagcggcgg cggcatcctc cgcaatgtgt ccagcctcgt    2040
cgccacccgt gaggactaca ggcaggtgct ccgggatcac aactgtctgc agacgctgct    2100
gcagcatctg acttcgcaca gcctgaccat cgtgagcaac gcgtgcggca cgctctggaa    2160
cctgtcggcc cgcagcgccc gtgaccagga gctgctgtgg gacctgggcg ccgtgggcat    2220
gctgcgtaat ctggtgcact ccaagcacaa gatgatcgcc atgggcagcg ccgccgccct    2280
gcgcaacctg ctggcccatc ggcccgccaa gcaccaggcg gccgccaccg ccgtgtcccc    2340
aggcagctgc gtgcccagcc tgtacgtgcg caagcagcgg gcgctggagg ccgagctgga    2400
cgcacggcac ctcgcgcagg cgctggagca cctggagaag cagggcccgc cggcagccga    2460
ggccgccact aagaagccgc tgccgcccct gcgacacctg gacggcctgg cccaagacta    2520
tgcttccgat tcgggctgct ttgacgacga cgatgcaccg tcatccctgg ctgcggccgc    2580
ggccaccggg gagccagcca gccctgccgc gctgtccctc ttcctgggca gcccttcct    2640
gcagggggcag gcgctggctc gcaccccgcc cacccgccga ggcggcaagg aggcagagaa    2700
ggacaccagt ggggaggcag ccgtggcggc caaggcaag gccaagctgg cgcttgcagt    2760
ggcgcgcatc gaccagctgg tggaggacat ctccgccctg cacacctcgt ccgacgatag    2820
cttcagcctc agctctggag acccgggaca ggaggcgcca cgggagggcc gcgcccagtc    2880
ctgctcgcca tgccgcggcc cggagggcgg gcggcgagag gcaggaagcc gggcgcaccc    2940
gctgctgcgg ctcaaggcgg cccacgcag cctctccaac gacagcctca acagcggcag    3000
tgccagcgac gggtactgcc cacgcgaaca tatgctgccc tgcccgctgg ccgcactggc    3060
ttcgcgccgc gaggaccccca ggtgtgggca gcctcggccc agccggcttg accttgacct    3120
gcccggctgc caggccgagc ccccggcccg cgaggccacc tccgccgacg cccgcgtgcg    3180
caccatcaag ctgtcgccta cctatcagca cgtgccactg cttgagggtg cctcaagggc    3240
gggtgcagag cccctcgcgg ggcctggaat tctccaggg gccccggaagc aggcctggct    3300
gccggcagac cacctgagca aggttcccga gaagctggcg gctgccccgc tgtctgtggc    3360
cagcaaggca ctgcagaaac tggcggcgca agagggcca ctctcgctgt cccgatgcag    3420
ctcccttttcc tcgctgtcct cggccggccg cccaggcccc agcgagggtg gtgacctgga    3480
tgacagtgac tcctccctgg aggggctgga ggaggccggc cccagcgagg ctgagctgga    3540
cagcacgtgg cgggcgcccg gggccacctc gctgcccgta gccattccgg ctccccggcg    3600
taaccgaggc cggggcctgg gggtggaaga cgccacgccg tccagctcgt cggagaacta    3660
cgtgcaggag acaccgcttg tgctgagccg ctgcagctct gtgagctcgc tgggcagctt    3720
cgagagcccg tccatcgcca gctccatccc cagtgaacct tgcagcgggc agggcagcgg    3780
caccatcagc cctagcgagc tgcccgacag ccccggacag accatgcctc ccagccggag    3840
caagacgcca ccgctggcgc ccgcgccaca gggtccccc gaggcacccc agttcagcct    3900
gcagtgggag agctacgtga agcgcttcct ggacatcgcc gactgccggg agcgctgccg    3960
gctgccatct gagctggacg caggcagcgt gcgctttacc gtggagaagc cagacgagaa    4020
cttctcgtgc gcctccagcc tcagcgcgct ggccttgcac gagcactacg tgcagcagga    4080
```

```
cgtggagctg cggctgctgc cctcggcctg ccccgagcgc ggcggggcg ccgggggcgc    4140 cggcctccac tttgcagggc accggcgcg ggaggagggg ccggcgccca cgggttctcg    4200
ccctcgcggc gccgcggacc aggagctgga actgctgcgg gagtgcctgg agccgccgt     4260 gcctgcccgg ctgcgcaagg tggcctccgc gctggtgcca ggtcgccgcg cactccccgt    4320
gcccgtctac atgttggtgc ccgccccggc cccggcccag gaggacgact cctgcactga    4380
ctccgcggag ggcacgccgg tcaacttctc tagcgccgcc tcgctcagcg acgagacgct    4440
gcagggaccc cccagggacc agcccggggg accagcgggc aggcaaagac ccaccggccg    4500 ccccaccctct gccagacagg ccatggggca ccggcacaag gcgggaggcg ccggccgcag   4560
cgcggagcag tctcggggcg cgggcaagaa cagagcaggg ctggagctgc ccctgggccg    4620
gcccccgagc gccccgcag acaaggacg ctcaaagccc ggccggaccc gcggggacgg     4680
ggcgctccag tcgctgtgcc tcacgacgcc cactgaggag gccgtgtact gcttctacgg    4740
caacgactcg gacgaggagc cccggcggc gcgcccacg ccaacccacc ggcgcacatc     4800
ggccatccct cgcgcttttta cgcgggagcg tccgcagggc cggaaggagg cccctgcccc    4860
gtccaaggct gcaccagctg ccccgccgcc cgcccggacc cagcccagcc tcattgctga    4920
cgagaccccg ccctgctact ccctgagctc ctccgccagc tccctcagcg agcccgagcc    4980
ctcggagccg ccggccgtcc atccacgagg ccgggagccc gcggtcacca aggacccggg    5040
cccaggaggc ggacgcgaca gctcgcccag cccgcgggcc gcggaggagc ttctgcagcg    5100
gtgcatcagc tcggccctgc ccaggcgccg gccccccgtg tctggcctgc ggcgccgcaa    5160
gccccgagcc acccggctgg atgagcggcc cgcagagggg tcccgggaac gcggcgagga    5220
ggcagcgggc tcggaccggg cctccgacct ggatagcgtg gagtggcgcg ccatccagga    5280
gggcgccaat tcaattgtca cgtggctgca ccaggcagca gctgccacgc gggaggcctc    5340
gtccgagtcc gactccatcc tgtccttcgt atccgggctg tcagtgggat ccaccctaca    5400
gccccccaag cacaggaagg gacgacaggc ggagggagaa atgggcagtg cccggcggcc    5460
agagaaaagg ggcgcagcct cagtcaagac cagcgggagc cccgttcccc ctgcaggccc    5520
cgagaagcca cgtggcacac agaagaccac gcccggggtg ccagctgtgc tccggggacg    5580
aacagtgatc tacgtcccca gcccggcacc ccgtgcccag cccaaaggga ccccccggccc    5640 ccgcgccaca ccgcggaagg tggcgccccc ttgcctggca cagcccgcgg ctccagccaa    5700
agtcccgagc cccgggcagc agcggtcgcg gagcctacac cggcctgcca agacctcgga    5760
gctggcgacg ctgagccagc cccccagaag cgccacaccg cccgcccgcc tcgccaagac    5820
cccctcctcc agctcctccc agacctcgcc cgcctcccag ccctgcccca gaaagcgccc    5880 cccgtcacc caggctgctg ggcccctgcc cggcccgga cctcccgg tgcccaaaac      5940 gccggcgcgc acccttctgg cgaagcagca caagacgcag agatcgcccg tgcggatccc    6000
gttcatgcag aggccggccc ggcgtggggcc gccaccgctg gctcgggcag tcccggagcc    6060 gggcccagg ggcgggcgg ggaccgaggc ggggcccggg gcgcgcgggg gccgcctggg       6120
cctggtgcgt gtggcctcag ccctctccag cggcagcgag tcctccgacc gctcgggctt    6180
ccggcgacag ctaaccttca tcaaggagtc gccgggcttg cggcgccgcc gctccgagct    6240 gtcctcgggcc gagtccgcgg cctctgcccc ccagggcgcc tcgccccgcc gcggccggcc    6300 ccgcgctgccc gccgtcttcc tctgctcctc gcgctgcgaa gagctccgag cggcacccccg   6360 gcagggcccg gccccggccc ggcagcggcc cccgcggccc cgaccagcc ctggcgagcg     6420 ccctgcccgg cgcaccacct ccgagagccc gtccgcctg cctgtgcgcg cgcccgccgc     6480
```

```
ccggccggag actgtcaagc gctacgcgtc gctgccgcac atcagcgtgg cccgcaggcc    6540
cgacggcgcc gtccccgcgg cccctgcctc agccgacgcc gcgcgccgca gcagcgacgg    6600
ggagccccgg ccgctcccca gggtggccgc gccgggcacg acctggcggc gcatccgaga    6660
tgaggacgtg ccccacatcc tgcgcagcac gcttcccgcc acggccctgc cactgcgggg    6720
ctccacgccc gaggacgccc cggccgggcc cccgccgcgc aagaccagcg acgccgtggt    6780
ccagaccgag gaggtcgccg cccccaagac caactccagc acgtcccgga gcctggagac    6840
cagggagccc cccggggccc cgccggcgg ccagctctcc ctcctcggca gcgacgtgga    6900
cggtcccagc ctcgccaagg ctcccatctc cgcacccttc gtgcacgagg gcctgggggt    6960
cgccgtgggg ggcttccccg ccagccggca cggctccccc agccgctcgg cccgagtacc    7020
ccccttcaac tatgtgccca gcccccatggt ggtcgcagcc accaccgact cggccgcgga    7080
gaaagccccg gccactgcct ccgccaccct cctggaatag tggcctaggc cggccttctg    7140
gaacgttctc tcccggccct gcggcgcggt ctggctgccc catgggcctg cgctgtagac    7200 gtccccata ggtcgcccca gggcctctgc ccacccgagc ccaccactc tcagaacccc    7260 cgcccagcgc acgcgacct cgcgcctcac cggaagacct tgcctctgtg ccgcggaggt    7320
ccaggaggaa acggggcggc cgctaggcct caagtcccga ccgtggagcg ctggcaaggg    7380
cgtcctggcc cagccctgag cgcgcggccc ttccctgtc ggaagccgtt gcttgacccc    7440
gggcgaggga ggcggtagcc tccgggtccg ggtctgggtc tgggtccgct gcttcgcagg    7500
gacagcgctg gggaggtgac ggcgcccgcc gcaggtgggg cgaggctggg ggagggcggc    7560
gccgcggcgg gcctgccagc tgggggcctt tgcggcgcgc aggggcgaag cctgtaatca    7620
ctgcagccgc cggtaattcg ctaatgaggg ctttgcaggg attgttttca ttctcagccc    7680
cagctgtggg agtgcgggtg ggggtgtggc cgagcccggg caggaagccc cgcccagacg    7740
gtgttcaggg aacccggagc ccaagcgctc cggcggagcc caaaagggtg ggggtgggag    7800
gggcagaggc caacggatcc ccctgcctgt cgcaccccctt ggcgggagac gggaaggcag    7860
cgggctgcgt acgatgggac cctggtgcag acgccgggcc ggctgacatt tggaccccat    7920
cccagaggag atgctggcta ccagctgggg cgaccccaag ggtcgctgga gtcagtatcg    7980
gcccggcgca ccgcggcgg gcgaggccaa tggaaaggag actgagggga gtcccggcag    8040
tgagcccgag gccctgggac ctggagcccg cgctggcctc tccccagcgg agcctgcacg    8100
ttacggagac catcacatgt gggcgtggtc agtgcccagg accgcaccgc tgctcatctt    8160 gtccctttc aattcccttc tggttcatga tgcataaagc gctaggccct agaactccag    8220
aaacagcaca gctggggcgg ggacccagcc ttgccctcca cccgaggctc tgggacaagg    8280
cgggaggttc gggggccttc cggcaggtga acgcagggct ggagagtatt tggtgccaga    8340
tgaggtgaaa gcttatagaa gggcctgagg ggctcggctg cctcatcccc tggcggggga    8400
ggctgggagc tgggcctcct gcgtggggtg ggactcgcag gggccgggtc tccgtgactg    8460
gggcaacgcc tcgtcctgca gagggagccg acgacctctt ttctgcagaa aagctccagc    8520
aggcgctgcc ttcacccacg gatctgccca ggctgaaggc acacgctcaa tgccccacgt    8580
gccttctcca ggaggaacga agcagggttt gagggttggg tggatggagc tcagaaggaa    8640
accccagccc caccacggat gacaccatcc ctcccgtccc atcccagca tgggcaaggc    8700 cagcctttct ggcagaagga gctgtcctca actcagggcc gctgtgagca aagctgaccc    8760 cagccccac ccccagttaa cactgctgct tctctgaatg catgtcacgc tgcaccccat    8820
gctccgggcc cacaccctgc aggacaagga gctccagaca ggacgtccat aagtcaccga    8880
```

```
ggtgtgccac ccagcaggtg ctggaggtgc ccaatgctcc ctcctaggac ctcgcagcca   8940
ggcaaggctg tcaggttgtt ttgggggaag agggggtcat ggatggctga gcagagagcg   9000
gggaaaatgc aggctgagtg gggcgacctc ctgcctgcca ggagccccct ttcaggacac   9060
agcgggggtc tcacacttgc tgtccccatc catgggccga gggggaacct ggtggtctct   9120
tctgagcttt tggacttggg gatgccaaac acgtgctcac cctcacactc gccccggccc   9180
gctgcgcccc taattgccaa agggtaggga aatggcgaag ccagccacca ggtcgctggt   9240
gacagggcca gggttatgca ggaaggtggt gcggcattgc cttccacata tgtaagtctc   9300
tgggcggcgc cctcccagct ccctgcctct gtttccccat gtgggccgtg gggaactccc   9360
agagctacct cttggggggag cgtggtggca gcgatgatgg ggagacgcct ggaagctcac   9420
agaacttggg tctggctggc tcctgcccgt gacgccttgc ccagcagcaa ggtgcgcaac   9480
atggctgcca gccccgcctc ccaccccac cccgagtcct gagctcactt tcgcctttctc   9540
catcccctgc cgtgggggcc acagccacac ctcaccgccc agtccagctg tctccagaag   9600
gggacaggca gtccgcggtc tctggacaat caactcaagg tacgcccact gcaaggcctc   9660
cctcccaccg cggcccctgc ctggccacct ggcctctctg caccagggtg acaaggggtc   9720
ctcgtctgcc ccccaatgct ccagggccag tcctaaggag ctgagggtct gaggacgcag   9780
ggagggtgga ggtgtcctga ggctgatgga cagtgaccgc cactggcccc caacatgacc   9840
acacgtgggt gctgaactcg gggcgccgtg cccaccggca tggtcctccc gagctccgac   9900
agcattacct cacccggccc catctgttgc cccggtccag ccctgatggc gcgcgcctgg   9960
tctgtctgat tcccctagcc gccaccccac gtttctgtac cgggtctctg cagtgttaaa  10020
cggacgtgta aatagtggta aatagtgaaa gcctgtcctt ccctaaatgt aaagccatct  10080
gtccggcgta aggacgacac cgtcagctgt ccgactcgca cacatttaat aaactgagct  10140
cttgcattgc c                                                       10151
```

<210> SEQ ID NO 72
<211> LENGTH: 2303
<212> TYPE: PRT
<213> ORGANISM: Homo sapiens

<400> SEQUENCE: 72

```
Met Ala Ser Ser Val Ala Pro Tyr Glu Gln Leu Val Arg Gln Val Glu
 1               5                  10                  15

Ala Leu Lys Ala Glu Asn Ser His Leu Arg Gln Glu Leu Arg Asp Asn
            20                  25                  30

Ser Ser His Leu Ser Lys Leu Glu Thr Glu Thr Ser Gly Met Lys Glu
        35                  40                  45

Val Leu Lys His Leu Gln Gly Lys Leu Glu Gln Glu Ala Arg Val Leu
    50                  55                  60

Val Ser Ser Gly Gln Thr Glu Val Leu Glu Gln Leu Lys Ala Leu Gln
65                  70                  75                  80

Met Asp Ile Thr Ser Leu Tyr Asn Leu Lys Phe Gln Pro Pro Thr Leu
                85                  90                  95

Gly Pro Glu Pro Ala Ala Arg Thr Pro Glu Gly Ser Pro Val His Gly
            100                 105                 110

Ser Gly Pro Ser Lys Asp Ser Phe Gly Glu Leu Ser Arg Ala Thr Ile
        115                 120                 125

Arg Leu Leu Glu Glu Leu Asp Arg Glu Arg Cys Phe Leu Leu Asn Glu
    130                 135                 140

Ile Glu Lys Glu Glu Lys Glu Lys Leu Trp Tyr Tyr Ser Gln Leu Gln
```

```
                145                 150                 155                 160
Gly Leu Ser Lys Arg Leu Asp Glu Leu Pro His Val Glu Thr Gln Phe
                    165                 170                 175
Ser Met Gln Met Asp Leu Ile Arg Gln Leu Glu Phe Glu Ala Gln
                    180                 185                 190
His Ile Arg Ser Leu Met Glu Glu Arg Phe Gly Thr Ser Asp Glu Met
                    195                 200                 205
Val Gln Arg Ala Gln Ile Arg Ala Ser Arg Leu Glu Gln Ile Asp Lys
                    210                 215                 220
Glu Leu Leu Glu Ala Gln Asp Arg Val Gln Gln Thr Glu Pro Gln Ala
225                 230                 235                 240
Leu Leu Ala Val Lys Ser Val Pro Val Asp Glu Asp Pro Glu Thr Glu
                    245                 250                 255
Val Pro Thr His Pro Glu Asp Gly Thr Pro Gln Pro Gly Asn Ser Lys
                    260                 265                 270
Val Glu Val Val Phe Trp Leu Leu Ser Met Leu Ala Thr Arg Asp Gln
                    275                 280                 285
Glu Asp Thr Ala Arg Thr Leu Leu Ala Met Ser Ser Ser Pro Glu Ser
                    290                 295                 300
Cys Val Ala Met Arg Arg Ser Gly Cys Leu Pro Leu Leu Leu Gln Ile
305                 310                 315                 320
Leu His Gly Thr Glu Ala Ala Gly Gly Arg Ala Gly Ala Pro Gly
                    325                 330                 335
Ala Pro Gly Ala Lys Asp Ala Arg Met Arg Ala Asn Ala Ala Leu His
                    340                 345                 350
Asn Ile Val Phe Ser Gln Pro Asp Gln Gly Leu Ala Arg Lys Glu Met
                    355                 360                 365
Arg Val Leu His Val Leu Glu Gln Ile Arg Ala Tyr Cys Glu Thr Cys
                    370                 375                 380
Trp Asp Trp Leu Gln Ala Arg Asp Gly Gly Pro Glu Gly Gly Gly Ala
385                 390                 395                 400
Gly Ser Ala Pro Ile Pro Ile Glu Pro Gln Ile Cys Gln Ala Thr Cys
                    405                 410                 415
Ala Val Met Lys Leu Ser Phe Asp Glu Glu Tyr Arg Arg Ala Met Asn
                    420                 425                 430
Glu Leu Gly Gly Leu Gln Ala Val Ala Glu Leu Leu Gln Val Asp Tyr
                    435                 440                 445
Glu Met His Lys Met Thr Arg Asp Pro Leu Asn Leu Ala Leu Arg Arg
                    450                 455                 460
Tyr Ala Gly Met Thr Leu Thr Asn Leu Thr Phe Gly Asp Val Ala Asn
465                 470                 475                 480
Lys Ala Thr Leu Cys Ala Arg Arg Gly Cys Met Glu Ala Ile Val Ala
                    485                 490                 495
Gln Leu Ala Ser Asp Ser Glu Glu Leu His Gln Val Val Ser Ser Ile
                    500                 505                 510
Leu Arg Asn Leu Ser Trp Arg Ala Asp Ile Asn Ser Lys Lys Val Leu
                    515                 520                 525
Arg Glu Ala Gly Ser Val Thr Ala Leu Val Gln Cys Val Leu Arg Ala
                    530                 535                 540
Thr Lys Glu Ser Thr Leu Lys Ser Val Leu Ser Ala Leu Trp Asn Leu
545                 550                 555                 560
Ser Ala His Ser Thr Glu Asn Lys Ala Ala Ile Cys Gln Val Asp Gly
                    565                 570                 575
```

-continued

```
Ala Leu Gly Phe Leu Val Ser Thr Leu Thr Tyr Lys Cys Gln Ser Asn
            580                 585                 590

Ser Leu Ala Ile Ile Glu Ser Gly Gly Ile Leu Arg Asn Val Ser
        595                 600                 605

Ser Leu Val Ala Thr Arg Glu Asp Tyr Arg Gln Val Leu Arg Asp His
    610                 615                 620

Asn Cys Leu Gln Thr Leu Leu Gln His Leu Thr Ser His Ser Leu Thr
625                 630                 635                 640

Ile Val Ser Asn Ala Cys Gly Thr Leu Trp Asn Leu Ser Ala Arg Ser
                645                 650                 655

Ala Arg Asp Gln Glu Leu Leu Trp Asp Leu Gly Ala Val Gly Met Leu
            660                 665                 670

Arg Asn Leu Val His Ser Lys His Lys Met Ile Ala Met Gly Ser Ala
        675                 680                 685

Ala Ala Leu Arg Asn Leu Leu Ala His Arg Pro Ala Lys His Gln Ala
    690                 695                 700

Ala Ala Thr Ala Val Ser Pro Gly Ser Cys Val Pro Ser Leu Tyr Val
705                 710                 715                 720

Arg Lys Gln Arg Ala Leu Glu Ala Glu Leu Asp Ala Arg His Leu Ala
                725                 730                 735

Gln Ala Leu Glu His Leu Glu Lys Gln Gly Pro Pro Ala Ala Glu Ala
            740                 745                 750

Ala Thr Lys Lys Pro Leu Pro Pro Leu Arg His Leu Asp Gly Leu Ala
        755                 760                 765

Gln Asp Tyr Ala Ser Asp Ser Gly Cys Phe Asp Asp Asp Ala Pro
    770                 775                 780

Ser Ser Leu Ala Ala Ala Ala Thr Gly Glu Pro Ala Ser Pro Ala
785                 790                 795                 800

Ala Leu Ser Leu Phe Leu Gly Ser Pro Phe Leu Gln Gly Gln Ala Leu
                805                 810                 815

Ala Arg Thr Pro Pro Thr Arg Arg Gly Gly Lys Glu Ala Glu Lys Asp
            820                 825                 830

Thr Ser Gly Glu Ala Ala Val Ala Ala Lys Ala Lys Ala Lys Leu Ala
        835                 840                 845

Leu Ala Val Ala Arg Ile Asp Gln Leu Val Glu Asp Ile Ser Ala Leu
    850                 855                 860

His Thr Ser Ser Asp Asp Ser Phe Ser Leu Ser Ser Gly Asp Pro Gly
865                 870                 875                 880

Gln Glu Ala Pro Arg Glu Gly Arg Ala Gln Ser Cys Ser Pro Cys Arg
                885                 890                 895

Gly Pro Glu Gly Gly Arg Arg Gly Ala Gly Ser Arg Ala His Pro Leu
            900                 905                 910

Leu Arg Leu Lys Ala Ala His Ala Ser Leu Ser Asn Asp Ser Leu Asn
        915                 920                 925

Ser Gly Ser Ala Ser Asp Gly Tyr Cys Pro Arg Glu His Met Leu Pro
    930                 935                 940

Cys Pro Leu Ala Ala Leu Ala Ser Arg Arg Glu Asp Pro Arg Cys Gly
945                 950                 955                 960

Gln Pro Arg Pro Ser Arg Leu Asp Leu Asp Leu Pro Gly Cys Gln Ala
                965                 970                 975

Glu Pro Pro Ala Arg Glu Ala Thr Ser Ala Asp Ala Arg Val Arg Thr
            980                 985                 990

Ile Lys Leu Ser Pro Thr Tyr Gln His Val Pro Leu Leu Glu Gly Ala
        995                 1000                1005
```

-continued

Ser Arg Ala Gly Ala Glu Pro Leu Ala Gly Pro Gly Ile Ser Pro
    1010                1015                1020

Gly Ala Arg Lys Gln Ala Trp Leu Pro Ala Asp His Leu Ser Lys
    1025                1030                1035

Val Pro Glu Lys Leu Ala Ala Ala Pro Leu Ser Val Ala Ser Lys
    1040                1045                1050

Ala Leu Gln Lys Leu Ala Ala Gln Glu Gly Pro Leu Ser Leu Ser
    1055                1060                1065

Arg Cys Ser Ser Leu Ser Ser Leu Ser Ser Ala Gly Arg Pro Gly
    1070                1075                1080

Pro Ser Glu Gly Gly Asp Leu Asp Asp Ser Asp Ser Ser Leu Glu
    1085                1090                1095

Gly Leu Glu Glu Ala Gly Pro Ser Glu Ala Glu Leu Asp Ser Thr
    1100                1105                1110

Trp Arg Ala Pro Gly Ala Thr Ser Leu Pro Val Ala Ile Pro Ala
    1115                1120                1125

Pro Arg Arg Asn Arg Gly Arg Gly Leu Gly Val Glu Asp Ala Thr
    1130                1135                1140

Pro Ser Ser Ser Ser Glu Asn Tyr Val Gln Glu Thr Pro Leu Val
    1145                1150                1155

Leu Ser Arg Cys Ser Ser Val Ser Ser Leu Gly Ser Phe Glu Ser
    1160                1165                1170

Pro Ser Ile Ala Ser Ser Ile Pro Ser Glu Pro Cys Ser Gly Gln
    1175                1180                1185

Gly Ser Gly Thr Ile Ser Pro Ser Glu Leu Pro Asp Ser Pro Gly
    1190                1195                1200

Gln Thr Met Pro Pro Ser Arg Ser Lys Thr Pro Pro Leu Ala Pro
    1205                1210                1215

Ala Pro Gln Gly Pro Pro Glu Ala Thr Gln Phe Ser Leu Gln Trp
    1220                1225                1230

Glu Ser Tyr Val Lys Arg Phe Leu Asp Ile Ala Asp Cys Arg Glu
    1235                1240                1245

Arg Cys Arg Leu Pro Ser Glu Leu Asp Ala Gly Ser Val Arg Phe
    1250                1255                1260

Thr Val Glu Lys Pro Asp Glu Asn Phe Ser Cys Ala Ser Ser Leu
    1265                1270                1275

Ser Ala Leu Ala Leu His Glu His Tyr Val Gln Gln Asp Val Glu
    1280                1285                1290

Leu Arg Leu Leu Pro Ser Ala Cys Pro Glu Arg Gly Gly Gly Ala
    1295                1300                1305

Gly Gly Ala Gly Leu His Phe Ala Gly His Arg Arg Arg Glu Glu
    1310                1315                1320

Gly Pro Ala Pro Thr Gly Ser Arg Pro Arg Gly Ala Ala Asp Gln
    1325                1330                1335

Glu Leu Glu Leu Leu Arg Glu Cys Leu Gly Ala Ala Val Pro Ala
    1340                1345                1350

Arg Leu Arg Lys Val Ala Ser Ala Leu Val Pro Gly Arg Arg Ala
    1355                1360                1365

Leu Pro Val Pro Val Tyr Met Leu Val Pro Ala Pro Ala Pro Ala
    1370                1375                1380

Gln Glu Asp Asp Ser Cys Thr Asp Ser Ala Glu Gly Thr Pro Val
    1385                1390                1395

Asn Phe Ser Ser Ala Ala Ser Leu Ser Asp Glu Thr Leu Gln Gly

```
                1400                1405                1410

Pro Pro Arg Asp Gln Pro Gly Gly Pro Ala Gly Arg Gln Arg Pro
    1415                1420                1425

Thr Gly Arg Pro Thr Ser Ala Arg Gln Ala Met Gly His Arg His
    1430                1435                1440

Lys Ala Gly Gly Ala Gly Arg Ser Ala Glu Gln Ser Arg Gly Ala
    1445                1450                1455

Gly Lys Asn Arg Ala Gly Leu Glu Leu Pro Leu Gly Arg Pro Pro
    1460                1465                1470

Ser Ala Pro Ala Asp Lys Asp Gly Ser Lys Pro Gly Arg Thr Arg
    1475                1480                1485

Gly Asp Gly Ala Leu Gln Ser Leu Cys Leu Thr Thr Pro Thr Glu
    1490                1495                1500

Glu Ala Val Tyr Cys Phe Tyr Gly Asn Asp Ser Asp Glu Glu Pro
    1505                1510                1515

Pro Ala Ala Ala Pro Thr Pro Thr His Arg Arg Thr Ser Ala Ile
    1520                1525                1530

Pro Arg Ala Phe Thr Arg Glu Arg Pro Gln Gly Arg Lys Glu Ala
    1535                1540                1545

Pro Ala Pro Ser Lys Ala Ala Pro Ala Ala Pro Pro Pro Ala Arg
    1550                1555                1560

Thr Gln Pro Ser Leu Ile Ala Asp Glu Thr Pro Pro Cys Tyr Ser
    1565                1570                1575

Leu Ser Ser Ser Ala Ser Ser Leu Ser Glu Pro Glu Pro Ser Glu
    1580                1585                1590

Pro Pro Ala Val His Pro Arg Gly Arg Glu Pro Ala Val Thr Lys
    1595                1600                1605

Asp Pro Gly Pro Gly Gly Gly Arg Asp Ser Ser Pro Ser Pro Arg
    1610                1615                1620

Ala Ala Glu Glu Leu Leu Gln Arg Cys Ile Ser Ser Ala Leu Pro
    1625                1630                1635

Arg Arg Arg Pro Pro Val Ser Gly Leu Arg Arg Arg Lys Pro Arg
    1640                1645                1650

Ala Thr Arg Leu Asp Glu Arg Pro Ala Glu Gly Ser Arg Glu Arg
    1655                1660                1665

Gly Glu Glu Ala Ala Gly Ser Asp Arg Ala Ser Asp Leu Asp Ser
    1670                1675                1680

Val Glu Trp Arg Ala Ile Gln Glu Gly Ala Asn Ser Ile Val Thr
    1685                1690                1695

Trp Leu His Gln Ala Ala Ala Thr Arg Glu Ala Ser Ser Glu
    1700                1705                1710

Ser Asp Ser Ile Leu Ser Phe Val Ser Gly Leu Ser Val Gly Ser
    1715                1720                1725

Thr Leu Gln Pro Pro Lys His Arg Lys Gly Arg Gln Ala Glu Gly
    1730                1735                1740

Glu Met Gly Ser Ala Arg Arg Pro Glu Lys Arg Gly Ala Ala Ser
    1745                1750                1755

Val Lys Thr Ser Gly Ser Pro Arg Ser Pro Ala Gly Pro Glu Lys
    1760                1765                1770

Pro Arg Gly Thr Gln Lys Thr Thr Pro Gly Val Pro Ala Val Leu
    1775                1780                1785

Arg Gly Arg Thr Val Ile Tyr Val Pro Ser Pro Ala Pro Arg Ala
    1790                1795                1800
```

-continued

| | | | | | | | | | | |
|---|---|---|---|---|---|---|---|---|---|---|
|Gln|Pro|Lys|Gly|Thr|Pro|Gly|Pro|Arg|Ala|Thr|Pro|Arg|Lys|Val|
| |1805| | | |1810| | | |1815| |
|Ala|Pro|Pro|Cys|Leu|Ala|Gln|Pro|Ala|Ala|Pro|Ala|Lys|Val|Pro|
| |1820| | | |1825| | | |1830| |
|Ser|Pro|Gly|Gln|Gln|Arg|Ser|Arg|Ser|Leu|His|Arg|Pro|Ala|Lys|
| |1835| | | |1840| | | |1845| |
|Thr|Ser|Glu|Leu|Ala|Thr|Leu|Ser|Gln|Pro|Pro|Arg|Ser|Ala|Thr|
| |1850| | | |1855| | | |1860| |
|Pro|Pro|Ala|Arg|Leu|Ala|Lys|Thr|Pro|Ser|Ser|Ser|Ser|Ser|Gln|
| |1865| | | |1870| | | |1875| |
|Thr|Ser|Pro|Ala|Ser|Gln|Pro|Leu|Pro|Arg|Lys|Arg|Pro|Pro|Val|
| |1880| | | |1885| | | |1890| |
|Thr|Gln|Ala|Ala|Gly|Ala|Leu|Pro|Gly|Pro|Gly|Ala|Ser|Pro|Val|
| |1895| | | |1900| | | |1905| |
|Pro|Lys|Thr|Pro|Ala|Arg|Thr|Leu|Leu|Ala|Lys|Gln|His|Lys|Thr|
| |1910| | | |1915| | | |1920| |
|Gln|Arg|Ser|Pro|Val|Arg|Ile|Pro|Phe|Met|Gln|Arg|Pro|Ala|Arg|
| |1925| | | |1930| | | |1935| |
|Arg|Gly|Pro|Pro|Pro|Leu|Ala|Arg|Ala|Val|Pro|Glu|Pro|Gly|Pro|
| |1940| | | |1945| | | |1950| |
|Arg|Gly|Arg|Ala|Gly|Thr|Glu|Ala|Gly|Pro|Gly|Ala|Arg|Gly|Gly|
| |1955| | | |1960| | | |1965| |
|Arg|Leu|Gly|Leu|Val|Arg|Val|Ala|Ser|Ala|Leu|Ser|Ser|Gly|Ser|
| |1970| | | |1975| | | |1980| |
|Glu|Ser|Ser|Asp|Arg|Ser|Gly|Phe|Arg|Arg|Gln|Leu|Thr|Phe|Ile|
| |1985| | | |1990| | | |1995| |
|Lys|Glu|Ser|Pro|Gly|Leu|Arg|Arg|Arg|Arg|Ser|Glu|Leu|Ser|Ser|
| |2000| | | |2005| | | |2010| |
|Ala|Glu|Ser|Ala|Ala|Ser|Ala|Pro|Gln|Gly|Ala|Ser|Pro|Arg|Arg|
| |2015| | | |2020| | | |2025| |
|Gly|Arg|Pro|Ala|Leu|Pro|Ala|Val|Phe|Leu|Cys|Ser|Ser|Arg|Cys|
| |2030| | | |2035| | | |2040| |
|Glu|Glu|Leu|Arg|Ala|Ala|Pro|Arg|Gln|Gly|Pro|Ala|Pro|Ala|Arg|
| |2045| | | |2050| | | |2055| |
|Gln|Arg|Pro|Pro|Ala|Ala|Arg|Pro|Ser|Pro|Gly|Glu|Arg|Pro|Ala|
| |2060| | | |2065| | | |2070| |
|Arg|Arg|Thr|Thr|Ser|Glu|Ser|Pro|Ser|Arg|Leu|Pro|Val|Arg|Ala|
| |2075| | | |2080| | | |2085| |
|Pro|Ala|Ala|Arg|Pro|Glu|Thr|Val|Lys|Arg|Tyr|Ala|Ser|Leu|Pro|
| |2090| | | |2095| | | |2100| |
|His|Ile|Ser|Val|Ala|Arg|Arg|Pro|Asp|Gly|Ala|Val|Pro|Ala|Ala|
| |2105| | | |2110| | | |2115| |
|Pro|Ala|Ser|Ala|Asp|Ala|Ala|Arg|Arg|Ser|Ser|Asp|Gly|Glu|Pro|
| |2120| | | |2125| | | |2130| |
|Arg|Pro|Leu|Pro|Arg|Val|Ala|Ala|Pro|Gly|Thr|Thr|Trp|Arg|Arg|
| |2135| | | |2140| | | |2145| |
|Ile|Arg|Asp|Glu|Asp|Val|Pro|His|Ile|Leu|Arg|Ser|Thr|Leu|Pro|
| |2150| | | |2155| | | |2160| |
|Ala|Thr|Ala|Leu|Pro|Leu|Arg|Gly|Ser|Thr|Pro|Glu|Asp|Ala|Pro|
| |2165| | | |2170| | | |2175| |
|Ala|Gly|Pro|Pro|Pro|Arg|Lys|Thr|Ser|Asp|Ala|Val|Val|Gln|Thr|
| |2180| | | |2185| | | |2190| |
|Glu|Glu|Val|Ala|Ala|Pro|Lys|Thr|Asn|Ser|Ser|Thr|Ser|Pro|Ser|
| |2195| | | |2200| | | |2205| |

```
Leu Glu Thr Arg Glu Pro Pro Gly Ala Pro Ala Gly Gly Gln Leu
    2210            2215                2220

Ser Leu Leu Gly Ser Asp Val Asp Gly Pro Ser Leu Ala Lys Ala
    2225            2230                2235

Pro Ile Ser Ala Pro Phe Val His Glu Gly Leu Gly Val Ala Val
    2240            2245                2250

Gly Gly Phe Pro Ala Ser Arg His Gly Ser Pro Ser Arg Ser Ala
    2255            2260                2265

Arg Val Pro Pro Phe Asn Tyr Val Pro Ser Pro Met Val Val Ala
    2270            2275                2280

Ala Thr Thr Asp Ser Ala Ala Glu Lys Ala Pro Ala Thr Ala Ser
    2285            2290                2295

Ala Thr Leu Leu Glu
    2300

<210> SEQ ID NO 73
<211> LENGTH: 2636
<212> TYPE: DNA
<213> ORGANISM: Homo sapiens

<400> SEQUENCE: 73
```

| | | | |
|---|---|---|---|
| cacccactag aaagccaccc gggttctcct tcatccccaa cgctcctcac ctagcccctg | 60 |
| tcctgagggt gccccctaacc ctggagccag ctttaaaggg gcaggcccct tctcctgccc | 120 |
| cagccccagc cccacccacc gggcccacat tctccgtctt ccaggtccag cgctccctca | 180 |
| cagaactccc ccgcaccttg tctcgctcgc tccgccccte cttcccagcc acagctagag | 240 |
| gtcccgggcg cacctgcaga gccggaggct tgctggggca tgcgctccat gaaggctctg | 300 |
| cagaaggccc tgagccgggc tggcagtcac tgcgggcgag gaggctgggg tcacccgagc | 360 |
| cggagccccc tccttggcgg gggcgtccgg caccacctca gtgaggccgc ggcgcagggc | 420 |
| agagagacgc cacacagcca ccagccgcag caccaggatc atgattcatc agaaagtggc | 480 |
| atgctgtccc gctgggtga tttgctcttt tacactattg ctgaaggaca ggaacgaatc | 540 |
| cctatccaca agttcaccac tgcactaaag gccactggac tgcagacatc agatcctcgg | 600 |
| ctccgagact gcatgagcga gatgcaccgc gtggtccaag agtccagtag tggtggcctc | 660 |
| ttggaccgag atctcttccg aaagtgtgtg agcagcaaca ttgtgctcct gacccaggca | 720 |
| ttccgaaaga gtttgtcat cctgattttt gaggagttca cgggccatgt ggatcgcatc | 780 |
| tttgaggatg tcaaagagct cactggaggc aaagtggcag cctacatccc tcagctggcc | 840 |
| aagtcaaacc cagacctgtg gggtgtctcc ctgtgcactg tggatggtca acggcactct | 900 |
| gtgggccaca caaagatccc cttctgcctg cagtcctgtg tgaagcccct cacctatgcc | 960 |
| atctccataa gcaccctagg cactgactac gtgcacaagt ttgtgggcaa agagccaagt | 1020 |
| ggcctgcgct acaacaagct ctcccctcaat gaggaaggaa tccccccataa ccccatggtc | 1080 |
| aatgctggtg ccattgttgt cagctccctg atcaagatgg actgtaacaa agcagagaag | 1140 |
| tttgattttg tgttgcagta tctcaacaaa atggctggga tgaatacat gggtttcagc | 1200 |
| aatgccacat tccagtcaga gaaggaaaca ggggatcgga attatgccat cggctattat | 1260 |
| ctcaaggaaa agaagtgctt tcctaagggg gtggacatga tggctgccct tgatctctac | 1320 |
| ttccagctgt gttctgtgga ggtcacttgt gaatcaggca gtgtcatggc agccaccctc | 1380 |
| gccaacggtg ggatctgccc catcacaggc gagagtgtgc tgagtgctga agcagtgcgc | 1440 |
| aacaccctca gcctcatgca ttcctgcggc atgtatgact tctctggcca gtttgccttc | 1500 |

-continued

```
cacgtgggcc tgccagccaa gtcagctgta tcaggagcca tcctcctggt ggtacccaat    1560
gtcatgggaa tgatgtgcct gtcaccccca ttggacaagc tggggaacag ccataggggg    1620
accagcttct gccagaagtt ggtgtctctc ttcaatttcc acaactatga caacctgagg    1680
cactgtgctc ggaagttaga cccacggcgt gaaggggcag aaattcggaa caagactgtg    1740
gtcaacctgt tatttgctgc ctatagtggc gatgtctcag ctcttcgaag gtttgccttg    1800
tcagccatgg atatggaaca gaaagactat gactcgcgca cagctctgca tgttgctgca    1860
gctgaaggac acatcgaagt tgttaaattc ctgatcgagg cttgcaaagt gaatcctttt    1920
gccaaggaca ggtggggcaa cattcccctg atgatgctg tgcagttcaa ccatctggag    1980
gtggtcaaac tgcttcaaga ttaccaggac tcctacacac tctctgaaac tcaggctgag    2040
gcagcagctg aggccctgtc caaagagaac ttagaaagca tggtatgagc acaggtcatg    2100
gacagcccct gctcaagaaa aagcatgagc tggccacaca tgtaatccat aaccaccaaa    2160
aatactatgg agagctacac tgcttcagtg gggaccaagc agtcatttgg tgacttaggc    2220
tagtgctttc tatgggagtc aaaataccc attccctcag cagacagagt acagagaagg    2280
gcctcagagg acacctgcag tacagctatc cagagagact gggcttcaag gtacagccta    2340
atggcttgcc ccactcaaaa ccatcccagc tcttcaccca ggtctcctct tcctctccct    2400
gaagaaacca tcatgagaga gatactctgg tggagggact ctagctacca tgcacatgta    2460
catatccaca gaatatggga agtgggaatg gctatataca tggctttagt agtctggaga    2520
aatctactcc ccttggccag gacatgctgc tgctactgct aacagccaat tttatagaca    2580
gagaaagtat tttgtgttca aataaacttt aattaccaaa tcaaaaaaaa aaaaaa       2636
```

<210> SEQ ID NO 74
<211> LENGTH: 602
<212> TYPE: PRT
<213> ORGANISM: Homo sapiens

<400> SEQUENCE: 74

```
Met Arg Ser Met Lys Ala Leu Gln Lys Ala Leu Ser Arg Ala Gly Ser
1               5                   10                  15

His Cys Gly Arg Gly Gly Trp Gly His Pro Ser Arg Ser Pro Leu Leu
            20                  25                  30

Gly Gly Gly Val Arg His His Leu Ser Glu Ala Ala Gln Gly Arg
        35                  40                  45

Glu Thr Pro His Ser His Gln Pro Gln His Gln Asp His Asp Ser Ser
    50                  55                  60

Glu Ser Gly Met Leu Ser Arg Leu Gly Asp Leu Leu Phe Tyr Thr Ile
65                  70                  75                  80

Ala Glu Gly Gln Glu Arg Ile Pro Ile His Lys Phe Thr Thr Ala Leu
                85                  90                  95

Lys Ala Thr Gly Leu Gln Thr Ser Asp Pro Arg Leu Arg Asp Cys Met
            100                 105                 110

Ser Glu Met His Arg Val Val Gln Glu Ser Ser Gly Gly Leu Leu
        115                 120                 125

Asp Arg Asp Leu Phe Arg Lys Cys Val Ser Ser Asn Ile Val Leu Leu
    130                 135                 140

Thr Gln Ala Phe Arg Lys Lys Phe Val Ile Pro Asp Phe Glu Glu Phe
145                 150                 155                 160

Thr Gly His Val Asp Arg Ile Phe Glu Asp Val Lys Glu Leu Thr Gly
                165                 170                 175

Gly Lys Val Ala Ala Tyr Ile Pro Gln Leu Ala Lys Ser Asn Pro Asp
```

-continued

```
                180                 185                 190
Leu Trp Gly Val Ser Leu Cys Thr Val Asp Gly Gln Arg His Ser Val
            195                 200                 205
Gly His Thr Lys Ile Pro Phe Cys Leu Gln Ser Cys Val Lys Pro Leu
            210                 215                 220
Thr Tyr Ala Ile Ser Ile Ser Thr Leu Gly Thr Asp Tyr Val His Lys
225                 230                 235                 240
Phe Val Gly Lys Glu Pro Ser Gly Leu Arg Tyr Asn Lys Leu Ser Leu
                245                 250                 255
Asn Glu Glu Gly Ile Pro His Asn Pro Met Val Asn Ala Gly Ala Ile
            260                 265                 270
Val Val Ser Ser Leu Ile Lys Met Asp Cys Asn Lys Ala Glu Lys Phe
            275                 280                 285
Asp Phe Val Leu Gln Tyr Leu Asn Lys Met Ala Gly Asn Glu Tyr Met
        290                 295                 300
Gly Phe Ser Asn Ala Thr Phe Gln Ser Glu Lys Glu Thr Gly Asp Arg
305                 310                 315                 320
Asn Tyr Ala Ile Gly Tyr Tyr Leu Lys Glu Lys Lys Cys Phe Pro Lys
                325                 330                 335
Gly Val Asp Met Met Ala Ala Leu Asp Leu Tyr Phe Gln Leu Cys Ser
                340                 345                 350
Val Glu Val Thr Cys Glu Ser Gly Ser Val Met Ala Ala Thr Leu Ala
            355                 360                 365
Asn Gly Gly Ile Cys Pro Ile Thr Gly Glu Ser Val Leu Ser Ala Glu
            370                 375                 380
Ala Val Arg Asn Thr Leu Ser Leu Met His Ser Cys Gly Met Tyr Asp
385                 390                 395                 400
Phe Ser Gly Gln Phe Ala Phe His Val Gly Leu Pro Ala Lys Ser Ala
                405                 410                 415
Val Ser Gly Ala Ile Leu Leu Val Pro Asn Val Met Gly Met Met
            420                 425                 430
Cys Leu Ser Pro Pro Leu Asp Lys Leu Gly Asn Ser His Arg Gly Thr
            435                 440                 445
Ser Phe Cys Gln Lys Leu Val Ser Leu Phe Asn Phe His Asn Tyr Asp
        450                 455                 460
Asn Leu Arg His Cys Ala Arg Lys Leu Asp Pro Arg Arg Glu Gly Ala
465                 470                 475                 480
Glu Ile Arg Asn Lys Thr Val Val Asn Leu Leu Phe Ala Ala Tyr Ser
                485                 490                 495
Gly Asp Val Ser Ala Leu Arg Arg Phe Ala Leu Ser Ala Met Asp Met
                500                 505                 510
Glu Gln Lys Asp Tyr Asp Ser Arg Thr Ala Leu His Val Ala Ala Ala
            515                 520                 525
Glu Gly His Ile Glu Val Val Lys Phe Leu Ile Glu Ala Cys Lys Val
            530                 535                 540
Asn Pro Phe Ala Lys Asp Arg Trp Gly Asn Ile Pro Leu Asp Asp Ala
545                 550                 555                 560
Val Gln Phe Asn His Leu Glu Val Val Lys Leu Leu Gln Asp Tyr Gln
                565                 570                 575
Asp Ser Tyr Thr Leu Ser Glu Thr Gln Ala Glu Ala Ala Glu Ala
                580                 585                 590
Leu Ser Lys Glu Asn Leu Glu Ser Met Val
            595                 600
```

<210> SEQ ID NO 75
<211> LENGTH: 1231
<212> TYPE: DNA
<213> ORGANISM: Homo sapiens

<400> SEQUENCE: 75

```
cgactctcac gtgaccagga gtcgacgtgt gcagaagtcc ttatagtcca gggcctgttt      60
ccctgtagca gctccttatt gctggagaag gagaaaagtg cccaagatcc tttcaggata     120
tttggttttt tgggcgcgac acaaatcgag gtgagggaag agagaggaaa atcccctgaa     180
tccctgcagg attaatttat tcaaaaagga aataaaaaat actcaatatg caaaagtctt     240
gtgaagaaaa tgagggaaaa ccacagaaca tgccaaaggc cgaggaagat cgccctttgg     300
aggatgtacc acaggaggca gaaggaaatc ctcaaccttc cgaagaaggc gtaagccagg     360
aagcagaagg aaaccccaga ggagggccga atcagcctgg ccagggattt aaagaggaca     420
cacccgttag gcatttggac cctgaagaaa tgataagagg agtagatgag cttgaaaggc     480
ttagggaaga gataagaaga gtaagaaaca agtttgtgat gatgcattgg aagcaaagac     540
attcacgcag ccgtccttat cctgtgtgct ttaggccttg aattcatttt tgcctaatat     600
taaaatctgg ccccagcttt ctttctgtta gcattttctg atgtatcttt gacctccatt     660
ttacttttaa tcatctgatg aaattttgtt ttaggtaatt tccttggtac cagcatctca     720
ttggattttg gattttgacc cattttccag gtctattttt caattggaaa ctttcacaca     780
tttgcatggg aatatgttca ttccatgttg taaagtaaaa cataacaggt tatggcaaag     840
cagcatattt aatatcagct cacatatgta ggataaaatt ccaaactttg tgtgtgtgcg     900
tgtgtgtata catacatcca tataacatat atcacaaact taaccaagct tatttctgtg     960
tggtgtgaaa ttttatttgt tttcttcttt ttgttctttt tgcttatatg tactttttaa    1020
tgaacacgtg tctcacacac aaaaagaatt aaggatttt tttacaagta agagtcaaat    1080
aatttgcaac cagcttatga gggcaatggg ggcacctaaa ctcttgatga agaactttta    1140
aaaagaaatg taaacctcaa attacctctg gatctcttag ccagaggaat aaactggcaa    1200
ttattacaga taaaaaaaaa aaaaaaaaaa a                                    1231
```

<210> SEQ ID NO 76
<211> LENGTH: 117
<212> TYPE: PRT
<213> ORGANISM: Homo sapiens

<400> SEQUENCE: 76

```
Met Gln Lys Ser Cys Glu Glu Asn Glu Gly Lys Pro Gln Asn Met Pro
1               5                   10                  15

Lys Ala Glu Glu Asp Arg Pro Leu Glu Asp Val Pro Gln Glu Ala Glu
            20                  25                  30

Gly Asn Pro Gln Pro Ser Glu Glu Gly Val Ser Gln Glu Ala Glu Gly
        35                  40                  45

Asn Pro Arg Gly Gly Pro Asn Gln Pro Gly Gln Gly Phe Lys Glu Asp
    50                  55                  60

Thr Pro Val Arg His Leu Asp Pro Glu Glu Met Ile Arg Gly Val Asp
65                  70                  75                  80

Glu Leu Glu Arg Leu Arg Glu Glu Ile Arg Arg Val Arg Asn Lys Phe
                85                  90                  95

Val Met Met His Trp Lys Gln Arg His Ser Arg Ser Arg Pro Tyr Pro
            100                 105                 110

Val Cys Phe Arg Pro
```

<210> SEQ ID NO 77
<211> LENGTH: 2213
<212> TYPE: DNA
<213> ORGANISM: Homo sapiens

<400> SEQUENCE: 77

| | | | | | |
|---|---|---|---|---|---|
| gcgggactcg | gccttctggg | cgcgcgcgac | gtcagtttga | gttctgtgtt | ctccccgccc | 60 |
| gtgtcccgcc | cgacccgcgc | ccgcgatgct | ggcgctgcgc | tgcggctccc | gctggctcgg | 120 |
| cctgctctcc | gtcccgcgct | ccgtgccgct | gcgcctcccc | gcggcccgcg | cctgcagcaa | 180 |
| gggctccggc | gacccgtcct | cttcctcctc | ctccgggaac | ccgctcgtgt | acctggacgt | 240 |
| ggacgccaac | gggaagccgc | tcggccgcgt | ggtgctggag | ctgaaggcag | atgtcgtccc | 300 |
| aaagacagct | gagaacttca | gagccctgtg | cactggtgag | aagggcttcg | gctacaaagg | 360 |
| ctccaccttc | cacagggtga | tcccttcctt | catgtgccag | gcgggcgact | tcaccaacca | 420 |
| caatggcaca | ggcgggaagt | ccatctacgg | aagccgcttt | cctgacgaga | actttacact | 480 |
| gaagcacgtg | gggccaggtg | tcctgtccat | ggctaatgct | ggtcctaaca | ccaacggctc | 540 |
| ccagttcttc | atctgcacca | taaagacaga | ctggttggat | ggcaagcatg | ttgtgttcgg | 600 |
| tcacgtcaaa | gagggcatgg | acgtcgtgaa | gaaaatagaa | tctttcggct | ctaagagtgg | 660 |
| gaggacatcc | aagaagattg | tcatcacaga | ctgtggccag | ttgagctaat | ctgtggccag | 720 |
| ggtgctggca | tggtggcagc | tgcaaatgtc | catgcaccca | ggtggccgcg | ttgggctgtc | 780 |
| agccaaggtg | cctgaaacga | tacgtgtgcc | cactccactg | tcacagtgtg | cctgaggaag | 840 |
| gctgctaggg | atgttagacc | tcggccagga | cccaccacat | tgcttcctaa | tacccaccct | 900 |
| tcctcacgac | ctcatttctg | ggcatctttg | tggacatgat | gtcacccacc | ccttgtcaag | 960 |
| cattgcctgt | gattgcccag | cccagattca | tctgtgcctt | ggacatggtg | atggtgatgg | 1020 |
| gttgccatcc | aagtgaaagt | cttttccttg | accaaggggg | acagtcagtt | ttgcaaaagg | 1080 |
| actctaatac | ctgtttaata | ttgtcttcct | aattgggata | atttaattaa | caagattgac | 1140 |
| tagaagtgaa | actgcaacac | taacttcccc | gtgctgtggt | gtgacctgag | ttggtgacac | 1200 |
| aggccacaga | ccccagagct | tggcttttga | aacacaactc | agggcttttg | tgaaggttcc | 1260 |
| cccgctgaga | tctttcctcc | tggttactgt | gaagcctgtt | ggtttgctgc | tgtcgttttt | 1320 |
| gaggagggcc | catgggggta | ggagcagttg | aacctgggaa | caaacctcac | ttgagctgtg | 1380 |
| cctagacaat | gtgaattcct | gtgttgctaa | cagaagtggc | ctgtaagctc | ctgtgctccg | 1440 |
| gagggaagca | tttcctggta | ggctttgatt | tttctgtgtg | ttaaagaaat | tcaatctact | 1500 |
| catgatgtgt | tatgcataaa | acatttctgg | aacatggatt | tgtgttcacc | ttaaatgtga | 1560 |
| aaataaatcc | tattttctat | ggaagactgg | tacctggttt | ctggaagagg | ggtctgtgac | 1620 |
| ttggagctga | tctttactga | gctcgccgtg | gcagatgcca | tgctcaggac | gttcatgtgg | 1680 |
| atggtttcat | gtcatcgtgc | tggcaacttg | tcctccctgc | cttagagatg | aggctcagac | 1740 |
| aaacgacctt | agcacccata | gcctatgcca | tgagcactgg | ctccaccctg | aatcccagct | 1800 |
| cctcccctta | gtgaccccaa | gtctgtttcc | ctcagctgca | taaggaggcg | atatagtttg | 1860 |
| aatatttgtc | cccagccaaa | tctcatgttg | aactgtaatc | cccagtgctg | gaggtggggc | 1920 |
| ctgctacgag | gtgtttggat | catggggacg | ggtatttcat | ggcttggtgc | tgttttcttg | 1980 |
| atggtgaatt | attgcaagat | acggtcattt | aaaattgtgt | ggcacctccc | cctgcccct | 2040 |
| tcttgctcct | gctttcacca | tgtgacatgc | ctgatccccc | ttcaccttt | gccatggtca | 2100 |

```
taagcttcct gaggcctccc tggaagctga gcagatgcca gcaccatgct tcctgtacat    2160
cctgcagaac cataagccaa ttaaacctt  ttaataataa aaaaaaaaaa aaa            2213

<210> SEQ ID NO 78
<211> LENGTH: 207
<212> TYPE: PRT
<213> ORGANISM: Homo sapiens

<400> SEQUENCE: 78

Met Leu Ala Leu Arg Cys Gly Ser Arg Trp Leu Gly Leu Leu Ser Val
1               5                   10                  15

Pro Arg Ser Val Pro Leu Arg Leu Pro Ala Ala Arg Ala Cys Ser Lys
            20                  25                  30

Gly Ser Gly Asp Pro Ser Ser Ser Ser Ser Gly Asn Pro Leu Val
        35                  40                  45

Tyr Leu Asp Val Asp Ala Asn Gly Lys Pro Leu Gly Arg Val Val Leu
    50                  55                  60

Glu Leu Lys Ala Asp Val Val Pro Lys Thr Ala Glu Asn Phe Arg Ala
65                  70                  75                  80

Leu Cys Thr Gly Glu Lys Gly Phe Gly Tyr Lys Gly Ser Thr Phe His
                85                  90                  95

Arg Val Ile Pro Ser Phe Met Cys Gln Ala Gly Asp Phe Thr Asn His
            100                 105                 110

Asn Gly Thr Gly Gly Lys Ser Ile Tyr Gly Ser Arg Phe Pro Asp Glu
        115                 120                 125

Asn Phe Thr Leu Lys His Val Gly Pro Gly Val Leu Ser Met Ala Asn
    130                 135                 140

Ala Gly Pro Asn Thr Asn Gly Ser Gln Phe Phe Ile Cys Thr Ile Lys
145                 150                 155                 160

Thr Asp Trp Leu Asp Gly Lys His Val Val Phe Gly His Val Lys Glu
                165                 170                 175

Gly Met Asp Val Val Lys Lys Ile Glu Ser Phe Gly Ser Lys Ser Gly
            180                 185                 190

Arg Thr Ser Lys Lys Ile Val Ile Thr Asp Cys Gly Gln Leu Ser
        195                 200                 205

<210> SEQ ID NO 79
<211> LENGTH: 1668
<212> TYPE: DNA
<213> ORGANISM: Homo sapiens

<400> SEQUENCE: 79
atgcccctca tttacataaa tattatacta gcatttacca tctcacttct aggaatacta      60
gtatatcgct cacacctcat atcctccta ctatgcctag aaggaataat actatcgctg     120
ttcattatag ctactctcat aaccctcaac acccactccc tcttagccaa tattgtgcct     180
attgccatac tagtctttgc cgcctgcgaa gcagcggtgg gcctagccct actagtctca     240
atctccaaca catatggcct agactacgta cataacctaa acctactcca atgctaaaac     300
taatcgtccc aacaattata ttactaccac tgacatgact ttccaaaaaa cacataattt     360
gaatcaacac aaccacccac agcctaatta ttagcatcat ccctctacta tttttaacc     420 aaatcaacaa caacctattt agctgttccc caacctttc ctccgacccc ctaacaaccc     480
ccctcctaat actaactacc tgactcctac ccctcacaat catggcaagc caacgccact     540
tatccagtga accactatca cgaaaaaaac tctacctctc tatactaatc tccctacaaa     600
tctccttaat tataacattc acagccacag aactaatcat attttatatc ttcttcgaaa     660
```

-continued

```
ccacacttat cccaccttg gctatcatca cccgatgagg caaccagcca gaacgcctga    720
acgcaggcac atacttccta ttctacaccc tagtaggctc ccttcccta ctcatcgcac     780 taatttacac tcacaacacc ctaggctcac taaacattct actactcact ctcactgccc    840
aagaactatc aaactcctga gccaataact taatatgact agcttacaca atagctttta   900
tagtaaagat acctctttac ggactccact tatgactccc taaagcccat gtcgaagccc    960
ccatcgctgg gtcaatagta cttgccgcag tactcttaaa actaggcggc tatggtataa   1020
tacgcctcac actcattctc aaccccctga caaaacacat agcctacccc ttccttgtac   1080
tatccctatg aggcataatt ataacaagct ccatctgcct acgacaaaca gacctaaaat   1140
cgctcattgc atactcttca atcagccaca tagccctcgt agtaacagcc attctcatcc   1200
aaaccccctg aagcttcacc ggcgcagtca ttctcataat cgcccacggg cttacatcct   1260
cattactatt ctgcctagca aactcaaact acgaacgcac tcacagtcgc atcataatcc   1320
tctctcaagg acttcaaact ctactcccac taatagcttt ttgatgactt ctagcaagcc   1380 tcgctaaccct cgccttaccc ccactatta acctactggg agaactctct gtgctagtaa    1440
ccacgttctc ctgatcaaat atcactctcc tacttacagg actcaacata ctagtcacag   1500
ccctatactc cctctacata tttaccacaa cacaatgggg ctcactcacc caccacatta   1560
acaacataaa accctcattc acacgagaaa acaccctcat gttcatacac ctatccccca   1620
ttctcctcct atccctcaac cccgacatca ttaccggggtt ttcctctt            1668
```

<210> SEQ ID NO 80
<211> LENGTH: 459
<212> TYPE: PRT
<213> ORGANISM: Homo sapiens

<400> SEQUENCE: 80

```
Met Leu Lys Leu Ile Val Pro Thr Ile Met Leu Leu Pro Leu Thr Trp
1               5                   10                  15

Leu Ser Lys Lys His Met Ile Trp Ile Asn Thr Thr Thr His Ser Leu
            20                  25                  30

Ile Ile Ser Ile Ile Pro Leu Leu Phe Phe Asn Gln Ile Asn Asn Asn
        35                  40                  45

Leu Phe Ser Cys Ser Pro Thr Phe Ser Ser Asp Pro Leu Thr Thr Pro
    50                  55                  60

Leu Leu Met Leu Thr Thr Trp Leu Leu Pro Leu Thr Ile Met Ala Ser
65                  70                  75                  80

Gln Arg His Leu Ser Ser Glu Pro Leu Ser Arg Lys Lys Leu Tyr Leu
                85                  90                  95

Ser Met Leu Ile Ser Leu Gln Ile Ser Leu Ile Met Thr Phe Thr Ala
            100                 105                 110

Thr Glu Leu Ile Met Phe Tyr Ile Phe Phe Glu Thr Thr Leu Ile Pro
        115                 120                 125

Thr Leu Ala Ile Ile Thr Arg Trp Gly Asn Gln Pro Glu Arg Leu Asn
    130                 135                 140

Ala Gly Thr Tyr Phe Leu Phe Tyr Thr Leu Val Gly Ser Leu Pro Leu
145                 150                 155                 160

Leu Ile Ala Leu Ile Tyr Thr His Asn Thr Leu Gly Ser Leu Asn Ile
                165                 170                 175

Leu Leu Leu Thr Leu Thr Ala Gln Glu Leu Ser Asn Ser Trp Ala Asn
            180                 185                 190

Asn Leu Met Trp Leu Ala Tyr Thr Met Ala Phe Met Val Lys Met Pro
```

```
                195                 200                 205
Leu Tyr Gly Leu His Leu Trp Leu Pro Lys Ala His Val Glu Ala Pro
    210                 215                 220

Ile Ala Gly Ser Met Val Leu Ala Ala Val Leu Leu Lys Leu Gly Gly
225                 230                 235                 240

Tyr Gly Met Met Arg Leu Thr Leu Ile Leu Asn Pro Leu Thr Lys His
                245                 250                 255

Met Ala Tyr Pro Phe Leu Val Leu Ser Leu Trp Gly Met Ile Met Thr
            260                 265                 270

Ser Ser Ile Cys Leu Arg Gln Thr Asp Leu Lys Ser Leu Ile Ala Tyr
        275                 280                 285

Ser Ser Ile Ser His Met Ala Leu Val Val Thr Ala Ile Leu Ile Gln
    290                 295                 300

Thr Pro Trp Ser Phe Thr Gly Ala Val Ile Leu Met Ile Ala His Gly
305                 310                 315                 320

Leu Thr Ser Ser Leu Leu Phe Cys Leu Ala Asn Ser Asn Tyr Glu Arg
                325                 330                 335

Thr His Ser Arg Ile Met Ile Leu Ser Gln Gly Leu Gln Thr Leu Leu
            340                 345                 350

Pro Leu Met Ala Phe Trp Trp Leu Leu Ala Ser Leu Ala Asn Leu Ala
        355                 360                 365

Leu Pro Pro Thr Ile Asn Leu Leu Gly Glu Leu Ser Val Leu Val Thr
    370                 375                 380

Thr Phe Ser Trp Ser Asn Ile Thr Leu Leu Thr Gly Leu Asn Met
385                 390                 395                 400

Leu Val Thr Ala Leu Tyr Ser Leu Tyr Met Phe Thr Thr Gln Trp
                405                 410                 415

Gly Ser Leu Thr His His Ile Asn Asn Met Lys Pro Ser Phe Thr Arg
            420                 425                 430

Glu Asn Thr Leu Met Phe Met His Leu Ser Pro Ile Leu Leu Leu Ser
        435                 440                 445

Leu Asn Pro Asp Ile Ile Thr Gly Phe Ser Ser
    450                 455

<210> SEQ ID NO 81
<211> LENGTH: 628
<212> TYPE: DNA
<213> ORGANISM: Homo sapiens

<400> SEQUENCE: 81
tgacccactt ccgttacttg ctgcggagga ccgtgggcag ccagggtcgg tgaaggatcc    60
caaaatggct gggcgaaaac ttgctctaaa aaccattgac tgggtagctt ttgcagagat   120 catacccag aaccaaaagg ccattgctag ttccctgaaa tcctggaatg agaccctcac   180
ctccaggttg gctgctttac ctgagaatcc accagctatc gactgggctt actacaaggc   240
caatgtggcc aaggctggct tggtggatga ctttgagaag aagtttaatg cgctgaaggt   300
tcccgtgcca gaggataaat atactgccca ggtggatgcc gaagaaaag aagatgtgaa   360 atcttgtgct gagtgggtgt ctctctcaaa ggccaggatt gtagaatatg agaaagagat   420
ggagaagatg aagaacttaa ttccatttga tcagatgacc attgaggact gaatgaagc   480 tttcccagaa accaaattag acaagaaaaa gtatccctat tggcctcacc aaccaattga   540
gaatttataa aattgagtcc aggaggaagc tctggccctt gtattacaca ttctggacat   600
taaaaataat aattatacag ttaaaaaa                                     628
```

<210> SEQ ID NO 82
<211> LENGTH: 161
<212> TYPE: PRT
<213> ORGANISM: Homo sapiens

<400> SEQUENCE: 82

```
Met Ala Gly Arg Lys Leu Ala Leu Lys Thr Ile Asp Trp Val Ala Phe
1               5                   10                  15

Ala Glu Ile Ile Pro Gln Asn Gln Lys Ala Ile Ala Ser Ser Leu Lys
            20                  25                  30

Ser Trp Asn Glu Thr Leu Thr Ser Arg Leu Ala Ala Leu Pro Glu Asn
        35                  40                  45

Pro Pro Ala Ile Asp Trp Ala Tyr Tyr Lys Ala Asn Val Ala Lys Ala
    50                  55                  60

Gly Leu Val Asp Asp Phe Glu Lys Lys Phe Asn Ala Leu Lys Val Pro
65                  70                  75                  80

Val Pro Glu Asp Lys Tyr Thr Ala Gln Val Asp Ala Glu Glu Lys Glu
                85                  90                  95

Asp Val Lys Ser Cys Ala Glu Trp Val Ser Leu Ser Lys Ala Arg Ile
            100                 105                 110

Val Glu Tyr Glu Lys Glu Met Glu Lys Met Lys Asn Leu Ile Pro Phe
        115                 120                 125

Asp Gln Met Thr Ile Glu Asp Leu Asn Glu Ala Phe Pro Glu Thr Lys
    130                 135                 140

Leu Asp Lys Lys Lys Tyr Pro Tyr Trp Pro His Gln Pro Ile Glu Asn
145                 150                 155                 160

Leu
```

<210> SEQ ID NO 83
<211> LENGTH: 1617
<212> TYPE: DNA
<213> ORGANISM: Homo sapiens

<400> SEQUENCE: 83

| | | | | | |
|---|---|---|---|---|---|
| ctgatgttcg | ccgaccgttg | actattctct | acaaaccaca | agacattgg | aacactatac | 60 |
| ctattattcg | gcgcatgagc | tggagtccta | ggcacagctc | taagcctcct | tattcgagcc | 120 |
| gagctgggcc | agccaggcaa | ccttctaggt | aacgaccaca | tctacaacgt | tatcgtcaca | 180 |
| gcccatgcat | ttgtaataat | cttcttcata | gtaataccca | tcataatcgg | aggctttggc | 240 |
| aactgactag | ttcccctaat | aatcggtgcc | cccgatatgg | cgtttcccg | cataaacaac | 300 |
| ataagcttct | gactcttacc | tccctctctc | ctactcctgc | tcgcatctgc | tatagtggag | 360 |
| gccggagcag | gaacaggttg | aacagtctac | cctcccttag | cagggaacta | ctcccaccct | 420 |
| ggagcctccg | tagacctaac | catcttctcc | ttacacctag | caggtgtctc | ctctatctta | 480 |
| ggggccatca | atttcatcac | aacaattatc | aatataaaac | ccctgccat | aacccaatac | 540 |
| caaacgcccc | tcttcgtctg | atccgtccta | atcacagcag | tcctacttct | cctatctctc | 600 |
| ccagtcctag | ctgctggcat | cactatacta | ctaacagacc | gcaacctcaa | caccaccttc | 660 |
| ttcgaccccg | ccggaggagg | agaccccatt | ctataccaac | acctattctg | attttcggt | 720 |
| caccctgaag | tttatattct | tatcctacca | ggcttcggaa | taatctccca | tattgtaact | 780 |
| tactactccg | gaaaaaaga | accatttgga | tacataggta | tggtctgagc | tatgatatca | 840 |
| attggcttcc | tagggtttat | cgtgtgagca | caccatatat | ttacagtagg | aatagacgta | 900 |
| gacacacgag | catatttcac | ctccgctacc | ataatcatcg | ctatccccac | cggcgtcaaa | 960 |

-continued

```
gtatttagct gactcgccac actccacgga agcaatatga aatgatctgc tgcagtgctc    1020
tgagccctag gattcatctt tcttttcacc gtaggtggcc tgactggcat tgtattagca    1080
aactcatcac tagacatcgt actacacgac acgtactacg ttgtagccca cttccactat    1140
gtcctatcaa taggagctgt atttgccatc ataggaggct tcattcactg atttccccta    1200
ttctcaggct acaccctaga ccaaacctac gccaaaatcc atttcactat catattcatc    1260
ggcgtaaatc taactttctt cccacaacac tttctcggcc tatccggaat gccccgacgt    1320
tactcggact accccgatgc atacaccaca tgaaacatcc tatcatctgt aggctcattc    1380
atttctctaa cagcagtaat attaataatt ttcatgattt gagaagcctt cgcttcgaag    1440
cgaaaagtcc taatagtaga agaaccctcc ataaacctgg agtgactata tggatgcccc    1500 ccacccctacc acacattcga agaaccgta tacataaat ctagacaaaa aaggaaggaa    1560
tcgaaccccc caaagctggt ttcaagccaa ccccatggcc tccatgactt tttcaaa      1617
```

<210> SEQ ID NO 84
<211> LENGTH: 513
<212> TYPE: PRT
<213> ORGANISM: Homo sapiens

<400> SEQUENCE: 84

```
Met Phe Ala Asp Arg Trp Leu Phe Ser Thr Asn His Lys Asp Ile Gly
1               5                   10                  15

Thr Leu Tyr Leu Leu Phe Gly Ala Trp Ala Gly Val Leu Gly Thr Ala
            20                  25                  30

Leu Ser Leu Leu Ile Arg Ala Glu Leu Gly Gln Pro Gly Asn Leu Leu
        35                  40                  45

Gly Asn Asp His Ile Tyr Asn Val Ile Val Thr Ala His Ala Phe Val
    50                  55                  60

Met Ile Phe Phe Met Val Met Pro Ile Met Ile Gly Gly Phe Gly Asn
65                  70                  75                  80

Trp Leu Val Pro Leu Met Ile Gly Ala Pro Asp Met Ala Phe Pro Arg
                85                  90                  95

Met Asn Asn Met Ser Phe Trp Leu Leu Pro Pro Ser Leu Leu Leu Leu
            100                 105                 110

Leu Ala Ser Ala Met Val Glu Ala Gly Ala Gly Thr Gly Trp Thr Val
        115                 120                 125

Tyr Pro Pro Leu Ala Gly Asn Tyr Ser His Pro Gly Ala Ser Val Asp
    130                 135                 140

Leu Thr Ile Phe Ser Leu His Leu Ala Gly Val Ser Ser Ile Leu Gly
145                 150                 155                 160

Ala Ile Asn Phe Ile Thr Thr Ile Ile Asn Met Lys Pro Pro Ala Met
                165                 170                 175

Thr Gln Tyr Gln Thr Pro Leu Phe Val Trp Ser Val Leu Ile Thr Ala
            180                 185                 190

Val Leu Leu Leu Leu Ser Leu Pro Val Leu Ala Ala Gly Ile Thr Met
        195                 200                 205

Leu Leu Thr Asp Arg Asn Leu Asn Thr Thr Phe Phe Asp Pro Ala Gly
    210                 215                 220

Gly Gly Asp Pro Ile Leu Tyr Gln His Leu Phe Trp Phe Phe Gly His
225                 230                 235                 240

Pro Glu Val Tyr Ile Leu Ile Leu Pro Gly Phe Gly Met Ile Ser His
                245                 250                 255

Ile Val Thr Tyr Tyr Ser Gly Lys Lys Glu Pro Phe Gly Tyr Met Gly
            260                 265                 270
```

```
Met Val Trp Ala Met Met Ser Ile Gly Phe Leu Gly Phe Ile Val Trp
            275                 280                 285

Ala His His Met Phe Thr Val Gly Met Asp Val Asp Thr Arg Ala Tyr
            290                 295                 300

Phe Thr Ser Ala Thr Met Ile Ile Ala Ile Pro Thr Gly Val Lys Val
305                 310                 315                 320

Phe Ser Trp Leu Ala Thr Leu His Gly Ser Asn Met Lys Trp Ser Ala
                325                 330                 335

Ala Val Leu Trp Ala Leu Gly Phe Ile Phe Leu Phe Thr Val Gly Gly
            340                 345                 350

Leu Thr Gly Ile Val Leu Ala Asn Ser Ser Leu Asp Ile Val Leu His
            355                 360                 365

Asp Thr Tyr Tyr Val Val Ala His Phe His Tyr Val Leu Ser Met Gly
            370                 375                 380

Ala Val Phe Ala Ile Met Gly Gly Phe Ile His Trp Phe Pro Leu Phe
385                 390                 395                 400

Ser Gly Tyr Thr Leu Asp Gln Thr Tyr Ala Lys Ile His Phe Thr Ile
                405                 410                 415

Met Phe Ile Gly Val Asn Leu Thr Phe Phe Pro Gln His Phe Leu Gly
            420                 425                 430

Leu Ser Gly Met Pro Arg Arg Tyr Ser Asp Tyr Pro Asp Ala Tyr Thr
            435                 440                 445

Thr Trp Asn Ile Leu Ser Ser Val Gly Ser Phe Ile Ser Leu Thr Ala
            450                 455                 460

Val Met Leu Met Ile Phe Met Ile Trp Glu Ala Phe Ala Ser Lys Arg
465                 470                 475                 480

Lys Val Leu Met Val Glu Glu Pro Ser Met Asn Leu Glu Trp Leu Tyr
                485                 490                 495

Gly Cys Pro Pro Pro Tyr His Thr Phe Glu Glu Pro Val Tyr Met Lys
                500                 505                 510

Ser
```

<210> SEQ ID NO 85
<211> LENGTH: 709
<212> TYPE: DNA
<213> ORGANISM: Homo sapiens

<400> SEQUENCE: 85

```
atggcacatg cagcgcaagt aggtctacaa gacgctactt cccctatcat agaagagctt      60
atcacctttc atgatcacgc cctcataatc attttcctta tctgcttcct agtcctgtat     120
gcccttttcc taacactcac aacaaaacta actaatacta acatctcaga cgctcaggaa     180
atagaaaccg tctgaactat cctgcccgcc atcatcctag tcctcatcgc cctcccatcc     240
ctacgcatcc tttacataac agacgaggtc aacgatccct cccttaccat caaatcaatt     300
ggccaccaat ggtactgaac ctacgagtac accgactacg gcggactaat cttcaactcc     360
tacatacttc cccattatt cctagaacca ggcgacctgc gactccttga cgttgacaat     420
cgagtagtac tcccgattga agcccccatt cgtataataa ttacatcaca agacgtcttg     480
cactcatgag ctgtccccac attaggctta aaaacagatg caattcccgg acgtctaaac     540
caaaccactt tcaccgctac acgaccgggg gtatactacg gtcaatgctc tgaaatctgt     600
ggagcaaacc acagtttcat gcccatcgtc ctagaattaa ttcccctaaa aatctttgaa     660
atagggcccg tatttaccct atagcacccc ctctaccccc tctagagcc                 709
```

<210> SEQ ID NO 86
<211> LENGTH: 227
<212> TYPE: PRT
<213> ORGANISM: Homo sapiens

<400> SEQUENCE: 86

Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
                20                  25                  30

Leu Ile Cys Phe Leu Val Leu Tyr Ala Leu Phe Leu Thr Leu Thr Thr
            35                  40                  45

Lys Leu Thr Asn Thr Asn Ile Ser Asp Ala Gln Glu Met Glu Thr Val
    50                  55                  60

Trp Thr Ile Leu Pro Ala Ile Ile Leu Val Leu Ile Ala Leu Pro Ser
65                  70                  75                  80

Leu Arg Ile Leu Tyr Met Thr Asp Glu Val Asn Asp Pro Ser Leu Thr
                85                  90                  95

Ile Lys Ser Ile Gly His Gln Trp Tyr Trp Thr Tyr Glu Tyr Thr Asp
            100                 105                 110

Tyr Gly Gly Leu Ile Phe Asn Ser Tyr Met Leu Pro Pro Leu Phe Leu
        115                 120                 125

Glu Pro Gly Asp Leu Arg Leu Leu Asp Val Asp Asn Arg Val Val Leu
    130                 135                 140

Pro Ile Glu Ala Pro Ile Arg Met Met Ile Thr Ser Gln Asp Val Leu
145                 150                 155                 160

His Ser Trp Ala Val Pro Thr Leu Gly Leu Lys Thr Asp Ala Ile Pro
                165                 170                 175

Gly Arg Leu Asn Gln Thr Thr Phe Thr Ala Thr Arg Pro Gly Val Tyr
            180                 185                 190

Tyr Gly Gln Cys Ser Glu Ile Cys Gly Ala Asn His Ser Phe Met Pro
        195                 200                 205

Ile Val Leu Glu Leu Ile Pro Leu Lys Ile Phe Glu Met Gly Pro Val
    210                 215                 220

Phe Thr Leu
225

<210> SEQ ID NO 87
<211> LENGTH: 781
<212> TYPE: DNA
<213> ORGANISM: Homo sapiens

<400> SEQUENCE: 87
atgacccacc aatcacatgc ctatcatata gtaaaaccca gcccatgacc cctaacaggg     60
gccctctcag ccctcctaat gacctccggc ctagccatgt gatttcactt ccactccata    120
acgctcctca tactaggcct actaaccaac acactaacca tataccaatg gtggcgcgat    180
gtaacacgag aaagcacata ccaaggccac cacacaccac ctgtccaaaa aggccttcga    240
tacgggataa tcctatttat tacctcagaa gtttttttct tcgcaggatt tttctgagcc    300
ttttaccact ccagcctagc cctacccccc aactaggagg gcactggcc cccaacaggc     360 atcaccccgc taaatcccct agaagtccca ctcctaaaca catccgtatt actcgcatca    420
ggagtatcaa tcacctgagc tcaccatagt ctaatagaaa acaaccgaaa ccaaataatt    480
caagcactgc ttattacaat tttactgggt ctctatttta ccctcctaca agcctcagag    540
tacttcgagt ctccctttcac catttccgac ggcatctacg gctcaacatt ttttgtagcc    600

| acaggcttcc acggacttca cgtcattatt ggctcaactt tcctcactat ctgcttcatc | 660 |
| cgccaactaa tatttcactt tacatccaaa catcactttg gcttcgaagc cgccgcctga | 720 |
| tactggcatt ttgtagatgt ggtttgacta tttctgtatg tctccatcta ttgatgaggg | 780 |
| t | 781 |

<210> SEQ ID NO 88
<211> LENGTH: 260
<212> TYPE: PRT
<213> ORGANISM: Homo sapiens

<400> SEQUENCE: 88

```
Met Thr His Gln Ser His Ala Tyr His Met Val Lys Pro Ser Pro Trp
1               5                   10                  15
Pro Leu Thr Gly Ala Leu Ser Ala Leu Leu Met Thr Ser Gly Leu Ala
                20                  25                  30
Met Trp Phe His Phe His Ser Met Thr Leu Leu Met Leu Gly Leu Leu
            35                  40                  45
Thr Asn Thr Leu Thr Met Tyr Gln Trp Trp Arg Asp Val Thr Arg Glu
        50                  55                  60
Ser Thr Tyr Gln Gly His His Thr Pro Pro Val Gln Lys Gly Leu Arg
65                  70                  75                  80
Tyr Gly Met Ile Leu Phe Ile Thr Ser Glu Val Phe Phe Ala Gly
                85                  90                  95
Phe Phe Trp Ala Phe Tyr His Ser Ser Leu Ala Pro Thr Pro Gln Leu
            100                 105                 110
Gly Gly His Trp Pro Pro Thr Gly Ile Thr Pro Leu Asn Pro Leu Glu
        115                 120                 125
Val Pro Leu Leu Asn Thr Ser Val Leu Leu Ala Ser Gly Val Ser Ile
130                 135                 140
Thr Trp Ala His His Ser Leu Met Glu Asn Asn Arg Asn Gln Met Ile
145                 150                 155                 160
Gln Ala Leu Leu Ile Thr Ile Leu Leu Gly Leu Tyr Phe Thr Leu Leu
                165                 170                 175
Gln Ala Ser Glu Tyr Phe Glu Ser Pro Phe Thr Ile Ser Asp Gly Ile
            180                 185                 190
Tyr Gly Ser Thr Phe Phe Val Ala Thr Gly Phe His Gly Leu His Val
        195                 200                 205
Ile Ile Gly Ser Thr Phe Leu Thr Ile Cys Phe Ile Arg Gln Leu Met
210                 215                 220
Phe His Phe Thr Ser Lys His His Gly Phe Glu Ala Ala Ala Trp
225                 230                 235                 240
Tyr Trp His Phe Val Asp Val Val Trp Leu Phe Leu Tyr Val Ser Ile
                245                 250                 255
Tyr Trp Trp Gly
            260
```

<210> SEQ ID NO 89
<211> LENGTH: 20
<212> TYPE: DNA
<213> ORGANISM: Artificial sequence
<220> FEATURE:
<223> OTHER INFORMATION: Description of the artificial sequence: oligonucleotide

<400> SEQUENCE: 89

| cacccgttcg cagtcgtccc | 20 |

```
<210> SEQ ID NO 90
<211> LENGTH: 18
<212> TYPE: DNA
<213> ORGANISM: Artificial sequence
<220> FEATURE:
<223> OTHER INFORMATION: Description of the artificial sequence:
      oligonucleotide

<400> SEQUENCE: 90
tcgccgtcct cgctttcc                                                      18

<210> SEQ ID NO 91
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 91
gaaatggaag ataaagtgac                                                    20

<210> SEQ ID NO 92
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 92
gttcttcatt tttgctttag                                                    20

<210> SEQ ID NO 93
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 93
aagattcgga gtttgggctg c                                                  21

<210> SEQ ID NO 94
<211> LENGTH: 18
<212> TYPE: DNA
<213> ORGANISM: Artificial sequence
<220> FEATURE:
<223> OTHER INFORMATION: Description of the artificial sequence:
      oligonucleotide

<400> SEQUENCE: 94
ccagccgcac caataagg                                                      18

<210> SEQ ID NO 95
<211> LENGTH: 18
<212> TYPE: DNA
<213> ORGANISM: Artificial sequence
<220> FEATURE:
<223> OTHER INFORMATION: Description of the artificial sequence:
      oligonucleotide

<400> SEQUENCE: 95
atgagcctgg tgagcctg                                                      18
```

```
<210> SEQ ID NO 96
<211> LENGTH: 18
<212> TYPE: DNA
<213> ORGANISM: Artificial sequence
<220> FEATURE:
<223> OTHER INFORMATION: Description of the artificial sequence:
      oligonucleotide

<400> SEQUENCE: 96
gagacgctgc cttctcaa                                                 18

<210> SEQ ID NO 97
<211> LENGTH: 19
<212> TYPE: DNA
<213> ORGANISM: Artificial sequence
<220> FEATURE:
<223> OTHER INFORMATION: Description of the artificial sequence:
      oligonucleotide

<400> SEQUENCE: 97
actacggggc ttgtgacgg                                                19

<210> SEQ ID NO 98
<211> LENGTH: 18
<212> TYPE: DNA
<213> ORGANISM: Artificial sequence
<220> FEATURE:
<223> OTHER INFORMATION: Description of the artificial sequence:
      oligonucleotide

<400> SEQUENCE: 98
cccgcaggac agccaggt                                                 18

<210> SEQ ID NO 99
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 99
ctgaatgaca ggtatcctaa g                                             21

<210> SEQ ID NO 100
<211> LENGTH: 18
<212> TYPE: DNA
<213> ORGANISM: Artificial sequence
<220> FEATURE:
<223> OTHER INFORMATION: Description of the artificial sequence:
      oligonucleotide

<400> SEQUENCE: 100
aggatgggtt ctggatgt                                                 18

<210> SEQ ID NO 101
<211> LENGTH: 7
<212> TYPE: RNA
<213> ORGANISM: Artificial Sequence
<220> FEATURE:
<223> OTHER INFORMATION: polyA tail

<400> SEQUENCE: 101 aaaaaaa                                                             7

<210> SEQ ID NO 102
<211> LENGTH: 13
<212> TYPE: DNA
```

```
<213> ORGANISM: Artificial Sequence
<220> FEATURE:
<223> OTHER INFORMATION: OligodT with XhoI cleavage site

<400> SEQUENCE: 102
ctcgagtttt ttt                                                        13

<210> SEQ ID NO 103
<211> LENGTH: 13
<212> TYPE: DNA
<213> ORGANISM: Artificial Sequence
<220> FEATURE:
<223> OTHER INFORMATION: polyA tail with XhoI cleavage site

<400> SEQUENCE: 103
aaaaaaactc gag                                                        13

<210> SEQ ID NO 104
<211> LENGTH: 5
<212> TYPE: DNA
<213> ORGANISM: Artificial Sequence
<220> FEATURE:
<223> OTHER INFORMATION: EcoR1 linker

<400> SEQUENCE: 104 aattc                                                                  5

<210> SEQ ID NO 105
<211> LENGTH: 8
<212> TYPE: DNA
<213> ORGANISM: Artificial Sequence
<220> FEATURE:
<223> OTHER INFORMATION: oligonucleotide

<400> SEQUENCE: 105 aaaaaaac                                                               8

<210> SEQ ID NO 106
<211> LENGTH: 12
<212> TYPE: DNA
<213> ORGANISM: Artificial Sequence
<220> FEATURE:
<223> OTHER INFORMATION: XhoI linker

<400> SEQUENCE: 106
tcgagttttt tt                                                         12
```